(12) United States Patent  (10) Patent No.: US 7,446,216 B2
Voskoboynikov et al.  (45) Date of Patent: Nov. 4, 2008

(54) HALOGEN SUBSTITUTED METALLOCENE COMPOUNDS FOR OLEFIN POLYMERIZATION

(75) Inventors: Alexander Z. Voskoboynikov, Moscow (RU); Alexey N. Ryahov, Moscow (RU); Mikhail V. Nikulin, Moscow (RU); Alexander V. Lygin, Moscow (RU); Vyatcheslav V. Izmer, Moscow (RU); Andrey F. Asachenko, Chelyabinsk (RU); Catalina L. Coker, Baytown, TX (US); Jo Ann M. Canich, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 88 days.

(21) Appl. No.: 11/300,054

(22) Filed: Dec. 14, 2005

(65) Prior Publication Data

US 2006/0183874 A1  Aug. 17, 2006

Related U.S. Application Data

(60) Provisional application No. 60/636,662, filed on Dec. 16, 2004.

(51) Int. Cl.
   *C08F 4/6392*  (2006.01)
   *C08F 4/6592*  (2006.01)
(52) U.S. Cl. .................. 556/53; 502/103; 502/152; 502/155; 526/160; 526/161; 526/165; 526/943
(58) Field of Classification Search ................ 556/53; 502/103, 152; 526/160, 161, 165, 943
See application file for complete search history.

(56) References Cited

U.S. PATENT DOCUMENTS

| | | | |
|---|---|---|---|
| 3,678,088 | A | 7/1972 | Hedberg et al. |
| 5,466,766 | A | 11/1995 | Patsidis et al. |
| 5,504,232 | A | 4/1996 | Winter et al. |
| 5,763,542 | A | 6/1998 | Winter et al. |
| 5,840,644 | A | 11/1998 | Küber et al. |
| 5,936,053 | A | 8/1999 | Fukuoka et al. |
| 6,075,171 | A | 6/2000 | Sullivan et al. |
| 6,087,292 | A * | 7/2000 | Winter et al. ............... 502/117 |
| 6,291,699 | B1 | 9/2001 | Birmingham et al. |
| 6,399,723 | B1 | 6/2002 | Burkhardt et al. |
| 6,414,095 | B1 | 7/2002 | Burkhardt et al. |
| 6,465,700 | B1 | 10/2002 | Sullivan et al. |
| 6,492,539 | B1 | 12/2002 | Bingel et al. |
| 6,737,487 | B2 | 5/2004 | Meverden |
| 7,214,746 | B2 | 5/2007 | Voskoboynikov et al. |
| 7,214,747 | B2 | 5/2007 | Voskoboynikov et al. |
| 7,276,567 | B2 | 10/2007 | Voskoboynikov et al. |
| 2002/0193535 | A1 | 12/2002 | Meverden et al. |
| 2004/0260107 | A1 | 12/2004 | Oberhoff et al. |
| 2006/0160967 | A1 | 7/2006 | Voskoboynikov et al. |
| 2006/0160968 | A1 | 7/2006 | Voskoboynikov et al. |

(Continued)

FOREIGN PATENT DOCUMENTS

EP  0 666 267  8/1995

(Continued)

OTHER PUBLICATIONS

MacDowell, Denis W.H., et al., "Keto-Enol Tautomerism in the Thiophene Analogues of Naphthacen-5-one," *J. Org. Chem.* 1982, 47, 705-709.

(Continued)

*Primary Examiner*—Caixia Lu
(74) *Attorney, Agent, or Firm*—Catherine L. Bell

(57) ABSTRACT

A metallocene compound is represented by the formula (1):

$$A_2Y_yMX_{n-2}$$

wherein:

M is a transition metal atom having a coordination number of n selected from Group 3, 4, 5 or 6 of the Periodic Table of Elements, or a lanthanide metal atom, or actinide metal atom;

each A is independently a substituted polycyclic arenyl ligand pi-bonded to M, each A ligand includes at least one halogen substituent directly bonded to an $sp^2$ carbon at a bondable ring position and, when each A is a substituted indenyl ligand and y is equal to one and the ligand includes at least one chloro, bromo or iodo substituent at the 4, 5, or 6 position of the indenyl ligand, then A also includes at least one other substituent in the indenyl ligand selected from hydrocarbyl, substituted hydrocarbyl, halogen, halocarbyl, substituted halocarbyl, silylcarbyl, substituted silylcarbyl, germylcarbyl, substituted germylcarbyl, or other heteroatom substituents wherein the heteroatom is bonded directly to a ring carbon of the ring structure ligand and is boron, a Group 15 atom, or a Group 16 atom, preferably boron, nitrogen, oxygen, phosphorus, or sulfur;

Y is an optional bridging group containing at least one Group 13, 14, 15, or 16 element and is bonded to any single position of the ring structure of A, y is zero or 1, indicating the absence (y=0) or presence (y=1) of Y; and the or each X is a univalent anionic ligand, or two X are joined and bound to the metal atom to form a metallocycle ring, or two X are joined to form a chelating ligand, a diene ligand, or an alkylidene ligand;

provided that when y is equal to 1, then A is not 5,6-dichloroindenyl or an indenyl group having a fluoro- or chloro substituent at the 7 position and a hydrocarbyl or substituted hydrocarbyl substituent at the 4 position, and provided further that when y is equal to 0, then A is not 5,6-difluoroindenyl.

21 Claims, 3 Drawing Sheets

U.S. PATENT DOCUMENTS

| | | | |
|---|---|---|---|
| 2007/0135593 A1 | 6/2007 | Voskoboynikov et al. |
| 2007/0135594 A1 | 6/2007 | Voskoboynikov et al. |
| 2007/0135595 A1 | 6/2007 | Voskoboynikov et al. |
| 2007/0135596 A1 | 6/2007 | Voskoboynikov et al. |
| 2007/0135597 A1 | 6/2007 | Voskoboynikov et al. |
| 2007/0135623 A1 | 6/2007 | Voskoboynikov et al. |

FOREIGN PATENT DOCUMENTS

| | | |
|---|---|---|
| EP | 0 582 195 B1 | 12/2000 |
| JP | 1995-216011 A | 8/1995 |
| JP | 11-080183 | 3/1999 |
| JP | 1999-080183 | 3/1999 |
| WO | 91/04257 | 4/1991 |
| WO | 02/092647 | 11/2002 |
| WO | 03/000744 | 1/2003 |

OTHER PUBLICATIONS

McEwen, Ian, et al., "Hydrogen Bonding of Hydroxy Groups to Carbanions in Indenide and Fluorenide Derivatized Alcohols Directly Observed by UV, IR, and NMR Spectroscopy," *J. Am. Chem. Soc.* 1993, 115, 3989-3996.

Halterman, Ronald L., et al., "Synthesis, Characterization, and Polymerization Properties of Bis(2-menthylindenyl)zirconium Dichloride and Bis(2-methyl-4,7-dimethylindenyl)zirconium Dichloride," *Organometallics* 2000, 19, 5464-5470.

Ryabov, Alexey N., et al., "Zirconium Complexes with Cyclopentadienyl Ligands Involving Fused a Thiophene Fragment," *Organometallics* 2002, 21, 2842-2855.

Zhang, Xingwang, et al., "General Synthesis of Racemic $Me_2Si$-Bridged Bis(indenyl) Zirconocene Complexes," *J. Am. Chem. Soc.* 2000, 122, 8093-8094.

Johnston, Randy F., et al., "Investigation of the Electrochemical Properties of Substituted Titanocene Dichlorides," *Electrochemica Acta* 1995, 40, 473-477.

Conway, Brian G., et al., "Formation and Reactivity of Halogen Derivatives of $\eta^5$-Cyclopentadienyl)thallium," *Organometallics* 1985, 4, 688-693.

Rausch, Marvin D., et al., "The Formation of Ring-Substituted Titanocene Derivatives Containing Chloro and Carbomethoxy Substituents," *J. Organometallic Chem.* 1988, 358, 161-168.

Finch, William C., et al., "Substituent Effects on the Cleavage Rates of Titanocene Metallocyclobutanes," *J. Am. Chem. Soc.* 1988, 110, 2406-2413.

Piccolrovazzi, Nicoletta, et al., "Electronic Effects in Homogenous Indenylzirconium Ziegler-Natta Catalysts," *Organometallics* 1990, 9, 3098-3105.

Schmid, Michael A., et al., "Unbridged Cyclopentadienyl-Fluorenyl Complexes of Zirconium as Catalysts for Homogenous Olefin Polymerization," *J. Organometallic Chem.* 1995, 501, 101-106.

Siedle, et al., "Synthesis of Unsymmetrical Ansa-Fluorenyl Metallocenes," *J. Mol. Catal. A. Chem.* 2004, 214(2), 187-198.

Linnolahti, et al., "Theoretical Study on the Factor Controlling the Accessibility of Cationic Metal Centers in Zirconocene Polymerization Catalysts," *Macromolecules* 2000, 33(25), 9205-9214.

\* cited by examiner

HALOGEN SUBSTITUTED METALLOCENE COMPOUNDS FOR OLEFIN POLYMERIZATION

CROSS REFERENCE TO RELATED APPLICATIONS

This application claims the benefit of U.S. Provisional Patent Application No. 60/636,662, filed on Dec. 16, 2004.

FIELD

This invention relates to halogen substituted metallocene compounds and their use in catalyst systems for olefin polymerization.

BACKGROUND

Various processes and catalysts exist for the homopolymerization or copolymerization of olefins. For many applications, it is desirable for a polyolefin to have a high weight average molecular weight while having a relatively narrow molecular weight distribution. A high weight average molecular weight, when accompanied by a narrow molecular weight distribution, provides a polyolefin with high strength properties.

Traditional Ziegler-Natta catalysts systems comprise a transition metal compound co-catalyzed by an aluminum alkyl and are typically capable of producing polyolefins having a high molecular weight, but with a broad molecular weight distribution.

More recently metallocene catalyst systems have been developed wherein the transition metal compound has one or more cyclopentadienyl, indenyl or fluorenyl ring ligands (typically two). Metallocene catalyst systems, when activated with cocatalysts, such as alumoxane, are effective to polymerize monomers to polyolefins having not only a high weight average molecular weight but also a narrow molecular weight distribution.

Particular focus has been directed to metallocenes containing substituted, bridged indenyl rings, since these materials are particularly effective in producing isotactic propylene polymers having high isotacticity and narrow molecular weight distribution. Considerable effort has been made toward obtaining metallocene produced propylene polymers having ever-higher molecular weight and melting point, while maintaining suitable catalyst activity. Researchers currently believe that there is a direct relationship between the way in which a metallocene is substituted, and the molecular structure of the resulting polymer. For the substituted, bridged indenyl type metallocenes, it is believed that the type and arrangement of substituents on the indenyl groups, as well as the type of bridge connecting the indenyl groups, determines such polymer attributes as molecular weight and melting point. Unfortunately, it is impossible at this time to accurately correlate specific substitution patterns with specific polymer attributes, though minor trends may be identified, from time to time.

For example, U.S. Pat. No. 5,840,644 describes certain metallocenes containing aryl-substituted indenyl derivatives as ligands, which are said to provide propylene polymers having high isotacticity, narrow molecular weight distribution and very high molecular weight.

Likewise, U.S. Pat. No. 5,936,053 describes certain metallocene compounds said to be useful for producing high molecular weight propylene polymers. These metallocenes have a specific hydrocarbon substituent at the 2 position and an unsubstituted aryl substituent at the 4 position, on each indenyl group of the metallocene compound.

In addition to hydrocarbon substituents, it is also known to include halogen substituents on metallocene compounds. For example, U.S. Pat. No. 3,678,088 discloses polychlorinated metallocenes having formulae $C_5H_{5-m}Cl_mMC_5H_5$ and $(C_5H_{5-n}Cl_n)_2M$ wherein M is iron, ruthenium or osmium, m is an integer from 3 to 5, inclusive and n is an integer from 2 to 5, inclusive. There is no disclosure of the polychlorinated metallocenes being used as olefin polymerization catalysts.

Similarly, chlorinated metallocenes including $(CpCl)_2TiCl_2$, $(CpCl)(Cp)TiCl_2$, $(CpCl)_2TiClMe$, and $(CpCl)(Cp)TiClMe$ are disclosed in J. Am. Chem. Soc. 1988, 110, 2406; J. Organometallic Chem. 1988, 358, 161; Organometallics 1985, 4, 688 and Electrochimica Acta, 1995, 40, 473.

Fluorinated bisindenyl metallocenes, particularly bis(4,7-difluoroindenyl)zirconium dichloride and bis(4,7-difluoroindenyl)zirconium dibenzyl, and their use in olefin polymerization are discussed in Organometallics, 1990, 9, 3098.

Brominated fluorenylcyclopentadienyl metallocenes, particularly (2,7-dibromofluorenyl)(cyclopentadienyl)zirconium dichloride, (2,7-dibromofluorenyl)(cyclopentadienyl) zirconium dimethyl and (2-bromofluorenyl) (cyclopentadienyl)zirconium dichloride, and their use in olefin polymerization are discussed in J. Organometallic Chem., 1995, 501, 101.

U.S. Patent Application Publication No. 2002/0193535 discloses a process for polymerizing propylene in the presence of a Group 3-5 transition metal catalyst having two indenoindolyl ligands, wherein the term "indenoindole" is defined to mean an organic compound that has both indole and indene rings in which the five-membered rings from each are fused. The indenoindole rings can be substituted with a variety of moieties, including halogen, and specifically disclosed and exemplified is bis(2-chloro-5-phenyl-5,10-dihydroindeno[1,2-b]-indolyl)zirconium dichloride U.S. Pat. Nos. 5,504,232, 5,763,542 and 6,087,292 disclose olefin polymerization catalysts based on bridged halogen substituted indenyls of Groups 4-6, such as Zr and Hf. Particularly exemplified are rac-dimethylsilanediylbis (5(6)-fluoroindenyl)zirconium dichloride (F mixed in 5 and 6 positions), rac-dimethylsilanediylbis(5-chloroindenyl)zirconium dichloride, rac-dimethylsilanediyl bis(4(7)-fluoroindenyl) zirconium dichloride (F mixed in 4 and 7 positions), and rac-dimethylsilanediylbis(5,6-dichloroindenyl)zirconium dichloride. The bridging groups are connected to the indenyl rings at 1-position.

JP1999-080183A discloses halogenated substituents on racemic carbon bridged bis-indenyl Group 4 transition metal complexes. The application focuses on the use of these complexes as pre-catalysts for the copolymerization of vinyl aromatic monomers (styrene). The only complexes exemplified are isopropylidene-bis(5- or 6-fluoroindenyl)zirconium bisdimethylamide, isopropylidene-bis(5- or 6-fluoroindenyl) zirconium dichloride, isopropylidene-bis(5-chloroindenyl) zirconium bisdimethylamide, and isopropylidene-bis(5-chloroindenyl)zirconium dichloride. The application gives preference to F>Cl>Br.

JP1995-216011A discloses olefin polymerization catalysts comprising bridged bis-indenyl Group 4-6 transition metal complexes, having halogen substituents either in the 2 or the 7 position on the indene ring. However, the only complexes exemplified are bridged bis-indenyl complexes having a fluoro- or chloro-substituent at the 7 position and a hydrocarbyl or substituted hydrocarbyl substituent at the 4 position.

U.S. Patent Application Publication No. 2004/0260107, published Dec. 23, 2004, discloses a large number of bridged indenyl substituted cyclopentadienyl complexes of Group 3 to 6 metals and indicates that the complexes are useful as olefin polymerization catalysts. Among the complexes specifically disclosed, but not synthesized, are dimethylsilanediyl(2-methyl-4-phenyl-7-chloroindenyl) (2-isopropyl-4-phenylindenyl)zirconium dichloride, dimethylsilanediyl (2-methyl-4-phenyl-7-bromoindenyl)(2-isopropyl-4-phenylindenyl)zirconium dichloride, dimethylsilanediyl(2-methyl-4-(1-naphthyl)-7-chloroindenyl)(2-isopropyl-4-(1-naphthyl)indenyl)zirconium dichloride, dimethylsilanediyl (2-methyl-4-(1-naphthyl)-7-bromoindenyl)(2-isopropyl-4-(1-naphthyl)indenyl)zirconium dichloride, dimethylsilanediyl(2-methyl-4-(p-t-butylphenyl)-7-chloroindenyl)(2-isopropyl-4-(p-t-butylphenyl)indenyl)zirconium dichloride and dimethylsilanediyl(2-methyl-4-(p-t-butylphenyl)-7-bromoindenyl)(2-isopropyl-4-(p-t-butylphenyl)indenyl)zirconium dichloride. Again, the bridging groups are connected to the indenyl rings at 1-position.

Since the effects of various substituents and bridging groups on the polymerization properties of metallocene catalysts is still largely an empirical matter; there is a continued interest in synthesizing and testing new metallocene structures.

SUMMARY

In one aspect, the invention resides in a metallocene compound represented by the formula (1):

$$A_2Y_yMX_{n-2}$$

wherein:

M is a transition metal atom having a coordination number of n selected from Group 3, 4, 5 or 6 of the Periodic Table of Elements, or a lanthanide metal atom, or actinide metal atom and preferably is a Group 4 transition metal selected from titanium, zirconium and hafnium;

each A is independently a substituted polycyclic arenyl ligand pi-bonded to M, each A ligand includes at least one halogen substituent directly bonded to an $sp^2$ carbon at a bondable ring position and, when each A is a substituted indenyl ligand and y is equal to one and the ligand includes at least one chloro, bromo or iodo substituent at the 4, 5, or 6 position of the indenyl ligand, then A also includes at least one other substituent in the indenyl ligand selected from hydrocarbyl, substituted hydrocarbyl, halogen, halocarbyl, substituted halocarbyl, silylcarbyl, substituted silylcarbyl, germylcarbyl, substituted germylcarbyl, or other heteroatom substituents wherein the heteroatom is bonded directly to a ring carbon of the ring structure ligand and is boron, a Group 15 atom, or a Group 16 atom, preferably boron, nitrogen, oxygen, phosphorus, or sulfur;

Y is an optional bridging group containing at least one Group 13, 14, 15, or 16 element and is bonded to any single position of the ring structure of A, y is zero or 1, indicating the absence (y=0) or presence (y=1) of Y; and the or each X is a univalent anionic ligand, or two X are joined and bound to the metal atom to form a metallocycle ring, or two X are joined to form a chelating ligand, a diene ligand, or an alkylidene ligand;

provided that when y is equal to 1, then A is not 5,6-dichloroindenyl or an indenyl group having a fluoro- or chloro substituent at the 7 position and a hydrocarbyl or substituted hydrocarbyl substituent at the 4 position, and provided further that when y is equal to 0, then A is not 5,6-difluoroindenyl.

In one embodiment, each A is independently a substituted fluorenyl ligand or a substituted cyclopentanaphthyl ligand and said at least one halogen substituent is a chloro, bromo or iodo substituent, preferably a chloro or bromo substituent.

In another embodiment, each A is independently a substituted indenyl ligand and said at least one halogen substituent is a chloro, bromo or iodo substituent, preferably a chloro or bromo substituent. Conveniently, each A is independently a substituted indenyl ligand, the at least one halogen substituent at the 4, 5, or 6 position of the indenyl ligand is a chloro, bromo or iodo substituent, preferably a chloro or bromo substituent, and said at least one other substituent is connected to the 2 position of the indenyl ligand.

In yet another aspect, the invention resides in an olefin polymerization catalyst system comprising (a) a metallocene compound as described herein and (b) an activator.

In still yet a further aspect, the invention resides in an olefin polymerization process comprising contacting at least one olefin with the olefin polymerization catalyst system described herein.

DEFINITIONS

Figure 1:
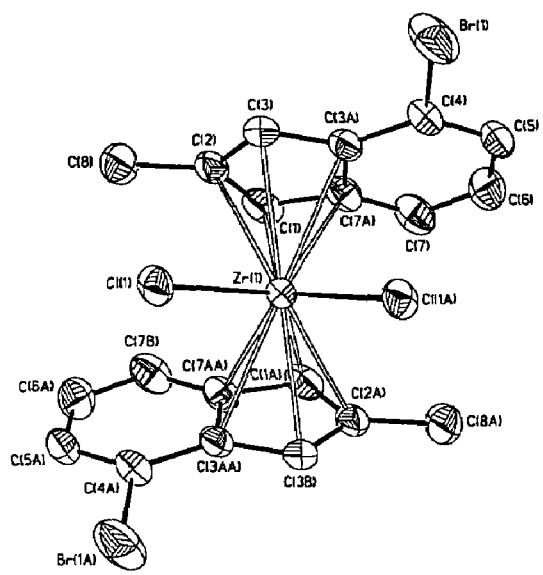
FIG. 1 is a representation of the molecular structure of rac-bis($\eta^5$-2-methyl-4-bromoindenyl)zirconium dichloride of Example 2.

As used herein, the numbering scheme for the Periodic Table Groups is the new notation as set out in CHEMICAL AND ENGINEERING NEWS, 63(5), 27 (1985). However, For purposes of this invention and the claims thereto the use of the capital letter Y in a formula herein is NOT meant to indicate yttrium.

As used herein, Me is methyl, Et is ethyl, Bu is butyl, t-Bu and $^tBu$ are tertiary butyl, Pr is propyl, iPr and $^iPr$ are isopropyl, Cy is cyclohexyl, THF (thf) is tetrahydrofuran, and Ph is phenyl.

The terms "hydrocarbyl radical," "hydrocarbyl" and "hydrocarbyl group" are used interchangeably throughout this document. Likewise the terms "group", "radical", and "substituent" are also used interchangeably in this document. For purposes of this disclosure, "hydrocarbyl radical" is defined to be a radical, which contains hydrogen atoms and up to 100 carbon atoms and which may be linear, branched, or cyclic, and when cyclic, aromatic or non-aromatic.

Substituted hydrocarbyl radicals are radicals in which at least one hydrogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-hydrocarbon atom or group has been inserted within the hydrocarbyl radical, such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halocarbyl radical, and two or more R* may join together to form a substituted or unsubstituted saturated, partially unsaturated or aromatic cyclic or polycyclic ring structure.

Halocarbyl radicals are radicals in which one or more hydrocarbyl hydrogen atoms have been substituted with at least one halogen (e.g. F, Cl, Br, I) or halogen-containing group (e.g. CF$_3$).

Substituted halocarbyl radicals are radicals in which at least one halocarbyl hydrogen or halogen atom has been substituted with at least one functional group such as NR*$_2$, OR*, SeR*, TeR*, PR*$_2$, AsR*$_2$, SbR*$_2$, SR*, BR*$_2$, SiR*$_3$, GeR*$_3$, SnR*$_3$, PbR*$_3$ and the like or where at least one non-carbon atom or group has been inserted within the halocarbyl radical such as —O—, —S—, —Se—, —Te—, —N(R*)—, =N—, —P(R*)—, =P—, —As(R*)—, =As—, —Sb(R*)—, =Sb—, —B(R*)—, =B—, —Si (R*)$_2$—, —Ge(R*)$_2$—, —Sn(R*)$_2$—, —Pb(R*)$_2$— and the like, where R* is independently a hydrocarbyl or halocarbyl radical provided that at least one halogen atom remains on the original halocarbyl radical. Additionally, two or more R* may join together to form a substituted or unsubstituted saturated, partially unsaturated or aromatic cyclic or polycyclic ring structure.

Silylcarbyl radicals (also called silylcarbyls) are groups in which the silyl functionality is bonded directly to the indicated atom or atoms. Examples include SiH$_3$, SiH$_2$R*, SiHR*$_2$, SiR*$_3$, SiH$_2$(OR*), SiH(OR*)$_2$, Si(OR*)$_3$, SiH$_2$(NR*$_2$), SiH(NR*$_2$)$_2$, Si(NR*$_2$)$_3$, and the like where R* is independently a hydrocarbyl or halocarbyl radical and two or more R* may join together to form a substituted or unsubstituted saturated, partially unsaturated or aromatic cyclic or polycyclic ring structure.

Germylcarbyl radicals (also called germylcarbyls) are groups in which the germyl functionality is bonded directly to the indicated atom or atoms. Examples include GeH$_3$, GeH$_2$R*, GeHR*$_2$, GeR*$_3$, GeH$_2$(OR*), GeH(OR*)$_2$, Ge(OR*)$_3$, GeH$_2$(NR*$_2$), GeH(NR*$_2$)$_2$, Ge(NR*$_2$)$_3$, and the like where R* is independently a hydrocarbyl or halocarbyl radical and two or more R* may join together to form a substituted or unsubstituted saturated, partially unsaturated or aromatic cyclic or polycyclic ring structure.

Polar radicals, functional groups, or polar groups are groups in which a heteroatom functionality is bonded directly to the indicated atom or atoms. They include heteroatoms of Groups 1-17 of the periodic table either alone or connected to other elements by covalent or other interactions such as ionic, van der Waals forces, or hydrogen bonding. Examples of functional groups include carboxylic acid, acid halide, carboxylic ester, carboxylic salt, carboxylic anhydride, aldehyde and their chalcogen (Group 14) analogues, alcohol and phenol, ether, peroxide and hydroperoxide, carboxylic amide, hydrazide and imide, amidine and other nitrogen analogues of amides, nitrile, amine and imine, azo, nitro, other nitrogen compounds, sulfur acids, selenium acids, thiols, sulfides, sulfoxides, sulfones, sulfonates, phosphines, phosphates, other phosphorus compounds, silanes, boranes, borates, alanes, aluminates. Functional groups may also be taken broadly to include organic polymer supports or inorganic support material such as alumina, and silica. Preferred examples of polar groups include NR*$_2$, OR*, SeR*, TeR*, PR*$_2$, AsR*$_2$, SbR*$_2$, SR*, BR*$_2$, SnR*$_3$, PbR*$_3$ and the like where R* is independently a hydrocarbyl, substituted hydrocarbyl, halocarbyl or substituted halocarbyl radical as defined above and two R* may join together to form a substituted or unsubstituted saturated, partially unsaturated or aromatic cyclic or polycyclic ring structure. Also preferred are sulfonate radicals, S(=O)$_2$OR*, where R* is defined as above. Examples include SO$_3$Me (mesylate), SO$_3$(4-tosyl) (tosylate), SO$_3$CF$_3$ (triflate), SO$_3$(n-C$_4$F$_9$) (nonaflate) and the like.

In using the terms "substituted or unsubstituted cyclopentadienyl ligand", "substituted or unsubstituted indenyl ligand", "substituted or unsubstituted fluorenyl ligand", "substituted or unsubstituted cyclopentanaphthyl ligand", "substituted or unsubstituted monocyclic arenyl ligand", or "substituted or unsubstituted polycyclic arenyl ligand", the substitution to the aforementioned ligand is on a bondable ring position, and each occurrence is selected from hydrocarbyl, substituted hydrocarbyl, halocarbyl, substituted halocarbyl, silylcarbyl, germylcarbyl, a halogen radical, or a polar group.

In some embodiments, the hydrocarbyl radical is independently selected from methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, triacontynyl, butadienyl, pentadienyl, hexadienyl, heptadienyl, octadienyl, nonadienyl, and decadienyl. Also included are isomers of saturated, partially unsaturated and aromatic cyclic and polycyclic structures wherein the radical may additionally be subjected to the types of substitutions described above. Examples include phenyl, methylphenyl, dimethylphenyl, ethylphenyl, diethylphenyl, propylphenyl, dipropylphenyl, benzyl, methylbenzyl, naphthyl, anthracenyl, cyclopentyl, cyclopentenyl, cyclohexyl, cyclohexenyl, methylcyclohexyl, cycloheptyl, cycloheptenyl, norbornyl, norbornenyl, adamantyl and the like. For this disclosure, when a radical is listed, it indicates that radical type and all other radicals formed when that radical type is subjected to the substitutions defined above. Alkyl, alkenyl and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

For nomenclature purposes, the following numbering schemes are used for cyclopentadienyl, indenyl, fluorenyl, and cyclopentanaphthyl (also termed benzindenyl). It should be noted that indenyl can be considered a cyclopentadienyl fused with a benzene ring. Analogously, fluorenyl can be considered a cyclopentadienyl with two phenyl rings fused onto the cyclopentadienyl ring. Each structure below is drawn and named as an anion.

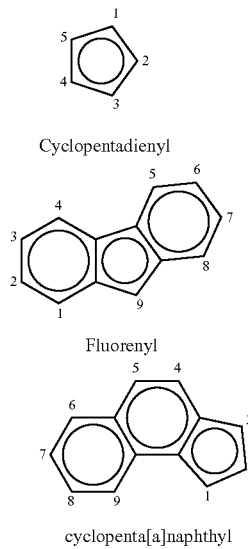

Cyclopentadienyl

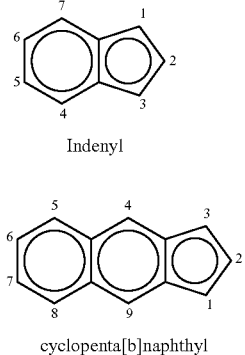

Indenyl

Fluorenyl cyclopenta[b]naphthyl cyclopenta[a]naphthyl

A similar numbering and nomenclature scheme is used for heterocyclopentadienyls, heterophenyls, heteropentalenyls, heterocyclopentapentalenyls, heteroindenyls, heterofluorenyls, heterocyclopentanaphthyls, heterocyclopentaindenyls, heterobenzocyclopentaindenyls, and the like, as illustrated below. Each structure is drawn and named as an anion.

Non-limiting examples of heterocyclopentadienyls include:

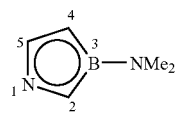

3-dimethylamino-1,3-azaborollide

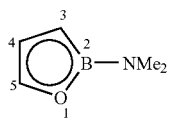

2-dimethylamino-1,2-oxaborollide

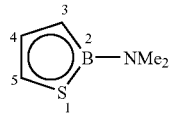

2-dimethylamino-1,2-thiaborollide

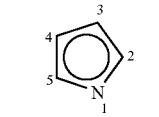

azacyclopentadienyl

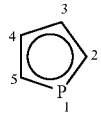

phosphacyclopentadienyl

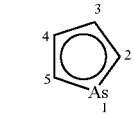

arsacyclopentadienyl

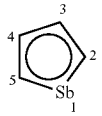

stibacyclopentadienyl

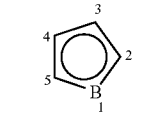

boracyclopentadienyl

Further non-limiting examples of heterocyclopentadienyls include 1,3-diazacyclopentadienyl, 1,3-diphosphacyclopentadienyl, 1,3-diarsacyclopentadienyl, 1,3-distibacyclopentadienyl, 1,3-diboracyclopentadienyl, 1,3-azaphosphacyclopentadienyl, 1,3-azaarsacylcopentadienyl, 1,3-azastibacyclopentadienyl, 1,3-azaboracyclopentadienyl, 1,3-arsaphosphacyclopentadienyl, 1,3-arsastibacyclopentadienyl, 1,3-arsaboracyclopentadienyl, 1,3-boraphosphacyclopentadienyl, 1,3-borastibacylcopentadienyl, 1,3-phosphastibacyclopentadienyl, 1,2-diazacyclopentadienyl, 1,2-diphosphacyclopentadienyl, 1,2-diarsacyclopentadienyl, 1,2-distibacyclopentadienyl, 1,2-diboracyclopentadienyl, 1,2-azaphosphacyclopentadienyl, 1,2-azaarsacylcopentadienyl, 1,2-azastibacyclopentadienyl, 1,2-azaboracyclopentadienyl, 1,2-arsaphosphacyclopentadienyl, 1,2-arsastibacyclopentadienyl, 1,2-arsaboracyclopentadienyl, 1,2-boraphosphacyclopentadienyl, 1,2-borastibacylcopentadienyl, 1,2-phosphastibacyclopentadienyl, 3-dihydrocarbylamino-1,3-azaborollide, 2-dihydrocarbylamino-1,2-oxaborollide, 2-dihydrocarbylamino-1,2-thiaborollide, 3-hydrocarbyloxy-1,3-azaborollide, 2-hydrocarbyloxy-1,2-oxaborollide, 2-hydrocarbyloxy-1,2-thiaborollide, 3-hydrocarbyl-1,3-azaborollide, 2-hydrocarbyl-1,2-oxaborollide, and 2-hydrocarbyl-1,2-thiaborollide, where hydrocarbyl is a "hydrocarbyl radical" as previously defined.

Non-limiting examples of heterophenyls include:

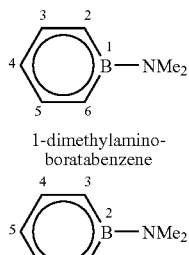

1-dimethylamino-boratabenzene

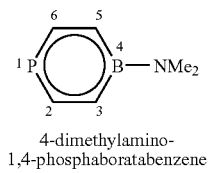

4-dimethylamino-1,4-phosphaboratabenzene

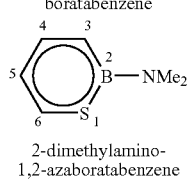

2-dimethylamino-1,2-azaboratabenzene

Further non-limiting examples of heterophenyls include 1-dihydrocarbylaminoboratabenzene, 4-dihydrocarbylamino-1,4-phosphaboratabenzene, 2-dihydrocarbylamino-1,2-azaboratabenzene, 1-hydrocarbyloxyboratabenzene, 4-hydrocarbyloxy-1,4-phosphaboratabenzene, 2-hydrocarbyloxy-1,2-azaboratabenzene, 1-hydrocarbylboratabenzene, 4-hydrocarbyl-1,4-phosphaboratabenzene, and 2-hydrocarbyl-1,2-azaboratabenzene, where hydrocarbyl is a "hydrocarbyl radical" as previously defined.

Non-limiting examples of heteropentalenyls include:

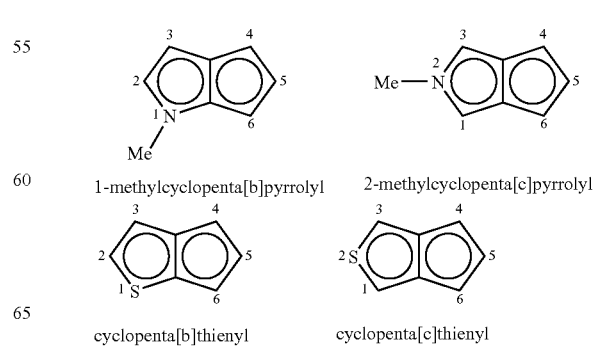

-continued

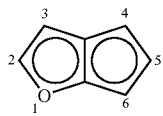
cyclopenta[b]furyl

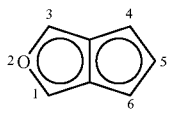
cyclopenta[c]furyl

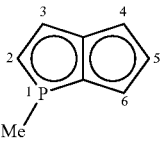
1-methylcyclopenta[b]phospholyl

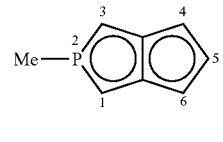
2-methylcyclopenta[c]phospholyl

Further non-limiting examples of heteropentalenyls include cyclopenta[b]selenophenyl, cyclopenta[c]selenophenyl, cyclopenta[b]tellurophenyl, cyclopenta[c]tellurophenyl, 1-hydrocarbylcyclopenta[b]arsolyl, 2-hydrocarbylcyclopenta[c]arsolyl, 1-hydrocarbylcyclopenta[b]stibolyl, 2-hydrocarbylcyclopenta[c]stibolyl, 1-hydrocarbylcyclopenta[b]pyrrolyl, 2-hydrocarbylcyclopenta[c]pyrrolyl, 1-hydrocarbylcyclopenta[b]phospholyl, and 2-hydrocarbylcyclopenta[c]phospholyl, where hydrocarbyl is a "hydrocarbyl radical" as previously defined.

Non-limiting examples of heterocylopentapentalenyls include the following, where Z and Q independently represent the heteroatoms O, S, Se, or Te, or heteroatom groups, NR, PR, AsR, or SbR where R** is hydrogen, or a hydrocarbyl, substituted hydrocarbyl, halocarbyl, substituted halocarbyl, silylcarbyl, or germylcarbyl substituent.

Non-limiting examples of heteroindenyls include:

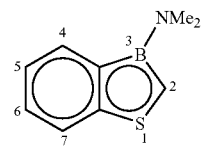
3-dimethylamino-1,3-benzothiaborollide

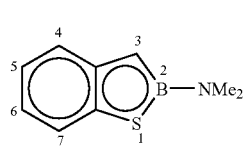
2-dimethylamino-1,2-benzothiaborollide

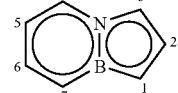
3a,7a-azaborindenyl

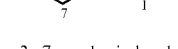
cyclopenta[b]pyridyl

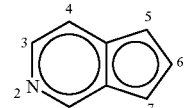
cyclopenta[c]pyridyl cyclopenta[c]phosphinyl

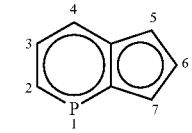
cyclopenta[b]phosphinyl

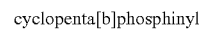

Further non-limiting examples of heteroindenyls include cyclopenta[b]arsinyl, cyclopenta[c]arsinyl, cyclopenta[b]stibinyl, cyclopenta[c]stibinyl, 3-dihydrocarbylamino-1,3-benzothiaborollide, 2-dihydrocarbylamino-1,2-benzothiaborollide, 3-hydrocarbyloxy-1,3-benzothiaborollide, 2-hydrocarbyloxy-1,2-benzothiaborollide, 3-hydrocarbyl-1,3-benzothiaborollide, and 2-hydrocarbyl-1,2-benzothiaborollide, where hydrocarbyl is a "hydrocarbyl radical" as previously defined.

Non-limiting examples of heterofluorenyls include:

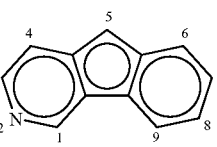
indeno[1,2-c]pyridyl

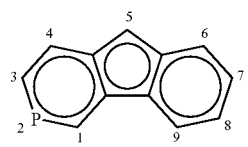
indeno[1,2-c]phosphinyl

Non-limiting examples of heterocyclopentanaphthyls include:

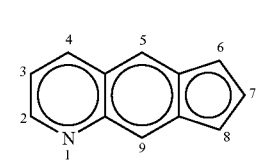
cyclopenta[g]quinolyl

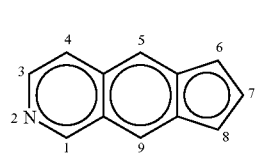
cyclopenta[g]isoquinolyl

Further non-limiting examples of heterocyclopentanaphthyls include cyclopenta[g]phosphinolyl, cyclopenta[g]isophosphinolyl, cyclopenta[g]arsinolyl, and cyclopenta[g]isoarsinolyl.

Non-limiting examples of heterocyclopentaindenyls include:

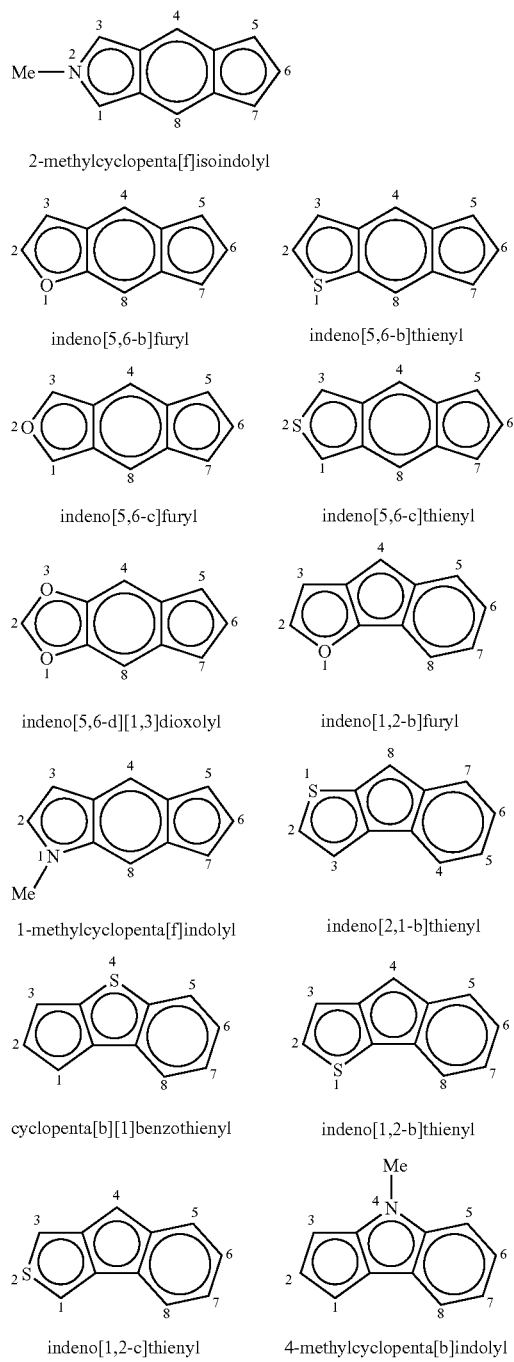

Further non-limiting examples of heterocyclopentaindenyls include 1-hydrocarbylcyclopenta[f]phosphindolyl, 2-hydrocarbylcyclopenta[f]isophosphindolyl, 1-hydrocarbylcyclopenta[f]arsindolyl, 2-hydrocarbylcyclopenta[f]isoarsindolyl, indeno[5,6-b]selenophenyl, indeno[5,6-b]tellurophenyl, indeno[5,6-c]selenophenyl, indeno[5,6-c]tellurophenyl, 2-hydrocarbylcyclopenta[f]isoindolyl, and 1-hydrocarbylcyclopenta[f]indolyl, where hydrocarbyl is a "hydrocarbyl radical" as previously defined.

Non-limiting examples of heterobenzocyclopentaindenyls include:

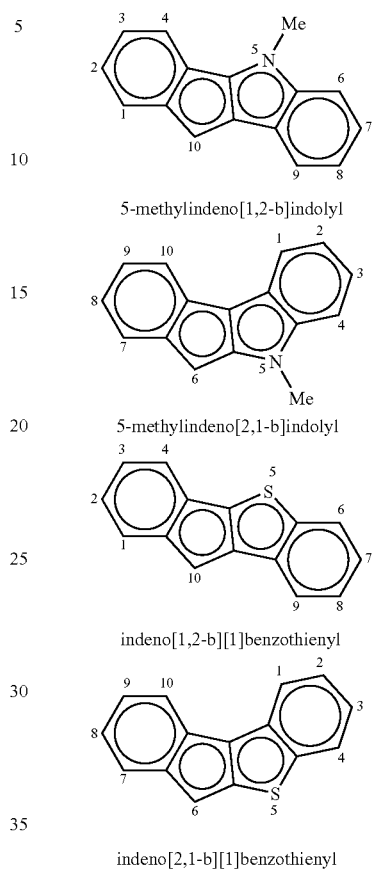

Further non-limiting examples of heterobenzocyclopentaindenyls include 5-hydrocarbylindeno[1,2-b]indolyl and 5-hydrocarbylindeno[2,1-b]indolyl, where hydrocarbyl is a "hydrocarbyl radical" as previously defined.

The term "arenyl" ligand is used herein to mean an unsaturated cyclic hydrocarbyl ligand that can consist of one ring, or two or more fused or catenated rings. Cyclopentadienyl ligands, indenyl ligands, and fluorenyl ligands are all examples of arenyl ligands.

The term "monocyclic arenyl ligand" is used herein to mean a substituted or unsubstituted monoanionic $C_5$ to $C_{100}$ hydrocarbyl ligand that contains an aromatic five-membered single hydrocarbyl ring (also referred to as a cyclopentadienyl ring).

The term "polycyclic arenyl ligand" is used herein to mean a substituted or unsubstituted monoanionic $C_8$ to $C_{103}$ hydrocarbyl ligand that contains an aromatic five-membered hydrocarbyl ring (also referred to as a cyclopentadienyl ring) that is fused to one or two partially unsaturated, or aromatic hydrocarbyl ring structures which may be fused to additional saturated, partially unsaturated, or aromatic hydrocarbyl rings.

Non-limiting examples of polycyclic arenyl ligands, named also as monoanionic ligands, include indenyl, 4,5-dihydroindenyl, 4,7-dihydroindenyl, 4,5,6,7-tetrahydroindenyl, fluorenyl, 1,2-dihydrotetrahydrofluorenyl, 1,4-dihydrotetrahydrofluorenyl, 3,4-dihydrotetrahydrofluorenyl, 1,2,3,4-tetrahydrofluorenyl, 1,2,5,6-tetrahydrofluorenyl, 1,2,7,8-tetrahydrofluorenyl, 3,4,5,6-tetrahydrofluorenyl, 1,4,5,8- tetrahydrofluorenyl, 1,2,3,4,5,6,7,8-octahydrofluorenyl, cyclopenta[b]naphthyl, 4,4a-dihydrocyclopenta[b]naphthyl, 5,6-dihydrocyclopenta[b]naphthyl, 5,8-dihydrocyclopenta[b]naphthyl, 4,9-dihydrocyclopenta[b]naphthyl, 4,4a,5,6-tetrahydrocyclopenta[b]naphthyl, 4,5,8,9-tetrahydrocyclopenta[b]naphthyl, 4,4a,7,8-tetrahydrocyclopenta[b]naphthyl, 4,4a,8a,9-tetrahydrocyclopenta[b]naphthyl, 5,6,7,8-tetrahydrocyclopenta[b]naphthyl, 4,4a,5,8-tetrahydrocyclopenta[b]naphthyl, 4,5,6,9-tetrahydrocyclopenta[b]naphthyl, 4,6,7,8-tetrahydrocyclopenta[b]naphthyl, 4,6,7,9-tetrahydrocyclopenta[b]naphthyl, 4,4a,5,9-tetrahydrocyclopenta[b]naphthyl, 4,4a,5,6,7,8-hexahydrocyclopenta[b]naphthyl, 4,4a,5,6,8a,9-hexahydrocyclopenta[b]naphthyl, 4,4a,5,8,8a,9-hexahydrocyclopenta[b]naphthyl, 4,5,6,7,8,9-hexahydrocyclopenta[b]naphthyl, 4,4a,5,6,7,9-hexahydrocyclopenta[b]naphthyl, 4,4a,5,6,7,8,8a,9-octahydrocyclopenta[b]naphthyl, cyclopenta[a]naphthyl, 4,5-dihydrocyclopenta[a]naphthyl, 6,7-dihydrocyclopenta[a]naphthyl, 8,9-dihydrocyclopenta[a]naphthyl, 5a,9a-dihydrocyclopenta[a]naphthyl, 6,9-dihydrocyclopenta[a]naphthyl, 7,9a-dihydrocyclopenta[a]naphthyl, 4,9a-dihydrocyclopenta[a]naphthyl, 5a,8-dihydrocyclopenta[a]naphthyl, 4,5,5a,9a-tetrahydrocyclopenta[a]naphthyl, 4,5,6,7-tetrahydrocyclopenta[a]naphthyl, 4,5,8,9-tetrahydrocyclopenta[a]naphthyl, 5a,6,7,9a-tetrahydrocyclopenta[a]naphthyl, 6,7,8,9-tetrahydrocyclopenta[a]naphthyl, 5a,8,9,9a-tetrahydrocyclopenta[a]naphthyl, 4,5,7,9a-tetrahydrocyclopenta[a]naphthyl, 5a,6,7,9a-tetrahydrocyclopenta[a]naphthyl, 7,8,9,9a-tetrahydrocyclopenta[a]naphthyl, 4,6,7,9a-tetrahydrocyclopenta[a]naphthyl, 4,8,9,9a-tetrahydrocyclopenta[a]naphthyl, 4,5,6,9-tetrahydrocyclopenta[a]naphthyl, 4,5,5a,8-tetrahydrocyclopenta[a]naphthyl, 5a,6,7,8-tetrahydrocyclopenta[a]naphthyl, 5a,6,9,9a-tetrahydrocyclopenta[a]naphthyl, 5a,6,7,8,9,9a-hexahydrocyclopenta[a]naphthyl, 4,6,7,8,9,9a-hexahydrocyclopenta[a]naphthyl, 4,5,7,8,9,9a-hexahydrocyclopenta[a]naphthyl, 4,5,5a,8,9,9a-hexahydrocyclopenta[a]naphthyl, 4,5,5a,6,9,9a-hexahydrocyclopenta[a]naphthyl, 4,5,5a,6,7,9a-hexahydrocyclopenta[a]naphthyl, 4,5,5a,6,7,8-hexahydrocyclopenta[a]naphthyl, 4,5,6,7,8,9-hexahydrocyclopenta[a]naphthyl, 4,5,5a,6,7,8,9,9a-hexahydrocyclopenta[a]naphthyl, 4,5,5a,6,7,8,9,9a-octahydrocyclopenta[a]naphthyl, 5,6-trimethyleneindenyl, 4,5-trimethyleneindenyl, 5,6-pentamethyleneindenyl, 4,5-pentamethyleneindenyl, 5,6-hexamethyleneindenyl, 4,5-hexamethyleneindenyl, 5,6-heptamethyleneindenyl, 4,5-heptamethyleneindenyl, 5,6-octamethyleneindenyl, 4,5-octamethyleneindenyl, 5,6-nonamethyleneindenyl, 4,5-nonamethyleneindenyl, 5,6-decamethyleneindenyl, 4,5-decamethyleneindenyl, 5,6-undecamethyleneindenyl, 4,5-undecamethyleneindenyl, 5,6-dodecamethyleneindenyl, 4,5-dodecamethyleneindenyl, 5,6-tridecamethyleneindenyl, 4,5-tridecamethyleneindenyl, 5,6-tetradecamethyleneindenyl, 4,5-tetradecamethyleneindenyl, 5,6-pentadecamethyleneindenyl, 4,5-pentadecamethyleneindenyl, 5,6-hexadecamethyleneindenyl, 4,5-hexadecamethyleneindenyl, 5,6-heptadecamethyleneindenyl, 4,5-heptadecamethyleneindenyl, 5,6-octadecamethyleneindenyl, 4,5-octadecamethyleneindenyl, 5,6-nonadecamethyleneindenyl, 4,5-nonadecamethyleneindenyl, 5,6-eicosamethyleneindenyl, 4,5-eicosamethyleneindenyl, (6Z,8Z,10Z)-cycloocta[e]indenyl, (5Z,7Z,9Z)-cycloocta[f]indenyl, (5E,7Z,9E,11Z,13E)-cyclododeca[f]indenyl, (6E,8Z,10E,12Z,14E)-cyclododeca[e]indenyl, benz[a]fluorenyl, benz[b]fluorenyl, benz[c]fluorenyl, naphth[2,3-a]fluorenyl, naphth[2,3-b]fluorenyl, naphth[2,3-c]fluorenyl, naphth[1,2-a]fluorenyl, naphth[1,2-b]fluorenyl, naphth[1,2-c]fluorenyl, 2,3-tetramethylenefluorenyl, 1,2-tetramethylenefluorenyl, 3,4-tetramethylenefluorenyl, 2,3-trimethylenefluorenyl, 1,2-trimethylenefluorenyl, 3,4-trimethylenefluorenyl, 2,3-pentamethylenefluorenyl, 1,2-pentamethylenefluorenyl, 3,4-pentamethylenefluorenyl, 2,3-hexamethylenefluorenyl, 1,2-hexamethylenefluorenyl, 3,4-hexamethylenefluorenyl, 2,3-heptamethylenefluorenyl, 1,2-heptamethylenefluorenyl, 3,4-heptamethylenefluorenyl, 2,3-octamethylenefluorenyl, 1,2-octamethylenefluorenyl, 3,4-octamethylenefluorenyl, 2,3-nonamethylenefluorenyl, 1,2-nonamethylenefluorenyl, 3,4-nonamethylenefluorenyl, 2,3-decamethylenefluorenyl, 1,2-decamethylenefluorenyl, 3,4-decamethylenefluorenyl, 2,3-undecamethylenefluorenyl, 1,2-undecamethylenefluorenyl, 3,4-undecamethylenefluorenyl, 2,3-dodecamethylenefluorenyl, 1,2-dodecamethylenefluorenyl, 3,4-dodecamethylenefluorenyl, 2,3-tetramethylene-6,7-tetramethylenefluorenyl, 1,2-tetramethylene-7,8-tetramethylenefluorenyl, 3,4-tetramethylene-5,6-tetramethylenefluorenyl, bis-benz[2,3;6,7]fluorenyl, bis-benz[2,3;5,6]fluorenyl, bis-benz[1,2;7,8]fluorenyl, bis-benz[1,2;5,6]fluorenyl, bis-benz[1,2;6,7]fluorenyl, bis-benz[1,2;7,8]fluorenyl, and bis-benz[3,4;5,6]fluorenyl, Partially hydrogenated polycyclic arenyl ligands retain the numbering scheme of the parent polycyclic arenyl ligand, namely the numbering schemes defined for indenyl, fluorenyl, cyclopenta[b]naphthyl, and cyclopenta[a]naphthyl ligands.

A "ring carbon atom" is a carbon atom that is part of a cyclic ring structure. By this definition, an indenyl fragment has nine ring carbon atoms. Whereas the monocyclic and polycyclic arene ligands described herein generally contain only ring carbon atoms, it is within the scope of the invention to replace one of more of the ring carbon atoms with a heteroatom, such as a boron atom, a Group 14 atom that is not carbon, a Group 15 atom, or a Group 16 atom. Preferred heteroatoms include boron, nitrogen, oxygen, phosphorus, and sulfur.

A "bondable ring position" is a ring position that is capable of bearing a substituent or bridging substituent. For example, cyclopenta[b]thienyl has five bondable ring positions (at the carbon atoms) and one non-bondable ring position (the sulfur atom); cyclopenta[b]pyrrolyl has six bondable ring positions (at the carbon atoms and at the nitrogen atom).

In the context of this document, "homopolymerization" would produce a polymer made from one monomer. For example, homopolymerization of propylene would produce homopolypropylene. Homopolymerization of ethylene would produce homopolyethylene. Likewise, "copolymerization" would produce polymers with more than one monomer type. For example, ethylene copolymers include polymers of ethylene with α-olefins, cyclic olefins and diolefins, vinylaromatic olefins, α-olefinic diolefins, substituted α-olefins, and/or acetylenically unsaturated monomers.

Non-limiting examples of α-olefins include ethylene, propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, and vinylnorbornane.

Non-limiting examples of cyclic olefins and diolefins include cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, and 1,5-diallylcyclooctane.

Non-limiting examples of vinylaromatic olefins include styrene, para-methylstyrene, para-t-butylstyrene, vinylnaphthylene, vinyltoluene, and divinylbenzene.

Non-limiting examples of α-olefinic dienes include 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1,11-dodecene, 1,13-tetradecene and 9-methyl-1,9-decadiene.

Substituted α-olefins (also called functional group containing α-olefins) include those containing at least one non-carbon Group 13 to 17 atom bound to a carbon atom of the substituted α-olefin where such substitution if silicon may be adjacent to the double bond or terminal to the double bond, or anywhere in between, and where inclusion of non-carbon and non-silicon atoms such as for example B, O, S, Se, Te, N, P, Ge, Sn, Pb, As, F, Cl, Br, or I, are contemplated, where such non-carbon or non-silicon moieties are sufficiently far removed from the double bond so as not to interfere with the coordination polymerization reaction with the catalyst and so to retain the generally hydrocarbyl characteristic. By sufficiently far removed from the double bond we intend that the number of carbon atoms, or the number of carbon and silicon atoms, separating the double bond and the non-carbon or non-silicon moiety is preferably 6 or greater, e.g. 7, or 8, or 9, or 10, or 11, or 12, or 13, or 14 or more. The number of such carbon atoms, or carbon and silicon atoms, is counted from immediately adjacent to the double bond to immediately adjacent to the non-carbon or non-silicon moiety. Examples include 8,8,8-trifluoro-1-octene, 8-methoxyoct-1-ene, 8-methylsulfanyloct-1-ene, 8-dimethylaminooct-1-ene, or combinations thereof. The use of functional group-containing α-olefins where the functional group is closer to the double bond is also within the scope of embodiments of the invention when such olefins may be incorporated in the same manner as are their α-olefin analogs. See, "Metallocene Catalysts and Borane Reagents in The Block/Graft Reactions of Polyolefins", T. C. Chung, et al, *Polym. Mater. Sci. Eng.*, v. 73, p. 463 (1995), and the masked α-olefin monomers of U.S. Pat. No. 5,153,282. Such monomers permit the preparation of both functional-group containing copolymers capable of subsequent derivatization, and of functional macromers which may be used as graft and block type polymeric segments. Copolymerization can also incorporate α-olefinic macromonomers of up to 2000 mer units.

For purposes of this disclosure, the term oligomer refers to compositions having 2-75 mer units and the term polymer refers to compositions having 76 or more mer units. A mer is defined as a unit of an oligomer or polymer that originally corresponded to the monomer(s) used in the oligomerization or polymerization reaction. For example, the mer of polyethylene would be ethylene.

The term "catalyst system" is defined to mean a catalyst precursor/activator pair. When "catalyst system" is used to describe such a pair before activation, it means the unactivated catalyst (precatalyst) together with an activator and, optionally, a co-activator. When it is used to describe such a pair after activation, it means the activated catalyst and the activator or other charge-balancing moiety.

The transition metal compound may be neutral as in a precatalyst, or a charged species with a counter ion as in an activated catalyst system.

Catalyst precursor is also often referred to as precatalyst, catalyst, catalyst compound, catalyst precursor, transition metal compound or transition metal complex. These words are used interchangeably. Activator and cocatalyst are also used interchangeably. A scavenger is a compound that is typically added to facilitate oligomerization or polymerization by scavenging impurities. Some scavengers may also act as activators and may be referred to as co-activators. A co-activator, that is not a scavenger, may also be used in conjunction with an activator in order to form an active catalyst. In some embodiments a co-activator can be pre-mixed with the transition metal compound to form an alkylated transition metal compound, also referred to as an alkylated invention compound.

Noncoordinating anion (NCA) is defined to mean an anion either that does not coordinate to the catalyst metal cation or that does coordinate to the metal cation, but only weakly. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon.

A stoichiometric activator can be either neutral or ionic. The terms ionic activator, and stoichiometric ionic activator can be used interchangeably. Likewise, the terms neutral stoichiometric activator, and Lewis acid activator can be used interchangeably.

DETAILED DESCRIPTION OF THE EMBODIMENTS

The present invention provides a series of bridged and unbridged metallocene compounds each containing two halogen substituted polycyclic arenyl ligands (preferably two identical halogen substituted polycyclic arenyl ligands) pi-bonded bonded to a transition metal. When combined with a suitable activator, these compounds show activity in the polymerization of olefins, such as ethylene and propylene.

In one embodiment, the invention provides a metallocene compound represented by the formula (1):

$$A_2Y_yMX_{n-2}$$

wherein:

M is a transition metal atom having a coordination number of n selected from Group 3, 4, 5 or 6 of the Periodic Table of Elements, or a lanthanide metal atom, or actinide metal atom and preferably is a Group 4 transition metal selected from titanium, zirconium and hafnium;

each A is independently a substituted polycyclic arenyl ligand pi-bonded to M, each A ligand includes at least one halogen substituent directly bonded to an $sp^2$ carbon at a bondable ring position and, when each A is a substituted indenyl ligand and y is equal to one and the ligand includes at least one chloro, bromo or iodo substituent at the 4, 5, or 6 position of the indenyl ligand, then A also includes at least one other substituent in the indenyl ligand selected from hydrocarbyl, substituted hydrocarbyl, halogen, halocarbyl, substituted halocarbyl, silylcarbyl, substituted silylcarbyl, germylcarbyl, substituted germylcarbyl, or other heteroatom substituents wherein the heteroatom is bonded directly to a ring carbon of the ring structure ligand and is boron, a Group 15 atom, or a Group 16 atom, preferably boron, nitrogen, oxygen, phosphorus, or sulfur;

Y is an optional bridging group containing at least one Group 13, 14, 15, or 16 element and is bonded to any single position of the ring structure of A, y is zero or 1, indicating the absence (y=0) or presence (y=1) of Y; and the or each X is a univalent anionic ligand, or two X are joined and bound to the metal atom to form a metallocycle ring, or two X are joined to form a chelating ligand, a diene ligand, or an alkylidene ligand;

provided that when y is equal to 1, then A is not 5,6-dichloroindenyl or an indenyl group having a fluoro- or chloro substituent at the 7 position and a hydrocarbyl or substituted hydrocarbyl substituent at the 4 position, and provided further that when y is equal to 0, then A is not 5,6-difluoroindenyl.

Conveniently, each A is independently a substituted fluorenyl ligand or a substituted cyclopentanaphthyl ligand and said at least one halogen substituent is a chloro, bromo or iodo substituent, preferably a chloro or bromo substituent.

Alternatively, each A is independently a substituted indenyl ligand and the at least one halogen substituent is a chloro, bromo, or iodo substituent, preferably a chloro or bromo substituent. In one embodiment, each A is independently a substituted indenyl ligand, the at least one halogen substituent at the 4, 5, or 6 position of the indenyl ligand is a chloro, bromo or iodo substituent, preferably a chloro or bromo substituent, and said at least one other substituent is connected to the 2 position of the indenyl ligand.

Conveniently, Y is present and is a bridging group containing boron or a Group 14, 15 or 16 element. Examples of suitable bridging groups include S, O, NR', PR', P(=S)R', AsR', SbR', O—O, S—S, R'N—NR', R'P—PR', O—S, O—NR', O—PR', S—NR', S—PR', R'N—PR', R'$_2$C, R'$_2$Si, R'$_2$Ge, R'$_2$CCR'$_2$, R'$_2$CCR'$_2$CR'$_2$, R'$_2$CCR'$_2$CR'$_2$CR'$_2$, R'C=CR'$_2$, R'C=CR'CR'$_2$, R'$_2$CCR'=CR'CR'$_2$, R'C=CR'CR'=CR', R'C=CR'CR'$_2$CR'$_2$, R'$_2$CSiR'$_2$, R'$_2$SiSiR'$_2$, R'$_2$CSiR'$_2$CR'$_2$, R'$_2$SiCR'$_2$SiR'$_2$, R'C=CR'SiR'$_2$, R'$_2$CGeR'$_2$, R'$_2$GeGeR'$_2$, R'$_2$CGeR'$_2$CR'$_2$, R'$_2$GeCR'$_2$GeR'$_2$, R'$_2$SiGeR'$_2$, R'C=CR'GeR'$_2$, R'B, R'$_2$C—BR', R'$_2$C—BR'—CR'$_2$, R'$_2$C—O—CR'$_2$, R'$_2$CR'$_2$C—O—CR'$_2$CR'$_2$, R'$_2$C—O—CR'$_2$CR'$_2$, R'$_2$C—O—CR'=CR', R'$_2$C—S—CR'$_2$, R'$_2$CR'$_2$C—S—CR'$_2$CR'$_2$, R'$_2$C—S—CR'$_2$CR'$_2$, R'$_2$C—S—CR'=CR', R'$_2$C—Se—CR'$_2$, R'$_2$CR'$_2$C—Se—CR'$_2$CR'$_2$, R'$_2$C—Se—CR'$_2$CR'$_2$, R'$_2$C—Se—CR'=CR', R'$_2$C—N=CR', R'$_2$C—NR'—CR'$_2$, R'$_2$C—NR'—CR'$_2$CR'$_2$, R'$_2$C—NR'—CR'=CR', R'$_2$CR'$_2$C—NR'—CR'$_2$CR'$_2$, R'$_2$C—P=CR', and R'$_2$C—PR'—CR'$_2$ where R' is hydrogen or a C$_1$-C$_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent. Preferred examples for the bridging group Y include O, S, NMe, Net, NPr, NPh, N-Ph-p-Me, PMe, PEt, PPr, PPh, P(=S)Ph, CH$_2$, CH$_2$CH$_2$, CH(CH$_3$)$_2$, SiMe$_2$, SiEt$_2$, SiPh$_2$, SiMePh, Si(CH$_2$)$_3$, and Si(CH$_2$)$_4$.

In a second embodiment, the invention provides a metallocene compound represented by the formula (2):

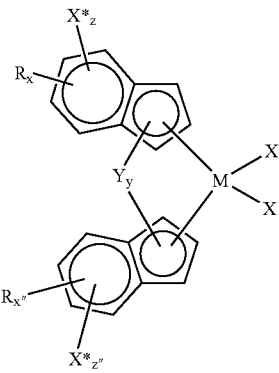

or formula (3):

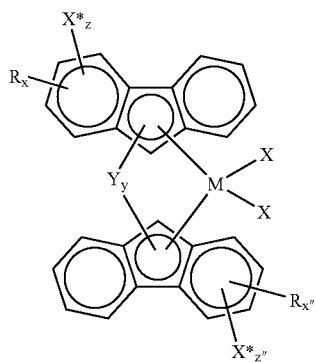

or formula (4):

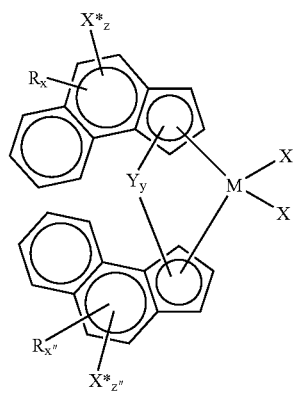

or formula (5):

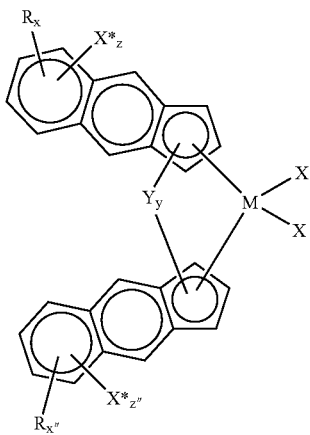

wherein

M is a group 3, 4, 5 or 6 transition metal atom, or a lanthanide metal atom, or actinide metal atom, preferably a Group 4 transition metal atom selected from titanium, zirconium or hafnium;

each R is bonded to any position of the ring structure ligand and is, independently, hydrogen, or a hydrocarbyl, substituted hydrocarbyl, halocarbyl, substituted halocarbyl, silylcarbyl, substituted silylcarbyl, germylcarbyl, substituted germylcarbyl, or other heteroatom substituents wherein the heteroatom is bonded directly to a ring carbon of the ring structure ligand and is boron, a Group 15 atom, or a Group 16 atom, preferably boron, nitrogen, oxygen, phosphorus, or sulfur, and optionally, two or more adjacent R may join together to form a substituted or unsubstituted, saturated, partially unsaturated, or aromatic cyclic or polycyclic substituent;

x and x" represent the number of R substituents bonded to the ring structure ligand; x and x" are, independently, 4, 5, 6, or 7 for formula (2); x and x" are, independently, 6, 7, 8, or 9 for each of formulae (3), (4) and (5);

each X* is bonded to any position of the ring structure ligand and is, independently, a chloro or bromo substitutent; provided that when y is equal to one, the ring structures are not both 5,6-dichloroindenyl or are not both an indenyl group having a fluoro- or chloro substituent at the 7 position and a hydrocarbyl or substituted hydrocarbyl substituent at the 4 position; provided that when y is equal to zero, the ring structures are not both 5,6-difluoroindenyl; and provided that when one X* substituent is bonded to the 4, 5, or 6 position of each indenyl ligand in formula (2), then at least one other substituent is selected from hydrocarbyl, substituted hydrocarbyl, halogen, halocarbyl, substituted halocarbyl, silylcarbyl, substituted silylcarbyl, germylcarbyl, substituted germylcarbyl, or other heteroatom substituents wherein the heteroatom is bonded directly to a ring carbon of the ring structure ligand and is boron, a Group 15 atom, or a Group 16 atom, preferably boron, nitrogen, oxygen, phosphorus, or sulfur;

z and z" represent the number of X* substituents bonded to its respective ring structure ligand; z and z" are, independently, 0, 1 or 2; z +z"=1, 2, 3, or 4;

Y is an optional bridging group bonded to any single position of each ring structure ligand and containing a Group 13, 14, 15, or 16 element;

y is 0 or 1, indicating the absence (y=0) or presence (y=1) of Y;

$x+y+z=7$, and $x''+y+z''=7$ for formula (2);

$x+y+z=9$, and $x''+y+z''=9$ for each of formulae (3), (4) and (5); and each X is a univalent anionic ligand, or two X are joined and bound to the metal atom to form a metallocycle ring, or two X are joined to form a chelating ligand, a diene ligand, or an alkylidene ligand.

Conveniently, each X* substituent is a chloro, bromo, or iodo substituent, preferably a chloro or bromo substituent.

Conveniently, Y is present and is a bridging group containing boron or a Group 14, 15 or 16 element. Examples of suitable bridging groups include S, O, NR', PR', P(=S)R', AsR', SbR', O—O, S—S, R'N—NR', R'P—PR', O—S, O—NR', O—PR', S—NR', S—PR', R'N—PR', $R'_2C$, $R'_2Si$, $R'_2Ge$, $R'_2CCR'_2$, $R'_2CCR'_2CR'_2$, $R'_2CCR'_2CR'_2CR'_2$, $R'C=CR'$, $R'C=CR'CR'_2$, $R'_2CCR'=CR'CR'_2$, $R'C=CR'CR'=CR'$, $R'C=CR'CR'_2CR'_2$, $R'_2CSiR'_2$, $R'_2SiSiR'_2$, $R'_2CSiR'_2CR'_2$, $R'_2SiCR'_2SiR'_2$, $R'C=CR'SiR'_2$, $R'_2CGeR'_2$, $R'_2GeGeR'_2$, $R'_2CGeR'_2CR'_2$, $R'_2GeCR'_2GeR'_2$, $R'_2SiGeR'_2$, $R'C=CR'GeR'_2$, $R'B$, $R'_2C$—$BR'$, $R'_2C$—$BR'$—$CR'_2$, $R'_2C$—$O$—$CR'_2$, $R'_2CR'_2C$—$O$—$CR'_2CR'_2$, $R'_2C$—$O$—$CR'_2CR'_2$, $R'_2C$—$O$—$CR'=CR'$, $R'_2C$—$S$—$CR'_2$, $R'_2CR'_2C$—$S$—$CR'_2CR'_2$, $R'_2C$—$S$—$CR'_2CR'_2$, $R'_2C$—$S$—$CR'=CR'$, $R'_2C$—$Se$—$CR'_2$, $R'_2CR'_2C$—$Se$—$CR'_2CR'_2$, $R'_2C$—$Se$—$CR'_2CR'_2$, $R'_2C$—$Se$—$CR'=CR'$, $R'_2C$—$N=CR'$, $R'_2C$—$NR'$—$CR'_2$, $R'_2C$—$NR'$—$CR'_2CR'_2$, $R'_2C$—$NR'$—$CR'=CR'$, $R'_2CR'_2C$—$NR'$—$CR'_2CR'_2$, $R'_2C$—$P=CR'$, and $R'_2C$—$PR'$—$CR'_2$ where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent. Preferred examples for the bridging group Y include O, S, NMe, Net, NPr, NPh, N-Ph-p-Me, PMe, PEt, PPr, PPh, P(=S)Ph, $CH_2$, $CH_2CH_2$, $CH(CH_3)_2$, $SiMe_2$, $SiEt_2$, $SiPh_2$, $SiMePh$, $Si(CH_2)_3$, and $Si(CH_2)_4$.

Examples of metallocene compounds according to the present invention include:

bis(2-bromoinden-1-yl)zirconium dichloride,
bis(3-bromoinden-1-yl)zirconium dichloride,
bis(2-chloroinden-1-yl)zirconium dichloride,
bis(2-methyl-4-bromoinden-1-yl)zirconium dichloride,
bis(2-bromo-4,7-dimethylindenyl)zirconium dichloride,
bis(3-bromo-5-methylcyclopenta[b]thienyl)zirconium dichloride,
rac-diethylsilyl-bis(4-bromo-2-methylindenyl)]($N^1$,$N^3$-diphenyl-1,3-propanediamido)zirconium,
rac-diethylsilyl-bis(4-bromo-2-methylindenyl)zirconium dichloride,
rac-dimethylsilanediyl-bis(2-bromoinden-1-yl)zirconium dichloride,
rac-dimethylsilanediyl-bis(3-bromoinden-1-yl)zirconium dichloride,
rac-dimethylsilanediyl-bis(2-chloroinden-1-yl)zirconium dichloride,
rac-dimethylsilanediyl-bis(4-bromo-2-methylinden-1-yl) zirconium dichloride,
rac-dimethylsilanediyl-bis(4-bromoinden-1-yl)zirconium dichloride
rac-dimethylsilanediyl-bis(4-bromo-2-isopropylinden-1-yl) zirconium dichloride, rac-dimethylsilanediyl-bis(4-bromo-2-phenylinden-1-yl)zirconium dichloride,
rac-dimethylsilanediyl-bis(4-chloro-2-methylinden-1-yl)zirconium dichloride,
rac-dimethylsilanediyl-bis(4-iodo-2-methylinden-1-yl)zirconium dichloride,
rac-dimethylsilanediyl-bis(4-bromo-2-methylinden-1-yl)zirconium dibromide,
rac-dimethylsilanediyl-bis(4-bromo-2-methylinden-1-yl)zirconium diiodide,
rac-dimethylsilanediyl-bis(4-bromo-2-methylinden-1-yl)zirconium difluoride,
rac-dimethylsilanediyl-bis(4-bromo-2-methylinden-1-yl)zirconium dihydride,
rac-dimethylsilanediyl-bis(4-bromo-2-methylinden-1-yl)dimethylzirconium,
rac-dimethylsilanediyl-bis(4-bromo-2-methylinden-1-yl)dibenzylzirconium,
rac-dimethylsilanediyl-bis(4-bromo-2-methylinden-1-yl)diphenylzirconium,
rac-dimethylsilanediyl-bis(4-bromo-2-methylinden-1-yl)-bis(dimethylamino)zirconium,
rac-dimethylsilanediyl-bis(4-bromo-2-methylinden-1-yl)($N^1,N^3$-diphenyl-1,3-propanediamino)zirconium,
rac-dimethylsilanediyl-bis(4-bromo-2-methylinden-1-yl)dimethoxyzirconium,
rac-dimethylsilanediyl-bis(4-bromo-2-methylinden-1-yl)(3,3',5,5'-tetra-tert-butyl-[1,1'-biphenyl]-2,2'-dioxo)zirconium,
rac-dimethylsilanediyl-bis(4-bromo-2,5-dimethylinden-1-yl)zirconium dichloride,
rac-dimethylsilanediyl-bis(4-bromo-2-methyl-6-phenylinden-1-yl)zirconium dichloride,
rac-dimethylsilanediyl-bis(4-bromo-6-isopropyl-2-methylinden-1-yl)zirconium dichloride,
rac-dimethylsilanediyl-bis(4-bromo-2-methyl-5,6,7,8-tetrahydrocyclopenta[b]naphth-1-yl)zirconium dichloride,
rac-dimethylsilanediyl-bis(5-bromo-2-methyl-6,7,8,9-tetrahydrocyclopenta[a]naphth-3-yl)zirconium dichloride,
rac-[dimethylsilyl-bis(5-bromo-2-methyl-6,7,8,9-tetrahydro-3H-cyclopenta[a]naphthalen-3-yl)]($N^1,N^3$-diphenyl-1,3-propanediamido)zirconium,
rac-dimethylsilanediyl-bis(4-bromo-2-methylcyclopenta[b]naphth-1-yl)zirconium dichloride
rac-dimethylsilanediyl-bis(7-bromo-2,4-dimethylcyclopenta[b]naphth-1-yl)zirconium dichloride
rac-dimethylsilanediyl-bis(4-bromo-6-trifluoromethyl-2-methylinden-1-yl)zirconium dichloride
rac-dimethylsilanediyl-bis(4-bromo-6-perfluorophenyl-2-methylinden-1-yl)zirconium dichloride
rac-dimethylsilanediyl-bis(4-bromo-6-trimethylsilyl-2-methylinden-1-yl)zirconium dichloride
rac-dimethylsilanediyl-bis(4,6-dibromo-2-methylinden-1-yl)zirconium dichloride
rac-dimethylsilanediyl-bis(4,6-dichloro-2-methylinden-1-yl)zirconium dichloride
rac-dimethylsilanediyl-bis(4-bromo-6-chloro-2-methylinden-1-yl)zirconium dichloride
rac-dimethylsilanediyl-bis(4-bromo-6-fluoro-2-methylinden-1-yl)zirconium dichloride
rac-dimethylsilanediyl-bis(5-bromo-2,4-dimethylinden-1-yl)zirconium dichloride
rac-dimethylsilanediyl-bis(6-bromo-2,4-dimethylinden-1-yl)zirconium dichloride
rac-dimethylsilanediyl-bis(7-bromo-2-methyl-4-phenylinden-1-yl)zirconium dichloride
meso-dimethylsilanediyl-bis(4-bromo-2-methylinden-1-yl)zirconium dichloride
meso-dimethylsilanediyl-bis(4-bromoinden-1-yl)zirconium dichloride
rac-isopropylidene-bis(4-bromo-2-methylinden-1-yl)zirconium dichloride
meso-isopropylidene-bis(4-bromo-2-methylinden-1-yl)zirconium dichloride
rac-methylidene-bis(4-bromo-2-methylinden-1-yl)zirconium dichloride
rac-diphenylmethylidene-bis(4-bromo-2-methylinden-1-yl)zirconium dichloride
rac-1,2-ethylidene-bis(4-bromo-2-methylinden-1-yl)zirconium dichloride
meso-1,2-ethylidene-bis(4-bromo-2-methylinden-1-yl)zirconium dichloride
rac-dimethylsilanediyl-bis[2-(4-bromophenyl)inden-1-yl]zirconium dichloride
meso-dimethylsilanediyl-bis[2-(4-bromophenyl)inden-1-yl]zirconium dichloride
meso-dimethylsilanediyl-bis[2-(4-bromophenyl)inden-1-yl]zirconium dichloride
rac-isopropylidene-bis[2-(4-bromophenyl)inden-1-yl]zirconium dichloride
rac-1,2-ethylidene-bis[2-(4-bromophenyl)inden-1-yl]zirconium dichloride
rac-methylidene-bis(4-bromo-2-inden-1-yl)zirconium dichloride
meso-methylidene-bis(4-bromo-2-inden-1-yl)zirconium dichloride
rac-dimethylsilanediyl-bis(2-bromofluoren-9-yl)zirconium dichloride
meso-dimethylsilanediyl-bis(2-bromofluoren-9-yl)zirconium dichloride
rac-dimethylsilanediyl-bis(2-iodofluoren-9-yl)zirconium dichloride
rac-dimethylsilanediyl-bis(2-chlorofluoren-9-yl)zirconium dichloride
dimethylsilanediyl-bis(2,7-dibromofluoren-9-yl)zirconium dichloride
rac-methylidenoe-bis(2-bromofluoren-9-yl)zirconium dichloride
rac-isopropylidene-bis(2-bromofluoren-9-yl)zirconium dichloride
rac-1,2-ethylidene-bis(2-bromofluoren-9-yl)zirconium dichloride
4,4'-sulfandiyl-bis(3-bromoindenyl)zirconium dichloride,
4,4'-sulfandiyl-bis(2-bromoindenyl)zirconium dichloride,
4,4'-sulfandiyl-bis(1-bromoindenyl)zirconium dichloride,
5,5'-sulfandiyl-bis(3-bromoindenyl)zirconium dichloride,
5,5'-sulfandiyl-bis(2-bromoindenyl)zirconium dichloride,
5,5'-sulfandiyl-bis(1-bromoindenyl)zirconium dichloride,
4,5'-sulfandiyl-bis(3-bromoindenyl)zirconium dichloride,
4,5'-sulfandiyl-bis(2-bromoindenyl)zirconium dichloride,
4,5'-sulfandiyl-bis(1-bromoindenyl)zirconium dichloride,
4,4'-oxadiyl-bis(7-bromo-1-phenylindenyl)zirconium dichloride,
4,4'-oxadiyl-bis(7-chloro-1-phenylindenyl)zirconium dichloride,
4,4'-oxadiyl-bis(7-iodo-1-phenylindenyl)zirconium dichloride,
4,4'-sulfandiyl-bis(7-bromo-1-phenylindenyl)zirconium dichloride,
4,4'-sulfandiyl-bis(7-chloro-1-phenylindenyl)zirconium dichloride,
4,4'-sulfandiyl-bis(7-iodo-1-phenylindenyl)zirconium dichloride, 4,4'-sulfandiyl-bis(6-bromo-1-phenylindenyl)zirconium dichloride,
4,4'-sulfandiyl-bis(5-bromo-1-phenylindenyl)zirconium dichloride,
4,4'-sulfandiyl-bis(7-bromo-1-phenylindenyl)zirconium dibromide,
4,4'-sulfandiyl-bis(7-bromo-1-phenylindenyl)zirconium difluoride,
4,4'-sulfandiyl-bis(7-bromo-1-phenylindenyl)zirconium diiodide,
4,4'-sulfandiyl-bis(7-bromo-1-phenylindenyl)zirconium dihydride,
4,4'-sulfandiyl-bis(7-bromo-1-phenylindenyl)dimethylzirconium,
4,4'-sulfandiyl-bis(7-bromo-1-phenylindenyl)dimethoxyzirconium,
4,4'-sulfandiyl-bis(7-bromo-1-phenylindenyl)bis(dimethylamino)zirconium,
4,4'-phenylphosphindiyl-bis(7-bromo-1-phenylindenyl)zirconium dichloride,
4,4'-phenylphosphindiyl-bis(7-chloro-1-phenylindenyl)zirconium dichloride,
4,4'-phenylphosphindiyl-bis(7-iodo-1-phenylindenyl)zirconium dichloride,
4,4'-(4-bromophenyl)phosphindiyl-bis(7-bromo-1-phenylindenyl)zirconium dichloride,
4,4'-phenylphosphindiyl-bis(7-bromo-1-phenylindenyl)zirconium dibromide,
4,4'-phenylphosphindiyl-bis(7-bromo-1-phenylindenyl)zirconium difluoride,
4,4'-phenylphosphindiyl-bis(7-bromo-1-phenylindenyl)zirconium diiodide,
4,4'-phenylphosphindiyl-bis(7-bromo-1-phenylindenyl)zirconium dihydride,
4,4'-phenylphosphindiyl-bis(7-bromo-1-phenylindenyl)dimethylzirconium,
4,4'-phenylphosphindiyl-bis(7-bromo-1-phenylindenyl)dimethoxyzirconium,
4,4'-phenylphosphindiyl-bis(7-bromo-1-phenylindenyl)bis(dimethylamino) zirconium,
4,4'-(4-bromophenyl)phosphindiyl-bis(7-bromo-1-phenylindenyl)zirconium dichloride,
4,4'-(4-chlorophenyl)phosphindiyl-bis(7-chloro-1-phenylindenyl)zirconium dichloride,
4,4'-(4-fluorophenyl)phosphindiyl-bis(7-iodo-1-phenylindenyl)zirconium dichloride,
4,4'-(4-iodophenyl)phosphindiyl-bis(7-fluoro-1-phenylindenyl)zirconium dichloride,
4,4'-sulfandiyl-bis(7-bromo-2-methylindenyl)zirconium dichloride,
4,4'-sulfandiyl-bis(7-bromoindenyl)zirconium dichloride,
4,4'-sulfandiyl-bis(7-bromofluorenyl)zirconium dichloride,
4,4'-sulfandiyl-bis(7-bromo-2,6-dimethylindenyl)zirconium dichloride,
4,4'-sulfandiyl-bis(7-bromo-6-ethyl-2-methylindenyl)zirconium dichloride,
4,4'-sulfandiyl-bis(7-bromo-5-phenylindenyl)zirconium dichloride,
4,4'-sulfandiyl-bis(7-bromo-5-phenyl-2-methylindenyl)zirconium dichloride,
4,4'-sulfandiyl-bis(7-bromo-2-methyl-6-o-tolylindenyl)zirconium dichloride,
4,4'-sulfandiyl-bis[7-bromo-2-methyl-2-(4-fluorophenyl)indenyl]zirconium dichloride,
4,4'-sulfandiyl-bis[7-bromo-2-methyl-2-(3-trifluoromethylphenyl)indenyl]zirconium dichloride,
4,4'-methylazandiyl-bis(7-bromo-1-phenylindenyl)zirconium dichloride,
4,4'-methylazandiyl-bis(7-chloro-1-phenylindenyl)zirconium dichloride,
4,4'-methylazandiyl-bis(7-iodo-1-phenylindenyl)zirconium dichloride,
4,4'-phenylazandiyl-bis(7-chloro-1-phenylindenyl)zirconium dichloride,
4,4'-phenylazandiyl-bis(7-iodo-1-phenylindenyl)zirconium dichloride,
4,4'-(thien-2-yl)azandiyl-bis(7-bromo-1-phenylindenyl)zirconium dichloride,
4,4'-(5-chlorothien-2-yl)azandiyl-bis(7-bromo-1-phenylindenyl)zirconium dichloride,
4,4'-(pyrid-2-yl)azandiyl-bis(7-bromo-1-phenylindenyl)zirconium dichloride,
4,4'-(4-bromopyrid-2-yl)azandiyl-bis(7-bromo-1-phenylindenyl)zirconium dichloride,
4,4'-(benzothien-3-yl)azandiyl-bis(7-bromo-1-phenylindenyl)zirconium dichloride,
5,5'-oxadiyl-bis(7-bromo-1-phenylindenyl)zirconium dichloride,
5,5'-oxadiyl-bis(7-chloro-1-phenylindenyl)zirconium dichloride,
5,5'-oxadiyl-bis(7-iodo-1-phenylindenyl)zirconium dichloride,
5,5'-sulfandiyl-bis(7-bromo-1-phenylindenyl)zirconium dichloride,
5,5'-sulfandiyl-bis(7-chloro-1-phenylindenyl)zirconium dichloride,
5,5'-sulfandiyl-bis(7-iodo-1-phenylindenyl)zirconium dichloride,
5,5'-sulfandiyl-bis(6-bromo-1-phenylindenyl)zirconium dichloride,
5,5'-sulfandiyl-bis(5-bromo-1-phenylindenyl)zirconium dichloride,
5,5'-sulfandiyl-bis(7-bromo-1-phenylindenyl)zirconium dibromide,
5,5'-sulfandiyl-bis(7-bromo-1-phenylindenyl)zirconium difluoride,
5,5'-sulfandiyl-bis(7-bromo-1-phenylindenyl)zirconium diiodide,
5,5'-sulfandiyl-bis(7-bromo-1-phenylindenyl)zirconium dihydride,
5,5'-sulfandiyl-bis(7-bromo-1-phenylindenyl)dimethylzirconium,
5,5'-sulfandiyl-bis(7-bromo-1-phenylindenyl)dimethoxyzirconium,
5,5'-sulfandiyl-bis(7-bromo-1-phenylindenyl)bis(dimethylamino)zirconium,
4,5'-oxadiyl-bis(7-bromo-1-phenylindenyl)zirconium dichloride,
4,5'-oxadiyl-bis(7-chloro-1-phenylindenyl)zirconium dichloride,
4,5'-oxadiyl-bis(7-iodo-1-phenylindenyl)zirconium dichloride,
4,5'-sulfandiyl-bis(7-bromo-1-phenylindenyl)zirconium dichloride,
4,5'-sulfandiyl-bis(7-chloro-1-phenylindenyl)zirconium dichloride,
4,5'-sulfandiyl-bis(7-iodo-1-phenylindenyl)zirconium dichloride,
4,5'-sulfandiyl-bis(6-bromo-1-phenylindenyl)zirconium dichloride,
4,5'-sulfandiyl-bis(5-bromo-1-phenylindenyl)zirconium dichloride, 4,5'-sulfandiyl-bis(7-bromo-1-phenylindenyl)zirconium dibromide,
4,5'-sulfandiyl-bis(7-bromo-1-phenylindenyl)zirconium difluoride,
4,5'-sulfandiyl-bis(7-bromo-1-phenylindenyl)zirconium diiodide,
4,5'-sulfandiyl-bis(7-bromo-1-phenylindenyl)zirconium dihydride,
4,5'-sulfandiyl-bis(7-bromo-1-phenylindenyl)dimethylzirconium,
4,5'-sulfandiyl-bis(7-bromo-1-phenylindenyl)dimethoxyzirconium,
4,5'-sulfandiyl-bis(7-bromo-1-phenylindenyl)bis(dimethylamino)zirconium,
rac-dimethylsilanediyl-bis(4-bromo-2-[5-methyl-2-thienyl]inden-1-yl)zirconium dichloride,
rac-dimethylsilanediyl-bis(4-bromo-2-[4-pyridyl]inden-1-yl)zirconium dichloride,
rac-dimethylsilanediyl-bis(4-bromo-2-methyl-6-[5-methyl-2-thienyl]inden-1-yl)zirconium dichloride,
rac-dimethylsilanediyl-bis(4-bromo-2-methyl-6-[4-pyridyl]inden-1-yl)zirconium dichloride,
rac-dimethylsilanediyl-bis(8-bromo-6-methylindeno[5,6-d][1,3]dioxol-5-yl)zirconium dichloride,
rac-dimethylsilanediyl-bis(4-bromo-2,3,6-trimethylindeno[5,6-b]thien-7-yl)zirconium dichloride,
rac-dimethylsilanediyl-bis(2-bromo-4,6-dimethylindeno[5,6-b]thien-7-yl)zirconium dichloride,
rac-dimethylsilanediyl-bis(4-bromo-1,2,3,6-tetramethylcyclopenta[f]indol-7-yl)zirconium dichloride,
rac-dimethylsilanediyl-bis(4-bromo-1-phenyl-2,3,6-triamethylcyclopenta[f]indol-7-yl)zirconium dichloride,
rac-dimethylsilanediyl-bis(5-bromo-7-methylcyclopenta[g]quinol-8-yl)zirconium dichloride,
rac-dimethylsilanediyl-bis(2-bromo-5,7-dimethylcyclopenta[g]quinol-8-yl)zirconium dichloride,
rac-dimethylsilanediyl-bis(4-bromo-6-methoxy-2-methylinden-1-yl)zirconium dichloride,
rac-dimethylsilanediyl-bis(4-bromo-6-dimethylamino-2-methylinden-1-yl)zirconium dichloride,
rac-dimethylsilanediyl-bis(4-bromo-6-methylsulfanyl-2-methylinden-1-yl)zirconium dichloride,
rac-dimethylsilanediyl-bis(4-bromo-6-dimethylphosphino-2-methylinden-1-yl)zirconium dichloride,
rac-dimethylsilanediyl-bis(4-bromo-6-trimethylgermyl-2-methylinden-1-yl)zirconium dichloride,
rac-dimethylgermanediyl-bis(4-bromo-2-methylinden-1-yl)zirconium dichloride,
rac-methylboranediyl-bis(4-bromo-2-methylinden-1-yl)zirconium dichloride,
rac-phenylboranediyl-bis(4-bromo-2-methylinden-1-yl)zirconium dichloride,
rac-methylphosphinediyl-bis(4-bromo-2-methylinden-1-yl)zirconium dichloride,
rac-methylphosphinediyl-bis(4-bromoinden-1-yl)zirconium dichloride,
meso-methylphosphinediyl-bis(4-bromoinden-1-yl)zirconium dichloride,
rac-phenylphosphinediyl-bis(4-bromo-2-methylinden-1-yl)zirconium dichloride,
rac-methylphosphinediyl-bis[2-(4-bromophenyl)inden-1-yl]zirconium dichloride,
rac-dimethylsilanediyl-bis[2-(4-bromo-2-pyridyl)inden-1-yl]zirconium dichloride,
rac-dimethylsilanediyl-bis[2-(5-bromo-2-thienyl)inden-1-yl]zirconium dichloride,
rac-dimethylsilanediyl-bis(3-bromo-5-methylcyclopenta[b]thien-6-yl)zirconium dichloride,
meso-dimethylsilanediyl-bis(3-bromo-5-methylcyclopenta[b]thien-6-yl)zirconium dichloride,
rac-dimethylsilanediyl-bis(3-chloro-5-methylcyclopenta[b]thien-6-yl)zirconium dichloride,
rac-dimethylsilanediyl-bis(3-bromo-5-methyl-2-phenylcyclopenta[b]thien-6-yl)zirconium dichloride,
rac-methylidene-bis(3-bromo-5-methylcyclopenta[b]thien-6-yl)zirconium dichloride,
rac-isopropylidene-bis(3-bromo-5-methylcyclopenta[b]thien-6-yl)zirconium dichloride,
rac-1,2-ethylidene-bis(3-bromo-5-methylcyclopenta[b]thien-6-yl)zirconium dichloride,
rac-methyl(4-bromophenyl)silanediyl-bis(3-bromo-5-methylcyclopenta[b]thien-6-yl)zirconium dichloride,
rac-dimethylsilanediyl-bis(3-bromo-5-methylcyclopenta[b]thien-6-yl)zirconium dibromide,
rac-dimethylsilanediyl-bis(3-bromo-5-methylcyclopenta[b]thien-6-yl)zirconium diiodide,
rac-dimethylsilanediyl-bis(3-bromo-5-methylcyclopenta[b]thien-6-yl)zirconium difluoride,
rac-dimethylsilanediyl-bis(3-bromo-5-methylcyclopenta[b]thien-6-yl)zirconium dihydride,
rac-dimethylsilanediyl-bis(3-bromo-5-methylcyclopenta[b]thien-6-yl)dimethylzirconium,
rac-dimethylsilanediyl-bis(3-bromo-5-methylcyclopenta[b]thien-6-yl)diphenylzirconium,
rac-dimethylsilanediyl-bis(3-bromo-5-methylcyclopenta[b]thien-6-yl)dibenzylzirconium,
rac-dimethylsilanediyl-bis(3-bromo-5-methylcyclopenta[b]thien-6-yl)-bis(dimethylamino)zirconium,
rac-dimethylsilanediyl-bis(3-bromo-5-methylcyclopenta[b]thien-6-yl)($N^1,N^3$-diphenyl-1,3-propanediamino)zirconium,
rac-dimethylsilanediyl-bis(3-bromo-5-methylcyclopenta[b]thien-6-yl)dimethoxyzirconium,
rac-dimethylsilanediyl-bis(3-bromo-5-methylcyclopenta[b]thien-6-yl)(3,3',5,5'-tetra-tert-butyl-[1,1'-biphenyl]-2,2'-dioxo)zirconium,
rac-dimethylsilanediyl-bis(1,3-dichlorocyclopenta[c]thien-4-yl)zirconium dichloride,
rac-dimethylsilanediyl-bis(8-bromo-2-methylcyclopenta[b][1]benzothien-3-yl)zirconium dichloride,
rac-dimethylsilanediyl-bis(8-chloro-2-methylcyclopenta[b][1]benzothien-3-yl)zirconium dichloride,
rac-dimethylsilanediyl-bis(8-iodo-2-methylcyclopenta[b][1]benzothien-3-yl)zirconium dichloride,
rac-dimethylsilanediyl-bis(3-bromo-5-methylcyclopenta[b]fur-6-yl)zirconium dichloride,
rac-dimethylsilanediyl-bis(2-bromo-1,5-dimethylcyclopenta[b]pyrrol-4-yl)zirconium dichloride,
rac-dimethylsilanediyl-bis(2-bromo-5-methyl-1-phenylcyclopenta[b]pyrrol-4-yl)zirconium dichloride,
rac-dimethylsilanediyl-bis(2-chloro-5-methyl-1-phenylcyclopenta[b]pyrrol-4-yl)zirconium dichloride,
rac-dimethylsilanediyl-bis(2-iodo-5-methyl-1-phenylcyclopenta[b]pyrrol-4-yl)zirconium dichloride,
rac-dimethylsilanediyl-bis(2-bromo-1,5-dimethylcyclopenta[b]phosphol-4-yl)zirconium dichloride,
rac-dimethylsilanediyl-bis(5-bromo-2,4-dimethylcyclopenta[b]indol-1-yl)zirconium dichloride,
rac-dimethylsilanediyl-bis(4-bromocyclopenta[b]pyrid-7-yl)zirconium dichloride,
rac-dimethylsilanediyl-bis(4-bromocyclopenta[b]phosphin-7-yl)zirconium dichloride, rac-4,4'-dimethylsilanediyl-bis(2,6-dibromo-1-dimethy-
lamino-1-boratabenzene)zirconium dichloride,
rac-2,2'-dimethylsilanediyl-bis(4-bromo-3-dimethylamino-
1,3-benzothiaborollide-2-yl)zirconium dichloride,
rac-dimethylsilanediyl-bis(4-bromo-3a,7a-azaborinden-1-
yl)zirconium dichloride,
rac-3,3'-dimethylsilanediyl-bis(7-bromo-2-dimethylamino-
1,2-benzothiaborollide)zirconium dichloride,
rac-5,5'-dimethylsilanediyl-bis(3-bromo-2-dimethylamino-
1,2-thiaborollide)zirconium dichloride,
rac-dimethylsilanediyl-bis(7-bromoindeno[1,2-c]pyrid-5-
yl)zirconium dichloride,
rac-dimethylsilanediyl-bis(3-bromoindeno[1,2-c]pyrid-5-
yl)zirconium dichloride,
rac-dimethylsilanediyl-bis(7-bromoindeno[1,2-c]phosphin-
5-yl)zirconium dichloride,
rac-dimethylsilanediyl-bis(2-bromoindeno[1,2-b]thien-4-
yl)zirconium dichloride,
rac-dimethylsilanediyl-bis(6-bromoindeno[2,1-b]thien-8-
yl)zirconium dichloride,
rac-dimethylsilanediyl-bis(6-bromoindeno[1,2-c]thien-8-yl)
zirconium dichloride,
rac-dimethylsilanediyl-bis(6-bromoindeno[1,2-b]thien-4-
yl)zirconium dichloride,
rac-dimethylsilanediyl-bis(6-bromo-2,3-dimethylindeno[1,
2-b]fur-4-yl)zirconium dichloride,
rac-dimethylsilanediyl-bis(2-bromoindeno[1,2-b][1]ben-
zothien-10-yl)zirconium dichloride,
rac-dimethylsilanediyl-bis(8-bromoindeno[1,2-b][1]ben-
zothien-10-yl)zirconium dichloride,
rac-dimethylsilanediyl-bis(8-bromoindeno[2,1-b][1]ben-
zothien-6-yl)zirconium dichloride,
rac-dimethylsilanediyl-bis(3-bromo-indeno[2,1-b][1]ben-
zothien-6-yl)zirconium dichloride,
rac-dimethylsilanediyl-bis(2-bromo-5-methylindeno[1,2-b]
indol-10-yl)zirconium dichloride,
rac-dimethylsilanediyl-bis(8-bromo-5-methylindeno[1,2-b]
indol-10-yl)zirconium dichloride,
rac-dimethylsilanediyl-bis(8-bromo-5-methylindeno[2,1-b]
indol-6-yl)zirconium dichloride,
rac-dimethylsilanediyl-bis(3-bromo-5-methylindeno[2,1-b]
indol-6-yl)zirconium dichloride,
4,4'-sulfandiyl-bis[7-bromo-2-methyl-6-(5-methylthien-2-
yl)indenyl]zirconium dichloride,
4,4'-sulfandiyl-bis[7-bromo-2-methyl-6-(5-methylfur-2-yl)
indenyl]zirconium dichloride,
4,4'-sulfandiyl-bis[7-bromo-2-methyl-2-(2-benzothienyl)in-
denyl]zirconium dichloride,
4,4'-sulfandiyl-bis[7-bromo-2-methyl-2-(2-benzofuryl)in-
denyl]zirconium dichloride,
3,3'-sulfandiyl-bis(2-bromo-5-methylcyclopenta[b]thienyl)
zirconium dichloride,
3,3'-sulfandiyl-bis(2-chloro-5-methylcyclopenta[b]thienyl)
zirconium dichloride,
3,3'-sulfandiyl-bis(2-iodo-5-methylcyclopenta[b]thienyl)
zirconium dichloride,
3,3'-sulfandiyl-bis(2-bromo-5-methylcyclopenta[b]thienyl)
zirconium dichloride,
3,3'-sulfandiyl-bis(2-bromo-5-methylcyclopenta[b]thienyl)
zirconium dibromide,
3,3'-sulfandiyl-bis(2-bromo-5-methylcyclopenta[b]thienyl)
zirconium diiodide,
3,3'-sulfandiyl-bis(2-bromo-5-methylcyclopenta[b]thienyl)
zirconium difluoride,
3,3'-sulfandiyl-bis(2-bromo-5-methylcyclopenta[b]thienyl)
zirconium dihydride,
3,3'-sulfandiyl-bis(2-bromo-5-methylcyclopenta[b]thienyl)
dimethylzirconium,
3,3'-sulfandiyl-bis(2-bromo-5-methylcyclopenta[b]thienyl)
diphenylzirconium,
3,3'-sulfandiyl-bis(2-bromo-5-methylcyclopenta[b]thienyl)
dibenzylzirconium,
3,3'-sulfandiyl-bis(2-bromo-5-methylcyclopenta[b]thienyl)-
bis(dimethylamino)zirconium,
3,3'-sulfandiyl-bis(2-bromo-5-methylcyclopenta[b]thienyl)
dimethoxyzirconium,
1,1'-sulfandiyl-bis(3-chlorocyclopenta[c]thienyl)zirconium
dichloride,
4,4'-sulfandiyl-bis(7-bromoindeno[1,2-c]pyridyl)zirconium
dichloride,
4,4'-sulfandiyl-bis(3-bromoindeno[1,2-c]pyridyl)zirconium
dichloride,
6,6'-sulfandiyl-bis(7-bromoindeno[1,2-c]pyridyl)zirconium
dichloride,
6,6'-sulfandiyl-bis(3-bromoindeno[1,2-c]pyridyl)zirconium
dichloride,
9,9'-sulfandiyl-bis(7-bromoindeno[1,2-c]pyridyl)zirconium
dichloride,
9,9'-sulfandiyl-bis(3-bromoindeno[1,2-c]pyridyl)zirconium
dichloride,
4,6'-sulfandiyl-bis(7-bromoindeno[1,2-c]pyridyl)zirconium
dichloride,
4,6'-sulfandiyl-bis(3-bromoindeno[1,2-c]pyridyl)zirconium
dichloride,
4,9'-sulfandiyl-bis(7-bromoindeno[1,2-c]pyridyl)zirconium
dichloride,
4,9'-sulfandiyl-bis(3-bromoindeno[1,2-c]pyridyl)zirconium
dichloride,
6,9'-sulfandiyl-bis(7-bromoindeno[1,2-c]pyridyl)zirconium
dichloride,
6,9'-sulfandiyl-bis(3-bromoindeno[1,2-c]pyridyl)zirconium
dichloride,
4,4'-sulfandiyl-bis(7-bromoindeno[1,2-c]phosphinyl)zirco-
nium dichloride,
3,3'-sulfandiyl-bis(2-bromoindeno[1,2-b]thienyl)zirconium
dichloride,
3,3'-sulfandiyl-bis(6-bromoindeno[1,2-b]thienyl)zirconium
dichloride,
5,5'-sulfandiyl-bis(2-bromoindeno[1,2-b]thienyl)zirconium
dichloride,
5,5'-sulfandiyl-bis(6-bromoindeno[1,2-b]thienyl)zirconium
dichloride,
8,8'-sulfandiyl-bis(2-bromoindeno[1,2-b]thienyl)zirconium
dichloride,
8,8'-sulfandiyl-bis(6-bromoindeno[1,2-b]thienyl)zirconium
dichloride,
3,5'-sulfandiyl-bis(2-bromoindeno[1,2-b]thienyl)zirconium
dichloride,
3,5'-sulfandiyl-bis(6-bromoindeno[1,2-b]thienyl)zirconium
dichloride,
3,8'-sulfandiyl-bis(2-bromoindeno[1,2-b]thienyl)zirconium
dichloride,
3,8'-sulfandiyl-bis(6-bromoindeno[1,2-b]thienyl)zirconium
dichloride,
5,8'-sulfandiyl-bis(2-bromoindeno[1,2-b]thienyl)zirconium
dichloride,
5,8'-sulfandiyl-bis(6-bromoindeno[1,2-b]thienyl)zirconium
dichloride,
3,3'-sulfandiyl-bis(2-bromoindeno[2,1-b]thienyl)zirconium
dichloride,
3,3'-sulfandiyl-bis(6-bromoindeno[2,1-b]thienyl)zirconium
dichloride, 4,4'-sulfandiyl-bis(2-bromoindeno[2,1-b]thienyl)zirconium dichloride,
4,4'-sulfandiyl-bis(6-bromoindeno[2,1-b]thienyl)zirconium dichloride,
7,7'-sulfandiyl-bis(2-bromoindeno[2,1-b]thienyl)zirconium dichloride,
7,7'-sulfandiyl-bis(6-bromoindeno[2,1-b]thienyl)zirconium dichloride,
3,4'-sulfandiyl-bis(2-bromoindeno[2,1-b]thienyl)zirconium dichloride,
3,4'-sulfandiyl-bis(6-bromoindeno[2,1-b]thienyl)zirconium dichloride,
3,7'-sulfandiyl-bis(2-bromoindeno[2,1-b]thienyl)zirconium dichloride,
3,7'-sulfandiyl-bis(6-bromoindeno[2,1-b]thienyl)zirconium dichloride,
4,7'-sulfandiyl-bis(2-bromoindeno[2,1-b]thienyl)zirconium dichloride,
4,7'-sulfandiyl-bis(6-bromoindeno[2,1-b]thienyl)zirconium dichloride,
1,1'-sulfandiyl-bis(3-bromoindeno[1,2-c]thienyl)zirconium dichloride,
1,1'-sulfandiyl-bis(6-bromoindeno[1,2-c]thienyl)zirconium dichloride,
3,3'-sulfandiyl-bis(1-bromoindeno[1,2-c]thienyl)zirconium dichloride,
3,3'-sulfandiyl-bis(6-bromoindeno[1,2-c]thienyl)zirconium dichloride,
4,4'-sulfandiyl-bis(3-bromoindeno[1,2-c]thienyl)zirconium dichloride,
4,4'-sulfandiyl-bis(6-bromoindeno[1,2-c]thienyl)zirconium dichloride,
7,7'-sulfandiyl-bis(3-bromoindeno[1,2-c]thienyl)zirconium dichloride,
7,7'-sulfandiyl-bis(6-bromoindeno[1,2-c]thienyl)zirconium dichloride,
1,3'-sulfandiyl-bis(6-bromoindeno[1,2-c]thienyl)zirconium dichloride,
1,4'-sulfandiyl-bis(3-bromoindeno[1,2-c]thienyl)zirconium dichloride,
1,4'-sulfandiyl-bis(6-bromoindeno[1,2-c]thienyl)zirconium dichloride,
1,7'-sulfandiyl-bis(3-bromoindeno[1,2-c]thienyl)zirconium dichloride,
1,7'-sulfandiyl-bis(6-bromoindeno[1,2-c]thienyl)zirconium dichloride,
3,4'-sulfandiyl-bis(1-bromoindeno[1,2-c]thienyl)zirconium dichloride,
3,4'-sulfandiyl-bis(6-bromoindeno[1,2-c]thienyl)zirconium dichloride,
3,7'-sulfandiyl-bis(1-bromoindeno[1,2-c]thienyl)zirconium dichloride,
3,7'-sulfandiyl-bis(6-bromoindeno[1,2-c]thienyl)zirconium dichloride,
4,7'-sulfandiyl-bis(3-bromoindeno[1,2-c]thienyl)zirconium dichloride,
4,7'-sulfandiyl-bis(6-bromoindeno[1,2-c]thienyl)zirconium dichloride,
3,3'-sulfandiyl-bis(2-bromoindeno[1,2-b]furyl)zirconium dichloride,
3,3'-sulfandiyl-bis(6-bromoindeno[1,2-b]furyl)zirconium dichloride,
5,5'-sulfandiyl-bis(2-bromoindeno[1,2-b]furyl)zirconium dichloride,
5,5'-sulfandiyl-bis(6-bromoindeno[1,2-b]furyl)zirconium dichloride,
8,8'-sulfandiyl-bis(2-bromoindeno[1,2-b]furyl)zirconium dichloride,
8,8'-sulfandiyl-bis(6-bromoindeno[1,2-b]furyl)zirconium dichloride,
3,5'-sulfandiyl-bis(2-bromoindeno[1,2-b]furyl)zirconium dichloride,
3,5'-sulfandiyl-bis(6-bromoindeno[1,2-b]furyl)zirconium dichloride,
3,8'-sulfandiyl-bis(2-bromoindeno[1,2-b]furyl)zirconium dichloride,
3,8'-sulfandiyl-bis(6-bromoindeno[1,2-b]furyl)zirconium dichloride,
5,8'-sulfandiyl-bis(2-bromoindeno[1,2-b]furyl)zirconium dichloride,
5,8'-sulfandiyl-bis(6-bromoindeno[1,2-b]furyl)zirconium dichloride,
6,6'-sulfandiyl-bis(2-bromo-5-methylindeno[1,2-b]indolyl)zirconium dichloride,
6,6'-sulfandiyl-bis(8-bromo-5-methylindeno[1,2-b]indolyl)zirconium dichloride,
9,9'-sulfandiyl-bis(2-bromo-5-methylindeno[1,2-b]indolyl)zirconium dichloride,
9,9'-sulfandiyl-bis(8-bromo-5-methylindeno[1,2-b]indolyl)zirconium dichloride,
6,9'-sulfandiyl-bis(2-bromo-5-methylindeno[1,2-b]indolyl)zirconium dichloride,
6,9'-sulfandiyl-bis(8-bromo-5-methylindeno[1,2-b]indolyl)zirconium dichloride,
7,7'-sulfandiyl-bis(8-bromo-5-methylindeno[2,1-b]indolyl)zirconium dichloride,
7,7'-sulfandiyl-bis(3-bromo-5-methylindeno[2,1-b]indolyl)zirconium dichloride,
10,10'-sulfandiyl-bis(8-bromo-5-methylindeno[2,1-b]indolyl)zirconium dichloride,
10,10'-sulfandiyl-bis(3-bromo-5-methylindeno[2,1-b]indolyl)zirconium dichloride,
7,10'-sulfandiyl-bis(8-bromo-5-methylindeno[2,1-b]indolyl)zirconium dichloride,
7,10'-sulfandiyl-bis(3-bromo-5-methylindeno[2,1-b]indolyl)zirconium dichloride,
3,3'-oxadiyl-bis(2-bromo-5-methylcyclopenta[b]thienyl)zirconium dichloride,
3,3'-methylazadiyl-bis(2-bromo-5-methylcyclopenta[b]thienyl)zirconium dichloride,
3,3'-phenylazadiyl-bis(2-bromo-5-methylcyclopenta[b]thienyl)zirconium dichloride, and
the hafnium and titanium analogs of the examples above.

Halogenated Metallocene Synthesis

The unbridged metal complexes of formula (1), where y=0, can be prepared through one of two general synthetic procedures. The first method involves a transmetallation reaction between a metal halide ($MX_n$) and a metal salt or non-transition metal derivative of a halo-substituted polycyclic ligand. Preferable metal halides include $TiCl_4$, $TiCl_3$, $ZrCl_4$, $ZrBr_4$, $ZrI_4$, $HfCl_4$, $LnCl_3$, $LnBr_3$, $LnI_3$ (where Ln is Sc, Y, La, or a lanthanide group metal), $VCl_3$, $NbCl_5$, $TaCl_5$, $CrCl_3$, $MoCl_5$, $WCl_6$, and the like. Preferable salts ($M'J_p$) of halo-substituted polycyclic ligands include Li, Na, K, Tl, and Mg salts, and the like. Preferable non-transition metal derivatives of halo-substituted polycyclic ligands include Si and Sn derivatives, and the like (Q derivatives). Two general examples of this first synthetic method are shown below, where Z is a heteroatom.

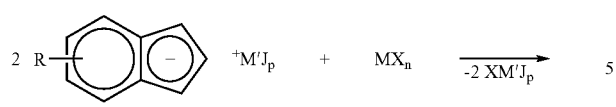

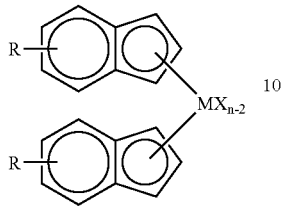

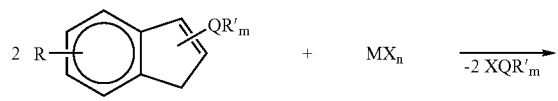

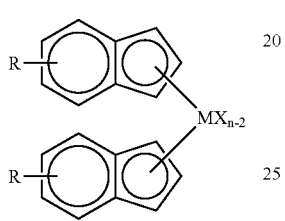

The following representative examples further illustrate this method.

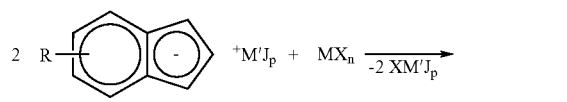

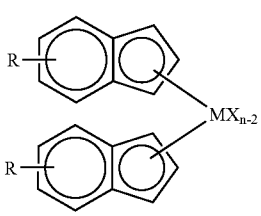

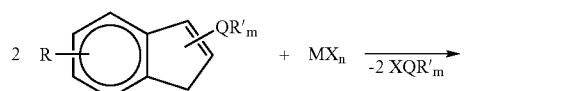

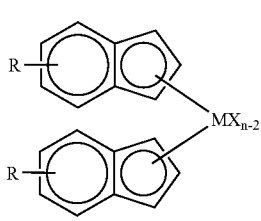

The second general procedure involves metallation of a halo-substituted polycyclic ligand by the respective transition metal derivatives, as shown below.

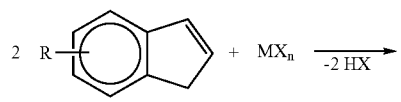

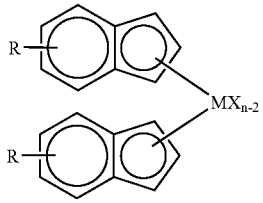

The following representative example illustrates this method.

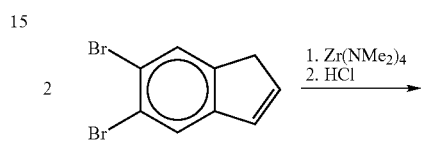

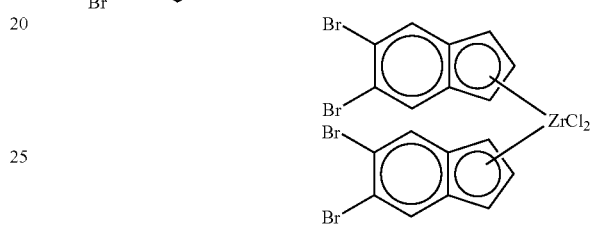

Metal complexes of formula (1) with y=1 can also be prepared by two general synthetic procedures. The first procedure involves a transmetallation reaction between a metal halide ($MX_n$) and a metal salt or non-transition metal derivative of the A-$Y_y$-A dianion. Preferable metal halides include $TiCl_4$, $TiCl_3$, $ZrCl_4$, $ZrBr_4$, $ZrI_4$, $HfCl_4$, $LnCl_3$, $LnBr_3$, $LnI_3$ (where Ln is Sc, Y, La, or lanthanide group metal), $VCl_3$, $NbCl_5$, $TaCl_5$, $CrCl_3$, $MoCl_5$, $WCl_6$, and the like. Preferable metal salts ($M'J_p$) of this dianion include Li, Na, K, Ti, and Mg salts, and the like. Preferable non-transition metal derivatives of this dianion include Si and Sn derivatives, and the like. The general scheme of this first synthetic procedure is shown below.

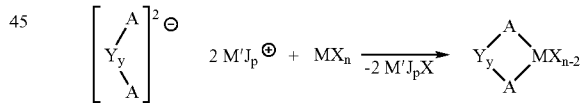

The following representative examples illustrate this method.

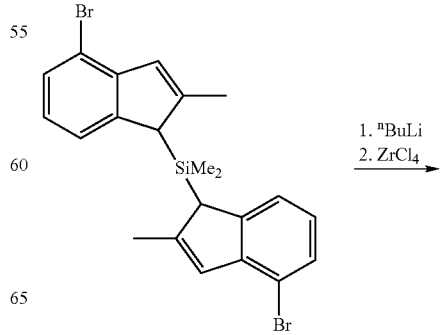

-continued

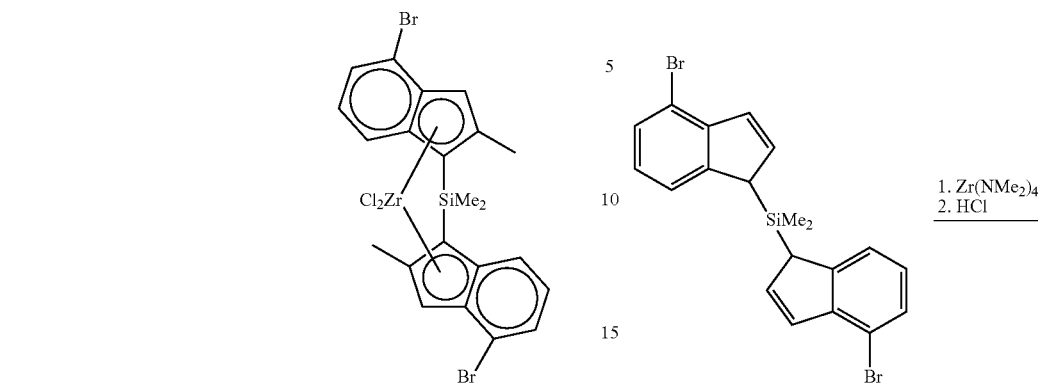

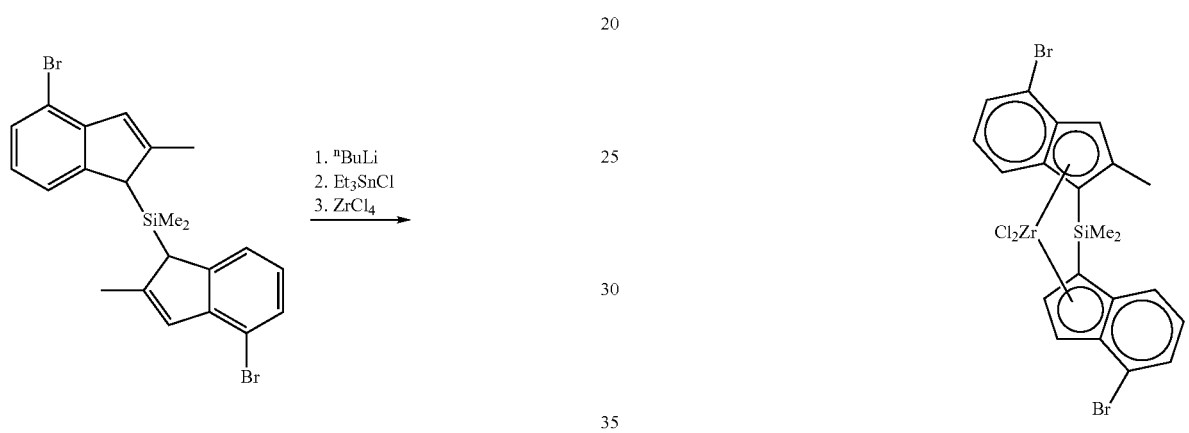

The following representative example illustrates this method.

The second general procedure involves metallation of the compounds of the following general formula HA-Y$_y$-AH by the respective transition metal derivatives, as shown below.

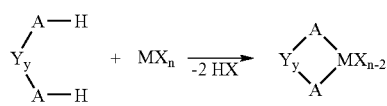

Activators and Catalyst Activation

The halogenated metallocene compounds of the invention are useful as catalyst precursors and, when activated with conventional activators, such as methyl alumoxane, form active catalysts for the polymerization or oligomerization of olefins. Activators that may be used include alumoxanes such as methyl alumoxane, modified methyl alumoxane, ethyl alumoxane, iso-butyl alumoxane and the like; Lewis acid activators include triphenyl boron, tris-perfluorophenyl boron, tris-perfluorophenyl aluminum and the like; Ionic activators include dimethylanilinium tetrakis perfluorophenyl borate, triphenyl carbonium tetrakis perfluorophenyl borate, dimethylanilinium tetrakis perfluorophenyl aluminate, and the like.

A co-activator is a compound capable of alkylating the transition metal complex, such that when used in combination with an activator, an active catalyst is formed. Co-activators include alumoxanes such as methyl alumoxane, modified alumoxanes such as modified methyl alumoxane, and aluminum alkyls such as trimethyl aluminum, tri-isobutyl aluminum, triethyl aluminum, and tri-isopropyl aluminum. Co-activators are typically only used in combination with Lewis acid activators and ionic activators when the pre-catalyst is not a dihydrocarbyl or dihydride complex.

The alumoxane component useful as an activator typically is an oligomeric aluminum compound represented by the general formula $(R^x$—Al—O$)_n$, which is a cyclic compound, or $R^x(R^x$—Al—O)$_n$AlR$^x{}_2$, which is a linear compound. In the general alumoxane formula, $R^x$ is independently a $C_1$-$C_{20}$ alkyl radical, for example, methyl, ethyl, propyl, butyl, pentyl, isomers thereof, and the like, and "n" is an integer from 1-50. Most preferably, $R^x$ is methyl and "n" is at least 4. Methyl alumoxane and modified methyl alumoxanes are most preferred. For further descriptions see, EP 0 279 586, EP 0 594 218, EP 0 561 476, WO94/10180 and U.S. Pat. Nos. 4,665,208, 4,874,734, 4,908,463, 4,924,018, 4,952,540, 4,968,827, 5,041,584, 5,091,352, 5,103,031, 5,157,137, 5,204,419, 5,206,199, 5,235,081, 5,248,801, 5,329,032, 5,391,793, and 5,416,229.

When an alumoxane or modified alumoxane is used, the catalyst-precursor-to-activator molar ratio is from about 1:3000 to 10:1; alternatively, 1:2000 to 10:1; alternatively 1:1000 to 10:1; alternatively, 1:500 to 1:1; alternatively 1:300 to 1:1; alternatively 1:200 to 1:1; alternatively 1:100 to 1:1; alternatively 1:50 to 1:1; alternatively 1:10 to 1:1. When the activator is an alumoxane (modified or unmodified), some embodiments select the maximum amount of activator at a 5000-fold molar excess over the catalyst precursor (per metal catalytic site). The preferred minimum activator to catalyst precursor ratio is 1:1 molar ratio.

Ionic activators (at times used in combination with a co-activator) may be used in the practice of this invention. Preferably, discrete ionic activators such as [Me$_2$PhNH][B(C$_6$F$_5$)$_4$], [Ph$_3$C][B(C$_6$F$_5$)$_4$], [Me$_2$PhNH][B((C$_6$H$_3$-3,5-(CF$_3$)$_2$))$_4$], [Ph$_3$C][B((C$_6$H$_3$-3,5-(CF$_3$)$_2$))$_4$], [NH$_4$][B(C$_6$H$_5$)$_4$] or Lewis acidic activators such as B(C$_6$F$_5$)$_3$ or B(C$_6$H$_5$)$_3$ can be used. Preferred co-activators, when used, are alumoxanes such as methyl alumoxane, modified alumoxanes such as modified methyl alumoxane, and aluminum alkyls such as tri-isobutyl aluminum, and trimethyl aluminum.

It is within the scope of this invention to use an ionizing or stoichiometric activator, neutral or ionic, such as tri (n-butyl) ammonium tetrakis(pentafluorophenyl)borate, a trisperfluorophenyl boron metalloid precursor or a trisperfluoronaphthyl boron metalloid precursor, polyhalogenated heteroborane anions (WO 98/43983), boric acid (U.S. Pat. No. 5,942, 459) or combination thereof.

Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl or mixtures thereof. Even more preferably, the three groups are halogenated, preferably fluorinated, aryl groups. Most preferably, the neutral stoichiometric activator is trisperfluorophenyl boron or trisperfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Ionic catalysts can be prepared by reacting a transition metal compound with an activator, such as B(C$_6$F$_6$)$_3$, which upon reaction with the hydrolyzable ligand (X') of the transition metal compound forms an anion, such as ([B(C$_6$F$_5$)$_3$(X')]$^-$), which stabilizes the cationic transition metal species generated by the reaction. The catalysts can be, and preferably are, prepared with activator components that are ionic compounds or compositions. However preparation of activators utilizing neutral compounds is also contemplated by this invention.

Compounds useful as an activator component in the preparation of the ionic catalyst systems used in the process of this invention comprise a cation, which is preferably a Bronsted acid capable of donating a proton, and a compatible non-coordinating anion which anion is relatively large (bulky), capable of stabilizing the active catalyst species which is formed when the two compounds are combined and said anion will be sufficiently labile to be displaced by olefinic diolefinic and acetylenically unsaturated substrates or other neutral Lewis bases such as ethers, nitriles and the like. Two classes of compatible non-coordinating anions have been disclosed in EPA 277,003 and EPA 277,004 published 1988: 1) anionic coordination complexes comprising a plurality of lipophilic radicals covalently coordinated to and shielding a central charge-bearing metal or metalloid core, and 2) anions comprising a plurality of boron atoms such as carboranes, metallacarboranes and boranes.

In a preferred embodiment, the stoichiometric activators include a cation and an anion component, and may be represented by the following formula:

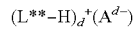

wherein L** is an neutral Lewis base;
H is hydrogen;
(L**-H)$^+$ is a Bronsted acid
A$^{d-}$ is a non-coordinating anion having the charge d-
d is an integer from 1 to 3.

The cation component, (L**-H)$_d{}^+$ may include Bronsted acids such as protons or protonated Lewis bases or reducible Lewis acids capable of protonating or abstracting a moiety, such as an alkyl or aryl, from the precatalyst after alkylation.

The activating cation (L-H)$_d{}^+$ may be a Bronsted acid, capable of donating a proton to the alkylated transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether, diethyl ether, tetrahydrofuran and dioxane, sulfoniums from thioethers, such as diethyl thioethers and tetrahydrothiophene, and mixtures thereof. The activating cation (L-H)$_d{}^+$ may also be a moiety such as silver, tropylium, carbeniums, ferroceniums and mixtures, preferably carboniums and ferroceniums; most preferably triphenyl carbonium.

The anion component A$^{d-}$ include those having the formula [M$^{k+}$Q$_n$]$^{d-}$ wherein k is an integer from 1 to 3; n is an integer from 2-6; n-k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

Illustrative, but not limiting examples of boron compounds which may be used as an activating cocatalyst in combination with a co-activator in the preparation of the improved catalysts of this invention are tri-substituted ammonium salts such as:

trimethylammonium tetraphenylborate,
triethylammonium tetraphenylborate,
tripropylammonium tetraphenylborate,
tri(n-butyl)ammonium tetraphenylborate,
tri(tert-butyl)ammonium tetraphenylborate,
N,N-dimethylanilinium tetraphenylborate,
N,N-diethylanilinium tetraphenylborate,
N,N-dimethyl-(2,4,6-trimethylanilinium)tetraphenylborate,
trimethylammonium tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate,
tri(sec-butyl)ammonium tetrakis(pentafluorophenyl)borate,
N,N-dimethylanilinium tetrakis(pentafluorophenyl)borate,
N,N-diethylanilinium tetrakis(pentafluorophenyl)borate,
N,N-dimethyl-(2,4,6-trimethylanilinium)tetrakis(pentafluorophenyl)borate,
trimethylammonium tetrakis-(2,3,4,6-tetrafluorophenyl)borate,
triethylammonium tetrakis-(2,3,4,6-tetrafluorophenyl)borate,
tripropylammonium tetrakis-(2,3,4,6-tetrafluorophenyl)borate,
tri(n-butyl)ammonium tetrakis-(2,3,4,6-tetrafluorophenyl)borate,
dimethyl(tert-butyl)ammonium tetrakis-(2,3,4,6-tetrafluorophenyl)borate,
N,N-dimethylanilinium tetrakis-(2,3,4,6-tetrafluorophenyl)borate,
N,N-diethylanilinium tetrakis-(2,3,4,6-tetrafluorophenyl)borate,
N,N-dimethyl-(2,4,6-trimethylanilinium)tetrakis-(2,3,4,6-tetrafluorophenyl)borate,
trimethylammonium tetrakis(perfluoronaphthyl)borate,
triethylammonium tetrakis(perfluoronaphthyl)borate,
tripropylammonium tetrakis(perfluoronaphthyl)borate,
tri(n-butyl)ammonium tetrakis(perfluoronaphthyl)borate,
tri(tert-butyl)ammonium tetrakis(perfluoronaphthyl)borate,
N,N-dimethylanilinium tetrakis(perfluoronaphthyl)borate,
N,N-diethylanilinium tetrakis(perfluoronaphthyl)borate,
N,N-dimethyl-(2,4,6-trimethylanilinium)tetrakis(perfluoronaphthyl)borate,
trimethylammonium tetrakis(perfluorobiphenyl)borate,
triethylammonium tetrakis(perfluorobiphenyl)borate,
tripropylammonium tetrakis(perfluorobiphenyl)borate,
tri(n-butyl)ammonium tetrakis(perfluorobiphenyl)borate,
tri(tert-butyl)ammonium tetrakis(perfluorobiphenyl)borate,
N,N-dimethylanilinium tetrakis(perfluorobiphenyl)borate,
N,N-diethylanilinium tetrakis(perfluorobiphenyl)borate,
N,N-dimethyl-(2,4,6-trimethylanilinium)tetrakis(perfluorobiphenyl)borate,
trimethylammonium tetrakis(3,5-bis(trifluoromethyl)phenyl)borate,
triethylammonium tetrakis(3,5-bis(trifluoromethyl)phenyl)borate,
tripropylammonium tetrakis(3,5-bis(trifluoromethyl)phenyl)borate,
tri(n-butyl)ammonium tetrakis(3,5-bis(trifluoromethyl)phenyl)borate,
tri(tert-butyl)ammonium tetrakis(3,5-bis(trifluoromethyl)phenyl)borate,
N,N-dimethylanilinium tetrakis(3,5-bis(trifluoromethyl)phenyl)borate,
N,N-diethylanilinium tetrakis(3,5-bis(trifluoromethyl)phenyl)borate,
N,N-dimethyl-(2,4,6-trimethylanilinium)tetrakis(3,5-bis(trifluoromethyl)phenyl)borate, and dialkyl ammonium salts such as:
di-(iso-propyl)ammonium tetrakis(pentafluorophenyl)borate, and
dicyclohexylammonium tetrakis(pentafluorophenyl)borate;

and other salts such as:
tri(o-tolyl)phosphonium tetrakis(pentafluorophenyl)borate,
tri(2,6-dimethylphenyl)phosphonium tetrakis(pentafluorophenyl)borate,
tropillium tetraphenylborate,
triphenylcarbenium tetraphenylborate,
triphenylphosphonium tetraphenylborate,
triethylsilylium tetraphenylborate,
benzene(diazonium)tetraphenylborate,
tropillium tetrakis(pentafluorophenyl)borate,
triphenylcarbenium tetrakis(pentafluorophenyl)borate,
triphenylphosphonium tetrakis(pentafluorophenyl)borate,
triethylsilylium tetrakis(pentafluorophenyl)borate,
benzene(diazonium)tetrakis(pentafluorophenyl)borate,
tropillium tetrakis-(2,3,4,6-tetrafluorophenyl)borate,
triphenylcarbenium tetrakis-(2,3,4,6-tetrafluorophenyl)borate,
triphenylphosphonium tetrakis-(2,3,4,6-tetrafluorophenyl)borate,
triethylsilylium tetrakis-(2,3,4,6-tetrafluorophenyl)borate,
benzene(diazonium)tetrakis-(2,3,4,6-tetrafluorophenyl)borate,
tropillium tetrakis(perfluoronaphthyl)borate,
triphenylcarbenium tetrakis(perfluoronaphthyl)borate,
triphenylphosphonium tetrakis(perfluoronaphthyl)borate,
triethylsilylium tetrakis(perfluoronaphthyl)borate,
benzene(diazonium)tetrakis(perfluoronaphthyl)borate,
tropillium tetrakis(perfluorobiphenyl)borate,
triphenylcarbenium tetrakis(perfluorobiphenyl)borate,
triphenylphosphonium tetrakis(perfluorobiphenyl)borate,
triethylsilylium tetrakis(perfluorobiphenyl)borate,
benzene(diazonium)tetrakis(perfluorobiphenyl)borate,
tropillium tetrakis(3,5-bis(trifluoromethyl)phenyl)borate,
triphenylcarbenium tetrakis(3,5-bis(trifluoromethyl)phenyl)borate,
triphenylphosphonium tetrakis(3,5-bis(trifluoromethyl)phenyl)borate,
triethylsilylium tetrakis(3,5-bis(trifluoromethyl)phenyl)borate, and
benzene(diazonium)tetrakis(3,5-bis(trifluoromethyl)phenyl)borate.

Most preferably, the ionic stoichiometric activator $(L^{**}-H)_d^+$ $(A^{d-})$ is N,N-dimethylanilinium tetrakis(perfluorophenyl)borate,
N,N-dimethylanilinium tetrakis(perfluoronaphthyl)borate,
N,N-dimethylanilinium tetrakis(perfluorobiphenyl)borate, N,N-dimethylanilinium tetrakis(3,5-bis(trifluoromethyl) phenyl)borate,
triphenylcarbenium tetrakis(perfluoronaphthyl)borate,
triphenylcarbenium tetrakis(perfluorobiphenyl)borate,
triphenylcarbenium tetrakis(3,5-bis(trifluoromethyl)phenyl) borate, or
triphenylcarbenium tetra(perfluorophenyl)borate.

In a preferred embodiment, the activator is trispentafluorophenylborane.

Invention catalyst precursors can also be activated with cocatalysts or activators that comprise non-coordinating anions containing metalloid-free cyclopentadienide ions. These are described in U.S. Patent Publication 2002/0058765 A1, published on 16 May 2002, and for the instant invention, require the addition of a co-activator to the catalyst precursor.

The term "non-coordinating anion" (NCA) means an anion that does not coordinate to the catalyst metal cation or that does coordinate to the metal cation, but only weakly. An NCA coordinates weakly enough that a neutral Lewis base, such as an olefinically or acetylenically unsaturated monomer can displace it from the catalyst center. "Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal complex cation in the sense of balancing its ionic charge at +1, yet retain sufficient lability to permit displacement by an ethylenically or acetylenically unsaturated monomer during polymerization. These types of cocatalysts sometimes use scavengers such as but not limited to tri-iso-butyl aluminum, tri-n-octyl aluminum, tri-n-hexyl aluminum, triethylaluminum or trimethylaluminum.

Invention process also can employ cocatalyst compounds or activator compounds that are initially neutral Lewis acids but form a cationic metal complex and a noncoordinating anion, or a zwitterionic complex upon reaction with the alkylated transition metal compounds. The alkylated invention compound is formed from the reaction of the catalyst precursor and the co-activator. For example, tris(pentafluorophenyl)boron or aluminum act to abstract a hydrocarbyl ligand to yield an invention cationic transition metal complex and stabilizing noncoordinating anion, see EP-A-0 427 697 and EP-A-0 520 732 for illustrations of analogous Group-4 metallocene compounds. Also, see the methods and compounds of EP-A-0 495 375. For formation of zwitterionic complexes using analogous Group 4 compounds, see U.S. Pat. Nos. 5,624,878; 5,486,632; and 5,527,929.

Additional neutral Lewis-acids are known in the art and are suitable for abstracting formal anionic ligands. See in particular the review article by E. Y.-X. Chen and T. J. Marks, "Cocatalysts for Metal-Catalyzed Olefin Polymerization: Activators, Activation Processes, and Structure-Activity Relationships", *Chem. Rev.*, 100, 1391-1434 (2000).

When the cations of noncoordinating anion precursors are Bronsted acids such as protons or protonated Lewis bases (excluding water), or reducible Lewis acids such as ferrocenium or silver cations, or alkali or alkaline earth metal cations such as those of sodium, magnesium or lithium, the catalyst-precursor-to-activator molar ratio may be any ratio. Combinations of the described activator compounds may also be used for activation.

When an ionic or neutral stoichiometric activator is used, the catalyst-precursor-to-activator molar ratio is from 1:10 to 1:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1:1; 1:5 to 10:1; 1:5 to 2:1; 1:5 to 3:1; 1:5 to 5:1; 1:1 to 1:1.2. The catalyst-precursor-to-co-activator molar ratio is from 1:100 to 100:1; 1:75 to 75:1; 1:50 to 50:1; 1:25 to 25:1; 1:15 to 15:1; 1:10 to 10:1; 1:5 to 5:1, 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1.

Preferred activators and activator/co-activator combinations include methylalumoxane, modified methylalumoxane, mixtures of methylalumoxane with dimethylanilinium tetrakis(pentafluorophenyl)borate or tris(pentafluorophenyl) boron, and mixtures of trimethyl aluminum with dimethylanilinium tetrakis(pentafluorophenyl)borate or tris (pentafluorophenyl)boron.

In some embodiments, scavenging compounds are used with stoichiometric activators. Typical aluminum or boron alkyl components useful as scavengers are represented by the general formula $R^xJZ_2$ where J is aluminum or boron, $R^x$ is as previously defined above, and each Z is independently $R^x$ or a different univalent anionic ligand such as halogen (Cl, Br, I), alkoxide ($OR^x$) and the like. Most preferred aluminum alkyls include triethylaluminum, diethylaluminum chloride, tri-isobutylaluminum, tri-n-octylaluminum, tri-n-hexylaluminum, trimethylaluminum and the like. Preferred boron alkyls include triethylboron. Scavenging compounds may also be alumoxanes and modified alumoxanes including methylalumoxane and modified methylalumoxane.

Mixed Catalysts

The metallocene compounds of the invention can also be used in mixed catalyst systems where, for example, the invention catalyst is used in conjunction with a "second catalyst" in the same reactor or in a series of reactors and where the invention catalyst produces oligomers, macromers, or polymers with olefinic end-groups, and the "second catalyst" incorporates these oligomers, macromers, or polymers into a polymer backbone as a copolymer with other monomers, such as ethylene, propylene, butene, and other C2 to C20 olefins. Alternatively, the invention catalyst can be used in conjunction with a second catalyst in the same reactor or in a series of reactors where the second catalyst produces oligomers, macromers, or polymers with olefinic end-groups, and the invention catalyst incorporates these oligomers, macromers, or polymers into a polymer backbone as a copolymer with other monomers, such as ethylene, propylene, butene, and other C2 to C20 olefins. The "second catalyst" can be of the same family as the invention catalyst, or can be from a completely different catalyst family. Likewise, the invention catalyst can be used in conjunction with a "second catalyst" in the same reactor or in a series of reactors where the invention catalyst and the "second catalyst" produces mixtures or blends of polymers.

Suitable additional olefin polymerization catalysts for use as the "second catalyst" in a mixed catalyst system include any of the compositions well known in the art to catalyze the olefin to polyolefin reaction. For example, the "second catalyst" can include any Group 4-6 metallocene compound, such as the bridged and unbridged compounds containing one or two cyclopentadienyl-containing ligands. Typical catalysts and their precursors are well known in the art. Suitable description appears in the patent literature, for example U. S. Pat. Nos. 4,871,705, 4,937,299, and 5,324,800, EP-A-0418044, EP-A-0591756, WO-A-92/00333 and WO-A-94/01471.

Mixed catalyst systems can also use non-cyclopentadienyl, Group 4 or 5 precursor compounds as the additional olefin polymerization catalyst. Non-cyclopentadienyl, Group 4 or 5 precursor compounds are activable to stable, discrete cationic complexes include those containing bulky, chelating, diamide ligands, such as described in U.S. Pat. No. 5,318,935 and "Conformationally Rigid Diamide Complexes: Synthesis and Structure of Tantalum (III) Alkyne Derivatives", D. H. McConville, et al, *Organometallics* 1995, 14, 3154-3156. U.S. Pat. No. 5,318,935 describes bridged and unbridged, bis-amido catalyst compounds of Group 4 metals capable of α-olefins polymerization. Bridged bis(arylamido) Group 4 compounds for olefin polymerization are described by D. H. McConville, et al., in *Organometallics* 1995, 14, 5478-5480. In addition, D. H. McConville, et al, *Macromolecules* 1996, 29, 5241-5243, describe bridged bis(arylamido) Group 4 compounds that are polymerization catalysts for 1-hexene. Cationic Group-3- or Lanthanide olefin polymerization complexes are disclosed in U.S. Pat. No. 6,403,773.

Mixed catalyst systems can also use transition metal catalyst precursors that have a 2+ oxidation state as the additional olefin polymerization catalyst. Typical $Ni^{2+}$ and $Pd^{2+}$ complexes are diimines, see "New Pd(II)- and Ni(II)-Based Catalysts for Polymerization of Ethylene and α-Olefins", M. Brookhart, et al, *J. Am. Chem. Soc.*, 1995, 117, 6414-6415, WO 96/23010 and WO 97/02298. See additionally the related bis(imino) Group 8 and 9 organometallic compounds described by V. C. Gibson and others in "Novel olefin polymerization catalysts based on iron and cobalt", *Chem. Commun.*, 849-850, 1998.

For a review of other potential catalysts used in combination or series with the invention catalysts, see S. D. Ittel and L. K. Johnson, Chem. Rev. 2000, 1000, 1169 and V. C. Gibson and S. K. Spitzmesser, Chem. Rev. 2003, 103, 283.

Supported Catalysts

The catalyst compounds of this invention may be placed on a support. To prepare uniform supported catalysts, the catalyst precursor is preferably dissolved in a suitable solvent and then the resultant solution is applied to or mixed with the support. The term "uniform supported catalyst" means that the catalyst precursor, the activator and or the activated catalyst approach uniform distribution upon the support's accessible surface area, including the interior pore surfaces of porous supports. Some embodiments of supported catalysts prefer uniform supported catalysts; other embodiments show no such preference.

Supported catalyst systems may be prepared by any method effective to support other coordination catalyst systems, effective meaning that the catalyst so prepared can be used for oligomerizing or polymerizing olefin in a heterogenous process. The catalyst precursor, activator, co-activator if needed, suitable solvent, and support may be added in any order or simultaneously.

By one method, the activator, dissolved in an appropriate solvent such as toluene may be stirred with the support material for 1 minute to 10 hours. The total solution volume may be greater than the pore volume of the support, but some embodiments limit the total solution volume below that needed to form a gel or slurry (about 90% to 400%, preferably about 100-200% of the pore volume). The mixture is optionally heated from 30-200° C. during this time. The catalyst precursor may be added to this mixture as a solid, if a suitable solvent is employed in the previous step, or as a solution. Or alternatively, this mixture can be filtered, and the resulting solid mixed with a catalyst precursor solution. Similarly, the mixture may be vacuum dried and mixed with a catalyst precursor solution. The resulting catalyst mixture is then stirred for 1 minute to 10 hours, and the catalyst is either filtered from the solution and vacuum dried or evaporation alone removes the solvent.

Alternatively, the catalyst precursor and activator may be combined in solvent to form a solution. Then the support is added, and the mixture is stirred for 1 minute to 10 hours. The total solution volume may be greater than the pore volume of the support, but some embodiments limit the total solution volume below that needed to form a gel or slurry (about 90% to 400%, preferably about 100-200% of the pore volume). After stirring, the residual solvent is removed under vacuum, typically at ambient temperature and over 10-16 hours. But greater or lesser times and temperatures are possible.

The catalyst precursor may also be supported absent the activator; in that case, the activator (and co-activator if needed) is added to a slurry process's liquid phase. For example, a solution of catalyst precursor may be mixed with a support material for a period of about 1 minute to 10 hours. The resulting precatalyst mixture may be filtered from the solution and dried under vacuum, or evaporation alone removes the solvent. The total, catalyst-precursor-solution volume may be greater than the support's pore volume, but some embodiments limit the total solution volume below that needed to form a gel or slurry (about 90% to 400%, preferably about 100-200% of the pore volume).

Additionally, two or more different catalyst precursors may be placed on the same support using any of the support methods disclosed above. Likewise, two or more activators or an activator and co-activator may be placed on the same support.

Suitable solid particle supports are typically comprised of polymeric or refractory oxide materials, each being preferably porous. Any support material that has an average particle size greater than 10 μm is suitable for use in this invention. Various embodiments select a porous support material, such as for example, talc, inorganic oxides, inorganic chlorides, for example magnesium chloride and resinous support materials such as polystyrene, polyolefin or polymeric compounds or any other organic support material and the like. Some embodiments select inorganic oxide materials as the support material including Group-2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as the activator component. But additional activator may also be used.

The support material may be pretreated by any number of methods. For example, inorganic oxides may be calcined, chemically treated with dehydroxylating agents such as aluminum alkyls and the like, or both.

As stated above, polymeric carriers will also be suitable in accordance with the invention, see for example the descriptions in WO 95/15815 and U.S. Pat. No. 5,427,991. The methods disclosed may be used with the catalyst complexes, activators or catalyst systems of this invention to adsorb or absorb them on the polymeric supports, particularly if made up of porous particles, or may be chemically bound through functional groups bound to or in the polymer chains.

The catalyst supports used herein suitably have a surface area of from 10-700 $m^2/g$, a pore volume of 0.1-4.0 cc/g and an average particle size of 10-500 μm. Some embodiments select a surface area of 50-500 $m^2/g$, a pore volume of 0.5-3.5 cc/g, or an average particle size of 20-200 μm. Other embodiments select a surface area of 100-400 m²/g, a pore volume of 0.8-3.0 cc/g, and an average particle size of 30-100 μm. Catalyst supports typically have a pore size of 10-1000 Angstroms, alternatively 50-500 Angstroms, or 75-350 Angstroms.

The catalyst precursors of the invention are generally deposited on a support at a loading level of 10-100 micromoles of catalyst precursor per gram of solid support; alternately 20-80 micromoles of catalyst precursor per gram of solid support; or 40-60 micromoles of catalyst precursor per gram of support. But greater or lesser values may be used provided that the total amount of solid catalyst precursor does not exceed the support's pore volume.

Monomers

When activated with a conventional activator, the halogenated metallocene compounds of the invention can be used to polymerize or oligomerize any unsaturated monomer or monomers. Preferred monomers include $C_2$ to $C_{100}$ olefins, preferably $C_2$ to $C_{60}$ olefins, preferably $C_2$ to $C_{40}$ olefins preferably $C_2$ to $C_{20}$ olefins, preferably $C_2$ to $C_{12}$ olefins. In some embodiments preferred monomers include linear, branched or cyclic alpha-olefins, preferably $C_2$ to $C_{100}$ alpha-olefins, preferably $C_2$ to $C_{60}$ alpha-olefins, preferably $C_2$ to $C_{40}$ alpha-olefins preferably $C_2$ to $C_{20}$ alpha-olefins, preferably $C_2$ to $C_{12}$ alpha-olefins. Preferred olefin monomers may be one or more of ethylene, propylene, butene, pentene, hexene, heptene, octene, nonene, decene, dodecene, 4-methylpentene-1, 3-methylpentene-1,3,5,5-trimethylhexene-1, and 5-ethylnonene-1.

In another embodiment the polymer produced herein is a copolymer of one or more linear or branched $C_3$ to $C_{30}$ prochiral alpha-olefins or $C_5$ to $C_{30}$ ring containing olefins or combinations thereof capable of being polymerized by either stereospecific and non-stereospecific catalysts. Prochiral, as used herein, refers to monomers that favor the formation of isotactic or syndiotactic polymer when polymerized using stereospecific catalyst(s).

Preferred monomers may also include aromatic-group-containing monomers containing up to 30 carbon atoms. Suitable aromatic-group-containing monomers comprise at least one aromatic structure, preferably from one to three, more preferably a phenyl, indenyl, fluorenyl, or naphthyl moiety. The aromatic-group-containing monomer further comprises at least one polymerizable double bond such that after polymerization, the aromatic structure will be pendant from the polymer backbone. The aromatic-group containing monomer may further be substituted with one or more hydrocarbyl groups including but not limited to $C_1$ to $C_{10}$ alkyl groups. Additionally two adjacent substitutions may be joined to form a ring structure. Preferred aromatic-group-containing monomers contain at least one aromatic structure appended to a polymerizable olefinic moiety. Particularly preferred aromatic monomers include styrene, alpha-methylstyrene, para-alkylstyrenes, vinyltoluenes, vinylnaphthalene, allyl benzene, and indene, especially styrene, para-methylstyrene, 4-phenyl-1-butene and allyl benzene.

Non aromatic cyclic group containing monomers can also be polymerized or oligomerized with the catalyst systems of the invention. These monomers can contain up to 30 carbon atoms. Suitable non-aromatic cyclic group containing monomers preferably have at least one polymerizable olefinic group that is either pendant on the cyclic structure or is part of the cyclic structure. The cyclic structure may also be further substituted by one or more hydrocarbyl groups such as, but not limited to, $C_1$ to $C_{10}$ alkyl groups. Preferred non-aromatic cyclic group containing monomers include vinylcyclohexane, vinylcyclohexene, cyclopentadiene, cyclopentene, 4-methylcyclopentene, cyclohexene, 4-methylcyclohexene, cyclobutene, vinyladamantane, norbornene, 5-methylnorbornene, 5-ethylnorbornene, 5-propylnorbornene, 5-butylylnorbornene, 5-pentylnorbornene, 5-hexylnorbornene, 5-heptylnorbornene, 5-octylnorbornene, 5-nonylnorbornene, 5-decylnorbornene, 5-phenylnorbornene, vinylnorbornene, ethylidene norbornene, 5,6-dimethylnorbornene, 5,6-dibutylnorbornene and the like.

Preferred diolefin monomers useful in this invention include any hydrocarbon structure, preferably $C_4$ to $C_{30}$, having at least two unsaturated bonds, wherein at least one, typically two, of the unsaturated bonds are readily incorporated into a polymer by either a stereospecific or a non-stereospecific catalyst(s). It is further preferred that the diolefin monomers be selected from alpha-omega-diene monomers (i.e. di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions.

Non-limiting examples of preferred polar unsaturated monomers useful in this invention include nitro substituted monomers including 6-nitro-1-hexene; amine substituted monomers including N-methylallylamine, N-allylcyclopentylamine, and N-allyl-hexylamine; ketone substituted monomers including methyl vinyl ketone, ethyl vinyl ketone, and 5-hexen-2-one; aldehyde substituted monomers including acrolein, 2,2-dimethyl-4-pentenal, undecylenic aldehyde, and 2,4-dimethyl-2,6-heptadienal; alcohol substituted monomers including allyl alcohol, 7-octen-1-ol, 7-octene-1,2-diol, 10-undecen-1-ol, 10-undecene-1,2-diol, 2-methyl-3-buten-1-ol; acetal, epoxide and or ether substituted monomers including 4-hex-5-enyl-2,2-dimethyl-[1,3]dioxolane, 2,2-dimethyl-4-non-8-enyl-[1,3]dioxolane, acrolein dimethyl acetal, butadiene monoxide, 1,2-epoxy-7-octene, 1,2-epoxy-9-decene, 1,2-epoxy-5-hexene, 2-methyl-2-vinyloxirane, allyl glycidyl ether, 2,5-dihydrofuran, 2-cyclopenten-1-one ethylene ketal, 11-methoxyundec-1-ene, and 8-methoxyoct-1-ene; sulfur containing monomers including allyl disulfide; acid and ester substituted monomers including acrylic acid, vinylacetic acid, 4-pentenoic acid, 2,2-dimethyl-4-pentenoic acid, 6-heptenoic acid, trans-2,4-pentadienoic acid, 2,6-heptadienoic acid, methyl acrylate, ethyl acrylate, tert-butyl acrylate, n-butyl acrylate, methacrylic acid, methyl methacrylate, ethyl methacrylate, tert-butyl methacrylate, n-butyl methacrylate, hydroxypropyl acrylate, acetic acid oct-7-enyl ester, non-8-enoic acid methyl ester, acetic acid undec-10-enyl ester, dodec-11-enoic acid methyl ester, propionic acid undec-10-enyl ester, dodec-11-enoic acid ethyl ester, and nonylphenoxypolyetheroxy acrylate; siloxy containing monomers including trimethyloct-7-enyloxy silane, and trimethylundec-10-enyloxy silane, polar functionalized norbornene monomers including 5-norbornene-2-carbonitrile, 5-norbornene-2-carboxaldehyde, 5-norbornene-2-carboxylic acid, cis-5-norbornene-endo-2,3-dicarboxylic acid, 5-norbornene-2,2,-dimethanol, cis-5-norbornene-endo-2,3-dicarboxylic anhydride, 5-norbornene-2-endo-3-endo-dimethanol, 5-norbornene-2-endo-3-exo-dimethanol, 5-norbornene-2-methanol, 5-norbornene-2-ol, 5-norbornene-2-yl acetate, 1-[2-(5-norbornene-2-yl)ethyl]-3,5,7,9,11,13,15-heptacyclopentylpentacyclo[9.5.1.1$^{3,9}$.1$^{5,15}$.1$^{7,13}$]octasiloxane, 2-benzoyl-5-norbornene, 2-acetyl-5-norbornene, 7-syn methoxymethyl-5-norbornen-2-one, 5-norbornen-2-ol, and 5-norbornen-2-yloxy-trimethylsilane, and partially fluorinated monomers including nonafluoro-1-hexene, allyl-1,1,2,2,-tetrafluoroethyl ether, 2,2,3,3-tetrafluoro-non-8-enoic acid ethyl ester, 1,1,2,2-tetrafluoro-2-(1,1,2,2-tetrafluoro-oct-7-enyloxy)-ethanesulfonyl fluoride, acrylic acid 2,2,3,3,4,4,5,5,6,6,7,7,8,8-pentadecafluorooctyl ester, and 1,1,2,2-tetrafluoro-2-(1,1,2,2,3,3,4,4-octafluoro-dec-9-enyloxy)-ethanesulfonyl fluoride.

In an embodiment herein, the process described herein is used to produce an oligomer of any of the monomers listed above. Preferred oligomers include oligomers of any $C_2$ to $C_{20}$ olefins, preferably $C_2$ to $C_{12}$ alpha-olefins, most preferably oligomers comprising ethylene, propylene and or butene are prepared. A preferred feedstock for the oligomerization process is the alpha-olefin, ethylene. But other alpha-olefins, including but not limited to propylene and 1-butene, may also be used alone or combined with ethylene. Preferred alpha-olefins include any $C_2$ to $C_{40}$ alpha-olefin, preferably any $C_2$ to $C_{20}$ alpha-olefin, preferably any $C_2$ to $C_{12}$ alpha-olefin, preferably ethylene, propylene, and butene, most preferably ethylene. Dienes may be used in the processes described herein, preferably alpha-omega-dienes are used alone or in combination with mono-alpha olefins.

In a preferred embodiment the process described herein may be used to produce homopolymers or copolymers. (For the purposes of this invention and the claims thereto a copolymer may comprise two, three, four or more different monomer units.) Preferred polymers produced herein include homopolymers or copolymers of any of the above monomers. In a preferred embodiment the polymer is a homopolymer of any $C_2$ to $C_{12}$ alpha-olefin. Preferably the polymer is a homopolymer of ethylene or a homopolymer of propylene. In another embodiment the polymer is a copolymer comprising ethylene and one or more of any of the monomers listed above. In another embodiment the polymer is a copolymer comprising propylene and one or more of any of the monomers listed above. In another preferred embodiment the homopolymers or copolymers described, additionally comprise one or more diolefin comonomers, preferably one or more $C_4$ to $C_{40}$ diolefins.

In another preferred embodiment the polymer produced herein is a copolymer of ethylene and one or more $C_3$ to $C_{20}$ linear, branched or cyclic monomers, preferably one or more $C_3$ to $C_{12}$ linear, branched or cyclic alpha-olefins. Preferably the polymer produced herein is a copolymer of ethylene and one or more of propylene, butene, pentene, hexene, heptene, octene, nonene, decene, dodecene, 4-methylpentene-1,3-methylpentene-1,3,5,5-trimethylhexene-1, cyclopentene, 4-methylcyclopentene, cyclohexene, and 4-methylcyclohexene.

In another preferred embodiment the polymer produced herein is a copolymer of propylene and one or more $C_2$ or $C_4$ to $C_{20}$ linear, branched or cyclic monomers, preferably one or more $C_2$ or $C_4$ to $C_{12}$ linear, branched or cyclic alpha-olefins. Preferably the polymer produced herein is a copolymer of propylene and one or more of ethylene, butene, pentene, hexene, heptene, octene, nonene, decene, dodecene, 4-methylpentene-1,3-methylpentene-1, and 3,5,5-trimethylhexene-1.

In a preferred embodiment, the polymer produced herein is a homopolymer of norbornene or a copolymer of norbornene and a substituted norbornene, including polar functionalized norbornenes.

In a preferred embodiment the copolymers described herein comprise at least 50 mole % of a first monomer and up to 50 mole % of other monomers.

In another embodiment, the polymer comprises:
(a) a first monomer present at from 40 to 95 mole %, preferably 50 to 90 mole %, preferably 60 to 80 mole %, and
(b) a comonomer present at from 5 to 60 mole %, preferably 10 to 40 mole %, more preferably 20 to 40 mole %, and
(c) a termonomer present at from 0 to 10 mole %, more preferably from 0.5 to 5 mole %, more preferably 1 to 3 mole %.

In a preferred embodiment the first monomer (a) comprises one or more of any $C_3$ to $C_8$ linear branched or cyclic alpha-olefins, including propylene, butene, (and all isomers thereof), pentene (and all isomers thereof), hexene (and all isomers thereof), heptene (and all isomers thereof), and octene (and all isomers thereof). Preferred monomers include propylene, 1-butene, 1-hexene, 1-octene, cyclopentene, cyclohexene, cyclooctene, hexadiene, cyclohexadiene and the like.

In a preferred embodiment the comonomer (b) comprises one or more of any $C_2$ to $C_{40}$ linear, branched or cyclic alpha-olefins (provided ethylene, if present, is present at 5 mole % or less), including ethylene, propylene, butene, pentene, hexene, heptene, and octene, nonene, decene, undecene, dodecene, hexadecene, butadiene, hexadiene, heptadiene, pentadiene, octadiene, nonadiene, decadiene, dodecadiene, styrene, 3,5,5-trimethylhexene-1,3-methylpentene-1,4-methylpentene-1, cyclopentadiene, and cyclohexene.

In a preferred embodiment the termonomer (c) comprises one or more of any $C_2$ to $C_{40}$ linear, branched or cyclic alpha-olefins, (provided ethylene, if present, is present at 5 mole % or less), including ethylene, propylene, butene, pentene, hexene, heptene, and octene, nonene, decene, undecene, dodecene, hexadecene, butadiene, hexadiene, heptadiene, pentadiene, octadiene, nonadiene, decadiene, dodecadiene, styrene, 3,5,5-trimethylhexene-1,3-methylpentene-1,4-methylpentene-1, cyclopentadiene, and cyclohexene.

In a preferred embodiment the monomers described above further comprise one or more dienes at up to 10 weight %, preferably at 0.00001 to 1.0 weight %, preferably 0.002 to 0.5 weight %, even more preferably 0.003 to 0.2 weight %, based upon the total weight of the composition. In some embodiments 500 ppm or less of diene is added to the polymerization, preferably 400 ppm or less, preferably or 300 ppm or less. In other embodiments at least 50 ppm of diene is added to the polymerization, or 100 ppm or more, or 150 ppm or more.

Polymerization Processes

Invention catalyst complexes are useful in polymerizing unsaturated monomers conventionally known to undergo metallocene-catalyzed polymerization such as solution, slurry, gas-phase, and high-pressure polymerization. Typically one or more transition metal compounds, one or more activators, and one or more monomers are contacted to produce polymer. These catalysts may be supported and as such will be particularly useful in the known, fixed-bed, movingbed, fluid-bed, slurry, solution, or bulk operating modes conducted in single, series, or parallel reactors.

One or more reactors in series or in parallel may be used in the present invention. The transition metal compound, activator and when required, co-activator, may be delivered as a solution or slurry, either separately to the reactor, activated in-line just prior to the reactor, or preactivated and pumped as an activated solution or slurry to the reactor. Polymerizations are carried out in either single reactor operation, in which monomer, comonomers, catalyst/activator/co-activator, optional scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors. In one preferred embodiment, the precatalyst is activated in the reactor in the presence of olefin.

Ethylene-alpha-olefin (including ethylene-cyclic olefin and ethylene-alpha-olefin-diolefin) elastomers of high molecular weight and low crystallinity can be prepared utilizing the catalysts of the invention under traditional solution processes or by introducing ethylene gas into a slurry utilizing the alpha-olefin or cyclic olefin or mixture thereof with other monomers, polymerizable and not, as a polymerization diluent in which the catalyst suspension is suspended. Typical ethylene pressures will be between 10 and 1000 psig (69-6895 kPa) and the polymerization diluent temperature will typically be between −10 and 160° C. The process can be carried out in a stirred tank reactor or a tubular reactor, or more than one reactor operated in series or in parallel. See the disclosure of U.S. Pat. No. 5,001,205 for general process conditions. All documents are incorporated by reference for description of polymerization processes, ionic activators and useful scavenging compounds.

The invention catalyst compositions can be used individually or can be mixed with other known polymerization catalysts to prepare polymer blends. Monomer and catalyst selection allows polymer blend preparation under conditions analogous to those using individual catalysts. Polymers having increased MWD for improved processing and other traditional benefits available from polymers made with mixed catalyst systems can thus be achieved.

Generally, when using invention catalysts, particularly when they are immobilized on a support, the complete catalyst system will additionally comprise one or more scavenging compounds. Here, the term scavenging compound means a compound that removes polar impurities from the reaction environment. These impurities adversely affect catalyst activity and stability. Typically, purifying steps are usually used before introducing reaction components to a reaction vessel. But such steps will rarely allow polymerization without using some scavenging compounds. Normally, the polymerization process will still use at least small amounts of scavenging compounds.

Typically, the scavenging compound will be an organometallic compound such as the Group-13 organometallic compounds of U.S. Pat. Nos. 5,153,157, 5,241,025 and WO-A-91/09882, WO-A-94/03506, WO-A-93/14132, and that of WO 95/07941. Exemplary compounds include triethyl aluminum, triethyl borane, tri-iso-butyl aluminum, methyl alumoxane, iso-butyl alumoxane, and tri-n-octyl aluminum. Those scavenging compounds having bulky or $C_6$-$C_{20}$ linear hydrocarbyl substituents connected to the metal or metalloid center usually minimize adverse interaction with the active catalyst. Examples include triethylaluminum, but more preferably, bulky compounds such as tri-iso-butyl aluminum, tri-iso-phenyl aluminum, and long-chain linear alkyl-substituted aluminum compounds, such as tri-n-hexyl aluminum, tri-n-octyl aluminum, or tri-n-dodecyl aluminum. When alumoxane is used as the activator, any excess over that needed for activation will scavenge impurities and additional scavenging compounds may be unnecessary. Alumoxanes also may be added in scavenging quantities with other activators, e.g., methylalumoxane, $[Me_2HNPh]^+[B(pfp)_4]^-$ or $B(pfp)_3$ (perfluorophenyl=pfp=$C_6F_5$).

In terms of polymer density, the polymers capable of production in accordance the invention, can range from about 0.85 to about 0.95, preferably from 0.87 to 0.93, more preferably 0.89 to 0.920. Polymer molecular weights can range from about 3000 Mn to about 2,000,000 Mn or greater. Molecular weight distributions can range from about 1.1 to about 50.0, with molecular weight distributions from 1.2 to about 5.0 being more typical. Pigments, antioxidants and other additives, as is known in the art, may be added to the polymer.

Gas Phase Polymerization

Generally, in a fluidized gas bed process used for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352, 749, 5,405,922, 5,436,304, 5,453,471, 5,462,999, 5,616,661 and 5,668,228 all of which are fully incorporated herein by reference.).

The reactor pressure in a gas phase process may vary from about 10 psig (69 kPa) to about 500 psig (3448 kPa), preferably from about 100 psig (690 kPa) to about 500 psig (3448 kPa), preferably in the range of from about 200 psig (1379 kPa) to about 400 psig (2759 kPa), more preferably in the range of from about 250 psig (1724 kPa) to about 350 psig (2414 kPa).

The reactor temperature in the gas phase process may vary from about 30° C. to about 120° C., preferably from about 60° C. to about 115° C., more preferably in the range of from about 70° C. to about 110° C., and most preferably in the range of from about 70° C. to about 95° C. In another embodiment when high density polyethylene is desired then the reactor temperature is typically between 70° C. and 105° C.

The productivity of the catalyst or catalyst system in a gas phase system is influenced by the partial pressure of the main monomer. The preferred mole percent of the main monomer, ethylene or propylene, preferably ethylene, is from about 25 to 90 mole percent and the comonomer partial pressure is in the range of from about 138 kPa to about 517 kPa, preferably about 517 kPa to about 2069 kPa, which are typical conditions in a gas phase polymerization process. Also in some systems the presence of comonomer can increase productivity.

In a preferred embodiment, the reactor utilized in the present invention is capable of producing more than 500 lbs of polymer per hour (227 Kg/hr) to about 200,000 lbs/hr (90,900 Kg/hr) or higher, preferably greater than 1000 lbs/hr (455 Kg/hr), more preferably greater than 10,000 lbs/hr (4540 Kg/hr), even more preferably greater than 25,000 lbs/hr (11, 300 Kg/hr), still more preferably greater than 35,000 lbs/hr (15,900 Kg/hr), still even more preferably greater than 50,000 lbs/hr (22,700 Kg/hr) and preferably greater than 65,000 lbs/ hr (29,000 Kg/hr) to greater than 100,000 lbs/hr (45,500 Kg/hr), and most preferably over 100,000 lbs/hr (45,500 Kg/hr).

Other gas phase processes contemplated by the process of the invention include those described in U.S. Pat. Nos. 5,627, 242, 5,665,818 and 5,677,375, and European publications EP-A-0794 200, EP-A-0 802 202 and EP-B-634 421 all of which are herein fully incorporated by reference.

In another preferred embodiment the catalyst system in is liquid form and is introduced into the gas phase reactor into a resin particle lean zone. For information on how to introduce a liquid catalyst system into a fluidized bed polymerization into a particle lean zone, please see U.S. Pat. No. 5,693,727, which is incorporated by reference herein.

Slurry Phase Polymerization

A slurry polymerization process generally operates between 1 to about 50 atmosphere pressure range (15 psig to 735 psig, 103 kPa to 5068 kPa) or even greater and temperatures in the range of 0° C. to about 120° C. In a slurry polymerization, a suspension of solid, particulate polymer is formed in a liquid polymerization diluent medium to which monomer and comonomers along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process should be operated above the reaction diluent critical temperature and pressure. Preferably, a hexane or an isobutane medium is employed.

In one embodiment, a preferred polymerization technique of the invention is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. The preferred temperature in the particle form process is within the range of about 85° C. to about 110° C. Two preferred polymerization methods for the slurry process are those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment, the slurry process is carried out continuously in a loop reactor. The catalyst, as a slurry in isobutane or as a dry free flowing powder, is injected regularly to the reactor loop, which is itself filled with circulating slurry of growing polymer particles in a diluent of isobutane containing monomer and comonomer. Hydrogen, optionally, may be added as a molecular weight control. The reactor is maintained at a pressure of 3620 kPa to 4309 kPa and at a temperature in the range of about 60° C. to about 104° C. depending on the desired polymer melting characteristics. Reaction heat is removed through the loop wall since much of the reactor is in the form of a double-jacketed pipe. The slurry is allowed to exit the reactor at regular intervals or continuously to a heated low pressure flash vessel, rotary dryer and a nitrogen purge column in sequence for removal of the isobutane diluent and all unreacted monomer and comonomers. The resulting hydrocarbon free powder is then compounded for use in various applications.

In another embodiment, the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

In another embodiment in the slurry process of the invention the total reactor pressure is in the range of from 400 psig (2758 kPa) to 800 psig (5516 kPa), preferably 450 psig (3103 kPa) to about 700 psig (4827 kPa), more preferably 500 psig (3448 kPa) to about 650 psig (4482 kPa), most preferably from about 525 psig (3620 kPa) to 625 psig (4309 kPa).

In yet another embodiment in the slurry process of the invention the concentration of predominant monomer in the reactor liquid medium is in the range of from about 1 to 10 weight percent, preferably from about 2 to about 7 weight percent, more preferably from about 2.5 to about 6 weight percent, most preferably from about 3 to about 6 weight percent.

Another process of the invention is where the process, preferably a slurry or gas phase process is operated in the absence of or essentially free of any scavengers, such as triethylaluminum, trimethylaluminum, tri-iso-butylaluminum and tri-n-hexylaluminum and diethyl aluminum chloride, dibutyl zinc and the like. This process is described in PCT publication WO 96/08520 and U.S. Pat. No. 5,712,352, which are herein fully incorporated by reference.

In another embodiment the process is run with scavengers. Typical scavengers include trimethyl aluminum, tri-iso-butyl aluminum and an excess of alumoxane or modified alumoxane.

In a preferred embodiment, hydrogen or other chain termination agent (such as phenylsilane) is added to the slurry polymerization.

Homogeneous, Bulk or Solution Phase Polymerization

The catalysts described herein can be used advantageously in homogeneous solution processes. Generally this involves polymerization in a continuous reactor in which the polymer formed and the starting monomer and catalyst materials supplied, are agitated to reduce or avoid concentration gradients. Suitable processes operate above the melting point of the polymers at high pressures, from 1 to 3000 bar (10-30,000 MPa), in which the monomer acts as diluent or in solution polymerization using a solvent.

Temperature control in the reactor is obtained by balancing the heat of polymerization and with reactor cooling by reactor jackets or cooling coils to cool the contents of the reactor, auto refrigeration, pre-chilled feeds, vaporization of liquid medium (diluent, monomers or solvent) or combinations of all three. Adiabatic reactors with pre-chilled feeds may also be used. The reactor temperature depends on the catalyst used. In general, the reactor temperature preferably can vary between about 0° C. and about 160° C., more preferably from about 10° C. to about 140° C., and most preferably from about 40° C. to about 120° C. In series operation, the second reactor temperature is preferably higher than the first reactor temperature. In parallel reactor operation, the temperatures of the two reactors are independent. The pressure can vary from about 1 mm Hg to 2500 bar (25,000 MPa), preferably from 0.1 bar to 1600 bar (1-16,000 MPa), most preferably from 1.0 to 500 bar (10-5000 MPa).

Each of these processes may also be employed in single reactor, parallel or series reactor configurations. The liquid processes comprise contacting olefin monomers with the above described catalyst system in a suitable diluent or solvent and allowing said monomers to react for a sufficient time to produce the desired polymers. Hydrocarbon solvents are suitable, both aliphatic and aromatic. Alkanes, such as hexane, pentane, isopentane, and octane, are preferred.

The process can be carried out in a continuous stirred tank reactor, batch reactor, or plug flow reactor, or more than one reactor operated in series or parallel. These reactors may have or may not have internal cooling and the monomer feed may or may not be refrigerated. See the general disclosure of U.S. Pat. No. 5,001,205 for general process conditions. See also, international application WO 96/33227 and WO 97/22639.

Medium and High Pressure Polymerizations

In the high pressure process for the polymerization of ethylene alone or in combination with $C_3$ to $C_{10}$ alpha-olefins and optionally other copolymerizable olefins, the temperature of the medium within which the polymerization reaction occurs is at least 120° C. and preferably above 140° C. and may range to 350° C., but below the decomposition temperature of said polymer product, typically from 310° C. to 325° C. Preferably, the polymerization is completed at a temperature within the range of 130° C. to 230° C. The polymerization is completed at a pressure above 200 bar (20 MPa), and generally at a pressure within the range of 500 bar (50 MPa) to 3500 bar (350 MPa). Preferably, the polymerization is completed at a pressure within the range from 800 bar (80 MPa) to 2500 bar (250 MPa).

For a medium pressure process, the temperature within which the polymerization reaction occurs is at least 80° C. and typically ranges from 80° C. to 250° C., preferably from 100° C. to 220° C., and should for a given polymer in the reactor, be above the melting point of said polymer so as to maintain the fluidity of the polymer-rich phase. The pressure can be varied between 100 and 1000 bar for ethylene homopolymers and from 30 bar (3 MPa) to 1000 bar (100 MPa), especially 50 bar (5 MPa) to 500 bar (50 MPa) for processes producing ethylene copolymers containing $C_3$ to $C_{10}$ olefins and optionally other copolymerizable olefins.

After polymerization and deactivation of the catalyst, the polymer product can be recovered by processes well known in the art. Any excess reactants may be flashed off from the polymer and the polymer obtained extruded into water and cut into pellets or other suitable comminuted shapes. For general process conditions, see the general disclosure of U.S. Pat. Nos. 5,084,534, 5,408,017, 6,127,497, 6,255,410, which are incorporated herein by reference.

In another embodiment, this invention also relates to:

1. A metallocene compound represented by the formula (1):

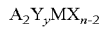

wherein:

M is a transition metal atom having a coordination number of n selected from Group 3, 4, 5 or 6 of the Periodic Table of Elements, or a lanthanide metal atom, or actinide metal atom;

each A is independently a substituted polycyclic arenyl ligand pi-bonded to M, each A ligand includes at least one halogen substituent directly bonded to an $sp^2$ carbon at a bondable ring position and, when each A is a substituted indenyl ligand and y is equal to one and the ligand includes at least one chloro, bromo or iodo substituent at the 4, 5, or 6 position of the indenyl ligand, then A also includes at least one other substituent in the indenyl ligand selected from hydrocarbyl, substituted hydrocarbyl, halogen, halocarbyl, substituted halocarbyl, silylcarbyl, substituted silylcarbyl, germylcarbyl, substituted germylcarbyl, or other heteroatom substituents wherein the heteroatom is bonded directly to a ring carbon of the ring structure ligand and is boron, a Group 15 atom, or a Group 16 atom, preferably boron, nitrogen, oxygen, phosphorus, or sulfur;

Y is an optional bridging group containing at least one Group 13, 14, 15, or 16 element and is bonded to any single position of the ring structure of A, y is zero or 1, indicating the absence (y=0) or presence (y=1) of Y; and the or each X is a univalent anionic ligand, or two X are joined and bound to the metal atom to form a metallocycle ring, or two X are joined to form a chelating ligand, a diene ligand, or an alkylidene ligand;

provided that when y is equal to 1, then A is not 5,6-dichloroindenyl or an indenyl group having a fluoro- or chloro substituent at the 7 position and a hydrocarbyl or substituted hydrocarbyl substituent at the 4 position, and provided further that when y is equal to 0, then A is not 5,6-difluoroindenyl.

2. The metallocene paragraph of claim 1 wherein each A is independently a substituted fluorenyl ligand or a substituted cyclopentanaphthyl ligand and said at least one halogen substituent is a chloro, bromo or iodo substituent.

3. The metallocene compound of paragraph 2 wherein said at least one halogen substituent is a chloro or bromo substituent.

4. The metallocene compound of paragraph 1 wherein each A is independently a substituted indenyl ligand and the at least one halogen substituent is a chloro, bromo, or iodo substituent.

5. The metallocene compound of paragraph 4 wherein said at least one halogen substituent is a chloro or bromo substituent.

6. The metallocene compound of paragraph 1 wherein each A is independently a substituted indenyl ligand, the at least one halogen substituent at the 4, 5, or 6 position of the indenyl ligand is a chloro, bromo, or iodo substituent, and said at least one other substituent is connected to the 2 position of the indenyl ligand.

7. The metallocene compound of paragraph 6 wherein said at least one halogen substituent is a chloro or bromo substituent.

8. A metallocene compound represented by the formula (2):

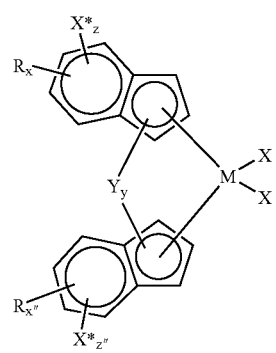

or formula (3):

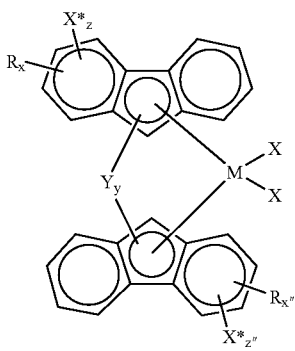

or formula (4):

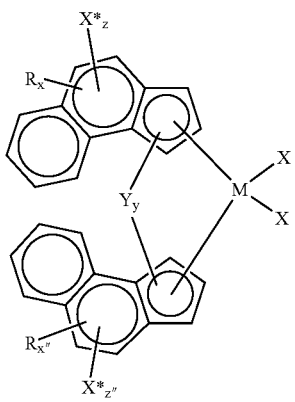

or formula (5):

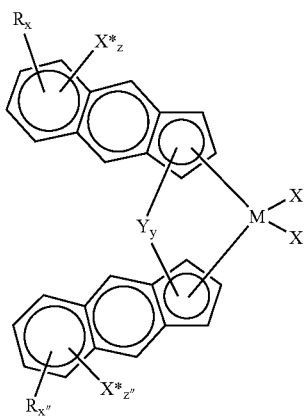

wherein

M is a group 3, 4, 5 or 6 transition metal atom, or a lanthanide metal atom, or actinide metal atom;

each R is bonded to any position of the ring structure ligand and is, independently, hydrogen, or a hydrocarbyl, substituted hydrocarbyl, halocarbyl, substituted halocarbyl, silylcarbyl, substituted silylcarbyl, germylcarbyl, substituted germylcarbyl, or other heteroatom substituents wherein the heteroatom is bonded directly to a ring carbon of the ring structure ligand and is boron, a Group 15 atom, or a Group 16 atom, preferably boron, nitrogen, oxygen, phosphorus, or sulfur, and optionally, two or more adjacent R may join together to form a substituted or unsubstituted, saturated, partially unsaturated, or aromatic cyclic or polycyclic substituent;

x and x" represent the number of R substituents bonded to the ring structure ligand; x and x" are, independently, 4, 5, 6, or 7 for formula (2); x and x" are, independently, 6, 7, 8, or 9 for each of formulae (3), (4) and (5);

each $X^*$ is bonded to any position of the ring structure ligand and is, independently, a chloro or bromo substitutent; provided that when y is equal to one, the ring structures are not both 5,6-dichloroindenyl or are not both an indenyl group having a fluoro- or chloro substituent at the 7 position and a hydrocarbyl or substituted hydrocarbyl substituent at the 4 position; provided that when y is equal to zero, the ring structures are not both 5,6-difluoroindenyl; and provided that when one $X^*$ substituent is bonded to the 4,5, or 6 position of each indenyl ligand in formula (2), then at least one other substituent is selected from hydrocarbyl, substituted hydrocarbyl, halogen, halocarbyl, substituted halocarbyl, silylcarbyl, substituted silylcarbyl, germylcarbyl, substituted germylcarbyl, or other heteroatom substituents wherein the heteroatom is bonded directly to a ring carbon of the ring structure ligand and is boron, a Group 15 atom, or a Group 16 atom, preferably boron, nitrogen, oxygen, phosphorus, or sulfur;

z and z" represent the number of $X^*$ substituents bonded to its respective ring structure ligand; z and z" are, independently, 0, 1 or 2; z+z"=1, 2, 3, or 4;

Y is an optional bridging group bonded to any single position of each ring structure ligand and containing a Group 13, 14, 15, or 16 element;

y is 0 or 1, indicating the absence (y=0) or presence (y=1) of Y;

$x+y+z=7$, and $x''+y+z''=7$ for formula (2);

$x+y+z=9$, and $x''+y+z''=9$ for each of formulae (3), (4) and (5); and each X is a univalent anionic ligand, or two X are joined and bound to the metal atom to form a metallocycle ring, or two X are joined to form a chelating ligand, a diene ligand, or an alkylidene ligand.

9. The metallocene compound of paragraph 8 wherein each $X^*$ substituent is a chloro, bromo, or iodo substituent.

10. The metallocene compound of paragraph 8 wherein each $X^*$ substituent is a chloro or bromo substituent.

11. The metallocene compound of any preceding paragraph 1 to 10 wherein M is a Group 4 transition metal selected from titanium, zirconium and hafnium.

12. The metallocene compound of any preceding paragraph 1 to 11 wherein Y is present and is a bridging group containing boron or a Group 14, 15 or 16 element.

13. The metallocene compound of any preceding paragraph 1 to 12 wherein Y is present and is selected from S, O, NR', PR', P(=S)R', AsR', SbR', O—O, S—S, R'N—NR', R'P—PR', O—S, O—NR', O—PR', S—NR', S—PR', R'N—PR', $R'_2C$, $R'_2Si$, $R'_2Ge$, $R'_2CCR'_2$, $R'_2CCR'_2CR'_2$, $R'_2CCR'_2CR'_2CR'_2$, R'C=CR', R'C=CR'CR'_2, $R'_2CCR'$=CR'CR'_2, R'C=CR'CR'=CR', R'C=CR'CR'_2CR'_2, $R'_2CSiR'_2$, $R'_2SiSiR'_2$, $R'_2CSiR'_2CR'_2$, $R'_2SiCR'_2SiR'_2$, R'C=CR'SiR'_2, $R'_2CGeR'_2$, $R'_2GeGeR'_2$, $R'_2CGeR'_2CR'_2$, $R'_2GeCR'_2GeR'_2$, $R'_2SiGeR'_2$, R'C=CR'GeR'_2, R'B, $R'_2C$—BR', $R'_2C$—BR'—$CR'_2$, $R'_2C$—O—$CR'_2$, R'$_2$CR'$_2$C—O—CR'$_2$CR'$_2$, R'$_2$C—O—CR'$_2$CR'$_2$, R'$_2$C—O—CR'=CR', R'$_2$C—S—CR'$_2$, R'$_2$CR'$_2$C—S—CR'$_2$CR'$_2$, R'$_2$C—S—CR'$_2$CR'$_2$, R'$_2$C—S—CR'=CR', R'$_2$C—Se—CR'$_2$, R'$_2$CR'$_2$C—Se—CR'$_2$CR'$_2$, R'$_2$C—Se—CR'$_2$CR'$_2$, R'$_2$C—Se—CR'=CR', R'$_2$C—N=CR', R'$_2$C—NR'—CR'$_2$, R'$_2$C—NR'—CR'$_2$CR'$_2$, R'$_2$C—NR'—CR'=CR', R'$_2$CR'$_2$C—NR'—CR'$_2$CR'$_2$, R'$_2$C—P=CR', and R'$_2$C—PR'—CR'$_2$ where R' is hydrogen or a C$_1$-C$_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.
14. The metallocene compound of any preceding paragraph 1 to 12 wherein Y is present and is selected from O, S, NMe, Net, NPr, NPh, N-Ph-p-Me, PMe, PEt, PPr, PPh, P(=S) Ph, CH$_2$, CH$_2$CH$_2$, CH(CH$_3$)$_2$, SiMe$_2$, SiEt$_2$, SiPh$_2$, SiMePh, Si(CH$_2$)$_3$, and Si(CH$_2$)$_4$, where Me is methyl and Ph is phenyl.
15. A metallocene compound selected from:
bis($\eta^5$-2-bromo-indenyl)zirconium dichloride,
rac-bis($\eta^5$-2-methyl-4-bromoinden-1-yl)zirconium dichloride,
meso-bis($\eta^5$-2-methyl-4-bromoinden-1-yl)zirconium dichloride,
rac-bis($\eta^5$-2-methyl-4-bromoinden-1-yl)hafnium dichloride,
meso-bis($\eta^5$-2-methyl-4-bromoinden-1-yl)hafnium dichloride,
rac-[dimethylsilyl-bis($\eta^5$-4-bromo-2-methylinden-1-yl)](N$^1$,N$^3$-diphenyl-1,3-propanediamido)zirconium,
rac-dimethylsilyl-bis($\eta^5$-4-bromo-2-methylinden-1-yl)zirconium dichloride,
meso-dimethylsilyl-bis($\eta^5$-4-bromo-2-methylinden-1-yl) zirconium dichloride,
meso-dimethylsilyl-bis($\eta^5$-4-bromo-2-methylinden-1-yl) hafnium dichloride,
rac-dimethylsilyl-bis($\eta^5$-4-bromo-2-methylinden-1-yl)zirconium dibromide,
4,4'-sulfandiyl-bis($\eta^5$-7-bromo-2-methylindenyl)zirconium dichloride,
4,4'-phenylphosphindiyl-bis($\eta^5$-7-bromo-2-methylindenyl) zirconium dichloride,
4,4'-phenylphosphinesulfide-bis($\eta^5$-7-bromo-2-methylindenyl)zirconium dichloride,
4,4'-tolylazandiyl-bis($\eta^5$-7-bromo-2-methylindenyl)zirconium dichloride,
4,4'-oxadiyl-bis($\eta^5$-7-bromo-2-methylindenyl)zirconium dichloride,
rac-[dimethylsilyl-bis($\eta^5$-5-bromo-2-methyl-6,7,8,9-tetrahydro-3H-cyclopenta[a]naphthalen-3-yl)](N$^1$,N$^3$-diphenyl-1,3-propanediamido)zirconium,
rac-[dimethylsilyl-bis($\eta^5$-5-bromo-2-methyl-6,7,8,9-tetrahydro-3H-cyclopenta[a]naphthalen-3-yl)]zirconium dichloride,
rac-diethylsilyl-bis($\eta^5$-5-bromo-2-methyl-6,7,8,9-tetrahydro-3H-cyclopenta[a]naphthalen-3-yl)zirconium dichloride,
rac-[diethylsilyl-bis($\eta^5$-4-bromo-2-methylinden-1-yl)](N$^1$,N$^3$-diphenyl-1,3-propanediamido)zirconium,
rac-diethylsilyl-bis($\eta^5$-4-bromo-2-methylinden-1-yl)zirconium dichloride,
rac-dimethylsilyl-bis($\eta^5$-4-bromo-2,6-dimethylinden-1-yl) zirconium dichloride,
bis($\eta^5$-2-bromo-4,7-dimethylinden-1-yl)zirconium dichloride,
rac-[dimethylsilyl-bis($\eta^5$-4-bromo-2-methyl-5,6,7,8,-tetrahydro-1H-cyclopenta[b]naphthalen-1-yl)]zirconium dichloride,
rac-dimethylsilyl-bis($\eta^5$-4-bromo-2,5-dimethylinden-1-yl) zirconium dichloride,
rac-dimethylsilyl-bis($\eta^5$-4-bromo-2,5-dimethylinden-1-yl) zirconium dichloride,
rac-dimethylsilyl-bis($\eta^5$-4-bromo-2-isopropylinden-1-yl) zirconium dichloride,
rac-dimethylsilyl-bis($\eta^5$-4-bromo-2-methyl-6-isopropylinden-1-yl)zirconium dichloride,
rac-dimethylsilyl-bis($\eta^5$-4,6-dichloro-2-methylinden-1-yl) zirconium dichloride,
rac-isopropylidene-bis($\eta^5$-4-bromo-3-methylinden-1-yl)zirconium dichloride,
meso-isopropylidene-bis($\eta^5$-4-bromo-3-methylinden-1-yl) zirconium dichloride,
rac-dimethylsilyl-bis($\eta^5$-4-bromo-6-fluoro-2-methylinden-1-yl)zirconium dichloride,
(2-bromoindenyl)($\eta^5$-2-mesityl-indenyl)zirconium dibromide,
(2-bromoindenyl)($\eta^5$-2-pyrrolidinyl-indenyl)zirconium dibromide,
(2-bromoindenyl)($\eta^5$-2-(3,5-dibromophenyl)-indenyl)zirconium dibromide, and
(2-bromoindenyl)($\eta^5$-2-phenylindenyl)zirconium dibromide.
16. A catalyst system comprising the metallocene compound of any preceding paragraph 1 to 15 and an activator.
17. A process for polymerizing olefins comprising contacting the catalyst system of paragraph 16 with at least one olefin.
18. The process of paragraph 17 wherein said at least one olefin comprises ethylene and/or propylene.

Experimental—Synthesis of Pre-Catalysts

All manipulations with air and moisture sensitive compounds were performed either in an atmosphere of thoroughly purified argon using a standard Schlenk technique or in a controlled atmosphere Glove Box (Vacuum Atmospheres Co.). Tetrahydrofuran (THF, Merck=Merck KGaA, Darmstadt, Germany) and diethyl ether (Merck) for synthesis were purified by distillation over LiAlH$_4$, and stored over sodium benzophenone ketyl under an inert atmosphere; prior to use, the solvents were distilled from the benzophenone ketyl. Hydrocarbon solvents such as toluene (Merck), hexanes (Merck), n-pentane (Acros), and C$_6$D$_6$ (Cambridge Isotope Laboratories, Inc., for NMR measurements) were typically distilled over CaH$_2$, and were stored over Na/K alloy under an inert atmosphere; prior to use, the solvents were distilled from the Na/K alloy. Dimethylether (DME, Acros) was purified by distillation over Na benzophenone ketyl. Methylene chloride (Merck) (and CCl$_2$D$_2$ for NMR measurements, Cambridge Isotope Laboratories, Inc.) was distilled and stored over CaH$_2$ under an inert atmosphere; prior to use, the solvent was distilled from the CaH$_2$. Sodium metal (Merck) was used as received. Chloroform-d (Merck) was distilled over P$_4$O$_{10}$ and stored over molecular sieves (3 Å). Anhydrous ethanol (Merck), methanol (Merck), methyl-tert-butyl ether (Acros=Acros Organics), acetone (Merck), dimethylsulfoxide (DMSO, Acros), anhydrous ZrCl$_4$ (Aldrich=Aldrich Chemical Co.), ZrCl$_4$(THF)$_2$ (Aldrich), anhydrous HfCl$_4$ (Aldrich), $^n$BuLi in hexanes (Chemetall=Chemetall Chemical Products), MeLi in ether (Aldrich), Et$_3$SnCl (Alfa Aesar), anhydrous K$_2$CO$_3$ (Merck), Pd(dba)$_2$ (Aldrich, dba=dibenzylidenacetone), NaBH$_4$ (Acros), anhydrous powdered AlCl$_3$ (Merck), methyl iodide (Acros), CuBr (Acros), para-toluene sulfonic acid (Aldrich), sodium nitrite (Merck), bromine (Merck), KOH (Merck), diethylmethylmalonate (Acros), 2-bromoisobutyryl bromide=2-bromo-2-methyl-propionyl bromide (Aldrich), tetraline (Acros), 2-bromobenzyl bromide (Aldrich), dichlorodimethylsilane (Merck), dichlorodiethylsilane (Aldrich), 1.0 M HCl in ether (Aldrich), p-bromoaniline (Acros), Silica Gel 60, 40-63 μm (Merck and Fluka), indanone-2 (Aldrich), pyrrolidine (Acros), tri(tert-butyl)phosphine (Strem), 12 M HCl (Reakhim, Moscow, Russia), $Na_2SO_4$ (Akzo Nobel), glacial acetic acid (Reakhim, Moscow, Russia), $Zr(NMe_2)_4$ (Aldrich), bromotrimethylsilane (Aldrich), HBr (47%, Merck), phenyldichlorophosphine (Aldrich), $NaSO_3$ (Merck), triisopropylborate (Alfa Aesar), $H_2O_2$ (Reakhim, Russia), sulfur (Merck), $Na_2CO_3$ (Reakhim, Moscow, Russia), para-toluidene (Acros), N-bromosuccinimide (Acros), benzoyl peroxide (Fluka), carbon tetrachloride (Reakhim, Moscow, Russia), sodium hydroxide (Reakhim, Moscow, Russia), tri(n-butyl) tin chloride (Aldrich), 2-bromo-4-fluorotoluene (Aldrich), diethylisopropylmalonate (Aldrich), sodium hydride (Aldrich), 2,4-dichloro-1-(chloromethyl)benzene (Fluka), $K_3PO_4$ (Fluka), potassium tert-butoxide (Acros), magnesium sulfate (Merck), CuCN (Merck), $NaHCO_3$ (Reakhim, Moscow, Russia), mesitylmagnesium bromide in THF (Aldrich), 1,3,5-tribromobenzene (Acros), acetic anhydride (Acros), $H_2SO_4$ (Reakhim, Moscow, Russia), Cu powder (Alfa Aesar), and 4-isopropylaniline (Acros) were used as obtained. Celite 503 (Fluka) was dried in vacuum at 180° C. Sulfur dichloride (Aldrich) and thionyl chloride (Merck) were distilled before use. Molecular sieves 4 A (Merck) were dried in vacuum at 250° C.

2-Bromo-1H-indene [(a) MacDowell, D. W. H.; Lindley, W. A. J. Org. Chem. 1982, 47, 705. (b) McEwen, I.; Rönnqvist, M.; Ahlberg, P. J. Am. Chem. Soc. 1993, 115, 3989. (c) Halterman, R. L.; Fahey, D. R.; Bailly, E. F.; Dockter, D. W.; Stenzel, O.; Shipman, J. L.; Khan, M. A.; Dechert, S.; Schumann, H. Organometallics 2000, 19, 5464], 2-phenyl-1H-indene [Sosnovskii, G. M.; Lugovskii, A. P.; Tishchenko, I. G. Z. Org. Khim. (Rus.) 1983, 19, 2143.], 2-bromo-4,7-dimethyl-1H-indene [Halterman, R. L.; Fahey, D. R.; Bailly, E. F.; Dockter, D. W.; Stenzel, O.; Shipman, J. L.; Khan, M. A.; Dechert, S.; Schumann, H. Organometallics 2000, 19, 5464], and ($N^1,N^3$-diphenyl-1,3-propanediamido)bis(tetrahydrofurano)zirconium dichloride [Zhang, X.; Zhu, Q.; Guzei, I. A.; Jordan, R. F. J. Am. Chem. Soc. 2000, 122, 8093] were prepared according to the published methods. 2-Bromoethylbenzene was obtained from 2-ethylaniline (Acros) as described in Hansch, C.; Geiger, C. J. Org. Chen. 1959, 24, 1025. 2-Bromo-1-(bromomethyl)-3-methylbenzene was obtained via bromination of 2-bromo-1,3-dimethylbenzene (Aldrich) by N-bromosucinimide in $CCl_4$ as described in Baker, R. W.; Foulkes, M. A.; Griggs, M.; Nguyen, B. N. Tetrahedron Lett. 2002, 43, 9319. 2,6-Dimethylindan-1-one was obtained via the "malonate" method from 4-methylbenzylchloride (Acros) as described in Fukuoka, M.; Yoshihira, K.; Natori, S.; Mihashi, K.; Nishi, M. Chem. Pharm. Bull. 1983, 31, 3113.

Analytical and semi-preparative liquid chromatography was performed using Waters Delta 600 HPLC system including 996 Photodiode Array Detector, Nova-Pack C18 or HR Silica (60A, 6 μm, 3.9 and 19×300 mm) and Symmetry C18 (5 μm, 4.6×250 mm) columns. MPLC (Medium Pressure Liquid Chromatography, pressure 5-15 bars) was performed using MPLC glass columns and fittings (Ace Glass), PD5130 pump drive equipped with J1 gear-well pump head (Heidolph), 996 Photodiode Array Detector and Fraction Collector II (Waters Corp.). $^1H$, and $^{13}C$ were recorded with a Brucker DPX-300 for 1-10% solutions in deuterated solvents. Chemical shifts for $^1H$ and $^{13}C$ were measured relatively to tetramethylsilane (TMS). In $^1H$ NMR spectra, the assignment was made on the evidence of double resonance and Nuclear Overhauser Effect (NOE) experiments. C, H microanalyses were done using CHN—O-Rapid analyzer (Heraecus Ltd., Banau, Germany).

EXAMPLE 1

Synthesis of bis($\eta^5$-2-bromo-indenyl)zirconium dichloride (1)

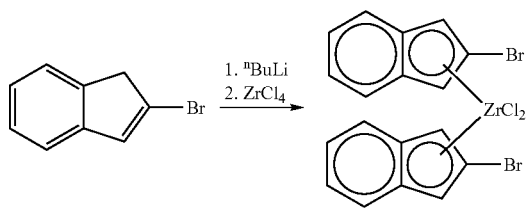

In the Glove Box, 32.0 ml of 1.6 M $^n$BuLi (51.2 mmol) in hexanes were added dropwise for 10 min at −30° C. to a solution of 10.0 g (51.3 mmol) of 2-bromoindene in 220 ml of hexanes. This mixture was stirred for 20 h at ambient temperature. The precipitate formed was filtered off, washed with 3×50 ml of hexanes, and dried in vacuum. This procedure gave 7.92 g (77%, 39.4 mmol) of the lithium salt of 2-bromoindene, which was then added at −100° C. to a suspension of 4.59 g (19.7 mmol) of $ZrCl_4$ in 200 ml of $CH_2Cl_2$. The reaction mixture was slowly warmed for 1 h to 20° C. and, then, stirred for 24 h at ambient temperature. The resulting mixture was filtered through Celite 503 and the filtrate was evaporated to about 70 ml. Crystals that precipitated at −30° C. were separated, washed with 3×20 ml of cold hexanes, and dried in vacuum. Yield 11.2 g (52%) of a yellow crystalline product.

Anal. calc. for $C_{18}H_{12}Br_2Cl_2Zr$: C, 39.29; H, 2.20. Found: C, 39.67; H, 2.39.

$^1H$ NMR ($CD_2Cl_2$): δ 7.46 (dd, J=6.6 Hz, J=3.2 Hz, 4H, 4,4',7,7'-H), 7.19 (dd, J=6.6 Hz, J=3.2 Hz, 4H, 5,5',6,6'-H), 6.48 (s, 4H, 1,1',3,3'-H).

$^{13}C$ NMR ($CD_2Cl_2$): δ 128.4, 127.8, 125.9, 110.1, 107.4.

EXAMPLE 2

Synthesis of mixture of rac- and meso-bis($\eta^5$-2-methyl-4-bromoinden-1-yl)zirconium dichlorides (2)

3-(2-Bromophenyl)-2-methylpropanoic acid, 3-(2-bromophenyl)-2-methylpropionyl chloride, and 4-bromo-2-methyl-1-indanone

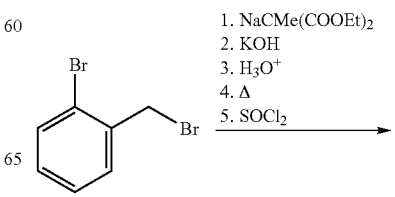

-continued

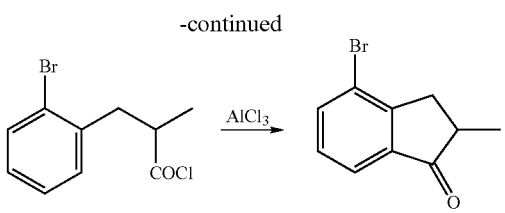

In a three-necked round-bottom 2000 ml flask equipped with a reflux condenser, dropping funnel with pressure-equalizing, and magnetic stirring bar, 20.5 g (0.89 mol) of sodium metal were dissolved in 450 ml of dry ethanol. To the resulting solution, 155 g (0.89 mol) of diethylmethylmalonate in 150 ml of dry ethanol was added dropwise within 15 minutes. This mixture was stirred for 15 minutes; then 186 g (0.89 mol) of o-bromobenzyl bromide was added, while vigorously stirring, at a rate that allowed the reaction mixture to maintain a gentle reflux. Additionally, this mixture was refluxed for 4 hours and cooled to room temperature. A solution of 151 g of potassium hydroxide in 400 ml of water was added. This mixture was refluxed for 3 hours to saponificate the ester formed. Ethanol and water were distilled off. To the residue, 500 ml of water and, then 12 M HCl (to pH 1) were added. The substituted methylmalonic acid that precipitated was separated, washed with 2×200 ml of cold water, and dried overnight on a watch glass. Crude 3-(2-bromophenyl)-2-methyl-propanoic acid was obtained after decarboxylation of this substituted methylmalonic acid by heating it for 2 hours at 160° C. The product was used without further purification. A mixture of this acid and 160 ml of SOCl$_2$ was stirred for 24 hours at ambient temperature. Thionyl chloride was distilled off. The crude 3-(2-bromophenyl)-2-methylpropionyl chloride dissolved in 270 ml of CH$_2$Cl$_2$ was added dropwise, while vigorously stirring, to a suspension of 136 g (1.02 mol) of AlCl$_3$ in 1350 ml of CH$_2$Cl$_2$ over 1 hour at 0° C. Then, this mixture was refluxed for 3 hours, cooled to ambient temperature, and poured on 500 cm$^3$ of ice. The organic layer was separated. The aqueous layer was extracted with 3×300 ml of methyl-tert-butyl ether. The combined organic fractions were dried over K$_2$CO$_3$ and evaporated to dryness. Fractional distillation gave the title indanone, b.p. 131-134° C./2 mm Hg. Yield 125.5 g (75%) of colorless solid.

Anal. calc. for C$_{10}$H$_9$BrO: C, 53.36; H, 4.03. Found: C, 53.19; H, 3.98.

$^1$H NMR (CDCl$_3$): δ 7.76 (d, J=7.6 Hz, 1H, 7-H), 7.71 (d, J=7.6 Hz, 1H, 5-H), 7.28 (t, J=7.6 Hz, 1H, 6-H), 3.36 (dd, J=17.5 Hz, J=7.6 Hz, 1H, 3-H), 2.70-2.82 (m, 1H, 2-H), 2.67 (dd, J=17.5 Hz, J=3.8 Hz, 1H, 3'-H), 1.34 (d, J=7.3 Hz, 3H, 2-Me).

$^{13}$C NMR (CDCl$_3$): δ 208.3, 152.9, 138.2, 137.2, 129.0, 122.6, 122.0, 41.8, 35.7, 16.0.

Mixture of 4- and 7-bromo-2-methyl-1H-indenes

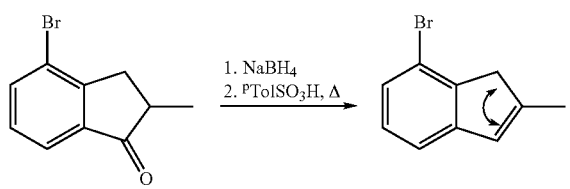

A total of 38.3 g (1.02 mol) of NaBH$_4$ were added in small portions over 2 hours to a solution of 116 g (0.52 mol) of 4-bromo-2-methyl-1-indanone in 950 ml of THF-methanol (2:1, vol.) at −5° C. (Caution: temperature must be lower than 0° C.). The mixture was stirred overnight at ambient temperature. The resulting mixture was poured on 1000 cm$^3$ of ice and acidified with 10% HCl to pH=4. The organic layer was separated, and the aqueous layer was extracted with 3×300 ml of methyl-tert-butyl ether. The organic fractions were combined and dried over K$_2$CO$_3$ and evaporated to dryness. To the residue 1500 ml of toluene were added. This toluene solution was treated with a catalytic amount of $^p$TolSO$_3$H (ca. 2 g) for 2 hours at reflux. Then this mixture was cooled to room temperature and passed through a short Silica Gel 60 column (40-63 μm, d 60 mm, l 40 mm). This column was additionally eluted with 250 ml of toluene. The chromatographed product was evaporated to dryness. Fractional distillation gave a mixture of the title indene, b.p. 104-108° C./5 mm Hg. Yield 100 g (93%) of colorless solid.

Anal. calc. for C$_{10}$H$_9$Br: C, 57.44; H, 4.34. Found: C, 57.59; H, 4.40.

$^1$H NMR (CDCl$_3$) of 7-bromo-2-methyl-1H-indene: δ 7.23 (dd, J=7.9 Hz, J=1.0 Hz, 1H, 6-H), 7.18 (dd, J=7.4 Hz, J=1.0 Hz, 1H, 4-H), 7.10 (m, 1H, 5-H), 6.51 (m, 1H, 3-H), 3.28 (m, 2H, 1,1'-H), 2.17 (s, 3H, 2-Me).

$^{13}$C NMR (CDCl$_3$) of 7-bromo-2-methyl-1H-indene: δ 147.3, 146.8, 143.3, 128.2, 127.1, 126.6, 118.7, 118.3, 44.2, 16.7.

Mixture of rac- and meso-bis(η$^5$-2-methyl-4-bromoindenyl)zirconium dichlorides (2)

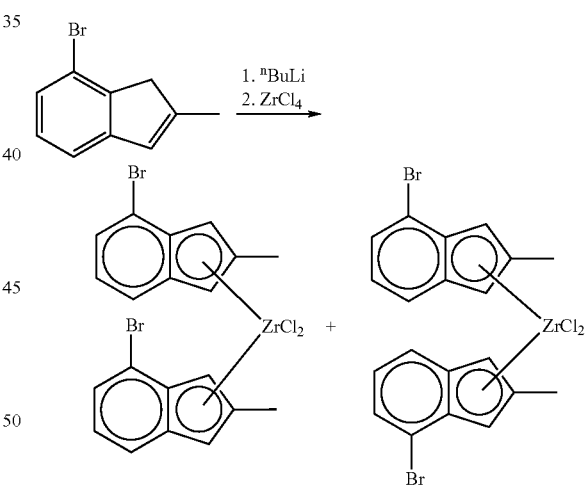

In the Glove Box to a solution of 3.50 g (16.7 mmol) of 2-methyl-7-bromoindene in 100 ml of toluene, 6.7 ml of 2.5 M $^n$BuLi (16.8 mmol) in hexanes were added. This mixture was stirred for 36 h and, then, added to a suspension of 1.95 g (8.35 mmol) of ZrCl$_4$ in 20 ml of toluene. The resulting mixture was stirred for 2 h at ambient temperature and, then, for 20 h at 90° C. This hot mixture was filtered through Celite 503; the filtrate was evaporated to dryness. The residue formed was re-crystallized from 40 ml of toluene. Yield 2.27 g (47%) of yellowish crystalline product as ca. 1 to 1 mixture of rac- and meso-complexes.

Anal. calc. for C$_{20}$H$_{16}$Br$_2$Cl$_2$Zr: C, 41.54; H, 2.79. Found: C, 41.69; H, 2.88.

$^1$H NMR (CD$_2$Cl$_2$): rac-complex, δ 7.54 (d, J=8.5 Hz, 2H, 6,6'-H), 7.43 (d, J=7.2 Hz, 2H, 5,5'-H), 7.00 (dd, J=8.5 Hz, J=7.2 Hz, 2H, 7,7'-H), 6.45 (m, 2H, 1,1'-H), 6.34 (m, 2H, 3,3'-H), 1.99 (s, 6H, 2,2'-Me);

$^1$H NMR (CD$_2$Cl$_2$): meso-complex, δ 7.57 (d, J=8.5 Hz, 2H, 6,6'-H), 7.40 (d, J=7.2 Hz, 2H, 5,5'-H), 6.98 (dd, J=8.5 Hz, J=7.2 Hz, 2H, 7,7'-H), 6.40 (m, 2H, 1,1'-H), 6.36 (m, 2H, 3,3'-H), 2.05 (s, 6H, 2,2'-Me).

The molecular structure of rac-bis(η$^5$-2-methyl-4-bromoindenyl)zirconium dichloride is shown in FIG. 1.

EXAMPLE 3

Synthesis of mixture of rac- and meso-bis(η$^5$-2-methyl-4-bromoinden-1-yl) hafnium dichlorides (3)

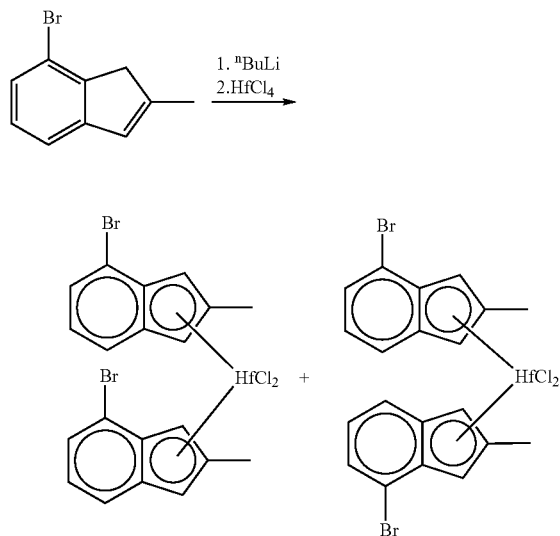

In the Glove Box 5.7 ml of 2.5 M $^n$BuLi (14.3 mmol) in hexanes were added to a solution of 3.00 g (14.3 mmol) of 2-methyl-7-bromoindene (from Example 2) in 100 ml of toluene. This mixture was stirred for 36 h and, then, added to a suspension of 2.29 g (7.15 mmol) of HfCl$_4$ in 20 ml of toluene. The resulting mixture was stirred for 2 h at ambient temperature and, then, for 20 h at 90° C. This hot mixture was filtered through Celite 503; the filtrate was evaporated to dryness. The residue formed was re-crystallized from 40 ml toluene. Yield 2.05 g (43%) of yellowish crystalline product as ca. 1 to 1 mixture of rac- and meso-complexes.

Anal. calc. for C$_{20}$H$_{16}$Br$_2$Cl$_2$Hf: C, 36.09; H, 2.42. Found: C, 36.31; H, 2.50.

$^1$H NMR (CD$_2$Cl$_2$): rac-complex, δ 7.54 (dt, J=8.5 Hz, J=0.9 Hz, 2H, 6,6'-H), 7.40 (dd, J=7.2 Hz, J=0.9 Hz, 2H, 5,5'-H), 6.97 (dd, J=8.5 Hz, J=7.2 Hz, 2H, 7,7'-H), 6.31 (m, 2H, 1,1'-H), 6.22 (m, 2H, 3,3'-H), 2.07 (s, 6H, 2,2'-Me);

$^1$H NMR (CD$_2$Cl$_2$): meso-complex, δ 7.45 (dt, J=8.5 Hz, J=0.9 Hz, 2H, 6,6'-H), 7.37 (dd, J=7.2 Hz, J=0.9 Hz, 2H, 5,5'-H), 6.96 (dd, J=8.5 Hz, J=7.2 Hz, 2H, 7,7'-H), 6.39 (m, 2H, 1,1'-H), 6.19 (m, 2H, 3,3'-H), 2.13 (s, 6H, 2,2'-Me).

Figure 2:
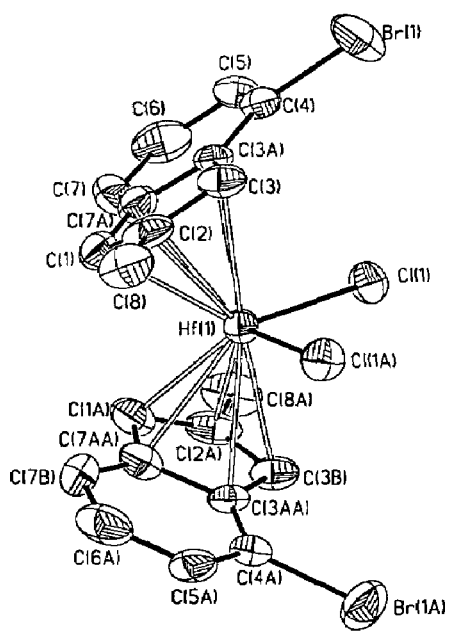
FIG. 2 is a representation of the molecular structure of rac-bis($\eta^5$-2-methyl-4-bromoindenyl)hafnium dichloride of Example 3.

The molecular structure of rac-bis(η$^5$-2-methyl-4-bromoindenyl)hafnium dichloride is shown in FIG. 2.

EXAMPLE 4

Synthesis of rac-[dimethylsilyl-bis(η$^5$-4-bromo-2-methylinden-1-yl)](N$^1$,N$^3$-diphenyl-1,3-propanediamido)zirconium (4)

Mixture of rac- and meso-bis(4-bromo-2-methyl-1H-inden-1-yl)(dimethyl)silanes

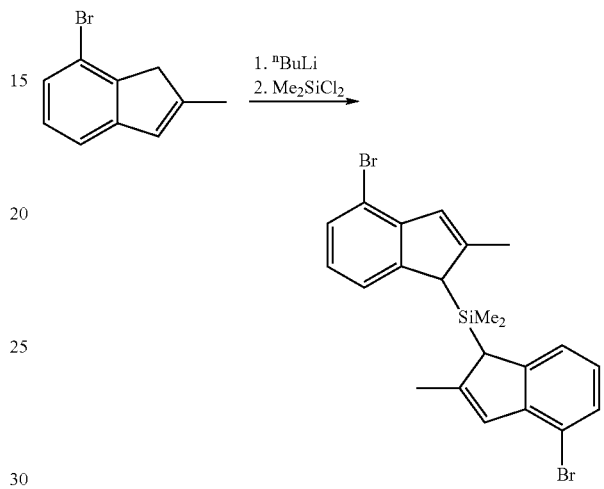

In an argon atmosphere, 23.9 ml of 2.00 M MeLi (47.8 mmol) in ether were added at 10° C. to a solution of 10.0 g (47.8 mmol) of 2-methyl-7-bromoindene (see Example 2) in 250 ml of diethyl ether. This mixture was stirred for 1 h at 20° C. and, then, cooled to 0° C. At this temperature, 2.89 ml (3.08 g, 23.9 mmol) of Me$_2$SiCl$_2$ were added. The resulting mixture was stirred for 2 h at ambient temperature; then 100 ml of water were added. The organic layer was separated, dried over K$_2$CO$_3$, and evaporated to dryness. The residue was treated with 25 ml of hexanes. The white solid that precipitated was filtered off, washed with 3×30 ml of hexanes, and dried in vacuum. Yield 5.37 g (47%) of white solid of ca. 1 to 1 mixture of rac- and meso-compounds.

Anal. calc. for C$_{22}$H$_{22}$Br$_2$Si: C, 55.71; H, 4.68. Found: C, 56.02; H, 4.77.

$^1$H NMR (CDCl$_3$): δ 7.36 (d, J=8.5 Hz, 2H, 5,5'-H in rac- or meso-compound), 7.34 (d, J=8.5 Hz, 2H, 5,5'-H in meso- or rac-compound), 7.32 (d, J=7.6 Hz, 2H, 7,7'-H in rac- or meso-compound), 7.23 (d, J=7.6 Hz, 2H, 7,7'-H in meso- or rac-compound), 6.95 (t, J=8.1 Hz, 2H, 6,6'-H in rac- or meso-compound), 6.93 (t, J=8.1 Hz, 2H, 6,6'-H in meso- or rac-compound), 6.70 (br.s, 4H, 3,3'-H in rac- and meso-compounds), 3.74 (s, 2H, CHSi, CHSi' in rac- or meso-compound), 3.73 (s, 2H, CHSi, CHSi' in meso- or rac-compound) 2.23 (d, 6H, J=1.2 Hz, 2,2'-Me in rac- or meso-compound), 2.17(d, 6H, J=1.2 Hz, 2,2'-Me in meso- or rac-compound), −0.19 (s, 3H, SiMe in meso-compound), −0.24 (s, 6H, SiMe$_2$ in rac-compound), −0.27 (s, 3H, SiMe' in meso-compound).

$^{13}$C NMR (CDCl$_3$): δ 148.4, 148.3, 145.9*, 145.1, 145.0, 128.4*, 126.5*, 124.2, 124.1, 121.8*, 114.1*, 48.6, 48.5, 17.9*, −5.4*, −5.6 (* two resonance of rac- and meso-isomers).

Rac-[dimethylsilyl-bis($\eta^5$-4-bromo-2-methylinden-1-yl)]($N^1$,$N^3$-diphenyl-1,3-propanediamido)zirconium (4)

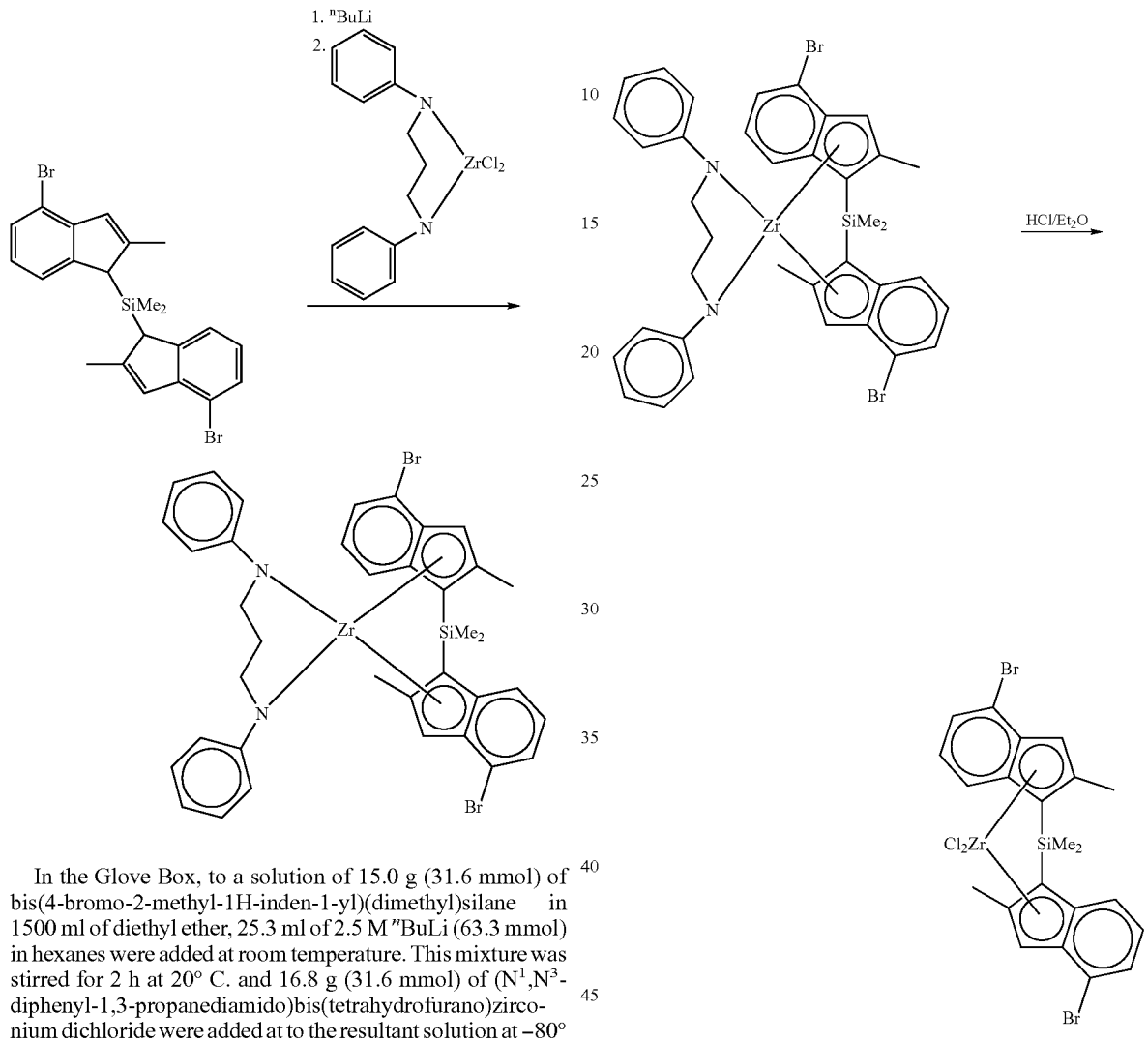

EXAMPLE 5

Synthesis of rac-dimethylsilyl-bis($\eta^5$-4-bromo-2-methylinden-1-yl)zirconium dichloride (5)

In the Glove Box, to a solution of 15.0 g (31.6 mmol) of bis(4-bromo-2-methyl-1H-inden-1-yl)(dimethyl)silane in 1500 ml of diethyl ether, 25.3 ml of 2.5 M $^n$BuLi (63.3 mmol) in hexanes were added at room temperature. This mixture was stirred for 2 h at 20° C. and 16.8 g (31.6 mmol) of ($N^1$,$N^3$-diphenyl-1,3-propanediamido)bis(tetrahydrofurano)zirconium dichloride were added at to the resultant solution at −80° C. The resulting mixture was stirred for 24 h at ambient temperature and, then, evaporated to dryness. The residue was treated with 700 ml of toluene. This toluene solution was filtered through Celite 503. The filtrate was evaporated to dryness. The crude product was washed with 4×150 ml of hexanes and dried in vacuum. This procedure gave 20.8 g (84%) of orange crystalline product.

Anal. calc. for $C_{37}H_{36}Br_2N_2SiZr$: C, 56.41; H, 4.61. Found: C, 56.64; H, 4.71.

$^1$H NMR ($CD_2Cl_2$): δ 7.93 (d, J=8.4 Hz, 2H, 5,5'-H in indenyl), 7.24 (m, 8H, 2,2',3,3',5,5',6,6'-H in N—$C_6H_5$), 7.09 (dd, J=8.4 Hz, J=7.2 Hz, 2H, 6,6'-H in indenyl), 7.00 (m, 2H, 4,4'-H in N—$C_6H_5$), 6.57 (d, J=7.2 Hz, 2H, 7,7'-H in indenyl), 6.30 (s, 2H, 3,3'-H in indenyl), 3.97 (dt, J=15.0 Hz, J=8.3 Hz, 2H, 1,3-H in propylidene), 3.01 (dt, J=15.0 Hz, J=3.2 Hz, 2H, 1',3'-H in propylidene), 2.08 (s, 6H, 2,2'-Me in indenyl), 1.39 (m, 2H, 2,2'-H in propylidene), 1.23 (s, 6H, $SiMe_2$).

$^{13}$C NMR ($C_6D_6$): δ 161.7, 132.1, 130.1, 129.5, 129.3, 128.4, 126.9, 125.2, 124.7, 123.6, 122.7, 119.2, 117.7, 59.0, 22.1, 18.8, 1.92.

In the Glove Box, 20.2 ml of cold 1.0 M solution of HCl in ether were added at −110° C. to a solution of 8.00 g (10.2 mmol) of rac-[dimethylsilyl-bis(4-bromo-2-methylinden-1-yl)]($N^1$,$N^3$-diphenyl-1,3-propanediamido)zirconium in 640 ml of diethyl ether-$CH_2Cl_2$ (1:1, vol.). This mixture was stirred and slowly warmed to ambient temperature during ca. 7 h. The yellow precipitate formed was filtered off, washed with 4×30 ml of $CH_2Cl_2$, and dried in vacuum. Yield 3.20 g (50%) of yellow solid.

Anal. calc. for $C_{22}H_{20}Br_2Cl_2SiZr$: C, 41.65; H, 3.18. Found: C, 41.50; H, 3.11.

$^1$H NMR ($CD_2Cl_2$): δ 7.60 (dt, J=8.7 Hz, J=0.8 Hz, 2H, 5,5'-H), 7.52 (dd, J=7.2 Hz, J=0.8 Hz, 2H, 7,7'-H), 6.87 (dd, J=8.7 Hz, J=7.2 Hz, 2H, 6,6'-H), 6.83 (m, 2H, 3,3'-H), 2.18 (d, J=0.5 Hz, 6H, 2,2'-Me), 1.26 (s, 6H, $SiMe_2$).

Figure 3:
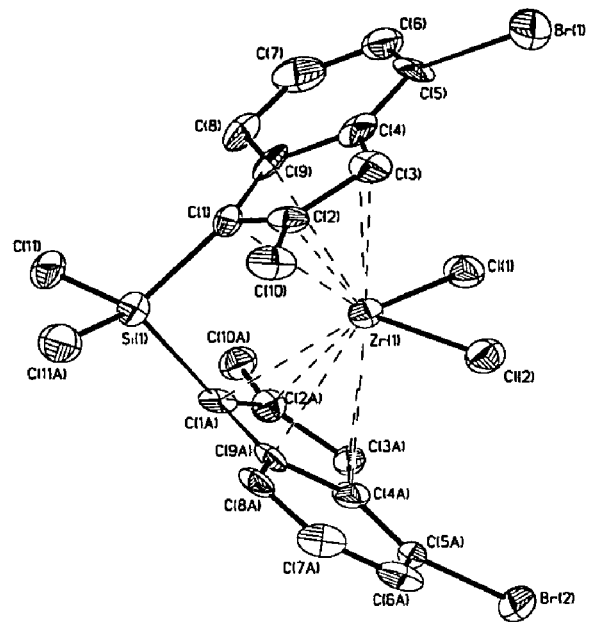
FIG. 3 is a representation of the molecular structure of rac-dimethylsilyl-bis($\eta^5$-4-bromo-2-methylindenyl)zirconium dichloride of Example 5.

The molecular structure of rac-dimethylsilyl-bis($\eta^5$-4-bromo-2-methylinden-1-yl)zirconium dichloride is shown in FIG. 3.

EXAMPLE 6

Synthesis of meso-dimethylsilyl-bis($\eta^5$-4-bromo-2-methylinden-1-yl)zirconium dichloride (6)

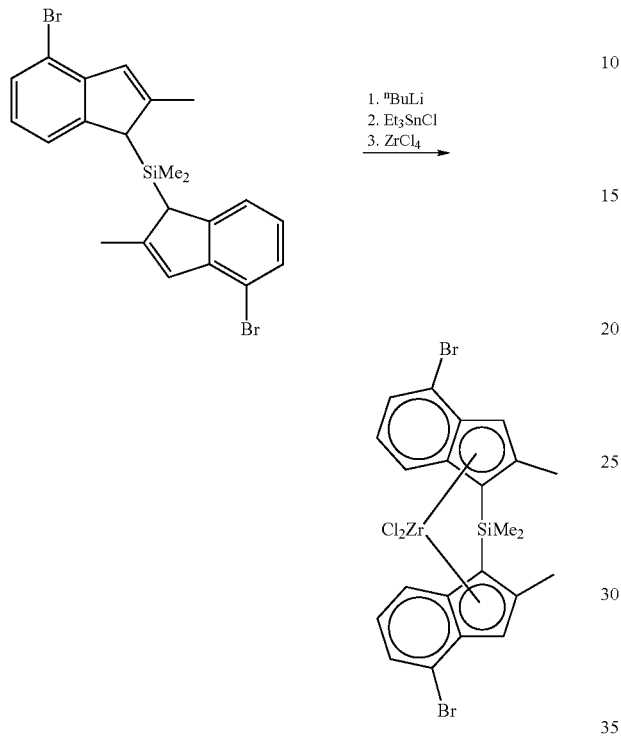

A total of 27.6 ml of 2.50 M $^n$BuLi (44.2 mmol) in hexanes were added by vigorous stirring for 5 min at −78° C. to a solution of 10.5 g (22.1 mmol) of bis(4-bromo-2-methyl-1H-inden-1-yl)(dimethyl)silanes from Example 4 in 150 ml of THF. This mixture was slowly warmed during ca. 1 h to ambient temperature and additionally stirred for 2 h at this temperature. Then, 10.7 g (44.2 mmol) of Et$_3$SnCl were added in one portion at −80° C. The resulting mixture was stirred for 3 h at room temperature and, then, evaporated to dryness. To the residue 100 ml of toluene were added, then the mixture was evaporated to dryness to eliminate THF traces. To the residue 220 ml of toluene were added. The suspension obtained was filtered through glass frit (G4). To the filtrate 5.15 g (22.1 mmol) of ZrCl$_4$ were added. The resulting mixture was stirred for 12 h at room temperature and, then, 30 h at reflux. Hot toluene suspension was filtered through glass frit (G4). The red crystals that precipitated at −30° C. from the filtrate were collected, washed with 3×25 ml of hot toluene, and dried in vacuum. This procedure gave 0.54 g of the title compound. The precipitate on the glass frit (obtained after the filtration of the hot toluene suspension) was washed with 4×40 ml of toluene and 3×25 ml of THF, then, dried in vacuum. This procedure gave 2.20 g of orange powder of the title product. Total yield 2.64 g (19%). No formation of the isomeric rac-dimethylsilyl-bis($\eta^5$-4-bromo-2-methylinden-1-yl)zirconium dichloride was observed during this synthesis.

Anal. calc. for $C_{22}H_{20}Br_2Cl_2SiZr$: C, 41.65; H, 3.18. Found: C, 41.84; H, 3.19.

$^1$H NMR (CD$_2$Cl$_2$): δ 7.57 (d, J=8.7 Hz, 2H, 5,5'-H), 7.26 (d, J=7.4 Hz, 2H, 7,7'-H), 6.70 (s, 2H, 3,3'-H), 6.59 (dd, J=8.7 Hz, J=7.4 Hz, 2H, 6,6'-H), 2.44 (s, 6H, 2,2'-Me), 1.37 (s, 3H, SiMe), 1.20 (s, 3H, SiMe').

EXAMPLE 7

Synthesis of meso-dimethylsilyl-bis($\eta^5$-4-bromo-2-methylinden-1-yl)hafnium dichloride (7)

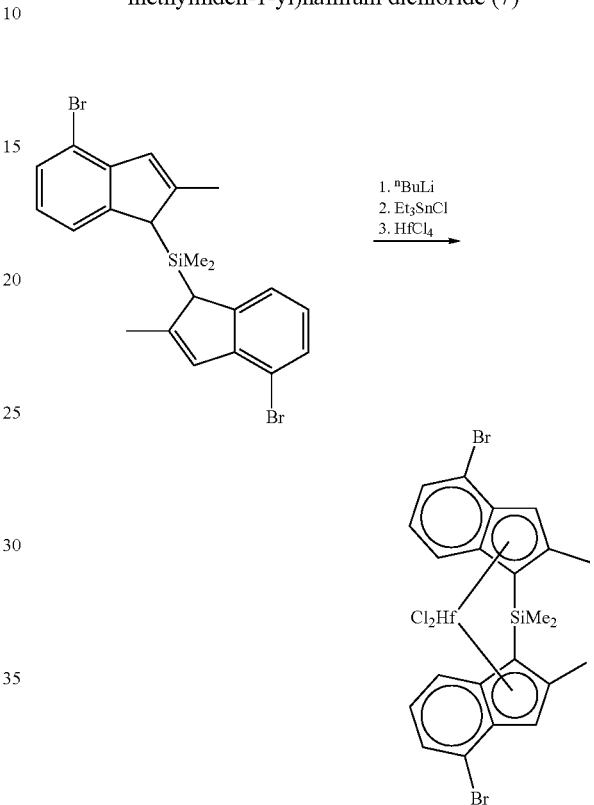

A total of 71.0 ml of 1.19 M MeLi (84.3 mmol) in diethyl ether were added by vigorous stirring for 5 min at −78° C. to a solution of 20.0 g (42.2 mmol) of bis(4-bromo-2-methyl-1H-inden-1-yl)(dimethyl)silanes in 300 ml of THF. This mixture was slowly warmed during ca. 1 h to ambient temperature and additionally stirred for 4 h at this temperature. Then, 22.0 g (91.1 mmol) of Et$_3$SnCl were added in one portion at −10° C. The resulting mixture was stirred overnight at room temperature and, then, evaporated to dryness. To the residue 150 ml of toluene were added, then the mixture was evaporated to dryness to eliminate ether traces. To the residue 250 ml of toluene were added. The suspension obtained was filtered through Celite 503. To the filtrate 13.5 g (42.2 mmol) of HfCl$_4$ were added at −40° C. The resulting mixture was stirred overnight at room temperature and, then, 4 h at reflux. The hot toluene suspension was filtered through glass frit (G4). The precipitate was washed with 100 ml of toluene and 2×50 ml of THF, then, dried in vacuum. Yield 3.80 g (16%) of orange powder of the title product.

Anal. calc. for $C_{22}H_{20}Br_2Cl_2SiHf$: C, 36.61; H, 2.79. Found: C, 36.85; H, 2.88.

$^1$H NMR (CD$_2$Cl$_2$): δ 7.60 (d, J=8.7 Hz, 2H, 5,5'-H), 7.24 (d, J=7.3 Hz, 2H, 7,7'-H), 6.60 (s, 2H, 3,3'-H), 6.56 (dd, J=8.7 Hz, J=7.3 Hz, 2H, 6,6'-H), 2.56 (s, 6H, 2,2'-Me), 1.37 (s, 3H, SiMeMe'), 1.21 (s, 3H, SiMeMe').

Figure 4:
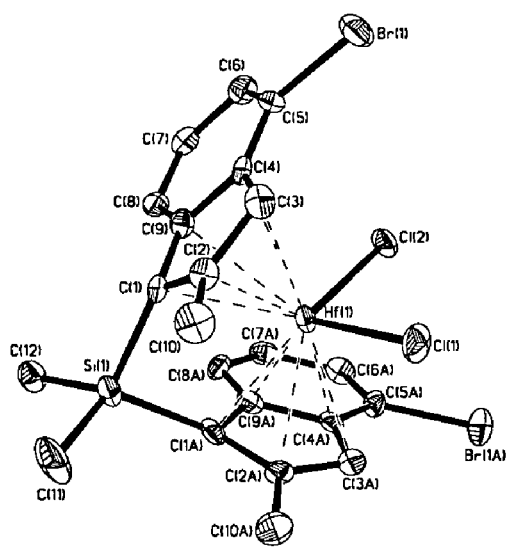
FIG. 4 is a representation of the molecular structure of meso-dimethylsilyl-bis($\eta^5$-4-bromo-2-methylindenyl) hafnium dichloride of Example 7.

The molecular structure of meso-dimethylsilyl-bis($\eta^5$-4-bromo-2-methylinden-1-yl)hafnium dichloride is shown in FIG. 4.

EXAMPLE 8

Synthesis of rac-dimethylsilyl-bis($\eta^5$-4-bromo-2-methylinden-1-yl)zirconium dibromide (8)

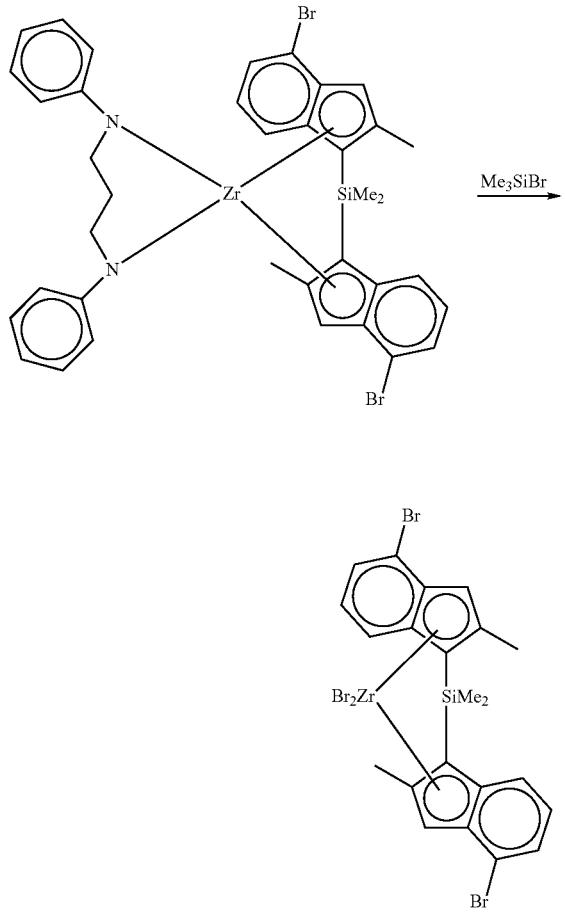

In the Glove Box (nitrogen atmosphere), to a solution of 1.00 g (1.27 mmol) of rac-[dimethylsilyl-bis(4-bromo-2-methylinden-1-yl)]($N^1,N^3$-diphenyl-1,3-propanediamido)zirconium in 5 ml of $CH_2Cl_2$, 1.00 ml (1.16 g, 7.58 mmol) of $Me_3SiBr$ was added at ambient temperature. This mixture was stirred for 24 hours. The yellow precipitate that formed was filtered off, washed with 3×10 ml of hexanes, and dried in vacuum. Yield 0.34 g (38%) of yellow solid.

Anal. calc. for $C_{22}H_{20}Br_4SiZr$: C, 36.53; H, 2.79. Found: C, 36.68; H, 2.85.

$^1$H NMR ($CD_2Cl_2$): δ 7.56 (dt, J=8.7 Hz, J=0.8 Hz, 2H, 5,5'-H), 7.53 (dd, J=7.2 Hz, J=0.6 Hz, 2H, 7,7'-H), 7.07 (br.s, 2H, 3,3'-H), 6.83 (dd, J=8.7 Hz, J=7.2 Hz, 2H, 6,6'-H), 2.12 (s, 6H, 2,2'-Me), 1.24 (s, 6H, $SiMe_2$).

EXAMPLE 9

Synthesis of 4,4'-sulfandiyl-bis($\eta^5$-7-bromo-2-methylindenyl)zirconium dichloride (9)

3,6-Dibromotoluene

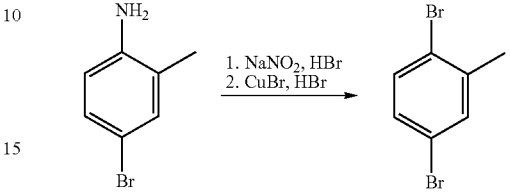

In a 2000 ml beaker 46.5 g (0.25 mol) of melted 2-methyl-4-bromoaniline were slowly added to 400 ml of 23% aqueous HBr. This mixture was stirred for 20 min using a mechanical stirrer, cooled to −5° C. Then a solution of 22.4 g (0.33 mol) of $NaNO_2$ in 130 ml of water was added dropwise for 1 h at this temperature. The diazonium reagent obtained was added in several portions to a solution of 35.9 g (0.25 mmol) of CuBr in 100 ml of 47% HBr at 0° C. The resulting mixture was warmed to 70° C., stirred for 30 min at this temperature, and, then, cooled to room temperature. The product was extracted with 3×200 ml of methyl-tert-butyl ether. The combined extract was dried over $K_2CO_3$ and evaporated to dryness. Firstly, the crude product was purified using a short Silica Gel 60 column (40-63 μm, d 60 mm, l 40 mm; eluent:hexanes). Fractional distillation gave a colorless oil, b.p. 100-102° C./10 mm Hg. Yield 36.1 g (58%).

Anal. calc. for $C_7H_6Br_2$: C, 33.64; H, 2.42. Found: C, 33.79; H, 2.50.

$^1$H NMR ($CDCl_3$): δ 7.39 (m, 1H, 5-H), 7.37 (m, 1H, 3-H), 7.18 (m, 1H, 6-H), 2.38 (s, 3H, Me).

$^{13}$C NMR ($CDCl_3$): δ 139.9, 133.6, 133.5, 130.3, 123.5, 120.9, 22.7.

3,6-Dibromobenzylbromide

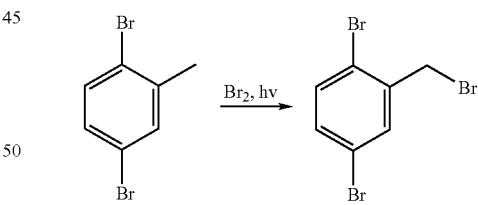

In a three-necked round-bottom 250 ml flask equipped with a reflux condenser, thermometer, dropping funnel with pressure-equalizing, and magnetic stirring bar 15.5 ml (47.9 g, 0.30 mmol) of bromine were added dropwise to 74.9 g (0.30 mol) of 3,6-dibromotoluene under exposure to 500 W lamp for 3 h at 190° C. The resulting mixture was cooled to room temperature. Fractional distillation gave a colorless liquid, b.p. 132-135° C./3 mm Hg. Yield 84.3 g (85%).

Anal. calc. for $C_7H_5Br_3$: C, 25.57; H, 1.53. Found: C, 25.81; H, 1.62.

$^1$H NMR ($CDCl_3$): δ 7.59 (m, 1H, 5-H), 7.43 (m, 1H, 3-H), 7.28 (m, 1H, 3-H), 4.52 (s, 2H, $CH_2$).

$^{13}$C NMR ($CDCl_3$): δ 138.9, 134.6, 134.0, 133.1, 123.0, 121.5, 32.2.

3-(2,5-Dibromophenyl)-2-methylpropanoic acid, 3-(2,5-dibromophenyl)-2-methylpropanoyl chloride, and 4,7-dibromo-2-methyl-1-indanone

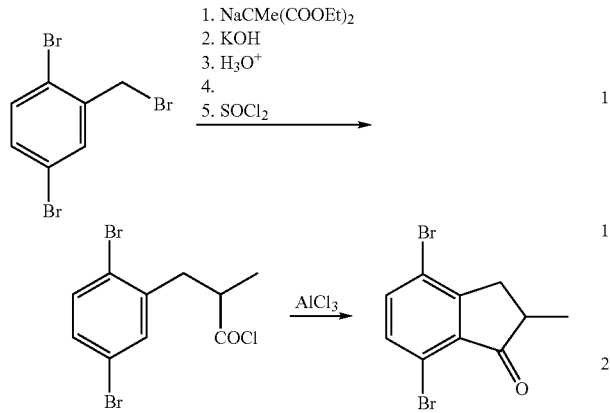

In a three-necked round-bottom 1000 ml flask equipped with a reflux condenser, dropping funnel with pressure-equalizing, and magnetic stirring bar 6.10 g (0.27 mol) of sodium metal were dissolved in 150 ml of dry ethanol. To the resulting solution 45.5 g (0.26 mol) of diethylmethylmalonate in 50 ml of dry ethanol were added dropwise within 10 min. This mixture was stirred for 15 min; then 84.3 g (0.26 mol) of 3,6-dibromobenzylbromide were added by vigorous stirring at a rate that allowed the reaction mixture to maintain a gentle reflux. Additionally, this mixture was refluxed for 4 h and, then, cooled to room temperature. A solution of 52.1 g of KOH in 140 ml of water was added. This mixture was refluxed for 3 h to saponificate the ester formed. Ethanol and water were distilled off. To the residue 200 ml of water and, then, 12 M HCl (to pH 1) were added. The substituted methylmalonic acid precipitated was separated, washed with 3×100 ml of cold water and dried overnight on a watch glass. Crude 3-(2,5-dibromophenyl)-2-methylpropanoic acid was obtained after decarboxylation of this substituted methylmalonic acid by heating it for 2 h at 160° C. This product was used without further purification. A mixture of this acid, 70 ml of $SOCl_2$, and 100 ml of $CH_2Cl_2$ was stirred for 3 h at reflux. Thionyl chloride and $CH_2Cl_2$ were distilled off. The residue was dried in vacuum and, then, dissolved in 95 ml of $CH_2Cl_2$. To a suspension of 47.0 g (0.35 mol) of $AlCl_3$ in 470 ml of $CH_2Cl_2$ the above-obtained solution of 3-(2,5-dibromophenyl)-2-methylpropanoyl chloride was added dropwise by vigorous stirring for 1 h at −20° C. This mixture was refluxed for 3 h, cooled to ambient temperature, and, then, poured on 500 $cm^3$ of ice. The organic layer was separated. The aqueous layer was extracted with 3×200 ml of methyl-tert-butyl ether. The combined organic fractions were dried over $K_2CO_3$ and evaporated to dryness. The crude 4,7-dibromo-2-methyl-1-indanone was purified by flash chromatography on Silica Gel 60 (40-63 μm, d 50 mm, h 250 mm; eluent:hexanes/methyl-tert-butyl ether (1:1, vol.)). Yield 54.1 g (70%).

Anal. calc. for $C_{10}H_8Br_2O$: C, 39.51; H, 2.65. Found: C, 39.40; H, 2.58.

$^1H$ NMR ($CDCl_3$): δ 7.52 (d, J=8.4 Hz, 1H, 6-H), 7.37 (d, J=8.4 Hz, 1H, 5-H), 3.27 (dd, J=17.7 Hz, J=8.0 Hz, 1H, 3-H), 3.73 (m, 1H, 2-H), 2.58 (dd, J=17.7 Hz, J=4.2 Hz, 1H, 3'-H), 1.31 (d, J=7.3 Hz, 3H, 2-Me).

$^{13}C$ NMR ($CDCl_3$): δ 205.5, 155.4, 137.6, 135.3, 133.9, 121.0, 118.6, 42.6, 35.3, 16.1.

4,7-Dibromo-2-methyl-1-indanol and a mixture of cis- and trans-4,7-dibromo-1-methoxy-2-methylindane

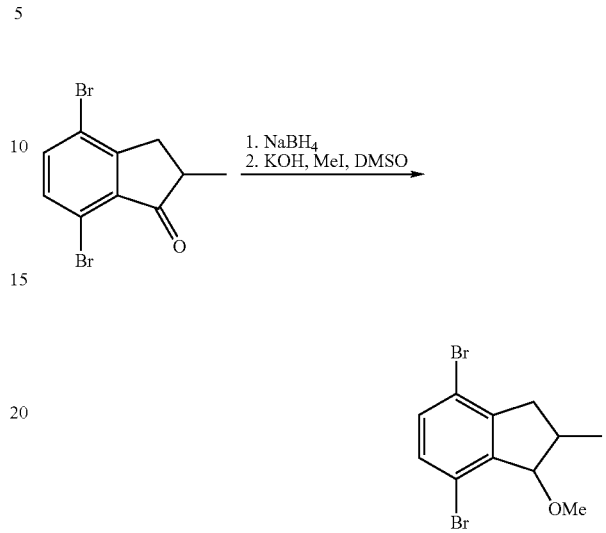

A total of 9.40 g (0.248 mol) of $NaBH_4$ were added in small portions at −5° C. to a solution of 54.1 g (0.178 mol) of 4,7-dibromo-2-methyl-1-indanone in 240 ml of THF-methanol (2:1, vol.). The resulting mixture was stirred overnight at ambient temperature and, then, poured on 500 $cm^3$ of ice. Then, 1 M HCl (to pH 4) was added. The organic layer was separated; and the aqueous layer was extracted with 3×200 ml of methyl-tert-butyl ether. The combined extract was dried over $K_2CO_3$ and evaporated to dryness. To a mixture of 40 g of KOH and 140 ml of DMSO 22.3 ml (50.8 g, 0.358 mol) of MeI was added at ambient temperature. Immediately, the crude 4,7-dibromo-2-methyl-1-indanol dissolved in 70 ml of DMSO was also added. The resulting mixture was stirred for 3 h and, then, poured on 2500 $cm^3$ of cold water. The organic layer was separated. The aqueous layer was extracted with 3×200 ml of methyl-tert-butyl ether. The combined extract was washed twice with 500 ml of water, dried over $K_2CO_3$, and evaporated to dryness. Fractional distillation gave a yellowish liquid, b.p. 121-125° C./2 mm Hg. Yield 50.1 g (88%) of 1 to 1 mixture of two diastereomeric compounds.

Anal. calc. for $C_{11}H_{12}Br_2O$: C, 41.28; H, 3.78. Found: C, 41.10; H, 3.69.

$^1H$ NMR ($CDCl_3$): δ 7.23 (m, 4H, 5,6-H in cis- and trans-products), 4.63 (d, J=5.6 Hz, 1H, 1-H in trans-product), 4.47 (d, J=1.5 Hz, 1H, 1-H in cis-product), 3.53 (s, 3H, MeO in trans- or cis-product), 3.45 (s, 3H, MeO in cis- or trans-product), 3.34 (dd, J=16.7 Hz, J=7.3 Hz, 1H, 3-H in trans- or cis-product), 2.98 (dd, J=16.4 Hz, J=7.6 Hz, 1H, 3-H in cis- or trans-product), 2.78 (dd, J=16.4 Hz, J=9.7 Hz, 1H, 3'-H in cis- or trans-product), 2.52 (m, 2H, 2-H in cis- and trans-products), 2.51 (dd, J=16.7 Hz, J=2.4 Hz, 1H, 3'-H in trans- or cis-product), 1.24 (d, J=7.0 Hz, 3H, 2-Me in trans- or cis-product), 1.06 (d, J=7.3 Hz, 3H, 2-Me in cis- or trans-product).

$^{13}C$ NMR ($CDCl_3$): δ 146.8, 146.0, 145.0, 142.8, 133.1, 132.7, 131.7, 131.4, 131.3, 131.1, 130.1, 129.7, 92.3, 86.8, 59.0, 57.0, 40.8 (two resonances), 38.5, 36.4, 19.5, 13.3.

Bis(4-bromo-2-methyl-1H-inden-7-yl)sulfide

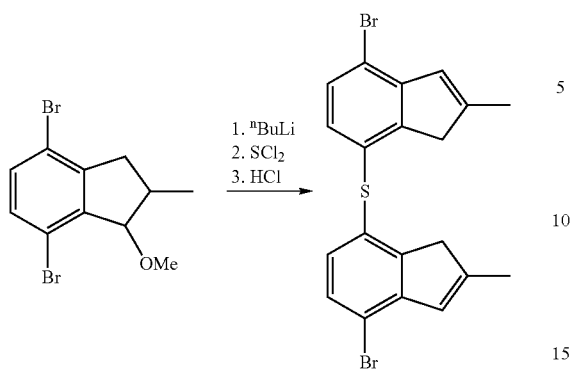

In a three-necked round-bottom 500 ml flask equipped with a reflux condenser, dropping funnel with pressure-equalizing, and magnetic stirring bar, 60.7 ml of 2.50 M $^n$BuLi (152 mmol) in hexanes were added dropwise to a solution of 48.55 g (152 mmol) of 4,7-dibromo-1-methoxy-2-methylindane in 250 ml of THF with vigorous stirring for 30 min at −78° C. Then a solution of 7.81 g (75.9 mmol) of freshly distilled $SCl_2$ in 50 ml of hexanes was added dropwise with vigorous stirring for 15 min at −94° C. The reaction mixture was warmed slowly for 1 h to ambient temperature; then 10 ml of water was added dropwise with vigorous stirring. The methoxydisulfide was extracted with 3×300 ml of diethyl ether. The combined extract was washed with 2×400 ml of cold water and evaporated to dryness. The residue was dissolved in a mixture of 250 ml of methanol and 250 ml of 12 M HCl. The resulting mixture was refluxed for 6 h and, then, cooled to ambient temperature. The crude product was extracted with 2×250 ml of $CH_2Cl_2$. The combined extract was evaporated to dryness; and the residue was purified using flash chromatography on Silica Gel 60 (40-63 μm, d 50 mm, l 500 mm; eluent:hexanes-$CH_2Cl_2$ (4:1, vol.)). Yield 7.65 g (23%) of white solid.

Anal. calc. for $C_{20}H_{16}Br_2S$: C, 53.59; H, 3.60. Found: C, 53.87; H, 3.77.

$^1$H NMR (CDCl$_3$): δ 7.11 (d, J=8.2 Hz, 2H, 5,5'-H), 6.90 (d, J=8.2 Hz, 2H, 6,6'-H), 6.67 (m, 2H, 3,3'-H), 3.32 (m, 4H, 1,1'-CH$_2$), 2.16 (m, 6H, 2,2'-Me).

$^{13}$C NMR (CDCl$_3$): δ 148.0, 143.7, 131.1, 128.6, 127.5, 126.0, 124.8, 117.3, 44.9, 16.9.

4,4'-sulfandiyl-bis(η$^5$-7-bromo-2-methylindenyl)zirconium dichloride (9)

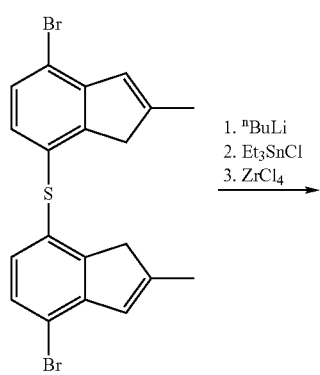

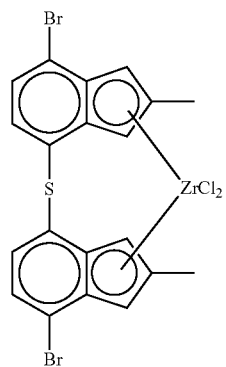

In the Glove Box, to a solution of 7.65 g (17.1 mmol) of bis(4-bromo-2-methyl-1H-inden-7-yl)sulfide in a mixture of 250 ml of diethyl ether and 70 ml of DME, 14.0 ml (35.0 mmol) of 2.50 M $^n$BuLi (35.0 mmol) in hexanes were added by vigorous stirring for 2 h at ambient temperature. This mixture was stirred additionally for 1 h; then 10.0 g (41.4 mmol) of Et$_3$SnCl were added in one portion. The resulting mixture was stirred overnight and, then, evaporated to dryness. The residue was dissolved in 250 ml of toluene. The suspension formed was filtered through a glass frit (G4). To the filtrate 4.18 g of ZrCl$_4$ were added. The resulting mixture was stirred for 7 h at 100° C. The hot suspension was filtered through a glass frit (G4). The red crystals that precipitated from the filtrate at 0° C. were separated, washed with 15 ml of cold toluene, and dried in vacuum. Yield 2.50 g (24% ).

Anal. calc. for $C_{20}H_{14}Br_2Cl_2SZr$: C, 39.49; H, 2.32. Found: C, 39.17; H, 2.22.

$^1$H NMR (CD$_2$Cl$_2$): δ 6.84 (d, J=7.5 Hz, 2H, 5,5'-H), 6.78 (d, J=7.5 Hz, 2H, 6,6'-H), 6.30 (d, J=2.4 Hz, 2H, 3,3'-H), 4.42 (d, J=2.4 Hz, 2H, 1,1'-H), 1.83 (s, 6H, 2,2'-Me).

Figure 5:
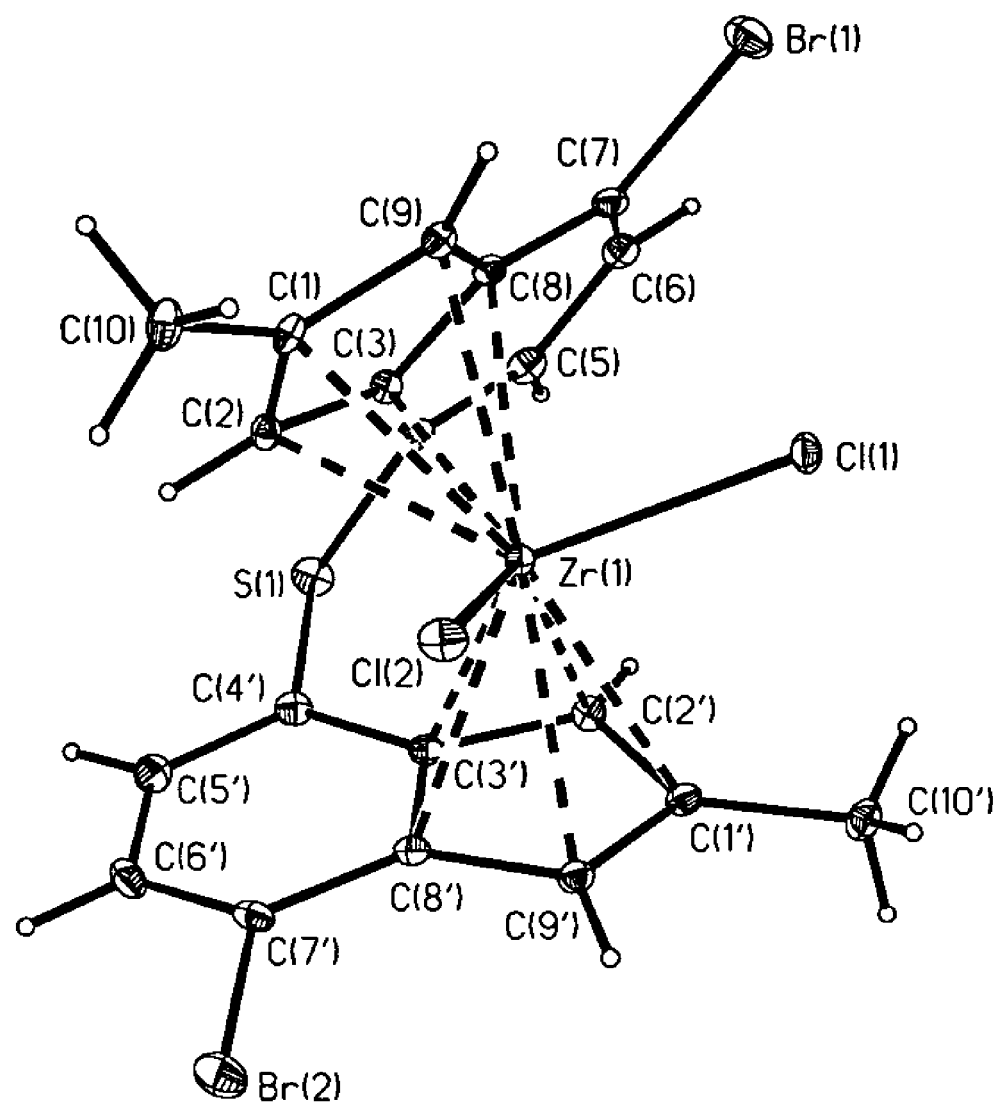
FIG. 5 is a representation of the molecular structure of sulfido-bis($\eta^5$-4-bromo-6-methylindenyl)zirconium dichloride of Example 9.

The molecular structure of sulfido-bis(η$^5$-4-bromo-6-methylindenyl)zirconium dichloride is shown in FIG. 5.

EXAMPLE 10

Synthesis of 4,4'-phenylphosphindiyl-bis(η$^5$-7-bromo-2-methylindenyl)zirconium dichloride (10)

Bis(4-bromo-2-methyl-1H-inden-7-yl)(phenyl)phosphine

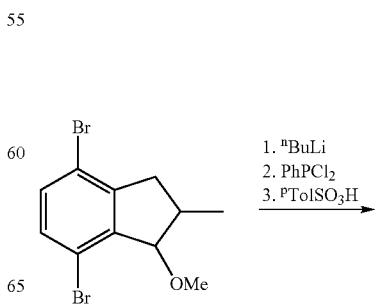

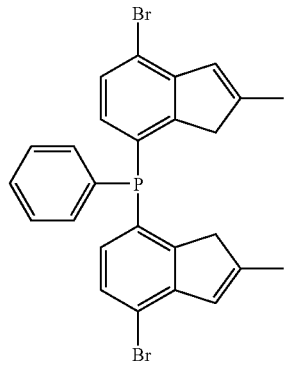

Under an argon atmosphere, in a 250 ml three-necked round-bottom flask equipped with a reflux condenser, dropping funnel with pressure-equalizing, and magnetic stirring bar, and containing a solution of 17.0 g (53.0 mmol) of 4,7-dibromo-1-methoxy-2-methylindane in 130 ml of THF, 21.2 ml of 2.50 M $^n$BuLi (53.0 mmol) in hexanes was added dropwise with vigorous stirring for 1 hour at −80° C. This mixture was additionally stirred for 2 hours at this temperature. Then, a solution of 9.51 g (53.0 mmol) of phenyldichlorophosphine in 30 ml of THF was added dropwise by vigorous stirring for 1 hour at −80° C. The reaction mixture was warmed slowly to ambient temperature and then stirred overnight at this temperature. The resulting mixture was evaporated to dryness. To the residue 250 ml of toluene and 7.0 g of para-toluenesulphonic acid were added. This mixture was refluxed for 5 hours, and then it was evaporated to dryness. The product was isolated using flash chromatography on Silica Gel 60 (40-63 μm, d 40 mm, l 400 mm; eluent:hexanes). Yield 8.08 g (58%) of white solid. On the evidence of NMR spectroscopy the product consists of three isomers with different positions of double bonds.

Anal. calc. for $C_{26}H_{21}Br_2P$: C, 59.57; H, 4.04. Found: C, 59.40; H, 3.95.

$^1$H NMR (CDCl$_3$): δ 7.22-7.36 (m, 5H,), 7.09-7.13 and 6.94-6.98 (two m, 2H,), 6.65-6.72 (m, 2H), 6.57-6.64 and 6.43-6.49 (two m, 2H), 3.27-3.35 (m, 4H), 2.08-2.12 (m, 6H).

4,4'-Phenylphosphindiyl-bis(η$^5$-7-bromo-2-methyl-indenyl)zirconium dichloride (10)

Under an argon atmosphere, to a solution of 5.24 g (10.0 mmol) of bis(4-bromo-2-methyl-1H-inden-7-yl)(phenyl)phosphine in 200 ml of ether, 8.00 ml of 2.5 M (10.0 mmol) of $^n$BuLi in hexanes was added over 10 minutes at ambient temperature. This mixture was stirred for 24 hours and then cooled to −80° C. Then, 3.77 g (10.0 mmol) of ZrCl$_4$(THF)$_2$ was added. The resulting mixture was stirred, slowly (over ca. 1 hour) heated to ambient temperature, and then further stirred for 24 hours. The resulting mixture was evaporated to dryness, and 100 ml of toluene was added. This mixture was stirred for 2 hours at 80° C. and then filtered using a funnel with a glass frit (G4) and jacket. The precipitate was washed with 5×100 ml of hot toluene. The combined toluene filtrate was evaporated to 100 ml. Crystals that precipitated at −30° C. were collected, washed with 2×20 ml of cold toluene, and dried in vacuum. Yield 3.52 g (51%) of yellow crystalline solid.

Anal. calc. for $C_{26}H_{19}Br_2Cl_2PZr$: C, 45.63; H, 2.80. Found: C, 45.47; H, 2.72.

$^1$H NMR (CD$_2$Cl$_2$): δ 7.83 (dd, J$_{PH}$=14.2 Hz, J=7.3 Hz, 1H, 6-H in indenyl), 7.40-7.55 (m, 6H, 5-H in indenyl and P-Ph), 7.28 (dd, J=7.5 Hz, J$_{PH}$=1.3 Hz, 1H, 5'-H in indenyl), 6.87 (dd, J=7.5 Hz, J$_{PH}$=3.8 Hz, 1H, 6'-H in indenyl), 6.57 (m, 1H, 3/3'-H), 6.53 (m, 1H, 1'/1-H), 4.70 (dd, J=2.5 Hz, J$_{PH}$=0.6 Hz, 1H, 3/3'-H), 4.36 (m, 1H, 1'/1-H), 2.13 (s, 3H, 2/2'-Me), 2.05 (s, 3H, 2'/2-Me).

EXAMPLE 11

Synthesis of 4,4'-phenylphosphinesulfide-bis(η$^5$-7-bromo-2-methylindenyl) zirconium dichloride (11)

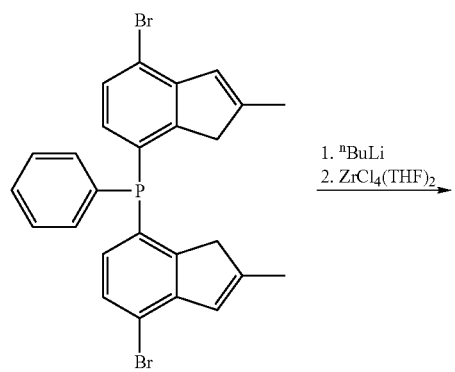

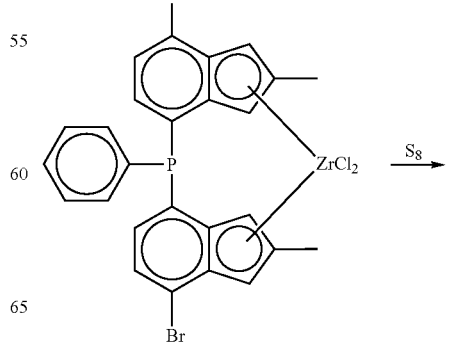

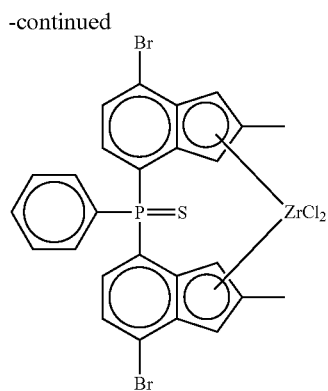

A mixture of 0.30 g (0.44 mmol) of 4,4'-phenylphosphido-bis(η$^5$-7-bromo-2-methylindenyl)zirconium dichloride and 13.7 mg (0.44 mmol) of sulfur in 20 ml of toluene was stirred for 20 h at 100° C. The resulting mixture was evaporated to dryness. The residue was washed with 8×30 ml of warm hexanes, and dried in vacuum. Yield 0.26 g (83%) of orange solid.

Anal. calc. for $C_{26}H_{21}Cl_2PSZr$: C, 55.90; H, 3.79. Found: C, 56.12; H, 3.93.

$^1$H NMR (CD$_2$Cl$_2$): δ 8.41 (dd, $J_{PH}$=17.4 Hz, J=7.5 Hz, 1H, 6-H in indenyl), 7.95-8.02 (m, 2H, 5,5'-H in indenyl), 7.75 (m, 1H, 6'-H in indenyl), 7.66-7.69 (m,1H, 4-H in PPh), 7.58-7.62 (m, 2H, 2,6-H in PPh), 7.40 (dd, J=7.5 Hz, $J_{PH}$=1.8 Hz, 1H, 4-H in indenyl), 7.15-7.25 (m, 2H, 3,5-H in PPh), 7.01 (dd, $J_{PH}$=14.8 Hz, J=7.5 Hz, 1H, 4'-H in indenyl), 6.70 (m, 1H, 3-H in indenyl), 6.80 (m, 1H, 3'-H in indenyl), 5.17 (d, J=2.5 Hz, 1H, 1-H in indenyl), 4.14 (d, J=2.5 Hz, 1H, 1'-H in indenyl), 2.20 (s, 3H, 2-Me), 2.14 (s, 3H, 2'-Me).

EXAMPLE 12

Synthesis of 4,4'-tolylazandiyl-bis(η$^5$-7-bromo-2-methylindenyl)zirconium dichloride (12)

4-Bromo-1-methoxy-2-methylindane

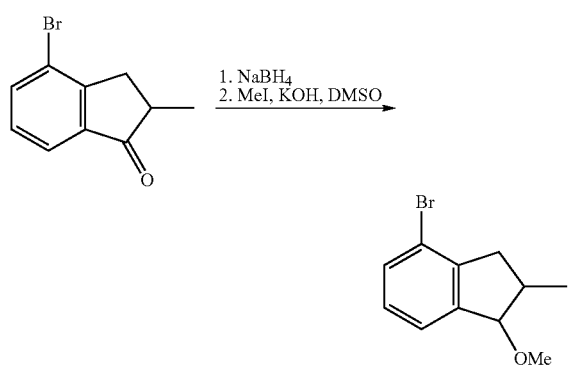

To a solution of 149.5 g (0.664 mol) of 4-bromo-2-methyl-1-indanone in 900 ml of THF-methanol (2:1, vol.), 37.6 g (0.995 mol) of NaBH$_4$ was added in small portions with vigorous stirring over 1.5 hours at 5° C. This mixture was stirred at room temperature for 12 hours and then added to 2 L of cold water. The hydrogenation product was extracted with 5×200 ml of dichloromethane, and the combined extract was evaporated to dryness. To 149 g (2.65 mol) of KOH in 420 ml of DMSO, 188 g (82.5 ml, 1.33 mol) of MeI, and a solution of the crude 4-bromo-2-methylindan-1-ol in 220 ml of DMSO were added. This mixture was stirred for 2 hours at ambient temperature; then, 92.0 g (40.4 ml, 0.664 mol) of MeI was added, and the mixture was additionally stirred for 2 hours. The resulting mixture was added to 2.5 L of cold water. The crude product was extracted with 5×200 ml of dichloromethane. The combined extract was dried over Na$_2$SO$_4$, and then evaporated to dryness. Fractional distillation gave a mixture of two diastereomeric compounds, b.p. 108° C./3 mm Hg. Yield, 148.5 g (93%) of a colorless oil.

Anal. calc. for $C_{11}H_{13}BrO$: C, 54.79; H, 5.43. Found: C, 54.86; H, 5.40.

$^1$H NMR (300 MHz, CDCl$_3$): δ 7.41 (d, J=7.9 Hz, 1H, 5-H of cis-product), 7.40 (d, J=7.9 Hz, 1H, 5-H of trans-product), 7.31 (d, J=7.2 Hz, 1H, 7-H of cis-product), 7.29 (d, J=7.2 Hz, 1H, 7-H of trans-product), 7.08 (m, 1H, 6-H of cis-product), 7.07 (m, 1H, 6-H of trans-product), 4.57 (d, J=5.8 Hz, 1H, CHOMe of trans-product), 4.45 (d, J=4.2 Hz, 1H, CHOMe of cis-product), 3.45 (m, 3H, OMe of cis-product), 3.40 (m, 3H, OMe of trans-product), 2.40-3.30 (m, 6H, CH$_2$ and CHMe of cis-products), 1.18 (m, 3H, CHMe of cis-product), 1.11 (m, 3H, CHMe of trans-product).

$^{13}$C{$^1$H} NMR (75 MHz, CDCl$_3$): δ 144.6, 144.1, 143.7, 143.4, 131.3, 131.2, 128.2, 127.8, 124.1, 123.9, 120.4 (two resonances), 91.9, 86.6, 56.9, 56.5, 39.7, 39.5, 39.0, 37.9, 19.2, 13.4.

N,N-bis(1-methoxy-2-methyl-2,3-dihydro-1H-inden-4-yl)-N-(4-methylphenyl)amine

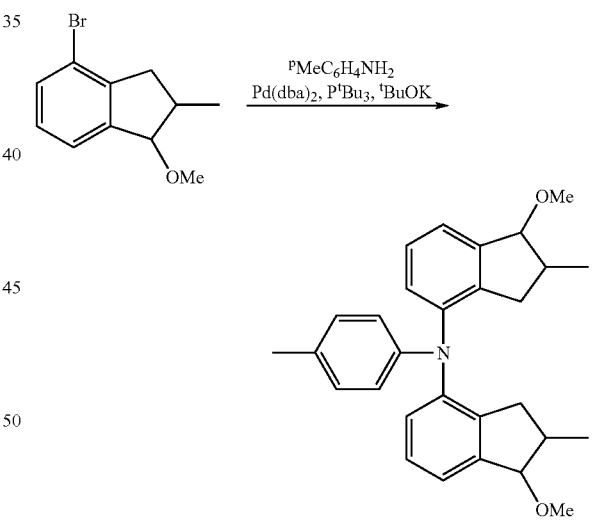

Under an argon atmosphere, a mixture of 12.1 g (50.0 mmol) of 4-bromo-1-methoxy-2-methylindane, 2.68 g (25.0 mmol) of para-toluidine, 16.8 g (150 mmol) of potassium tert-butoxide, 575 mg (1.0 mmol) of Pd(dba)$_2$, 404 mg (2.0 mmol) of tris(tert-butyl)phosphine, and 300 ml of toluene were refluxed for 9 hours. Then, this mixture was evaporated to dryness. The product was isolated using flash chromatography on Silica Gel 60 (40-63 μm, d 50 mm, 1500 mm; eluent: dichloromethane). Yield 7.92 g (74%) of yellow oil of a mixture of isomeric compounds.

Anal. calc. for $C_{29}H_{33}NO_2$: C, 81.46; H, 7.78. Found: C, 81.70; H, 7.97.

77

N,N-Bis(4-bromo-2-methyl-1H-inden-7-yl)-N-(4-methylphenyl)amine

78

4,4'-tolylazandiyl-bis($\eta^5$-7-bromo-2-methylindenyl)zirconium dichloride (12)

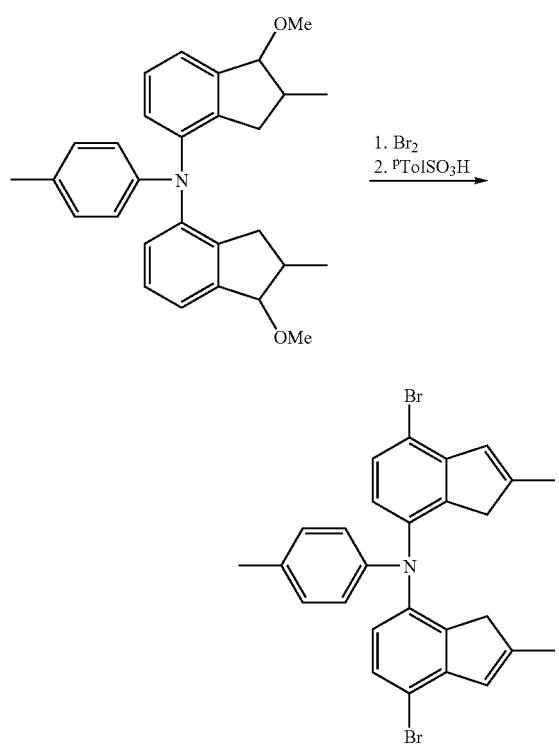

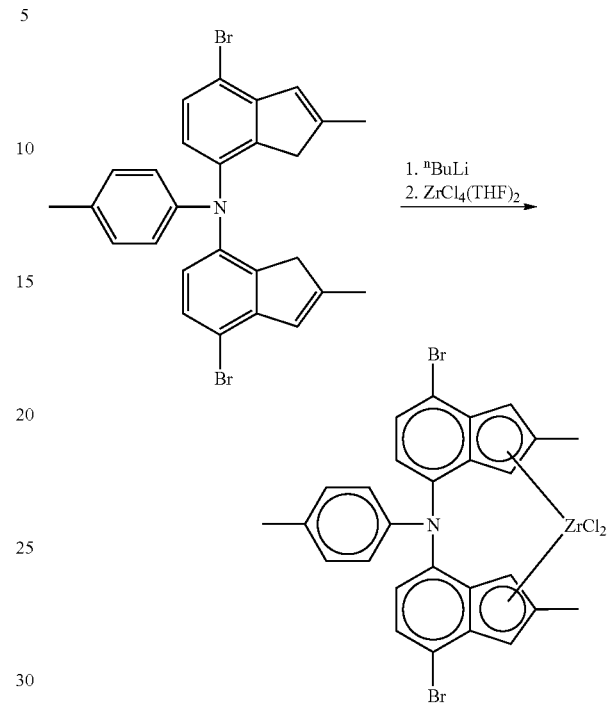

To a solution of 5.44 g (12.7 mmol) of N,N-bis(2-methyl-1H-inden-7-yl)-N-(4-methylphenyl)amine in 90 ml of dichloromethane, a solution of 1.31 ml (4.06 g, 25.4 mmol) of bromine in 30 ml of dichloromethane was added dropwise, while vigorously stirring, over 1.5 hour at 0° C. This mixture was stirred overnight at ambient temperature. Then, this mixture was washed with aqueous $Na_2SO_3$ to remove bromine traces. The organic layer was separated, dried over $Na_2SO_4$, and evaporated to dryness. To the oil obtained, 120 ml of toluene and 150 mg of para-toluenesulphonic acid were added. This mixture was refluxed for 5 hours. Each hour during this process a new portion of 150 mg of para-toluenesulphonic was added. The resulting mixture was passed through a short Silica Gel 60 column (40-63 μm, d 50 mm, l 40 mm). The Silica Gel layer was additionally eluted with 200 ml of methyl-tert-butyl ether. The combined solution was evaporated to dryness. The product was isolated using flash chromatography on Silica Gel 60 (40-63 μm, d 50 mm, l 70 mm; eluent: hexanes). Yield 4.70 g (71%). On the evidence of $^1$H NMR spectrum, the product consists of one major isomer (>80%) and two minor isomers.

Anal. calc. for $C_{27}H_{23}Br_2N$: C, 62.21; H, 4.45. Found: C, 62.01; H, 4.64.

$^1$H NMR ($CDCl_3$), major isomer: δ 7.09 (d, J=7.4 Hz, 2H, 5-H in indenyls), 6.96-7.03 (m, 2H, 2,6-H in phenyl), 6.73-6.80 (m, 2H, 3,5-H in phenyl), 6.65 (d, J=7.4 Hz, 2H, 6-H in indenyls), 6.51 (m, 3-H in indenyls), 2.76 (m, 4H, $CH_2$ in indenyls), 2.76 (s, 3H, 4-Me in phenyl), 2.03 (m, 6H, 2-Me in indenyls).

Under an argon atmosphere, to a solution of 3.97 g (7.62 mmol) of N,N-bis(4-bromo-2-methyl-1H-inden-7-yl)-N-(4-methylphenyl)amine in 150 ml of ether, 6.10 ml of 2.5 M (15.2 mmol) of $^n$BuLi in hexanes was added over 10 minutes at 0° C. This mixture was stirred for 2 hours at room temperature and then cooled to −80° C. Then, 2.87 g (7.62 mmol) of $ZrCl_4(THF)_2$ was added. The resulting mixture was stirred, slowly (over ca. 1 hour) heated to ambient temperature, and then further stirred for 24 hours. The resulting mixture was evaporated to dryness, and 100 ml of toluene was added. This mixture was heated to 80° C. and then filtered using a funnel with a glass frit (G4) and jacket. The filtrate was evaporated to dryness. The residue was recrystallized from 100 ml of a mixture of toluene and hexanes (1:2; vol.). Yield 1.76 g (34%) of yellow crystalline solid.

Anal. calc. for $C_{27}H_{21}Br_2Cl_2NZr$: C, 47.59; H, 3.11. Found: C, 47.55; H, 3.18.

EXAMPLE 13

Synthesis of 4,4'-oxadiyl-bis($\eta^5$-7-bromo-2-methylindenyl)zirconium dichloride (13)

1-Methoxy-2-methyl-4-indanol

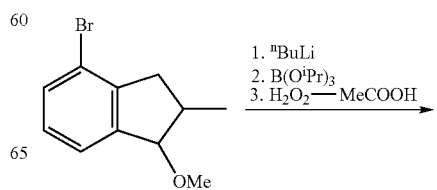

-continued

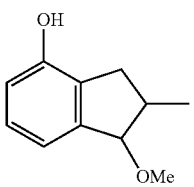

To a solution of 20.0 g (83.0 mmol) of 4-bromo-1-methoxyindane in 200 ml of THF, 33.2 ml of 2.5 M "BuLi (83.0 mmol) in hexanes was added with vigorous stirring over 1 hour at −78° C. under an argon atmosphere. Then, 28.7 ml (23.4 g, 124 mmol) of triisopropylborate was added at this temperature. The resulting mixture was slowly warmed to ambient temperature, and then 7.15 ml (7.50 g, 125 mmol) of glacial acetic acid was added. The resulting mixture was cooled to 0° C., and then 27.6 ml of 10% $H_2O_2$ was added. This mixture was stirred for ca. 30 minutes at room temperature, and then 300 ml of water was added. The product was extracted with 3×150 ml of $CH_2Cl_2$. The combined extract was dried over $Na_2SO_4$ and evaporated to dryness. The analytically pure product was obtained by flash chromatography on Silica Gel 60 (40-63 μm, d 50 mm, 1 350 mm, eluant: hexanes-ether=2:1, vol.). Yield, 9.90 g (67%).

Anal. calc. for $C_{11}H_{14}O_2$: C, 74.13; H, 7.92. Found: C, 74.26; H, 8.00.

$^1$H NMR (300 MHz, CDCl$_3$): δ 7.06 (m, 1H, 6-H), 6.96 (d, J=7.4 Hz, 1H, 5-H), 6.63 (dd, J=7.8 Hz, J=0.8 Hz, 1H, 7-H), 5.68 (br.s, 1H, OH), 4.53 (d, J=5.7 Hz, 1H, CHOMe), 3.42 (s, 3H, OMe), 2.81-2.89 (m, 1H, CHH'), 2.54-2.65 (m, 2H, CHH' and CHMe), 1.13 (d, J=6.8 Hz, 3H, CHMe).

$^{13}$C{$^1$H} NMR (75 MHz, CDCl$_3$): δ 152.3, 144.6, 129.0, 127.6, 117.5, 114.8, 86.3, 56.7, 38.7, 34.2, 13.6.

1-Methoxy-4-[(1-methoxy-2-methyl-2,3-dihydro-1H-inden-4-yl)oxy]-2-methylindane

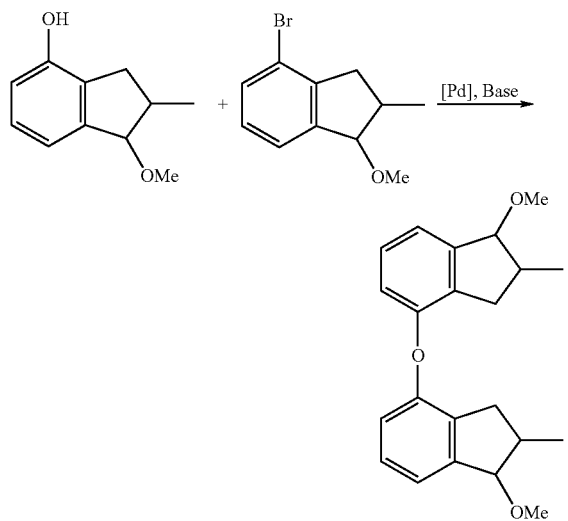

To a mixture of 14.6 g (60.5 mmol) of 4-bromo-1-methoxy-2-methylindane, 10.8 g (60.5 mmol) of 1-methoxy-2-methyl-4-indanol, 38.5 g (181 mmol) K$_3$PO$_4$, and 200 ml of toluene, a mixture of 696 mg (1.21 mmol) Pd(dba)$_2$ and 825 mg (2.42 mmol) of 2-di(tert-butyl)phosphino-2'-(N,N-dimethylamino)biphenyl was added under an argon atmosphere. This mixture was stirred for 14 hours at 100° C. Then, 300 ml of water was added. The organic layer was separated, and the aqueous layer was extracted with 3×100 ml of $CH_2Cl_2$. The combined extract was washed with 2×100 ml of water, dried over K$_2$CO$_3$, and evaporated to dryness. The analytically pure product was obtained using flash chromatography on Silica Gel 60 (40-63 μm, d 50 mm, 1 400 mm, eluant: hexanes-dichloromethane=1:1, vol.). Yield, 12.4 g (61%). On the evidence of NMR spectra, the product consists of a mixture of isomers.

Anal. calc. for $C_{22}H_{26}O_3$: C, 78.07; H, 7.74. Found: C, 77.99; H, 7.79.

$^1$H NMR (300 MHz, CDCl$_3$): δ 7.11-7.19 (m, 4H, 5,6-H), 6.69-6.76 (m, 2H, 7-H), 4.41-4.57 (m, 2H, CHOMe), 3.42-3.49 (m, 6H, OMe), 2.79-3.17 (m, 2H, CHH'), 2.44-2.67 (m, 4H, CHH' and CHMe), 1.06-1.18 (m, 6H, CHMe).

Bis(4-bromo-2-methyl-1H-inden-7-yl)ether

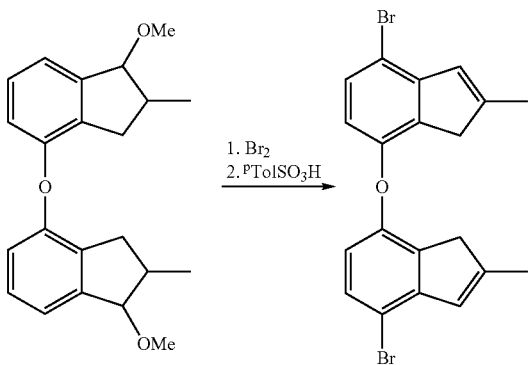

To a solution of 8.34 g (24.6 mmol) of bis(2-methyl-1H-inden-7-yl)ether in 90 ml of dichloromethane, a solution of 2.53 ml (7.86 g, 49.2 mmol) of bromine in 30 ml of dichloromethane was added dropwise, while vigorously stirring, over 1.5 hour at 0° C. This mixture was further stirred overnight at ambient temperature. Then, this mixture was washed by aqueous Na$_2$SO$_3$ to remove bromine traces. The organic layer was separated, dried over Na$_2$SO$_4$, and evaporated to dryness. To the oil obtained, 200 ml of toluene and 0.90 g of para-toluenesulphonic acid were added. This mixture was refluxed for 9 hours. Each hour during this process a new portion of 0.50 g of para-toluenesulphonic was added. The resulting mixture was passed through a short Silica Gel 60 column (40-63 μm, d 50 mm, 1 40 mm). The Silica Gel layer was additionally eluted with 400 ml of methyl-tert-butyl ether. The combined solution was evaporated to dryness. The product was isolated using flash chromatography on Silica Gel 60 (40-63 μm, d 65 mm, 1700 mm; eluent: hexanes). Yield 5.41 g (51%).

Anal. calc. for $C_{20}H_{16}Br_2O$: C, 55.59; H, 3.73. Found: C, 55.62; H, 3.81.

$^1$H NMR (CDCl$_3$): δ 7.25 (d, J=8.6 Hz, 2H, 5,5'-H), 6.56 (m, 2H, 3,3'-H), 6.51 (d, J=8.6 Hz, 2H, 6,6'-H), 3.31 (m, 4H, CH$_2$), 2.13 (m, 6H, 2,2'-Me).

4,4'-oxadiyl-bis($\eta^5$-7-bromo-2-methylindenyl)zirconium dichloride (13)

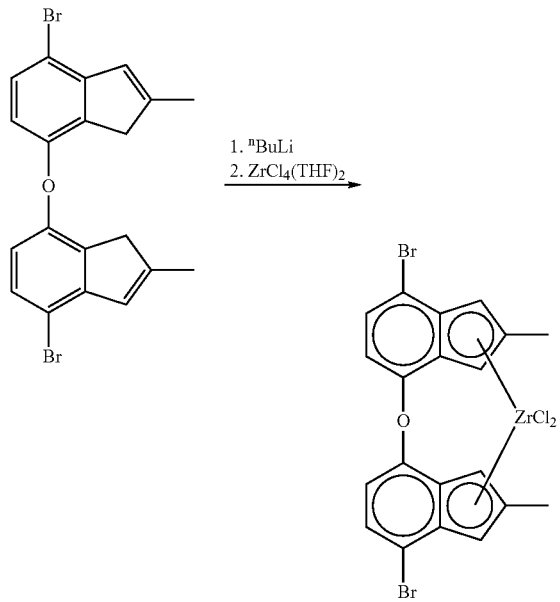

Under an argon atmosphere, to a solution of 3.02 g (6.99 mmol) of bis(4-bromo-2-methyl-1H-inden-7-yl)ether in 140 ml of ether, 5.59 ml of 2.5 M (14.0 mmol) of $^n$BuLi in hexanes was added over 10 minutes at 0° C. This mixture was stirred for 24 hours and then cooled to −80° C. Then, 2.64 g (6.99 mmol) of ZrCl$_4$(THF)$_2$ was added. The resulting mixture was stirred, slowly (over ca. 1 hour) heated to ambient temperature, and then further stirred for 24 hours at this temperature. The resulting mixture was evaporated to dryness, and 100 ml of toluene was added. This mixture was heated to 80° C. and then filtered using a funnel with a glass frit (G4) and jacket. The precipitate was washed with 2×50 ml of hot toluene. The combined toluene filtrate was evaporated to 100 ml. Crystals that precipitated at −30° C. were collected, washed with 2×20 ml of hexanes, and dried in vacuum. Yield 1.44 g (35%) of yellow crystalline solid.

Anal. calc. for C$_{20}$H$_{14}$Br$_2$Cl$_2$OZr: C, 40.56; H, 2.38. Found: C, 40.63; H, 2.41.

$^1$H NMR (CD$_2$Cl$_2$): δ 7.45 (d, J=7.6 Hz, 2H, 6,6'-H), 7.12 (d, J=7.6 Hz, 2H, 5,5'-H), 6.54 (s, 2H, 1,1'-H), 4.46 (s, 2H, 3,3'-H), 2.13 (s, 6H, 2,2'-Me).

EXAMPLE 14

Synthesis of rac-[dimethylsilyl-bis($\eta^5$-5-bromo-2-methyl-6,7,8,9-tetrahydro-3H-cyclopenta[a]naphthalen-3-yl)](N$^1$,N$^3$-diphenyl-1,3-propanediamido) zirconium (14)

2-Methyl-1,2,6,7,8,9-hexahydro-3H-cyclopenta[a]naphthalen-3-one and 2-methyl-2,3,5,6,7,8-hexahydro-1H-cyclopenta[b]naphthalen-1-one

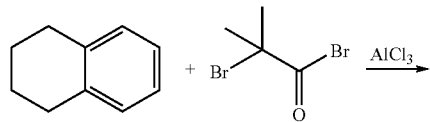

-continued

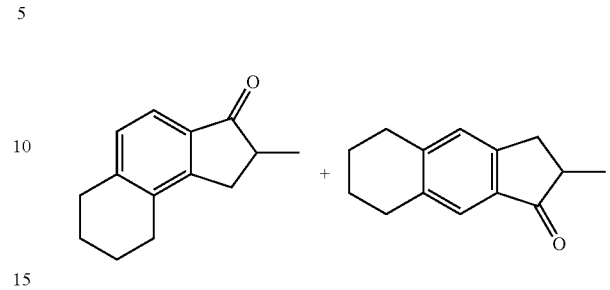

A total of 145 g (0.63 mol) of 2-bromo-2-methylpropanoyl bromide were added dropwise to a suspension of 223 g (1.67 mol) AlCl$_3$ in 200 ml of CH$_2$Cl$_2$ with vigorous stirring for 15 min at 0° C. This mixture was stirred for 45 min at this temperature; then a solution of 83.4 g (0.63 mol) of tetraline in 200 ml of CH$_2$Cl$_2$ was added dropwise. The mixture was slowly warmed to ambient temperature, stirred additionally overnight, and, then, poured on 1000 cm$^3$ of ice. The organic layer was separated, the aqueous layer was extracted with 3×300 ml of CH$_2$Cl$_2$. The combined organic fractions were dried over MgSO$_4$ and evaporated to dryness. Fractional distillation gave a yellowish mixture of the title indanones, b.p. 183-190° C./7 mm Hg. This mixture was recrystallized from 300 ml of n-hexane. Crystals of 2-methyl-1,2,6,7,8,9-hexahydro-3H-cyclopenta[a]naphthalen-3-one that precipitated at −30° C. were filtered off, washed with 2×25 ml of cold n-hexane, and dried in vacuum. Yield 56.5 g (45%). The filtrate was evaporated to dryness and dried in vacuum. This procedure gave 39.3 g (31%) of pure 2-methyl-2,3,5,6,7,8-hexahydro-1H-cyclopenta[b]naphthalen-1-one.

2-Methyl-1,2,6,7,8,9-hexahydro-3H-cyclopenta[a]naphthalen-3-one.

Anal. calc. for C$_{14}$H$_{16}$O: C, 83.96; H, 8.05. Found: C, 83.79; H, 8.16.

$^1$H NMR (CDCl$_3$): δ 7.46 (d, J=7.9 Hz, 1H, 9-H), 7.06 (d, J=7.9 Hz, 1H, 8-H), 3.18 (dd, J=17.3 Hz, J=7.9 Hz, 1H, 3-H), 2.81 (m, 2H, 7,7'-H), 2.66 (m, 3H, 2,4,4'-H), 2.48 (dd, J=17.3 Hz, J=3.5 Hz, 1H, 3'-H), 1.83 (m, 4H, 5,5',6,6'-H), 1.28 (d, J=7.3 Hz, 3H, 2-Me).

$^{13}$C NMR (CDCl$_3$): δ 209.3, 153.1, 144.4, 134.4, 133.7, 128.8, 120.5, 41.9, 33.4, 30.1, 25.4, 22.6, 22.5, 16.5.

2-Methyl-2,3,5,6,7,8-hexahydro-1H-cyclopenta[b]naphthalen-1-one.

Anal. calc. for C$_{14}$H$_{16}$O: C, 83.96; H, 8.05. Found: C, 84.20; H, 8.14.

$^1$H NMR (CDCl$_3$): δ 7.42 (s, 1H, 9-H), 7.09 (s, 1H, 4-H), 3.26 (dd, J=16.7 Hz, J=7.6 Hz, 1H, 3-H), 2.78 (m, 3H, 2,8,8'-H), 2.63 (m, 2H, 5,5'-H), 2.59 (dd, J=16.7 Hz, J=3.8 Hz, 1H, 3'-H), 1.77 (m, 4H, 6,6',7,7'-H), 1.25 (d, J=7.3 Hz, 2-Me).

$^{13}$C NMR (CDCl$_3$): δ 209.0, 150.3, 145.2, 136.6, 133.9, 126.5, 123.8, 42.0, 34.3, 30.2, 29.2, 22.8, 22.7, 16.3.

5-Bromo-2-methyl-1,2,6,7,8,9-hexahydro-3H-cyclopenta[a]naphthalen-3-one

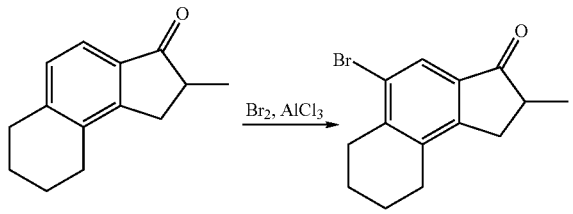

In a three-necked round-bottom 500 ml flask equipped with a reflux condenser, dropping funnel with pressure-equalizing, and mechanical stirrer a solution of 55.0 g (0.275 mol) of 2-methyl-1,2,6,7,8,9-hexahydro-3H-cyclopenta[a]naphthalen-3-one in 50 ml of $CH_2Cl_2$ was added dropwise with vigorous stirring for 1 h at −10° C. to a suspension of 92 g (0.69 mol) of $AlCl_3$ in 100 ml of $CH_2Cl_2$. This mixture was stirred additionally for 1 h at this temperature; then 14.2 ml (44.0 g, 0.275 mol) of bromine was added dropwise with vigorous stirring for 1 h. The resulting mixture was stirred for 2 h at −10° C. and then overnight at ambient temperature, and, then, it was poured on 1000 cm³ of cold water. The organic layer was separated, the aqueous layer was extracted with 3×200 ml of methyl-tert-butyl ether. The combined extract was washed with saturated aqueous $Na_2SO_3$ to eliminate bromine and with aqueous $Na_2CO_3$. It was then dried over $K_2CO_3$, and evaporated to dryness. Fractional distillation gave a yellowish liquid, b.p. 195-198° C./4 mm Hg. Yield 58.3 g (76%).

Anal. calc. for $C_{14}H_{15}BrO$: C, 60.23; H, 5.42. Found: C, 60.41; H, 5.56.

$^1$H NMR ($CDCl_3$): δ 7.75 (s, 1H, 9-H), 3.17 (dd, J=17.4 Hz, J=7.8 Hz, 1H, 3-H), 2.79 (m, 2H, 7,7'-H), 2.69 (m, 3H, 2,4, 4'-H), 2.47 (dd, J=17.4 Hz, J=3.7 Hz, 1H, 3'-H), 1.84 (m, 4H, 5,5',6,6'-H), 1.30 (d, J=7.6 Hz, 3H, 2-Me).

5-Bromo-2-methyl-2,3,6,7,8,9-hexahydro-1H-cyclopenta[a]naphthalen-3-ol and 5-bromo-2-methyl-6,7,8,9-tetrahydro-1H-cyclopenta[a]naphthalene

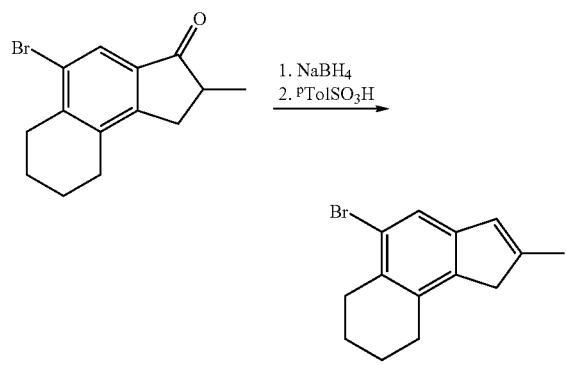

A total of 9.40 g (0.246 mol) of $NaBH_4$ were added for 1 h at −5° C. (Caution: temperature must be lower 0° C.) to a solution of 49.2 g (0.176 mol) of 5-bromo-2-methyl-1,2,6,7,8,9-hexahydro-3H-cyclopenta[a]naphthalen-3-one in 225 ml of THF-methanol (2:1, vol.). The mixture was stirred overnight at ambient temperature. The resulting mixture was poured on 500 cm³ of ice and acidified with 1 M HCl to pH=4. The organic layer was separated, the aqueous layer was extracted with 3×200 ml of methyl-tert-butyl ether. The combined extract was dried over $K_2CO_3$ and evaporated to dryness. To the yellowish oil obtained 1000 ml of toluene were added. This toluene solution was treated with a catalytic amount of $^p$TolSO$_3$H (ca. 0.5 g) for 2 h at reflux. It was then cooled to room temperature and evaporated to dryness. The crude product was purified using flash chromatography on Silica Gel 60 (40-63 μm, d 50 mm, 1 400 mm; eluent: hexanes). Yield 42.3 g (92%) of white crystalline product.

Anal. calc. for $C_{14}H_{15}Br$: C, 63.89; H, 5.74. Found: C, 63.64; H, 5.65.

$^1$H NMR ($CDCl_3$): δ 7.37 (s, 1H, 4-H), 6.43 (m, 1H, 3-H), 3.10 (s, 2H, 1,1'-H), 2.84 (m, 2H, 6,6'-H), 2.73 (m, 2H, 9,9'-H), 2.22 (s, 3H, 2-Me), 1.88 (m, 4H, 7,7',8,8'-H).

$^{13}$C NMR ($CDCl_3$): δ 146.5, 144.7, 141.3, 134.4, 131.4, 126.8, 124.2, 121.8, 41.6, 30.8, 27.7, 24.0, 23.1, 17.3.

Mixture of rac- and meso-bis($\eta^5$-5-bromo-2-methyl-6,7,8,9-tetrahydro-3H-cyclopenta[a]naphthalen-3-yl)(dimethyl)silanes

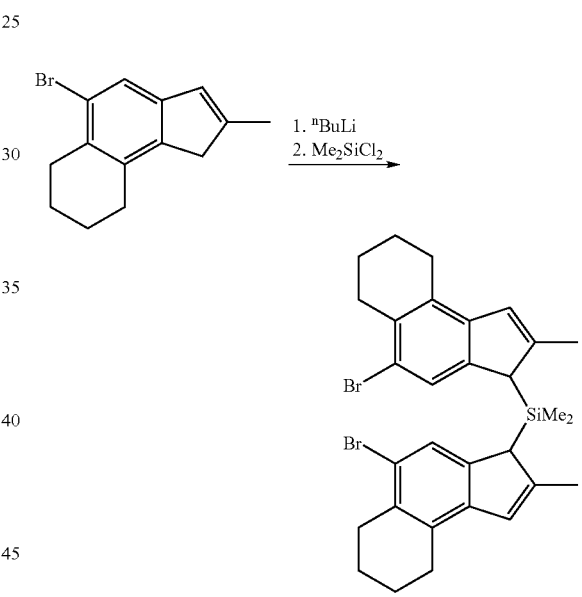

In an argon atmosphere, 40.0 ml of 2.50 M $^n$BuLi (100 mmol) in hexanes were added dropwise at 0° C. to a solution of 26.3 g (100 mmol) of 5-bromo-2-methyl-6,7,8,9-tetrahydro-1H-cyclopenta[a]naphthalene in 800 ml of diethyl ether. This mixture was stirred additionally for 5 h at 20° C. and, then, cooled to 0° C. At this temperature, 6.06 ml (6.45 g, 50 mmol) of $Me_2SiCl_2$ were added. The resulting mixture was stirred overnight at ambient temperature and, then, filtered through a glass frit (G4). The filtrate was evaporated to dryness. The residue was recrystallized from 150 ml of hot acetone. White crystalline material that precipitated at 0° C. was filtered off, washed with 20 ml of cold acetone, and dried in vacuum. Yield 15.2 g (52%).

Anal. calc. for $C_{30}H_{34}Br_2Si$: C, 61.86; H, 5.88. Found: C, 62.07; H, 5.96.

$^1$H NMR ($CDCl_3$): rac-compound, δ 7.27 (s, 2H, 9,9'-H), 6.57 (m, 2H, 3,3'-H), 3.51 (m, 2H, 1,1'-H), 2.81 (m, 4H, 4,4'-$CH_2$), 2.75 (m, 4H, 7,7'-$CH_2$), 2.15 (s, 6H, 2,2'-Me), 1.81 (m, 8H, 5,5',6,6'-$CH_2$), −0.23 (s, 6H, $SiMe_2$); meso-compound, δ 7.33 (s, 2H, 9,9'-H), 6.59 (m, 2H, 3,3'-H), 3.51 (m, 2H, 1,1'-H), 2.83 (m, 4H, 4,4'-CH$_2$), 2.77 (m, 4H, 7,7'-CH$_2$), 2.21 (s, 6H, 2,2'-Me), 1.83 (m, 8H, 5,5',6,6'-CH$_2$), −0.17 (s, 3H, SiMe), −0.27 (s, 3H, SiMe').

$^{13}$C NMR (CDCl$_3$): δ 147.0, 146.9, 143.3, 143.2, 142.9 (two resonances), 132.6, 132.5, 130.4, 130.3, 124.4 (two resonances), 124.3 (two resonances), 120.7, 120.5, 47.0 (two resonances), 30.4, 30.3, 27.2 (two resonances), 23.4 (two resonances), 22.7 (two resonances), 18.0 (two resonances), −4.9, −5.2, −5.5.

Rac-[dimethylsilyl-bis(η$^5$-5-bromo-2-methyl-6,7,8,9-tetrahydro-3H-cyclopenta[a]naphthalen-3-yl)](N$^1$,N$^3$-diphenyl-1,3-propanediamido)zirconium (14)

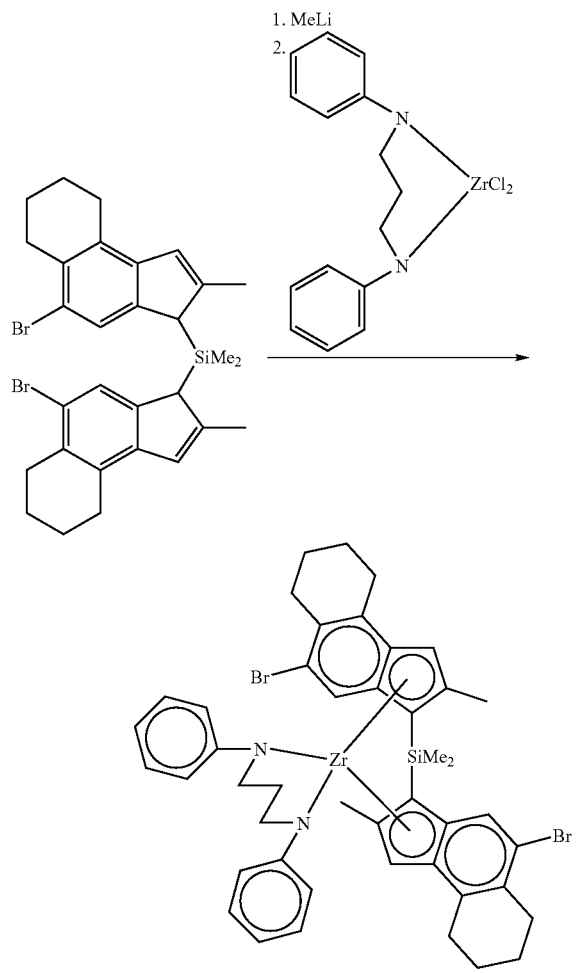

In the Glove Box, 8.0 ml of 1.88 M MeLi (15.1 mmol) in ether were added at room temperature to a solution of 4.39 g (7.53 mmol) of bis(5-bromo-2-methyl-6,7,8,9-tetrahydro-3H-cyclopenta[a]naphthalen-3-yl)(dimethyl) silane in 350 ml of diethyl ether. This mixture was stirred for 2 h at 20° C. To the solution obtained 4.00 g (7.53 mmol) of (N$^1$,N$^3$-diphenyl-1,3-propanediamido)bis-(tetrahydrofurano)zirconium dichloride were added at −80° C. The resulting mixture was stirred for 24 h at ambient temperature and, then, evaporated to dryness. The residue was treated with 300 ml of toluene. This toluene solution was filtered through Celite 503. The filtrate was evaporated to dryness. The crude product was washed with 4×100 ml of hexanes and dried in vacuum. This procedure gave 5.46 g (81%) of orange crystalline product.

Anal. calc. for C$_{45}$H$_{48}$Br$_2$N$_2$SiZr: C, 60.32; H, 5.40. Found: C, 60.74; H, 5.53.

$^1$H NMR (CD$_2$Cl$_2$): δ 7.92 (s, 2H, 9,9'-H in indenyl), 7.19 (m, 4H, 3,3',5,5'-H in N—C$_6$H$_5$), 6.89 (m, 2H, 4,4'-H in N—C$_6$H$_5$), 6.44 (m, 4H, 2,2',6,6'-H in N—C$_6$H$_5$), 6.02 (s, 2H, 3,3'-H in indenyl), 3.44 (dt, J=14.9 Hz, J=8.2 Hz, 2H, 1,3-H in propylidene), 2.85 (dt, J=14.9 Hz, J=3.2 Hz, 2H, 1',3'-H in propylidene), 2.35-2.82 (m, 8H, 4,4',7,7'-CH$_2$ in indenyl), 1.70 and 1.26 (two multiplets, 10H, 5,5',6,6'-CH$_2$ in indenyl and 2,2'-H in propylidene), 2.00 (s, 6H, 2,2'-Me in indenyl), 1.11 (s, 6H, SiMe$_2$).

$^{13}$C NMR (CD$_2$Cl$_2$): δ 163.0, 135.1, 133.0, 131.8, 130.7, 129.8, 128.1, 126.3 (two resonances), 125.9, 125.8, 123.1, 115.5, 59.6, 31.7, 30.1, 24.8, 24.3, 23.8, 20.0, 3.6.

EXAMPLE 15

Synthesis of rac-[dimethylsilyl-bis(η$^5$-5-bromo-2-methyl-6,7,8,9-tetrahydro-3H-cyclopenta[a]naphthalen-3-yl)]zirconium dichloride (15)

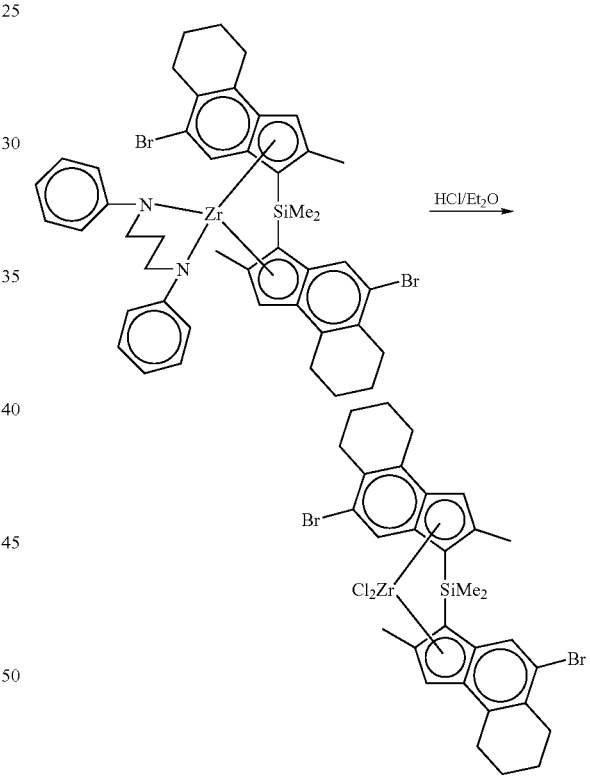

In the Glove Box, 10.1 ml of cold 1.0 M solution of HCl in ether were added dropwise at −110° C. to a solution of 5.00 g (5.50 mmol) of rac-[dimethylsilyl-bis(5-bromo-2-methyl-6,7,8,9-tetrahydro-3H-cyclopenta[a]naphthalene-3-yl)](N$^1$,N$^3$-diphenyl-1,3-propanediamido)zirconium in 320 ml of diethyl ether-CH$_2$Cl$_2$ (1:1, vol.). This mixture was stirred and slowly warmed during ca. 7 h to ambient temperature and, then, evaporated to dryness. The residue was washed with 4×20 ml of CH$_2$Cl$_2$ and dried in vacuum. Yield 1.89 g (46%) of yellow crystalline product.

Anal. calc. for C$_{30}$H$_{32}$Br$_2$Cl$_2$SiZr: C, 48.52; H, 4.34. Found: C, 48.80; H, 4.47.

$^1$H NMR (CD$_2$Cl$_2$): δ 7.69 (s, 2H, 9,9'-H), 6.66 (s, 2H, 3,3'-H), 3.53 (m, 4H, 4,4'- or 7,7'-CH$_2$), 2.71 (m, 4H, 7,7'- or 4,4'-CH$_2$), 2.09 (s, 6H, 2,2'-Me), 1.77 (m, 8H, 5,5',6,6'-CH$_2$), 1.23 (s, 6H, SiMe$_2$).

EXAMPLE 16

Synthesis of rac-diethylsilyl-bis(η$^5$-5-bromo-2-methyl-6,7,8,9-tetrahydro-3H-cyclopenta[a]naphthalen-3-yl)zirconium dichloride (16)

Bis(5-bromo-2-methyl-6,7,8,9-tetrahydro-3H-cyclopenta[a]naphthalen-3-yl)diethylsilane

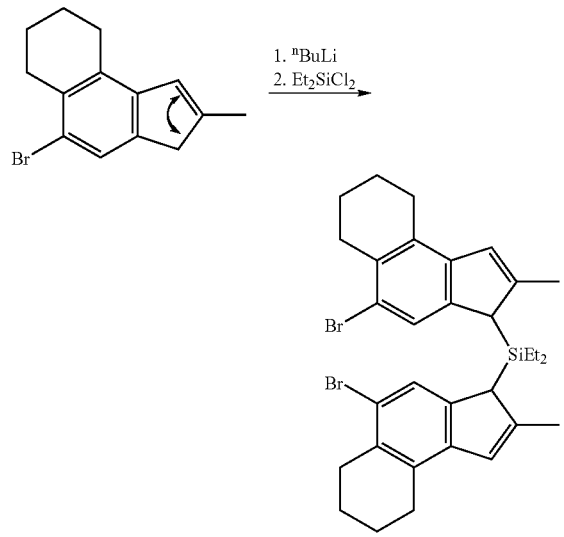

To a solution of 14.0 g (53.2 mmol) of a mixture of 5-bromo-2-methyl-6,7,8,9-tetrahydro-1(3)H-cyclopenta[a]naphthalenes in 500 ml of ether, 143 mg (1.60 mmol) of CuCN was added. The mixture was cooled to −20° C., and 23.4 ml (58.5 mmol) of 2.5 M $^n$BuLi in hexanes was added while vigorously stirring. Next, the resulting mixture was allowed to warm to room temperature, and a solution of 4.60 g (29.3 mmol) of Et$_2$SiCl$_2$ in 100 ml of THF was added dropwise over 20 min. The mixture was stirred for 36 h, and then 100 ml of water was added. The organic layer was separated, the aqueous layer was extracted with 3×100 ml of ether. The combined organic fractions were dried over K$_2$CO$_3$ and then evaporated to dryness. The product was isolated by flash chromatography on Silica Gel 60 (40-63 um, d 50 mm, l 300 mm, eluent—hexanes). Yield 7.10 g (44%) of pure racemic product.

Anal. calc. for C$_{32}$H$_{38}$Br$_2$Si: C, 62.95; H, 6.27. Found: C, 63.09; H, 6.40.

$^1$H NMR (CDCl$_3$): rac-compound, δ 6.94 (s, 2H, 9,9'-H), 6.44 (m, 2H, 3,3'-H), 3.28 (m, 2H, 1,1'-H), 2.76 (m, 8H, 4,4',7,7'-CH$_2$), 2.11 (m, 6H, 2,2'-Me), 1.81 (m, 8H, 5,5',6,6'-CH$_2$), 0.67-0.90 (m, 10H, SiEt$_2$); meso-compound, δ 7.28 (s, 2H, 9,9'-H), 6.49 (m, 2H, 3,3'-H), 3.24 (m, 2H, 1,1'-H), 2.76 (m, 8H, 4,4',7,7'-CH$_2$), 2.07 (m, 6H, 2,2'-Me), 1.81 (m, 8H, 5,5',6,6'-CH$_2$), 0.67-0.90 (m, 10H, SiEt$_2$).

Rac-[diethylsilyl-bis(η$^5$-5-bromo-2-methyl-6,7,8,9-tetrahydrocyclopenta[a]naphthyl)](N$^1$,N$^3$-diphenyl-1,3-propanediamido)zirconium

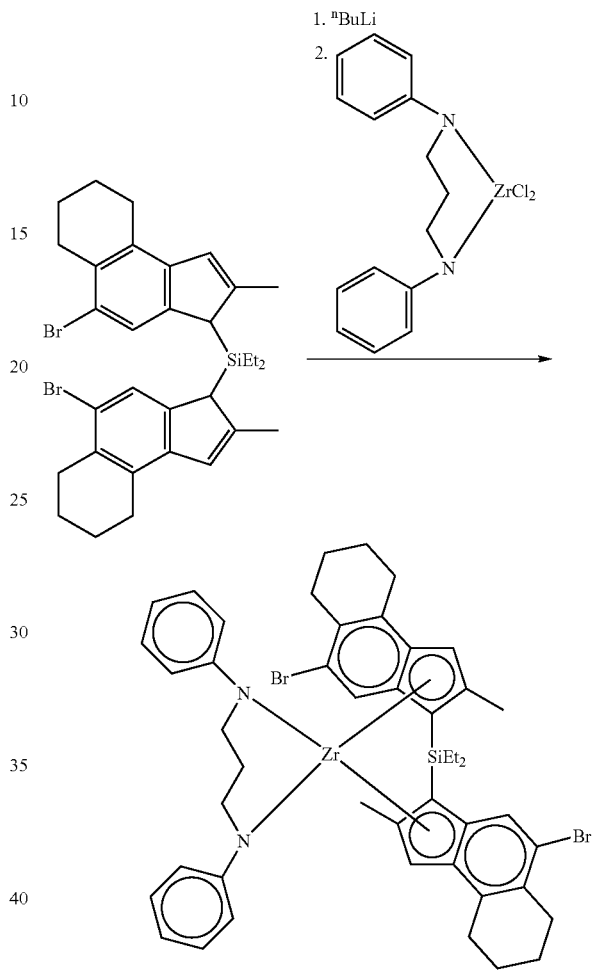

In the Glove Box, to a solution of 5.00 g (8.19 mmol) of bis(5-bromo-2-methyl-6,7,8,9-tetrahydro-3H-cyclopenta[a]naphthalen-3-yl)(diethyl)silane in 250 ml of diethyl ether, 6.55 ml (63.3 mmol) of 2.5 M $^n$BuLi in hexanes was added at room temperature. This mixture was stirred for 3 h at 20° C. To the solution obtained, 4.34 g (8.19 mmol) of (N$^1$,N$^3$-diphenyl-1,3-propanediamido)bis(tetrahydrofurano)zirconium dichloride was added at −80° C. The resulting mixture was stirred for 48 h at ambient temperature and, then, evaporated to dryness. The residue was treated with 200 ml of toluene. This toluene solution was filtered through Celite 503. The filtrate was evaporated to dryness. The crude product was recrystallized from 20 ml of warm dichloromethane. Crystals that precipitated at room temperature were collected, washed with 5 ml of cold dichloromethane, and dried in vacuum. Yield 2.72 g (36%) of orange crystalline product.

Anal. calc. for C$_{47}$H$_{52}$Br$_2$N$_2$SiZr: C, 61.09; H, 5.67. Found: C, 60.87; H, 5.43.

$^1$H NMR (CD$_2$Cl$_2$): δ 7.92 (s, 2H, 9,9'-H in indenyl), 7.22 (m, 4H, 3,3',5,5'-H in Ph), 6.93(m, 2H, 4,4'-H in Ph), 6.47 (m, 4H, 2,2',6,6'-H in Ph), 6.07 (m, 2H, 3,3'-H in indenyl), 3.47 (dt, J=14.7 Hz, J=8.5 Hz, 2H, 1,3-H in propylidene), 2.84-2.90 (m, 4H, 7,7'-CH$_2$ in indenyl), 2.72-2.80 (m, 2H, 1',3'-H in propylidene), 2.60-2.66 (m, 2H, 4 or 4'-CH$_2$ in indenyl), 2.42-2.50 (m, 2H, 4' or 4-CH$_2$ in indenyl), 2.02 (s, 6H, 2,2'-Me), 1.63-1.72 (m, 14H, 5,5',6,6'-CH$_2$ in indenyl and Si(CH$_2$CH$_3$)$_2$), 1.32 (t, J=7.8 Hz, 6H, Si(CH$_2$CH$_3$)$_2$).

Rac-diethylsilyl-bis($\eta^5$-5-bromo-2-methyl-6,7,8 9-tetrahydro-3H-cyclopenta[a]naphthalen-3-yl)zirconium dichloride (16)

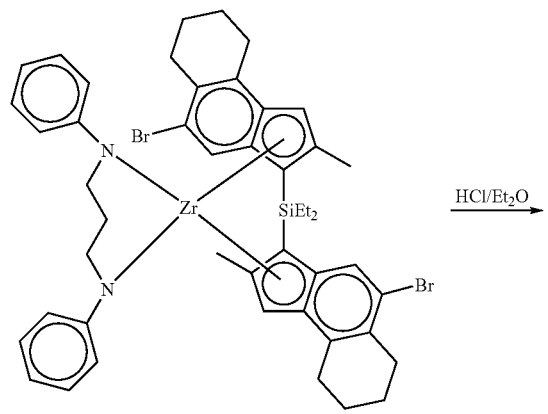

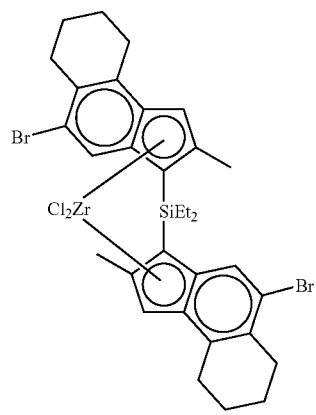

In the Glove Box, to a solution of 1.45 g (1.67 mmol) of rac-[diethylsilyl-bis($\eta^5$-5-bromo-2-methyl-6,7,8,9-tetrahydrocyclopenta[a]naphthyl)](N$^1$,N$^3$-diphenyl-1,3-propanediamido)zirconium in 100 ml of diethyl ether-CH$_2$Cl$_2$ (1:1, vol.), 3.50 ml of cold 1.0 M solution of HCl in ether was added at −80° C. This mixture was stirred and slowly warmed to ca. −10° C. during ca. 5 h and then evaporated (at this temperature) to dryness. The residue was washed with 6×15 ml of hot toluene. The combined washings were evaporated to dryness, and the residue was washed with 3×15 ml of hexanes and dried in vacuum. Yield 489 mg (38%) of yellow solid.

Anal. calc. for C$_{32}$H$_{36}$Br$_2$Cl$_2$SiZr: C, 49.87; H, 4.71. Found: C, 50.01; H, 4.85.

H NMR (C$_6$D$_6$): δ 7.87 (s, 2H, 9,9'-H), 6.63 (s, 2H, 3,3'-H), 2.94 (m, 2H, 4 or 7-CH$_2$), 2.69 (m, 4H, 7 or 4-CH$_2$ and 4' or 7'-CH$_2$), 2.38 (m, 2H, 7' or 4'-CH$_2$) 2.12 (s, 6H, 2,2'-Me), 1.43-1.72 (m, 12H, SiCH$_2$Me$_2$ and 5,5',6,6'-CH$_2$) 1.11 (t, J=7.8 Hz, 6H, SiCH$_2$Me$_2$).

EXAMPLE 17

Synthesis of rac-[diethylsilyl-bis($\eta^5$-4-bromo-2-methylinden-1-yl)](N$^1$,N$^3$-diphenyl-1,3-propanediamido)zirconium (17)

Mixture of rac- and meso-bis(4-bromo-2-methyl-1H-inden-1-yl)(diethyl)silanes

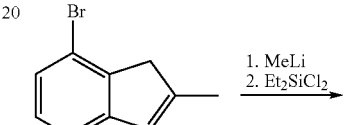

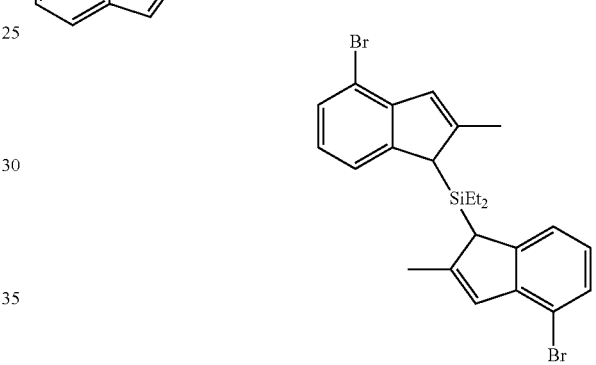

In an argon atmosphere, 22.0 ml of 2.18 M MeLi (48.0 mmol) in ether were added at room temperature to a solution of 10.0 g (47.8 mmol) of 2-methyl-7-bromoindene (see Example 2) in 200 ml of diethyl ether. This mixture was stirred for 2 h at 20° C. and, then, cooled to 5° C. At this temperature, 3.60 ml (4.55 g, 23.9 mmol) of Et$_2$SiCl$_2$ were added. The resulting mixture was stirred for 3 days at ambient temperature; then 100 ml of water were added. The organic layer was separated, dried over K$_2$CO$_3$, and evaporated to dryness. The crude product was purified by MPHPLC on SilicaGel 60 (40-63 μm; d 40 mm, l 400 mm; eluent: hexanes, 70 ml/min). Yield 6.10 g (50%) of yellowish oil of ca. 1 to 1 mixture of rac- and meso-compounds.

Anal. calc. for C$_{24}$H$_{26}$Br$_2$Si: C, 57.38; H, 5.22. Found: C, 57.60; H, 5.32.

$^1$H NMR (CDCl$_3$): δ 7.24-7.36 (m, 4H, 5,5'-H in rac- and meso-compounds), 7.07-7.20 (m, 4H, 7,7'-H in rac- and meso-compounds), 6.90 (t, J=7.6 Hz, 2H, 6,6'-H in rac- or meso-compound), 6.85 (t, J=7.7 Hz, 2H, 6,6'-H in meso- or rac-compound), 6.62 (m, 2H, 3,3'-H in rac- or meso-compound), 6.56 (m, 3,3'-H in meso-or rac-compound), 3.52 (m, 2H, 1,1'-H in rac- or meso-compound), 3.47 (m, 2H, 1,1'-H in meso-or rac-compound), 2.07 (m, 6H, 2,2'-Me in rac- or meso-compound), 2.01 (m, 6H, 2,2'-Me in meso-or rac-compound), 1.02-0.62 (m, 20H, SiEt$_2$ in rac- and meso-compounds).

$^{13}$C NMR (CDCl$_3$): δ 148.7, 148.5, 146.2, 146.1, 128.3 (two resonances), 128.2, 128.1, 126.7, 126.6 (two resonances), 125.5, 123.9, 123.8, 121.9, 121.8, 48.7, 48.4, 46.3, 46.2, 17.7, 17.5, 7.2, 3.5.

Rac-[diethylsilyl-bis($\eta^5$-4-bromo-2-methylinden-1-yl)]($N^1$,$N^3$-diphenyl-1,3-propanediamido)zirconium (17)

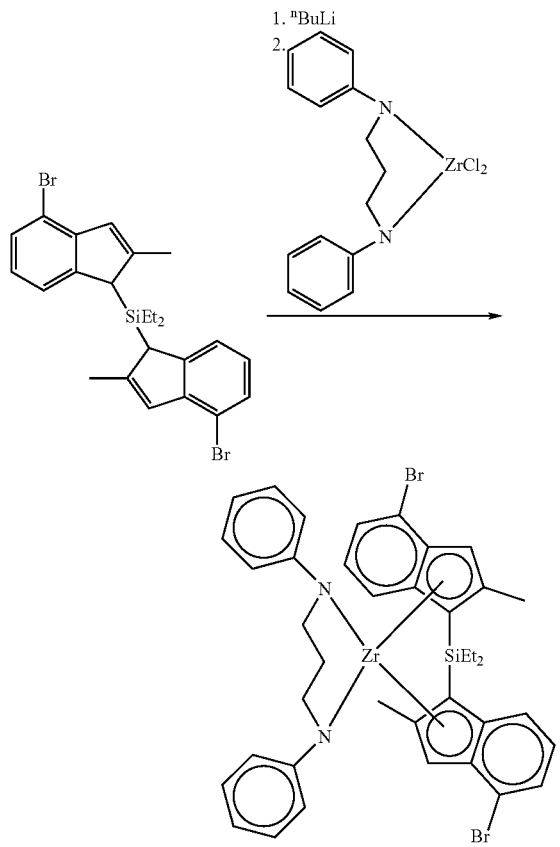

In the Glove Box, 7.00 ml of 2.5 M $^n$BuLi (17.5 mmol) in hexanes were added at room temperature to a solution of 4.40 g (8.80 mmol) of bis(4-bromo-2-methyl-1H-inden-1-yl)(diethyl)silane in 600 ml of diethyl ether. This mixture was stirred for 24 h at 20° C. To the solution obtained 4.67 g (8.80 mmol) of ($N^1$,$N^3$-diphenyl-1,3-propanediamido)bis(tetrahydrofurano)zirconium dichloride were added at −80° C. The resulting mixture was stirred for 24 h at ambient temperature and, then, evaporated to dryness. The residue was treated with 200 ml of toluene. This toluene solution was filtered through Celite 503. The filtrate was evaporated to dryness. The crude product was washed with 3×70 ml of hexanes and dried in vacuum. This procedure gave 4.11 g (57%) of orange crystalline product.

Anal. calc. for $C_{39}H_{40}Br_2N_2SiZr$: C, 57.41; H, 4.94. Found: C, 57.83; H, 5.09.

$^1$H NMR (CD$_2$Cl$_2$): δ 7.82 (d, J=8.4 Hz, 2H, 5,5'-H), 7.12-7.20 (m, 8H, 2,2',3,3',5,5',6,6'-H in N—C$_6$H$_5$), 7.02 (t, J=7.9 Hz, 2H, 6,6'-H), 6.92 (t, J=7.3 Hz, 2H, 4,4'-H in N—C$_6$H$_5$), 6.49 (d, J=7.7 Hz, 2H, 7,7'-H), 6.24 (s, 2H, 3,3'-H), 3.90 (dt, J=15.0 Hz, J=8.4 Hz, 2H, 1,3-H in propylidene), 2.95 (dt, J=15.0 Hz, J=2.7 Hz, 2H, 1',3'-H in propylidene), 1.98 (s, 6H, 2,2'-Me), 1.75 (m, 2H, 2,2'-H in propylidene), 1.22-1.37 (m, 10H, SiEt$_2$).

$^{13}$C NMR (CD$_2$Cl$_2$): δ 162.7, 134.1, 131.2, 130.9, 129.6, 128.2, 126.3, 126.0, 125.3, 125.1, 123.6, 120.1, 118.9, 60.2, 23.2, 20.0, 8.1, 6.8.

EXAMPLE 18

Synthesis of rac-diethylsilyl-bis($\eta^5$-4-bromo-2-methylinden-1-yl)zirconium dichloride (18)

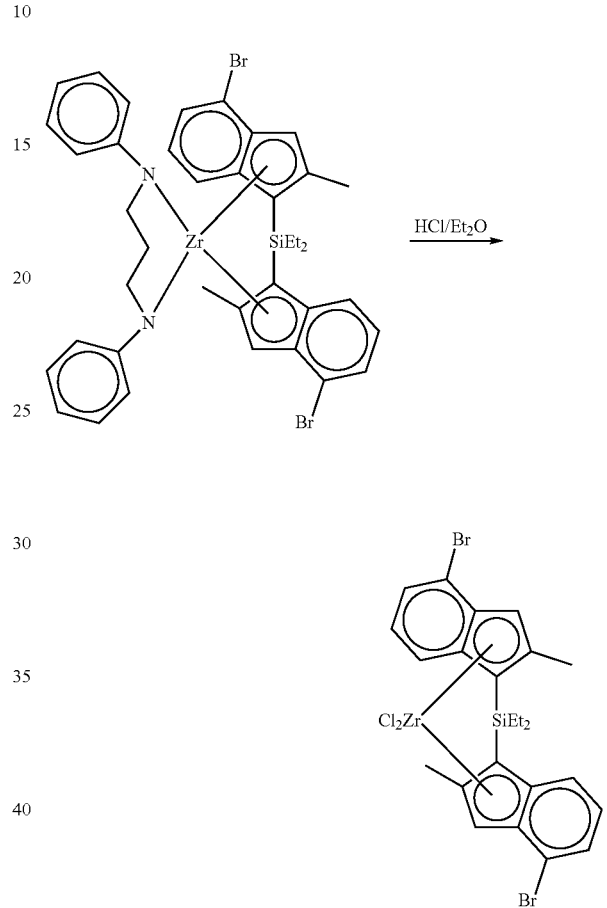

In the Glove Box, 2.20 ml of cold 1.0 M solution of HCl in ether were added at −110° C. to a solution of 1.00 g (1.23 mmol) of rac-[diethylsilyl-bis(4-bromo-2-methylinden-1-yl)]($N^1$,$N^3$-diphenyl-1,3-propanediamido)zirconium in 80 ml of diethyl ether-CH$_2$Cl$_2$ (1:1, vol.). This mixture was stirred and slowly warmed to ambient temperature during ca. 5 h. The resulting mixture was evaporated to dryness. The crude product was washed with 3×5 ml of toluene and 3×5 ml of hexanes, then, dried in vacuum. Yield 170 mg (21%) of yellow solid.

Anal. calc. for $C_{24}H_{24}Br_2Cl_2SiZr$: C, 43.51; H, 3.65. Found: C, 43.85; H, 3.78.

$^1$H NMR (CD$_2$Cl$_2$): δ 7.56 (d, J=8.7 Hz, 2H, 5,5'-H), 7.52 (d, J=7.2 Hz, 2H, 7,7'-H), 6.87 (dd, J=8.7 Hz, J=7.2 Hz, 2H, 6,6'-H), 6.84 (m, 2H, 3,3'-H), 2.17 (s, 6H, 2,2'-Me), 1.80 (m, J=8.0 Hz, 6H, CH$_2$Me), 1.38 (t, J=8.0 Hz, 6H, CH$_2$Me).

$^{13}$C NMR (CD$_2$Cl$_2$): δ 137.7, 135.1, 131.3, 131.2, 129.6, 127.8, 126.1, 124.0, 121.5, 20.0, 7.8, 6.9.

EXAMPLE 19

Synthesis of rac-dimethylsilyl-bis(η⁵-4-bromo-2,6-dimethylinden-1-yl)zirconium dichloride (19)

4-Bromo-2,6-dimethylindan-1-one

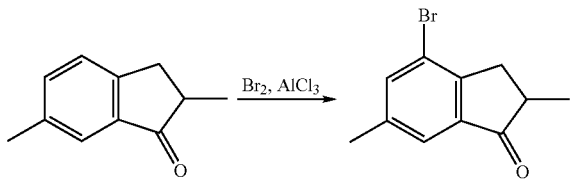

To a suspension of 334 g (2.50 mol) of anhydrous AlCl$_3$ (powder) in 400 ml of dry dichloromethane, a solution of 160 g (1.00 mol) of 2,6-dimethylindan-1-one in 200 ml of dichloromethane was added dropwise while vigorously stirring for 30 min at 0° C. This mixture was stirred for 1 h at ambient temperature, and then a solution of 51.6 ml (161 g, 1.01 mol) of bromine in 800 ml of dichloromethane was added while vigorously stirring for 2 h. The resulting mixture was stirred for 12 h and then poured on 700 cm³ of ice. The mixture was acidified by saturated HCl to pH 1, the organic layer was separated, and the aqueous layer was extracted with 3×350 ml of dichloromethane. The combined organic fractions were dried over K$_2$CO$_3$ and then evaporated to dryness. From the residue, 71.0 g of the starting indanone was distilled off in vacuum (bp 89-91 mm Hg), and the solid material left in the rectification flask was recrystallized from 600 ml of hot hexanes. Crystals that precipitated at room temperature were collected. The pure title product was then isolated by flash chromatography on Silica Gel 60 (40-63 um, d 50 mm, l 200 mm, eluent: hexanes-dichloromethane, 10:1, vol.). Yield 44.0 g (18%).

Anal. calc. for C$_{11}$H$_{11}$BrO: C, 55.25; H, 4.64. Found: C, 55.34; H, 4.75.

¹H NMR (CDCl$_3$): δ 7.55 (s, 1H, 7-H), 7.45 (s, 1H, 5-H), 3.26 (dd, J=17.5 Hz, J=7.8 Hz, 1H, 3-H), 2.64-2.76 (m, 1H, 2-H), 2.57 (dd, J=17.5 Hz, J=3.7 Hz, 1H, 3'-H), 2.36 (m, 3H, 6-Me), 1.29 (d, J=7.5 Hz, 3H, 2-Me).

¹³C NMR (CDCl$_3$): δ 208.4, 150.3, 139.6, 138.2, 122.9, 121.6, 42.3, 35.5, 20.8, 16.2.

7-Bromo-2,5-dimethyl-1H-indene

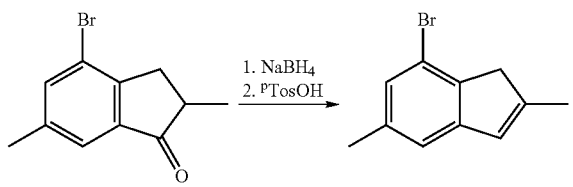

To a solution of 32.5 g (136 mmol) of 4-bromo-2,6-dimethylindan-1-one in 370 ml of a mixture of THF-methanol (2:1, vol.), 11.8 g (312 mmol) of NaBH$_4$ was added in small portions while vigorously stirring for 2 h at 0° C. This mixture was stirred for 12 h at room temperature and then added to 1000 ml of cold water. The organic layer was separated, the aqueous layer was extracted with 3×300 ml of methyl-tert-butyl ether. The combined organic fractions were dried over K$_2$CO$_3$ and then evaporated to dryness. The residue was dissolved in 700 ml of toluene, and 2.0 g of p-TosOH was added. The resulting solution was refluxed for 1 h using a Dean-Stark trap to remove the water formed, and then it was passed through a short Silica Gel 60 column (40-63 um, d 100 mm, l 80 mm, eluent: hexanes). This column was additionally washed with 250 ml of toluene. The combined organic fractions were evaporated to dryness. The product was isolated by flash chromatography on Silica Gel 60 (40-63 um, d 60 mm, l 150 mm, eluent: hexanes). Yield 24.6 g (81%).

Anal. calc. for C$_9$H$_6$Br$_4$Zr: C, 59.22; H, 4.97. Found: C, 59.41; H, 5.09.

¹H NMR (CDCl$_3$): δ 6.94 (s, 1H, 6-H), 6.81 (s, 1H, 4-H), 6.27 (m, 1H, 3-H), 3.04 (s, 2H, 1-H), 2.22 (s, 3H, 5-Me), 2.00 (d, J=1.5 Hz, 3H, 2-Me).

Bis(4-bromo-2,6-dimethyl-1H-inden-1-yl)(dimethyl)silane

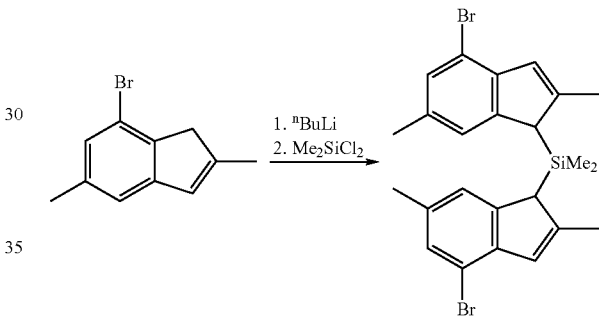

To a solution of 10.2 g (45.7 mmol) of 7-bromo-2,5-dimethyl-1H-indene in 400 ml of ether, 18.3 ml (45.7 mmol) of 2.5 M ″BuLi in hexanes was added at room temperature. This mixture was stirred for 12 h, and then 2.96 g (22.9 mmol) of dichlorodimethylsilane was added while vigorously stirring. The resulting mixture was stirred for 24 h, and then 100 ml of water was added. The organic layer was separated, dried over Na$_2$SO$_4$, and evaporated to dryness. The residue was recrystallized from 70 ml of acetone. Crystals that precipitated at −30° C. were collected and dried in vacuum. Yield 6.20 g (54%) of ca. 2 to 1 mixture of the respective rac- and meso-bis-indenylsilanes.

Anal. calc. for C$_{24}$H$_{26}$Br$_2$Si: C, 57.38; H, 5.22. Found: C, 57.17; H, 5.28.

¹H NMR (CDCl$_3$): δ 7.20 (s, 2H, 5,5'-H in rac-isomer), 7.18 (s, 2H, 5,5'-H in meso-isomer), 7.03 (s, 2H, 7,7'-H in meso-isomer), 7.01 (s, 2H, 7,7'-H in rac-isomer), 6.65 (s, 2H, 3,3'-H in rac- and meso-isomers), 3.67 (s, 2H, 1,1'-H in meso-isomer), 3.65 (s, 2H, 1,1'-H in rac-isomer), 2.32 (s, 6H, 6,6'-Me in rac- and meso-isomers), 2.21 (m, 6H, 2,2'-Me in meso-isomer), 2.18 (m, 6H, 2,2'-Me in rac-isomer), −0.16 (s, 3H, SiMeMe in meso-isomer), −0.23 (s, 6H, SiMe$_2$ in rac-isomer), −0.26 (s, 3H, SiMeMe in meso-isomer).

¹³C NMR (CDCl$_3$): δ, rac-isomer 147.1, 146.2, 142.5, 134.1, 129.1, 126.2, 122.8, 113.6, 48.3, 21.2, 17.9, −5.3.

95

Rac-[dimethylsilyl-bis($\eta^5$-4-bromo-2,6-dimethylinden-1-yl)]($N^1,N^3$-diphenyl-1,3-propanediamido)zirconium

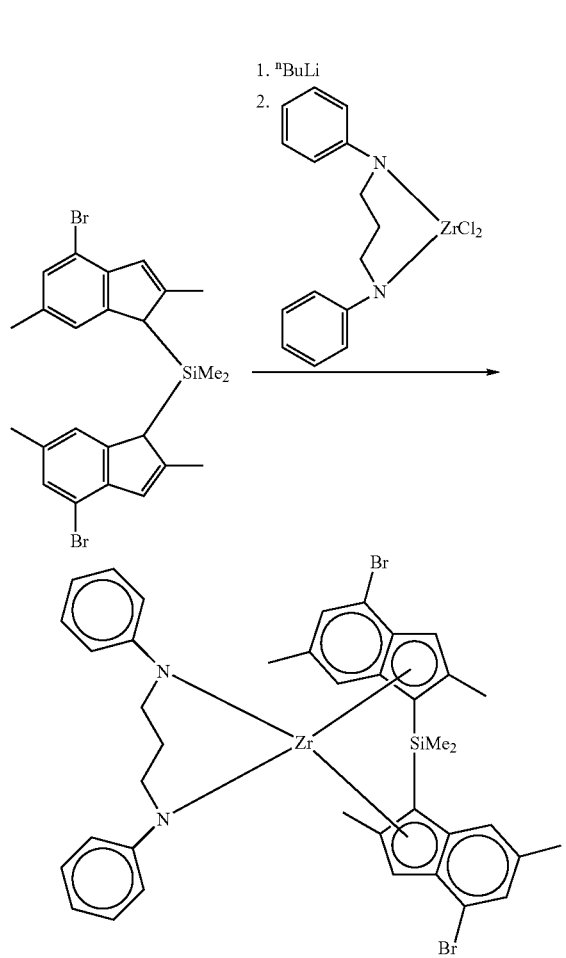

In the Glove Box, to a solution of 5.00 g (9.95 mmol) of bis(4-bromo-2,6-dimethyl-1H-inden-1-yl)(dimethyl)silane in 600 ml of diethyl ether, 8.00 ml (20.0 mmol) of 2.5 M $^n$BuLi in hexanes was added at room temperature. This mixture was stirred for 2 h at 20° C. To the solution obtained 5.28 g (9.95 mmol) of ($N^1,N^3$-diphenyl-1,3-propanediamido)bis(tetrahydrofurano)zirconium dichloride was added at –80° C. The resulting mixture was stirred for 48 h at ambient temperature and, then, evaporated to dryness. The residue was treated with 200 ml of toluene. This toluene solution was filtered through Celite 503. The filtrate was evaporated to dryness. The residue was washed with 4×50 ml of hexanes and dried in vacuum. Yield 4.20 g (52%) of orange crystalline product.

Anal. calc. for $C_{39}H_{40}Br_2N_2SiZr$: C, 57.41; H, 4.94. Found: C, 57.66; H, 5.13.

$^1$H NMR (CD$_2$Cl$_2$): δ 7.61 (m, 2H, 7,7'-H in indenyl), 7.18 (t, J=7.4 Hz, 4H, 3,3',5,5'-H in Ph), 7.04 (s, 2H, 5,5'-H in indenyl), 6.92 (t, J=7.4 Hz, 2H, 4,4'-H in Ph), 6.44 (d, J=7.4 Hz, 4H, 2,2',6,6'-H in Ph), 6.17 (s, 2H, 3,3'-H in indenyl), 3.88 (dt, J=14.7 Hz, J=8.5 Hz, 2H, 1,3-H in propylidene), 2.98 (dt, J=14.7 Hz, J=3.6 Hz, 2H, 1',3'-H in propylidene), 2.47 (s, 6H, 6,6'-Me), 2.04 (s, 6H, 2,2'-Me), 1.34 (m, 2H, 2,2'-H in propylidene), 1.18 (s, 6H, SiMe$_2$).

96

Rac-dimethylsilyl-bis($\eta^5$-4-bromo-2,6-dimethylinden-1-yl)zirconium dichloride (19)

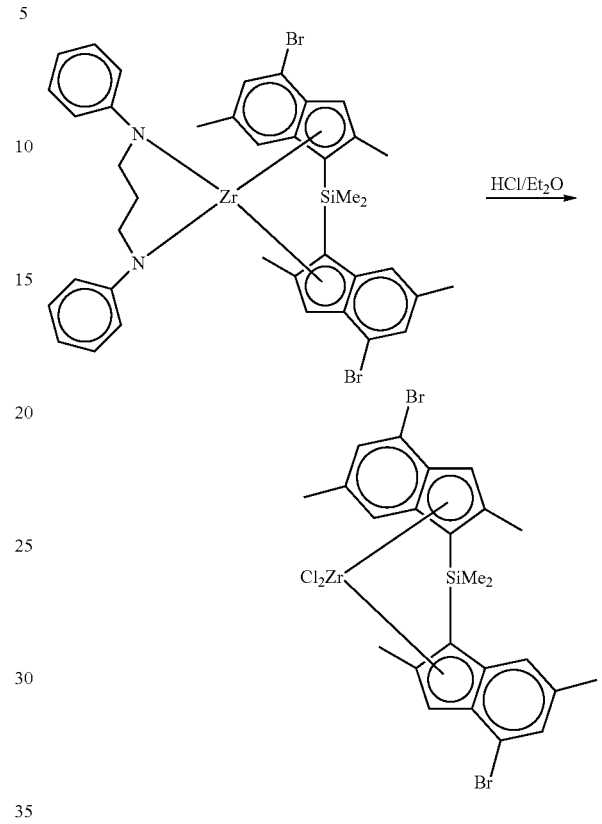

In the Glove Box, to a solution of 2.00 g (2.45 mmol) of rac-[dimethylsilyl-bis($\eta^5$-4-bromo-2,6-dimethylinden-1-yl)]($N^1,N^3$-diphenyl-1,3-propanediamido)zirconium in 160 ml of diethyl ether-CH$_2$Cl$_2$ (1:1, vol.), 4.40 ml of cold 1.0 M solution of HCl in ether was added at –80° C. This mixture was stirred and slowly warmed to ca. –10° C. over ca. 5 h and then it was evaporated (at this temperature) to dryness. The residue was washed with 5×10 ml of dichloromethane using a centrifuge to separate the precipitate. This precipitate was dried in vacuum. Yield 650 mg (40%) of yellow solid.

Anal. calc. for $C_{24}H_{24}Br_2Cl_2SiZr$: C, 43.51; H, 3.65. Found: C, 43.70; H, 3.79.

$^1$H NMR (CD$_2$Cl$_2$): δ 7.43 (m, 2H, 5,5'-H), 7.36 (m, 2H, 7,7'-H), 6.80 (m, 2H, 3,3'-H), 2.31 (s, 6H, 6-CH$_3$), 2.20 (s, 6H, 2-CH$_3$), 1.28 (s, 6H, SiMe$_2$).

EXAMPLE 20

Synthesis of bis($\eta^5$-2-bromo-4,7-dimethylinden-1-yl)zirconium dichloride (20)

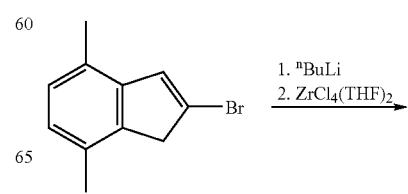

-continued

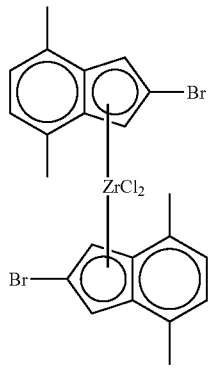

To a solution of 10.0 g (44.8 mmol) of 2-bromo-4,7-dimethyl-1H-indene in 200 ml of hexanes, 17.9 ml (44.8 mmol) of 2.5 M $^n$BuLi in hexanes was added. The reaction mixture was stirred for 12 h at room temperature, and then the precipitate formed was filtered off using a glass frit (G3) funnel and dried in vacuum. This procedure gave 8.60 g (84%) of the lithium salt of 2-bromo-4,7-dimethyl-1H-indene. Next, to a suspension of 7.08 g (18.8 mmol) of $ZrCl_4(THF)_2$ in 200 ml of dichloromethane, 8.60 g (37.5 mmol) of the above-obtained lithium salt was added. The resulting mixture was stirred for 24 h and then filtered through a glass frit (G4). The precipitate was additionally washed with 3×30 ml of dichloromethane. The combined filtrate was evaporated to dryness. The residue was recrystallized from 100 ml of dichloromethane. Crystals that precipitated at −30° C. were collected, washed with 3×50 ml of hexanes, and dried in vacuum. Yield 2.80 g (25%).

Anal. calc. for $C_{22}H_{20}Br_2Cl_2Zr$: C, 43.58; H, 3.32 Found: C, 43.40; H, 3.23.

$^1$H NMR ($CD_2Cl_2$): δ 6.87 (m, 4H, 5,5',6,6'-H), 6.65 (s, 4H, 1,1',3,3'-H), 2.35 (s, 12H, 4,4',7,7'-$CH_3$).

EXAMPLE 21

Synthesis of rac-[dimethylsilyl-bis($\eta^5$-4-bromo-2-methyl-5,6,7,8,-tetrahydro-1H-cyclopenta[b]naphthalen-1-yl)]zirconium dichloride (21)

4-Bromo-2-methyl-2,3,5,6,7,8-hexahydro-1H-cyclopenta[b]naphthalen-1-one

To a mixture of 43.0 g (322 mmol) of $AlCl_3$ in 50 ml of dichloromethane, a solution of 26.4 g (132 mmol) of 2-methyl-2,3,5,6,7,8-hexahydro-1H-cyclopenta[b]naphthalen-1-one in 25 ml of dichloromethane was added dropwise, while vigorously stirring, over 10 min at 0° C. Then, 6.8 ml (21.1 g, 132 mmol) of bromine was added dropwise over 1 h at this temperature. The resulting mixture was stirred overnight at this temperature and then added to 400 ml of cold water. The organic layer was separated, and the aqueous layer was extracted with 3×150 ml of methyl-tert-butyl ether. The combined organic fractions were washed with aqueous $Na_2CO_3$, dried over $K_2CO_3$, and evaporated to dryness. Fractional distillation gave the title product, b.p. 165-175° C./1 mm Hg. Yield 19.3 g (53%) of yellowish oil.

Anal. calc. for $C_{14}H_{15}BrO$: C, 60.23; H, 5.42. Found: C, 60.02; H, 5.35.

$^1$H NMR ($CDCl_3$): δ 7.39 (s, 1H, 9-H), 3.26 (dd, J=17.3 Hz, J=7.9 Hz, 1H, 3-H), 2.80 (m, 4H, 5,5',8,8'-H), 2.68 (m, 1H, 2-H), 2.58 (dd, J=17.3 Hz, J=3.9 Hz, 1H, 3'-H), 1.71-1.89 (m, 4H, 6,6',7,7'-H), 1.30 (d, J=7.3 Hz, 3H, 2-Me).

9-Bromo-2-methyl-5,6,7,8-tetrahydro-1H-cyclopenta[b]naphthalene (17)

To a solution of 18.2 g (65.3 mmol) of 4-bromo-2-methyl-2,3,5,6,7,8-hexahydro-1H-cyclopenta[b]naphthalen-1-one in 100 ml of THF-methanol (2:1, vol.), 3.47 g (91.3 mmol) of $NaBH_4$ was added, while vigorously stirring, over 1 h at 0° C. This mixture was stirred overnight at room temperature and then added to 300 ml of cold water and acidified with 1 M HCl to pH 1. The organic layer was separated, and the aqueous layer was extracted with 2×100 ml of methyl-tert-butyl ether. The combined extract was dried over $K_2CO_3$ and evaporated to dryness, and 300 ml of toluene was added to the yellowish oil obtained. This toluene solution was treated with a catalytic amount of $^p$TolSO$_3$H (ca. 0.5 g) for 15 h at reflux, cooled to room temperature, and evaporated to dryness. The crude product was purified using flash chromatography on Silica Gel 60 (40-63 μm, d 70 mm, l 150 mm; eluent: hexanes). Yield 14.1 g (82%) of white crystalline solid.

Anal. calc. for $C_{14}H_{15}Br$: C, 63.89; H, 5.74. Found: C, 63.50; H, 5.69. $^1$H NMR ($CDCl_3$): δ 6.90 (s, 1H, 4-H), 6.42 (m, 1H, 3-H), 3.25 (s, 2H, 1,1'-H), 2.78 (m, 4H, 5,5',8,8'-H), 2.13 (s, 3H, 2-Me), 1.78 (m, 4H, 6,6',7,7'-H). $^{13}C\{^1H\}$ NMR ($CDCl_3$): δ 145.4, 142.8, 141.1, 137.3, 130.8, 126.5, 121.5, 119.2, 44.4, 30.2, 29.6, 23.3, 22.7, 16.4.

Rac-bis(4-bromo-2-methyl-5,6,7,8-tetrahydro-1H-cyclopenta[b]naphthalen-1-yl)(dimethyl)silane

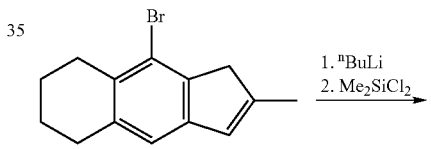

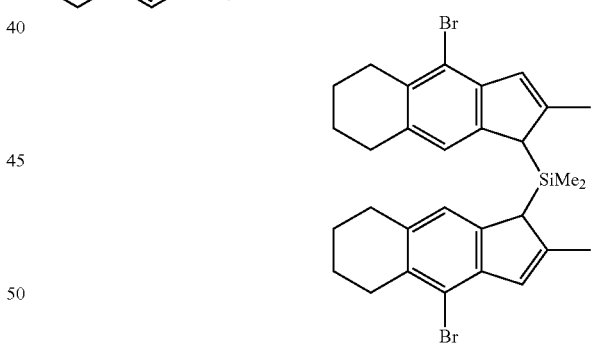

To a solution of 8.14 g (30.9 mmol) of 9-bromo-2-methyl-5,6,7,8-tetrahydro-1H-cyclopenta[b]naphthalene in 250 ml of ether, 12.4 ml (31.0 mmol) of 2.5 M $^n$BuLi in hexanes was added at room temperature. The mixture was stirred for 12 h at this temperature, cooled to 0° C., and then 1.99 g (15.5 mmol) of dichlorodimethylsilane was added. The resulting mixture was stirred for 24 h at ambient temperature, and then 100 ml of water was added. The organic layer was separated, dried over $Na_2SO_4$, and evaporated to dryness. The residue was washed with 3×20 ml of ether and dried in vacuum. Yield 3.27 g (42%) of pure rac-bis(4-bromo-2-methyl-5,6,7,8-tetrahydro-1H-cyclopenta[b]naphthalen-1-yl)(dimethyl)silane.

Anal. calc. for $C_{30}H_{34}Br_2Si$: C, 61.86; H, 5.88. Found: C, 62.03; H, 5.73.

$^1$H NMR (CDCl$_3$): δ 6.91 (s, 2H, 9,9'-H), 6.88 (s, 2H, 3,3'-H), 3.62 (s, 2H, 1,1'-H), 2.71-2.80 (m, 8H, 5,5',8,8'-CH$_2$), 2.18 (s, 6H, 2-Me), 1.69-1.87 (m, 8H, 6,6',7,7'-CH$_2$), −0.23 (s, 6H, SiMe$_2$).

Rac-[dimethylsilyl-bis(η$^5$-4-bromo-2-methyl-5,6,7,8-tetrahydrocyclopenta[b]naphthalen-1-yl)](N$^1$,N$^3$-diphenyl-1,3-propanediamido)zirconium

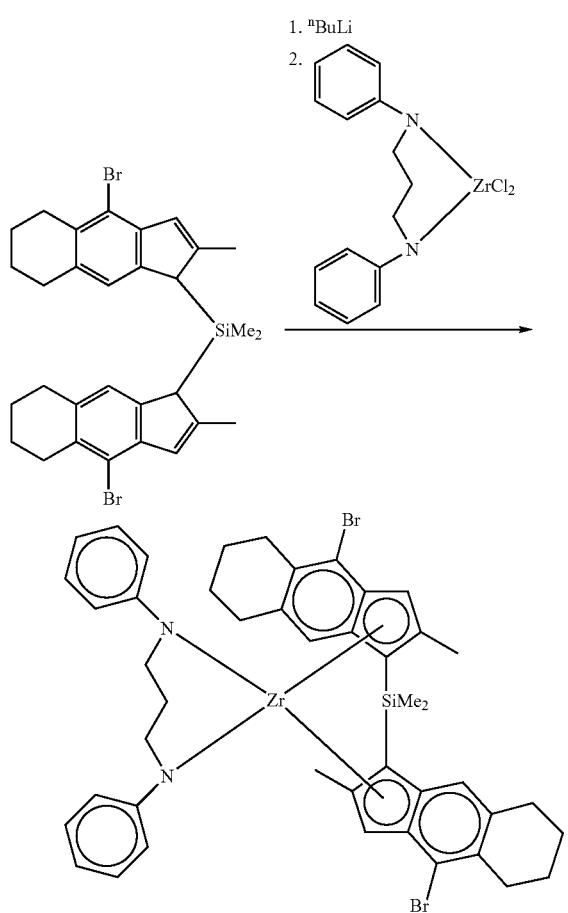

In the Glove Box, to a solution of 3.04 g (5.22 mmol) of rac-bis(4-bromo-2-methyl-5,6,7,8-tetrahydro-1H-cyclopenta[b]naphthalen-1-yl)(dimethyl)silane in 150 ml of diethyl ether, 4.18 ml (10.5 mmol) of 2.5 M $^n$BuLi in hexanes was added at room temperature. This mixture was stirred for 2 h at 20° C. To the solution obtained, 2.77 g (5.22 mmol) of (N$^1$,N$^3$-diphenyl-1,3-propanediamido)bis(tetrahydrofurano)zirconium dichloride was added at −80° C. The resulting mixture was stirred for 16 h at ambient temperature and, then, evaporated to dryness. The residue was treated with 100 ml of toluene. This toluene solution was filtered through Celite 503. The Celite layer was additionally washed with 3×20 ml of toluene. The combined filtrate was evaporated to dryness. The residue was washed with 4×15 ml of hexanes and dried in vacuum. Yield 2.53 g (54%) of orange solid.

Anal. calc. for C$_{45}$H$_{48}$Br$_2$N$_2$SiZr: C, 60.32; H, 5.40. Found: C, 60.58; H, 5.57.

$^1$H NMR (CD$_2$Cl$_2$): δ 7.55 (s, 2H, 9,9'-H in indenyl), 7.19 (m, 4H, 3,3',5,5'-H in Ph), 6.92 (m, 2H, 4,4'-H in Ph), 6.46 (m, 4H, 2,2',6,6'-H in Ph), 6.15 (m, 2H, 3,3'-H in indenyl), 3.84 (dt, J=15.0 Hz, J=8.2 Hz, 2H, 1,3-H in propylidene), 2.56-3.05 (m, 10H, 1',3'-H in propylidene and 5,5',8,8'-CH$_2$ in indenyl), 2.02 (m, 6H, 2,2'-CH$_3$ in indenyl), 1.69-1.84 (m, 8H, 6,6',7,7'-CH$_2$ in indenyl), 1.33-1.36 (m, 2H, 2,2'-H in propylidene), 1.16 (s, 6H, SiMe$_2$).

$^{13}$C NMR (CD$_2$Cl$_2$): δ 162.8, 137.0, 134.6, 132.9, 130.8, 129.5, 128.8, 125.8, 124.1 (two resonances), 123.0, 121.6, 117.2, 59.8, 33.0, 32.0, 24.9, 24.5, 23.4, 20.1, 3.8.

Rac-[dimethylsilyl-bis(η$^5$-4-bromo-2-methyl-5,6,7,8,-tetrahydro-1H-cyclopenta[b]naphthalen-1-yl)]zirconium dichloride (21)

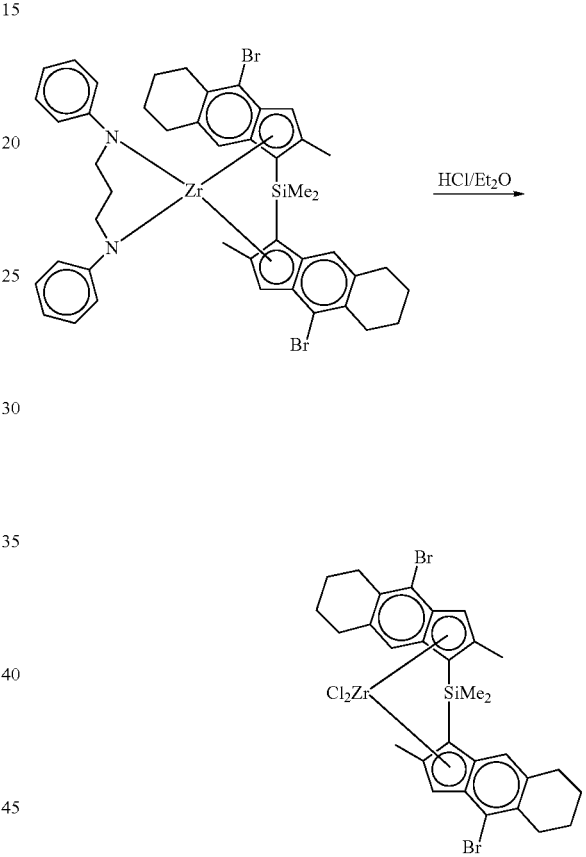

In the Glove Box, to a solution of 2.50 g (2.79 mmol) of rac-[dimethylsilyl-bis(η$^5$-4-bromo-2-methyl-5,6,7,8 tetrahydrocyclopenta[b]naphthalen-1-yl)](N$^1$,N$^3$-diphenyl-1,3-propanediamido)zirconium in 200 ml of diethyl ether-CH$_2$Cl$_2$ (1:1, vol.), 5.02 ml of cold 1.0 M solution of HCl in ether was added at −95° C. for 10 min. This mixture was stirred and slowly warmed to ca. 0° C. during ca. 6 h and then evaporated (at this temperature) to dryness. The residue was washed with 4×8 ml of dichloromethane using a centrifuge to separate the precipitate. This precipitate was dried in vacuum. Yield 0.66 g (32%) of yellow solid.

Anal. calc. for C$_{30}$H$_{32}$Br$_2$Cl$_2$SiZr: C, 48.52; H, 4.34. Found: C, 48.68; H, 4.47.

$^1$H NMR (CD$_2$Cl$_2$): δ 7.33 (s, 2H, 9,9'-H), 6.79 (s, 2H, 3,3'-H), 2.69-3.11 (m, 8H, 5,5',8,8'-CH$_2$), 2.23 (s, 6H, 2-Me), 1.72-1.91 (m, 8H, 6,6',7,7'-CH$_2$), 1.30 (s, 6H, SiMe$_2$).

EXAMPLE 22

Synthesis of rac-dimethylsilyl-bis($\eta^5$-4-bromo-2,5-dimethylinden-1-yl)zirconium dichloride (22)

3-(2-Bromo-3-methylphenyl)-2-methylpropanoic acid, 3-(2-bromo-3-methylphenyl)-2-methylpropionyl chloride, and 4-bromo-2,5-dimethyl-1-indanone

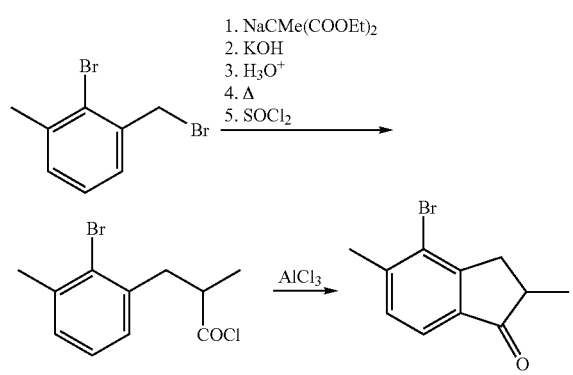

In a three-necked round-bottom 500 ml flask equipped with a reflux condenser, dropping funnel with pressure-equalizing, and magnetic stirring bar, 5.95 g (0.26 mol) of sodium metal was dissolved in 200 ml of dry ethanol. To the resulting solution 45.1 g (0.26 mol) of diethylmethylmalonate were added dropwise over 15 minutes. This mixture was further stirred for 15 minutes; then, 62.1 g (0.24 mol) of 2-bromo-1-(bromomethyl)-3-methylbenzene in 50 ml of ethanol were added by vigorous stirring at a rate that allowed the reaction mixture to maintain a gentle reflux. Additionally, this mixture was refluxed for 4 hours and then it was cooled to room temperature. A solution of 51.8 g of potassium hydroxide in 150 ml of water was added. This mixture was refluxed for 3 hours to saponificate the ester formed. Ethanol and water were distilled off. To the residue 200 ml of water, and then 12 M HCl (to pH 1) were added. The substituted methylmalonic acid that precipitated was separated, washed with 2×60 ml of cold water, and dried overnight on a watch glass. Crude 3-(2-bromo-3-methylphenyl)-2-methylpropanoic acid was obtained after decarboxylation of this substituted methylmalonic acid by heating it for 2 hours at 160° C. The product was used without further purification. Mixture of this acid and 60 ml of $SOCl_2$ was stirred for 24 hours at ambient temperature. Thionyl chloride was distilled off. The crude 3-(2-bromo-3-methylphenyl)-2-methylpropionyl chloride dissolved in 200 ml of $CH_2Cl_2$ was added dropwise by vigorous stirring to a suspension of 37.7 g (0.28 mol) of $AlCl_3$ in 800 ml of $CH_2Cl_2$ for 1 hour at 0° C. Then, this mixture was refluxed for 3 hours, cooled to ambient temperature, and poured on 300 cm³ of ice. The organic layer was separated. The aqueous layer was extracted with 3×100 ml of methyl-tert-butyl ether. The combined organic fractions were dried over $K_2CO_3$ and evaporated to dryness. Fractional distillation gave the title indanone, b.p. 120-121° C./1 mm Hg. Yield 47.6 g (85%) of colorless solid.

Anal. calc. for $C_{11}H_{11}BrO$: C, 55.25; H, 4.64. Found: C, 55.35; H, 4.66.

$^1$H NMR ($CDCl_3$): δ 7.64 (d, J=7.8 Hz, 1H, 7-H), 7.22 (d, J=7.8 Hz, 1H, 6-H), 3.29 (dd, J=17.6 Hz, J=7.9 Hz, 1H, 3-H), 2.70 (m, 1H, 2-H), 2.59 (dd, J=17.6 Hz, J=3.9 Hz, 1H, 3'-H), 2.45 (s, 3H, 5-Me), 1.28 (d, J=7.6 Hz, 2-Me).

$^{13}C\{^1H\}$ NMR ($CDCl_3$): δ 208.1, 153.8, 145.1, 136.1, 130.3, 124.1, 122.3, 42.2, 36.5, 23.1, 16.2.

A mixture of 4-bromo-2,5-dimethyl-1H- and 7-bromo-2,6-dimethyl-1H-indenes

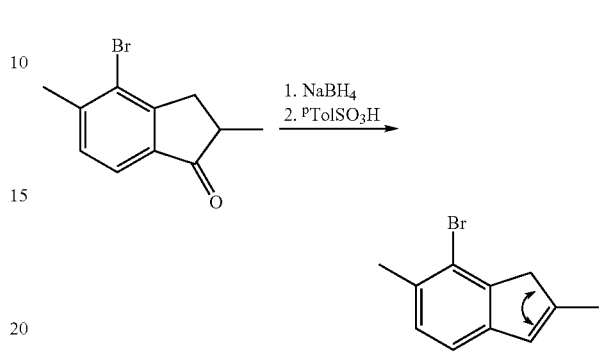

To a solution of 47.6 g (199 mmol) of 4-bromo-2,5-dimethyl-1-indanone in 270 ml of THF-methanol (2:1, vol.), 11.3 g (299 mmol) of $NaBH_4$ was added over 1 hour at −5° C. (Caution: temperature must be lower 0° C.). The mixture was stirred overnight at ambient temperature, then diluted with 300 ml of water, and acidified with 10% HCl to pH=1. The crude product was extracted with 3×200 ml of $CH_2Cl_2$. This extract was evaporated to dryness. To the white solid obtained 500 ml of toluene was added. This toluene solution was treated with a catalytic amount of $^P$TolSO$_3$H (ca. 2 g) for 2 hours at reflux using a Dean-Stark head. It was then cooled to room temperature, washed with aqueous $NaHCO_3$, dried over $Na_2SO_4$, and evaporated to dryness. The product was isolated by flash chromatography on Silica Gel 60 (40-63 μm, d 30 mm, l 300 mm; eluent: hexanes). Yield 38.7 g (87%) of white crystalline product.

Anal. calc. for $C_{11}H_{11}Br$: C, 59.22; H, 4.97. Found: C, 59.40; H, 5.04.

$^1$H NMR ($CDCl_3$) of 4-bromo-2,5-dimethyl-1H-indene: δ 7.03 (m, 1H, 7-H in indenyl), 6.97 (d, J=7.4 Hz, 1H, 6-H on indenyl), 6.36 (m, 1H, 3-H in indenyl), 3.22 (m, 2H, $CH_2$), 2.35 (s, 3H, 5-Me in indenyl), 2.09 (m, 3H, 2-Me in indenyl); 7-bromo-2,6-dimethyl-1H-indene: δ 7.03 (m, 1H, 4-H in indenyl), 7.00 (d, J=7.5 Hz, 1H, 5-H on indenyl), 6.40 (m, 1H, 3-H in indenyl), 3.20 (m, 2H, $CH_2$), 2.38 (s, 3H, 6-Me in indenyl), 2.09 (m, 3H, 2-Me in indenyl).

$^{13}C$ NMR ($CDCl_3$) of 7-bromo-2,6-dimethyl-1H-indene: δ 145.6, 144.6, 144.0, 132.5, 128.7, 126.9, 121.0, 118.3, 44.8, 22.3, 16.6.

Bis(4-bromo-2,5-dimethyl-1H-inden-1-yl)(dimethyl)silane

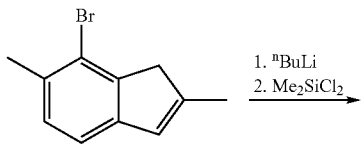

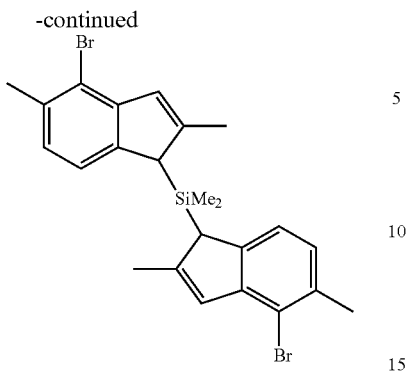

In an argon atmosphere (argon atmosphere), to a solution of 10.0 g (44.8 mmol) of a mixture of 4-bromo-2,5-dimethyl-1H- and 7-bromo-2,6-dimethyl-1H-indenes in 400 ml of diethyl ether, 17.9 ml of 2.5 M "BuLi (44.8 mmol) in hexanes was added at ambient temperature. This mixture was stirred overnight at room temperature, and then 2.72 ml (2.89 g, 22.4 mmol) of $Me_2SiCl_2$ was added. The resulting mixture was stirred for 24 hours at ambient temperature; then 50 ml of water was added. The organic layer was separated, dried over $Na_2SO_4$, and evaporated to dryness. The residue was washed with 3×30 ml of hexanes and dried in vacuum. Yield 7.02 g (61%) of white solid.

Anal. calc. for $C_{24}H_{26}Br_2Si$: C, 57.38; H, 5.22. Found: C, 57.55; H, 5.34.

$^1$H NMR (CDCl$_3$): δ 7.53 (d, J=7.5 Hz, 2H, 7,7'-H in rac-compound), 7.41 (d, J=7.5 Hz, 2H, 7,7'-H in meso-compound), 7.25 (d, J=7.5 Hz, 2H, 6,6'-H in rac-compound), 7.22 (d, J=7.5 Hz, 2H, 6,6'-H in meso-compound), 7.02 (m, 4H, 3,3'-H in rac- and meso-compounds), 4.02 (s, 2H, 1,1'-H in rac-compound), 3.99 (s, 2H, 1,1'-H in meso-compound), 2.74 (s, 6H, 5,5'-Me in rac-compound), 2.72 (s, 6H, 5,5'-Me in meso-compound), 2.51 (m, 6H, 2,2'-Me in meso-compound), 2.46 (m, 6H, 2,2'-Me in rac-compound), 0.08 (s, 3H, SiMe in meso-compound), 0.015 (s, 3H, SiMe' in meso-compound), 0.006 (s, 6H, SiMe$_2$ in rac-compound).

Rac-[dimethylsilyl-bis(η$^5$-4-bromo-2,5-dimethylinden-1-yl)](N$^1$,N$^3$-diphenyl-1,3-propanediamido)zirconium (22)

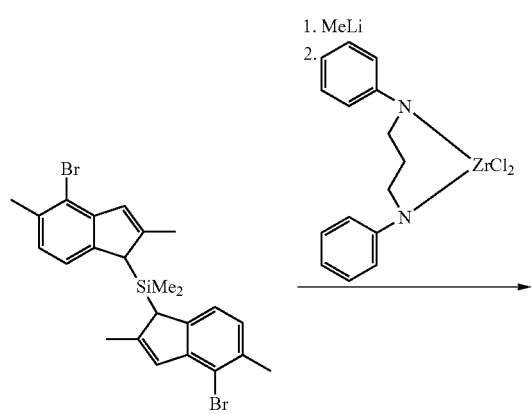

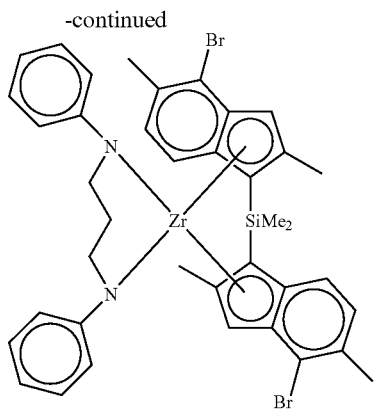

In the Glove Box (nitrogen atmosphere), to a solution of 7.00 g (13.9 mmol) of bis(4-bromo-2,5-dimethyl-1H-inden-1-yl)(dimethyl)silane in 700 ml of diethyl ether, 13.9 ml of 2.0 M MeLi (27.8 mmol) in ether was added at room temperature. This mixture was stirred for 24 hours at 20° C. To the solution obtained, 7.40 g (13.9 mmol) of (N$^1$,N$^3$-diphenyl-1,3-propanediamido)bis(tetrahydrofurano)zirconium dichloride was added at −70° C. The resulting mixture was stirred for 24 hours at ambient temperature, and then evaporated to dryness. The residue was treated with 300 ml of hot toluene. This hot toluene solution was filtered through Celite 503. The filtrate was evaporated to dryness. The crude product was washed with 5×70 ml of hexanes and dried in vacuum. This procedure gave 8.04 g (71%) of orange crystalline product.

Anal. calc. for $C_{39}H_{40}Br_2N_2SiZr$: C, 57.41; H, 4.94. Found: C, 57.63; H, 5.10.

$^1$H NMR (CD$_2$Cl$_2$): δ 7.73 (d, J=8.5 Hz, 2H, 7,7'-H in indenyl), 7.17 (m, 4H, 3,3',5,5'-H in N—C$_6$H$_5$), 7.01 (d, J=8.5 Hz, 2H, 6,6'-H in indenyl), 6.92 (m, 2H, 4,4'-H in N—C$_6$H$_5$), 6.50 (m, 4H, 2,2',6,6'-H in N—C$_6$H$_5$), 6.16 (s, 2H, 3,3'-H in indenyl), 3.83 (dt, J=14.9 Hz, J=8.3 Hz, 2H, 1,3-H in propylidene), 2.81 (dt, J=14.9 Hz, J=2.9 Hz, 2H, 1',3—-H in propylidene), 2.31 (s, 6H, 5,5'-Me in indenyl), 1.95 (s, 6H, 2,2'-Me in indenyl), 1.23-1.34 (m, 2H, 2,2'-H in propylidene), 1.12 (s, 6H, SiMe$_2$).

$^{13}$C NMR (CD$_2$Cl$_2$): δ 163.0, 134.1, 133.0, 132.0, 129.6, 128.8, 128.6, 126.1, 124.8, 123.5, 120.6, 118.2, 95.5, 60.0, 23.6, 23.2, 19.8, 3.5.

EXAMPLE 23

Synthesis of rac-dimethylsilyl-bis(η$^5$-4-bromo-2,5-dimethylinden-1-yl)zirconium dichloride (23)

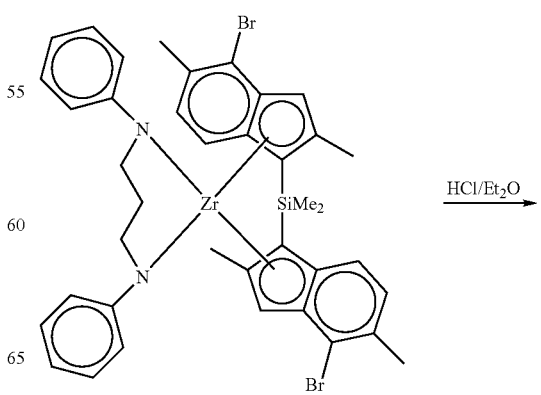

-continued

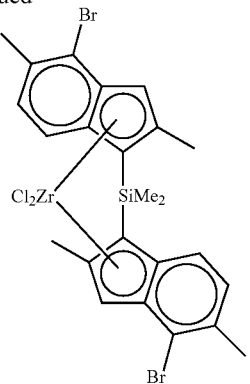

In the Glove Box (nitrogen atmosphere), to a solution of 7.52 g (9.22 mmol) of rac-[dimethylsilyl-bis(4-bromo-2,5-dimethylinden-1-yl)]($N^1,N^3$-diphenyl-1,3-propanediamido) zirconium in 640 ml of diethyl ether-$CH_2Cl_2$ (1:1, vol.), 18.4 ml of cold 1.0 M solution of HCl in ether was added at −110° C. This mixture was stirred and slowly warmed to ambient temperature during ca. 7 hours. The reaction mixture was evaporated to dryness. The residue was washed with 3×20 ml of $CH_2Cl_2$ and dried in vacuum. Yield 2.54 mg (42%) of yellow solid.

Anal. calc. for $C_{24}H_{24}Br_2Cl_2SiZr$: C, 43.51; H, 3.65. Found: C, 43.77; H, 3.69.

$^1$H NMR ($CD_2Cl_2$): δ 7.48 (d, J=8.7 Hz, 2H, 7,7'-H), 6.89 (d, J=8.7 Hz, 2H, 6,6'-H), 6.77 (s, 2H, 3,3'-H), 2.48 (s, 6H, 5,5'-Me), 2.16 (s, 6H, 2,2'-M 1.23 (s, 6H, $SiMe_2$).

$^{13}$C NMR ($CD_2Cl_2$): δ 138.8, 136.9, 136.0, 130.3, 125.4, 124.8, 123.1, 121.7, 97.2, 23.8, 20.0, 3.5.

EXAMPLE 24

Synthesis of rac-dimethylsilyl-bis($\eta^5$-4-bromo-2-isopropylinden-1-yl)zirconium dichloride (24)

4-Bromo-2-isopropylindan-1-one

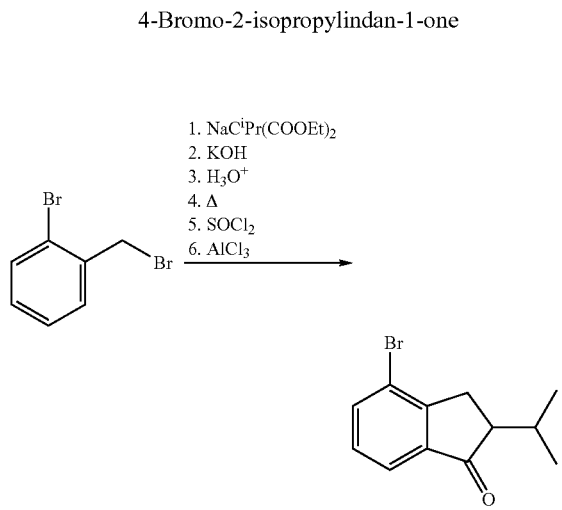

To a solution of 99.1 g (0.49 mol) of diethyl isopropylmalonate in 500 ml of THF, 11.7 g (0.49 mol) of sodium hydride was added. This mixture was refluxed for 1 h and then cooled to room temperature. Next, 120 g (0.49 mol) of 2-bromobenzylbromide was added, and the resulting mixture was refluxed for 3 h. This mixture was cooled to ambient temperature and filtered through a glass frit (G2). The precipitate (NaBr) was additionally washed with 3×100 ml of THF. The combined filtrate was evaporated to dryness. The residue was dissolved in 400 ml of ethanol and 160 g of potassium hydroxide and 50 ml of water were added. The resulting mixture was refluxed for 4 h, and then 200 ml of water was added. Ethanol was distilled off at atmospheric pressure. The resulting aqueous solution was acidified with 5 M HCl to pH 1. The precipitate obtained at −30° C. was filtered off, washed with 100 ml of water, and dried in air. The dibasic acid was decarboxylated by heating for 2 h at 160° C. The product obtained was dissolved in 600 ml of dichloromethane, and 600 ml of $SOCl_2$ was added. The mixture was refluxed for 3 h and then evaporated to dryness. The residue was dissolved in 270 ml of dry dichloromethane, and the solution obtained was added dropwise to a suspension of 136 g (1.02 mol) of $AlCl_3$ in 1350 ml of dichloromethane for 1 h at 0° C., while vigorously stirring. Next, the reaction mixture was refluxed for 3 h, cooled to ambient temperature, poured on 500 cm³ of ice, and, finally, acidified with 8M HCl to pH 3. The organic layer was separated, the aqueous layer was washed with 3×300 ml of methyl-tert-butyl ether. The combined organic fractions were dried over $K_2CO_3$ and then evaporated to dryness. The product was isolated by vacuum distillation (bp 154-157° C./3 mm Hg). Yield 73.4 g (60%).

Anal. calc. for $C_{12}H_{13}BrO$: C, 56.94; H, 5.18. Found: C, 56.78; H, 5.02.

$^1$H NMR ($CDCl_3$): δ 7.73 (d, J=7.7 Hz, 1H, 7-H), 7.67 (d, J=7.7 Hz, 1H, 5-H), 7.25 (t, J=7.7 Hz, 1H, 6-H), 3.09 (dd, J=17.7 Hz, J=8.0 Hz, 1H, 3-H), 2.66-2.72 (m, 1H, 2-H), 2.66 (dd, J=17.7 Hz, J=4.2 Hz, 1H, 3'-H), 2.36-2.46 (m, 1H, $CHMe_2$), 1.07 (d, J=6.7 Hz, 3H, $CH_3$), 0.80 (d, J=6.6 Hz, 3H, $CH_3'$).

$^{13}$C NMR ($CDCl_3$): δ 207.6, 153.6, 139.4, 137.1, 128.9, 122.3, 122.0, 53.0, 29.4, 29.0, 20.6, 17.3.

7-Bromo-2-isopropyl-1H-indene

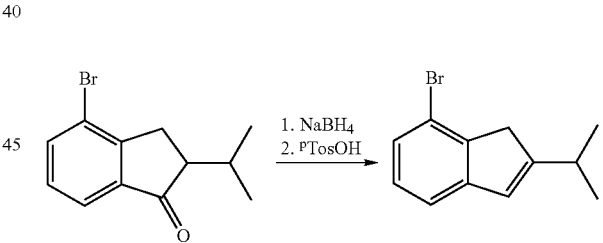

To a solution of 73.4 g (0.29 mol) of 4-bromo-2-isopropylindan-1-one in 530 ml of a mixture of THF-methanol (2:1, vol.), 22.0 g (0.58 mol) of $NaBH_4$ was added in small portions while vigorously stirring for 2 h at 0° C. This mixture was stirred for 12 h at room temperature and then added to 600 ml of cold water. The organic layer was separated, the aqueous layer was extracted with 3×300 ml of methyl-tert-butyl ether. The combined organic fractions were dried over $K_2CO_3$ and then evaporated to dryness. The residue was dissolved in 1500 ml of toluene, and 2.0 g of p-TosOH was added. The resulting solution was refluxed for 2 h using a Dean-Stark trap to remove the water formed, and then it was passed through a short Silica Gel 60 column (40-63 um, d 100 mm, l 80 mm, eluent: hexanes). This column was additionally washed with 250 ml of toluene. The combined organic fractions were evaporated to dryness. The product was isolated by vacuum distillation (bp 128-132° C./4 mm Hg). Yield 57.8 g (84%).

Anal. calc. for $C_{12}H_{13}Br$: C, 60.78; H, 5.53. Found: C, 60.85; H, 5.49.

$^1$H NMR (CDCl$_3$): δ 7.32 (d, J=7.8 Hz, 1H, 5-H), 7.28 (d, J=7.8 Hz, 1H, 7-H), 7.17 (t, J=7.8 Hz, 1H, 6-H), 6.61 (m, 1H, 3-H in indenyl), 3.41 (br.s., 2H, 1-H), 2.86 (sep, J=6.9 Hz, 1H, CHMe$_2$), 1.32 (d, J=6.9 Hz, 6H, CHMe$_2$).

Bis(4-bromo-2-isopropyl-1H-inden-1-yl)(dimethyl)silane

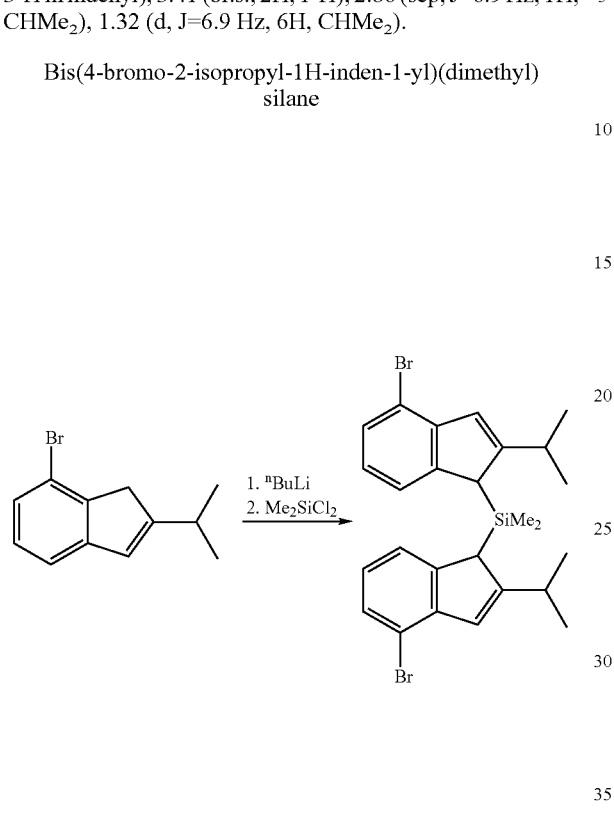

Rac-dimethylsilyl-bis(η$^5$-4-bromo-2-isopropylinden-1-yl)zirconium dichloride (24)

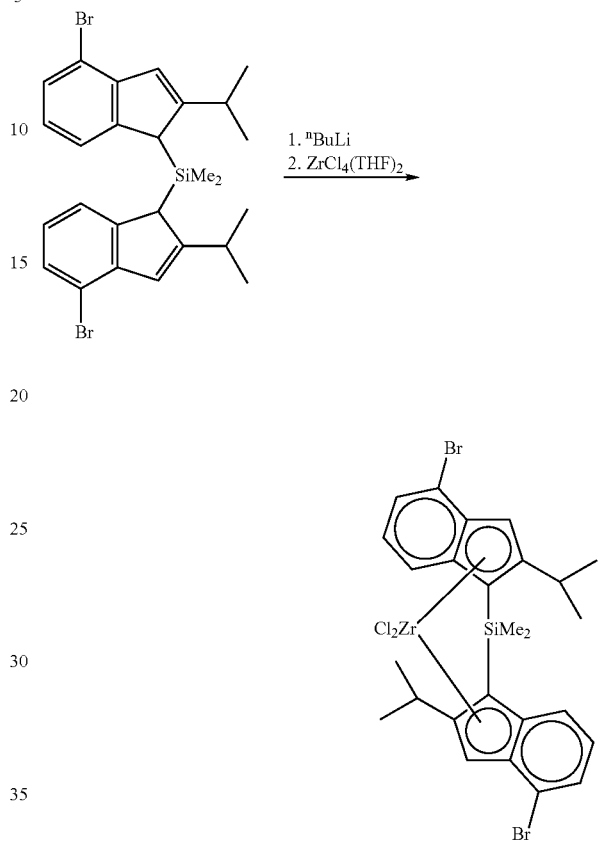

To a solution of 23.7 g (100 mmol) of 4-bromo-2-isopropyl-1H-indene in 600 ml of ether, 40.0 ml (100 mmol) of 2.5 M $^n$BuLi in hexanes was added at room temperature. The mixture was stirred for 24 h at this temperature, and then 6.45 g (50.0 mmol) of dichlorodimethylsilane was added. The resulting mixture was stirred for 36 h at ambient temperature, and then 200 ml of water was added. The organic layer was separated, dried over Na$_2$SO$_4$, and evaporated to dryness. The product was isolated by MPLC on Silica Gel 60 (40-63 um, d 50 mm, l 500 mm; eluent—hexanes). Yield 16.6 g (63%) of a ca. 4:3 mixture of rac- and meso-products.

Anal. calc. for $C_{26}H_{30}Br_2Si$: C, 58.87; H, 5.70. Found: C, 59.03; H, 5.59.

$^1$H NMR (CDCl$_3$): δ 7.38 (d, J=7.6 Hz, 2H, 7,7'-H in meso-isomer), 7.35 (m, 4H, 5,5',7,7'-H in rac-isomer), 7.21 (d, J=7.6 Hz, 2H, 5,5'-H in meso-isomer), 6.98 (t, J=7.8 Hz, 2H, 6,6'-H in rac-isomer), 6.92 (t, J=7.6 Hz, 2H, 6,6'-H in meso-isomer), 6.68 (m, 2H, 3,3'-H in rac- and meso-isomers), 3.86 (s, 2H, 1,1'-H in rac-isomer), 3.78 (s, 2H, 1,1'-H in meso-isomer), 2.57 (m, 2H, CHMe$_2$ in rac- and meso-isomers), 1.32 (d, J=6.9 Hz, 3H, CHMeCH$_3$ in meso-isomer), 1.28 (d, J=6.9 Hz, 3H, CHMeCH$_3$ in rac-isomer), 1.12 (d, J=6.9 Hz, 3H, CHMeCH$_3$ in meso-isomer), 1.05 (d, J=6.9 Hz, 3H, CHMeCH$_3$ in rac-isomer), −0.10 (s, 3H, SiMeMe in meso-isomer), −0.18 (s, 3H, SiMeMe in meso-isomer), −0.19 (s, 6H, SiMe$_2$ in rac-isomer).

$^{13}$C NMR (CDCl$_3$): δ 160.2, 145.8, 145.7, 144.9, 144.7, 128.4, 124.2, 124.1, 122.4, 122.3, 121.9, 121.8, 114.6, 110.2, 46.4, 29.7, 24.7, 24.5, 21.0, −3.48, −3.91, −4.63.

To a solution of 14.7 g (27.7 mmol) of bis(4-bromo-2-isopropyl-1H-inden-1-yl)(dimethyl)silane in 600 ml of diethyl ether, 34.6 ml of 1.6 M (55.4 mmol) $^n$BuLi in hexanes was added at room temperature. This mixture was stirred at ambient temperature for 24 hours and then cooled to −30° C. Next, 10.4 g (27.7 mmol) of ZrCl$_4$(THF)$_2$ was added at this temperature. The resulting mixture was slowly warmed (for ca. 2 hours) to ambient temperature, stirred at this temperature for 24 h, and then evaporated to dryness. The residue was suspended in 400 ml of hot toluene, and this suspension was filtered through a glass frit (G4). The precipitate was additionally washed with 3×15 ml of hot toluene. The combined filtrate was evaporated to dryness. The residue was washed with 5×50 ml of hexanes and dried in vacuum. This procedure gave 6.08 g of a mixture of rac- and meso-complexes. This mixture was dissolved in ca. 50 ml of warm dichloromethane, and this warm solution was filtered through a glass frit (G4). The first portion of pure rac-complex is precipitated at ambient temperature (ca. 25° C.) after 2-4 weeks. The crystalline product was separated, washed with 5 ml of diethyl ether, and dried in vacuum. This procedure gave 1.88 g (10%) of pure rac-complex.

Anal. calc. for $C_{26}H_{28}Br_2Cl_2SiZr$: C, 45.22; H, 4.09. Found: C, 45.29; H, 4.00.

$^1$H NMR (CD$_2$Cl$_2$): δ rac-complex, 7.59 (d, J=8.7 Hz, 2H, 7,7'-H), 7.54 (dd, J=7.3 Hz, J=0.5 Hz, 2H, 5,5'-H), 6.89 (m, 2H, 3,3'-H), 6.88 (dd, J=8.7 Hz, J=7.3 Hz, 2H, 6,6'-H), 3.09 (sep, J=6.6 Hz, 2H, CHMe$_2$, CH'Me$_2$), 1.32 (s, 6H, SiMe$_2$), 1.15 (d, J=6.6 Hz, CHMeMe), 1.12 (d, J=6.6 Hz, CHMeMe);

meso-complex, 7.61 (m, 2H, 7,7'-H), 7.32 (dd, J=7.3 Hz, J=0.6 Hz, 2H, 5,5'-H), 6.89 (m, 2H, 3,3'-H), 6.63 (dd, J=8.4 Hz, J=7.3 Hz, 2H, 6,6'-H), 3.05-3.17 (m, 2H, $CHMe_2$, CH'$Me_2$), 1.46 (d, J=6.6 Hz, CHMeMe), 1.43 (s, 6H, SiMeMe), 1.28 (s, 6H, SiMeMe), 1.22 (d, J=6.6 Hz, CHMeMe).

$^{13}C$ NMR ($CD_2Cl_2$): δ rac-complex, 151.1, 134.3, 131.0, 129.5, 127.8, 125.4, 122.3, 116.6, 86.1, 32.1, 30.5, 20.9, 4.8.

EXAMPLE 25

Synthesis of rac-dimethylsilyl-bis($\eta^5$-4-bromo-2-methyl-6-isopropylinden-1-yl)zirconium dichloride (25)

2-Bromo-4-isopropylaniline

A mixture of 99 g (0.73 mol) of 4-isopropylaniline (Acros) and 300 ml of acetic acid was refluxed for 1 h; then, 75 g of acetic anhydride was added dropwise while vigorously stirring. The resulting solution was cooled to 50° C., and 37.4 ml of bromine was added dropwise, while vigorously stirring, over ca. 30 min. Then, 370 ml of 12 M HCl was added and this mixture was refluxed until a precipitate was formed. This precipitate was separated, washed with 2×150 ml of methyl-tert-butyl ether, and dried in vacuum. A mixture of the solid obtained and a solution of 112 g of KOH in 300 ml of water was stirred at 50-60° C. for 1 h. The organic layer was separated, and the aqueous layer was extracted with 2×150 ml of methyl-tert-butyl ether. The combined extract was dried over $K_2CO_3$ and evaporated to dryness. Fractional distillation gave the title product, b.p. 107-111° C./3 mm Hg. Yield 83.7 g (77%) of yellowish oil.

Anal. calc. for $C_9H_{12}BrN$: C, 50.49; H, 5.65. Found: C, 50.45; H, 5.69.

$^1H$ NMR ($CDCl_3$): δ 7.26 (d, J=2.0 Hz, 1H, 3-H), 6.95 (dd, J=8.1 Hz, J=2.0 Hz, 1H, 5-H), 6.68 (d, J=8.1 Hz, 1H, 6-H), 3.89 (br.s, 2H, $NH_2$), 2.77 (sept, J=6.9 Hz, $CHMe_2$), 1.18 (d, J=6.9 Hz, 6H, $CHMe_2$).

1-Bromo-3-isopropylbenzene

To a mixture of 1000 ml of 96% ethanol and 94 ml of 98% $H_2SO_4$, 117 g (0.55 mol) of 2-bromo-4-isopropylaniline was added, while vigorously stirring, at −5° C. over 15 min. Then, a solution of 63 g of $NaNO_2$ in 125 ml of water was added at this temperature over 1 h, and the resulting mixture was stirred for about 30 min longer. Then, 12 g of copper powder was added. The reaction mixture was refluxed for 4 h and then filtered through a glass frit (G3). The filtrate was poured into 2500 $cm^3$ of cold water. The organic product was extracted with 4×400 ml of dichloromethane. The combined extract was dried over $K_2CO_3$ and evaporated to dryness. Fractional distillation gave the title product, b.p. 64-67° C./3 mm Hg. Yield 117.4 g (75%) of yellowish oil.

Anal. calc. for $C_9H_{11}Br$: C, 54.30; H, 5.57. Found: C, 54.44; H, 5.49.

$^1H$ NMR ($CDCl_3$): δ 7.37 (m, 1H, 2-H), 7.28-7.34 (m, 1H, 5-H), 7.15-7.16 (m, 1H, 6-H), 7.14 (d, J=1.0 Hz, 1H, 2-H), 2.87 (sept, J=6.9 Hz, 1H, $CHMe_2$), 1.24 (d, J=6.9 Hz, 6H, $CHMe_2$).

7-Bromo-5-isopropyl-2-methyl-1-indanone

To a mixture of 34.9 g (0.26 mol) of $AlCl_3$ and 350 ml of dichloromethane, a solution of 50.9 g (0.22 mol) of 2-bromo-2-methylpropanoyl bromide in 120 ml of dichloromethane was added dropwise, while vigorously stirring, at −10° C. Then, a solution of 40.0 g (0.20 mol) of 1-bromo-3-isopropylbenzene in 70 ml of dichloromethane was added dropwise at this temperature. The resulting mixture was refluxed for 12 h and then poured onto 2000 $cm^3$ of ice. The organic product was extracted with 4×300 ml of dichloromethane. The combined extract was dried over $K_2CO_3$ and evaporated to dryness. Fractional distillation gave the title product, b.p. 130-135° C./1.5 mm Hg. Yield 36.2 g (67%).

Anal. calc. for $C_{13}H_{15}BrO$: C, 58.44; H, 5.66. Found: C, 58.40; H, 5.67.

$^1H$ NMR ($CDCl_3$): δ 7.37 (s, 1H, 6-H), 7.23 (s, 1H, 4-H), 3.31 (dd, J=16.7 Hz, J=8.0 Hz, 1H, 3-H), 2.94 (sept, J=6.8 Hz, 1H, $CHMe_2$), 2.71 (m, 1H, 2-H), 2.65 (m, 1H, 3'-H), 1.30 (d, J=7.4 Hz, 3H, 2-Me), 1.27 (d, J=6.8 Hz, 6H, $CHMe_2$).

4-Bromo-6-isopropyl-2-methyl-1H-indene

To a solution of 22.2 g (83.2 mmol) of 7-bromo-5-isopropyl-2-methyl-1-indanone in 120 ml of THF-methanol (2:1, vol.), 5.06 g (133 mmol) of $NaBH_4$ was added, while vigorously stirring, over 3 h at 0° C. This mixture was stirred overnight at room temperature; then, 300 ml of cold water was added and the resulting mixture was acidified with 1 M HCl to pH 1. The organic layer was separated, and the aqueous layer was extracted with 3×150 ml of dichloromethane. The combined extract was dried over $K_2CO_3$ and evaporated to dryness, and 200 ml of toluene was added to the yellowish oil obtained. This toluene solution was treated with a catalytic amount of $^pTolSO_3H$ (ca. 0.2 g) for 1 h at reflux, cooled to room temperature, and evaporated to dryness. The crude product was purified using flash chromatography on Silica Gel 60 (40-63 µm, d 40 mm, 1400 mm; eluent: hexanes). Yield 19.6 g (94%).

Anal. calc. for $C_{13}H_{15}Br$: C, 62.17; H, 6.02. Found: C, 61.99; H, 6.08.

$^1H$ NMR ($CDCl_3$): δ 7.20 (s, 1H, 5-H), 7.13 (s, 1H, 7-H), 6.52 (m, 1H, 3-H), 3.32 (s, 2H, 1,1'-H), 2.86 (sept, J=6.9 Hz, 1H, $CHMe_2$), 2.12 (m, 3H, 2-Me) 1.23 (d, J=6.9 Hz, 6H, $CHMe_2$). $^{13}C\{^1H\}$ NMR ($CDCl_3$): δ 146.5, 146.4, 144.9, 143.6, 127.4, 126.5, 120.6, 113.4, 43.7, 33.9, 24.2, 16.8.

Bis(4-bromo-6-isopropyl-2-methyl-1H-inden-1-yl)(dimethyl)silane

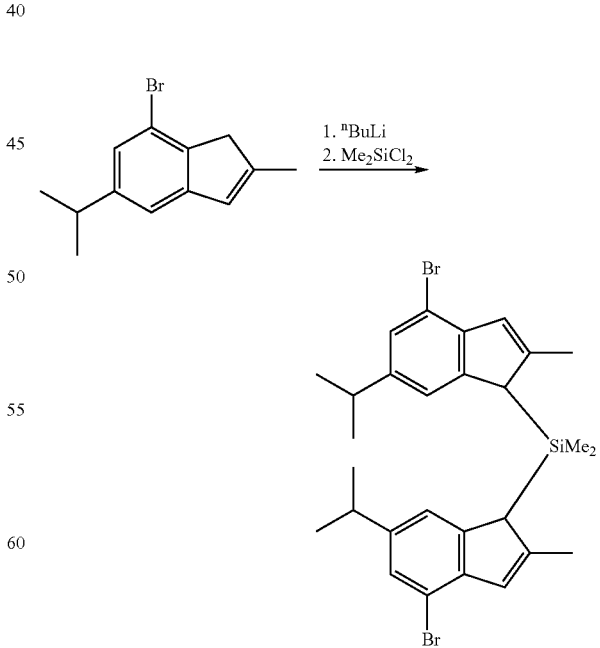

To a solution of 10.0 g (39.8 mmol) of 4-bromo-6-isopropyl-2-methyl-1H-indene in 400 ml of ether, 15.9 ml (39.8 mmol) of 2.5 M $^n$BuLi in hexanes was added at room temperature. The mixture was stirred for 3 h at this temperature, and then 2.57 g (19.9 mmol) of dichlorodimethylsilane was added. The resulting mixture was stirred for 96 h at ambient temperature, and then 50 ml of water was added. The organic layer was separated, dried over $Na_2SO_4$, and evaporated to dryness. The product was isolated by MPLC on Silica Gel 60 (40-63 um, d 50 mm, 1500 mm; eluent—hexanes). Yield 4.83 g (43%) of a ca. 6:5 mixture of rac- and meso-products.

Anal. calc. for $C_{28}H_{34}Br_2Si$: C, 60.22; H, 6.14. Found: C, 60.09; H, 6.29.

$^1$H NMR ($CDCl_3$): δ 7.22 (m, 2H, 5,5'-H of rac- and meso-isomers), 7.12 (br.s., 2H, 7,7'-H of rac-isomer), 7.09 (br.s., 2H, 7,7'-H of meso-isomer), 6.65 (br.s., 2H, 3,3'-H of meso-isomer), 6.63 (br.s., 2H, 7,7'-H of rac-isomer), 3.65 (s, 2H, 1,1'-H of rac- and meso-isomers), 2.87 (m, 2H, $CHMe_2$ of rac- and meso-isomers), 2.16-2.18 (m, 6H, $CH_3$ of rac- and meso-isomers), 1.20-1.23 (m, 12H, $(CH_3)_2CH$), −0.15 (s, 3H, SiMe of meso-isomer), −0.21 (s, 6H, $SiMe_2$ of rac-isomer), −0.29 (s, 3H, SiMe' of meso-isomer).

$^{13}$C NMR ($CDCl_3$): δ 147.6, 147.4, 146.2*, 145.6*, 142.9, 142.8, 126.7*, 126.2, 126.1, 120.3*, 113.7*, 48.5, 48.4, 33.9*, 31.6, 24.3, 24.2*, 24.1, 22.6, 17.9, 14.1, −4.8, −5.0, −5.1 (* two resonances).

Rac-[dimethylsilyl-bis($\eta^5$-4-bromo-6-isopropyl-2-methylinden-1-yl)]($N^1,N^3$-diphenyl-1,3-propanediamido)zirconium In the Glove Box, to a solution of 4.83 g (8.65 mmol) of rac-/meso-bis(4-bromo-6-isopropyl-2-methyl-1H-inden-1-yl)(dimethyl)silane in 400 ml of diethyl ether, 3.46 ml (8.66 mmol) of 2.5 M $^n$BuLi in hexanes was added at room temperature. This mixture was stirred for 24 h at 20° C. To the solution obtained, 4.59 g (8.65 mmol) of ($N^1,N^3$-diphenyl-1,3-propanediamido)bis(tetrahydrofurano)zirconium dichloride was added at −90° C. The resulting mixture was stirred for 48 h at ambient temperature and, then, evaporated to dryness. The residue was treated with 200 ml of toluene. This toluene solution was filtered through Celite 503. The Celite layer was additionally washed with 100 ml of toluene. The combined filtrate was evaporated to dryness. The residue was washed with 3×30 ml of hexanes. The hexanes extract was evaporated to dryness, and the residue was washed with 3×10 ml of n-pentane and then dried in vacuum. Yield 1.00 g (13%) of orange solid.

Anal. calc. for $C_{43}H_{48}Br_2N_2SiZr$: C, 59.23; H, 5.55. Found: C, 59.39; H, 5.69.

$^1$H NMR ($CD_2Cl_2$): δ 7.69 (m, 2H, 7,7'-H in indenyl), 7.17 (m, 4H, 3,3',5,5'-H in Ph), 7.15 (d, J=1.0 Hz, 2H, 5,5'-H in indenyl), 6.94 (m, 2H, 4,4'-H in Ph), 6.44 (m, 4H, 2,2',6,6'-H in Ph), 6.21 (m, 2H, 3,3'-H in indenyl), 3.95 (dt, J=14.7 Hz, J=8.6 Hz, 2H, 1,3-H in propylidene), 3.03 (sep, J=6.9 Hz, 2H, $CHMe_2$), 3.00 (dt, J=14.7 Hz, J=3.3 Hz, 2H, 1',3'-H in propylidene), 1.99 (s, 6H, 2,2'-$CH_3$), 1.41 (d, J=6.9 Hz, 6H, $MeCHCH_3$), 1.36 (m, 2H, 2,2'-H in propylidene), 1.34 (d, J=6.9 Hz, 6H, $MeCHCH_3$'), 1.20 (s, 6H, $SiMe_2$).

$^{13}$C NMR ($CD_2Cl_2$): δ 162.6, 146.7, 132.9, 131.7, 129.8, 129.5, 129.0, 126.1, 123.5, 121.1, 119.9, 117.8, 96.1, 60.1, 35.6, 25.4, 24.4, 23.1, 20.1, 3.7.

Rac-dimethylsilyl-bis($\eta^5$-4-bromo-2-methyl-6-isopropylinden-1-yl)zirconium dichloride (25)

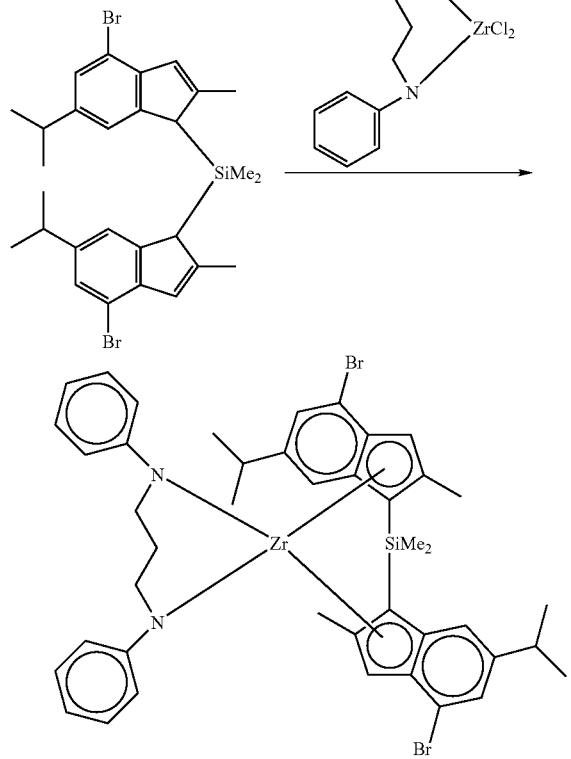

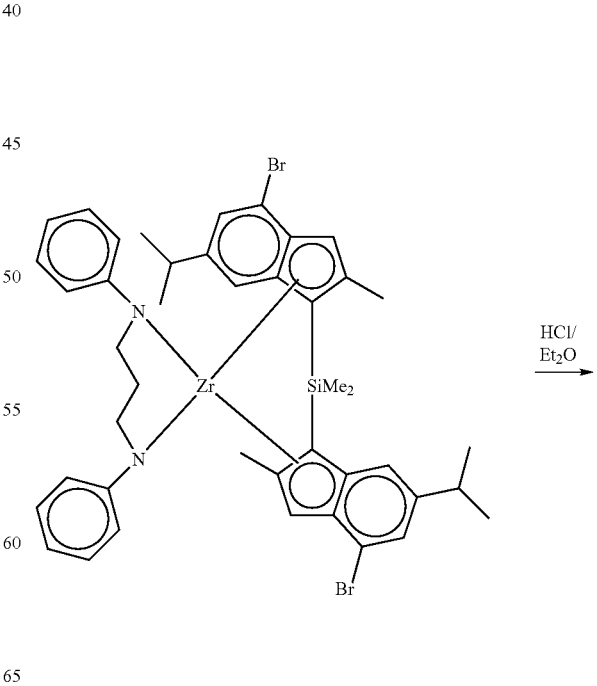

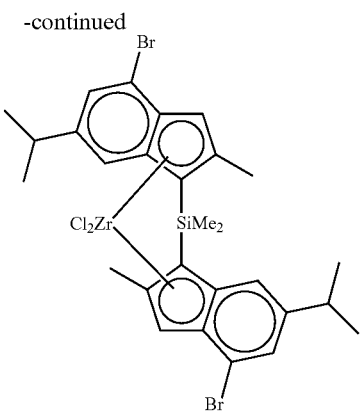

In the Glove Box, to a solution of 1.00 g (1.15 mmol) of rac-[dimethylsilyl-bis($\eta^5$-4-bromo-6-isopropyl-2-methylinden-1-yl)]($N^1$,$N^3$-diphenyl-1,3-propanediamido)zirconium in 80 ml of diethyl ether-$CH_2Cl_2$ (1:1, vol.), 2.42 ml of cold 1.0 M solution of HCl in ether was added at −90° C. over 5 min. This mixture was stirred and slowly warmed to ca. 0° C. during ca. 3 h and then evaporated (at this temperature) to dryness. The residue was washed with 30 ml of a 1:1 mixture of dichloromethane and hexanes, 20 ml of ether, and 2×10 ml of n-pentane, and then it was dissolved in 50 ml of hot toluene. This toluene solution was filtered through a glass frit (G4) and evaporated to dryness. The residue was recrystallized from 25 ml of dichloromethane. Crystals that precipitated at −30° C. were collected, washed with 5 ml of cold dichloromethane, and dried in vacuum. Yield 0.31 g (38%) of orange crystalline solid.

Anal. calc. for $C_{28}H_{32}Br_2Cl_2SiZr$: C, 46.80; H, 4.49. Found: C, 46.89; H, 4.57.

$^1$H NMR ($CDCl_3$): δ 7.49 (m, 2H, 5,5'-H), 7.40 (m, 2H, 7,7'-H), 6.79 (m, 2H, 3,3'-H), 2.85 (m, 2H, CHMe$_2$), 2.22 (s, 6H, CH$_3$), 1.30 (s, 6H, SiMe$_2$), 1.22 (d, J=2.3 Hz, 6H, MeCHCH$_3$), 1.20 (d, J=2.3 Hz, 6H, MeCHCH$_3$).

$^{13}$C NMR ($CDCl_3$): δ 148.8, 136.5, 133.5, 132.0, 131.2, 129.8, 123.2, 121.9, 121.1, 86.4, 36.0, 24.7, 24.6, 20.0.

EXAMPLE 26

Synthesis of rac-dimethylsilyl-bis($\eta^5$-4,6-dichloro-2-methylinden-1-yl)zirconium dichloride (26)

4,6-Dichloro-2-methylindan-1-one

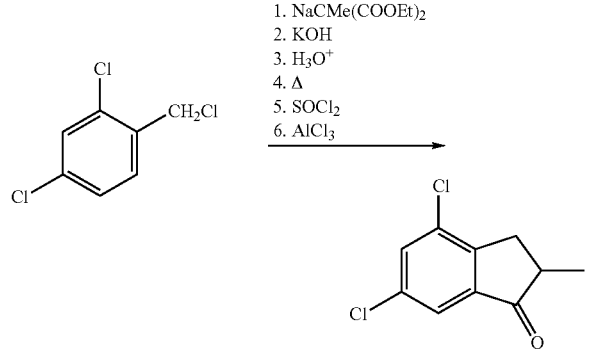

To a solution of sodium ethoxide in ethanol obtained from 4.80 g (0.21 mol) of sodium and 120 ml of anhydrous ethanol, a solution of 36.5 g (0.21 mol) of diethyl methylmalonate in 50 ml of ethanol was added dropwise while vigorously stirring for 15 min. Then, 39.1 g (0.20 mol) of 2,4-dichloro-1-(chloromethyl)benzene was added dropwise with such a rate, so the reaction mixture would be slowly refluxing. The resulting mixture was additionally refluxed for 4 h, then cooled to room temperature, and a solution of 40 g of potassium hydroxide in 100 ml of water was added. This mixture was refluxed for 3 h, and then ethanol was distilled off at atmospheric pressure. The solution obtained was cooled to ambient temperature and acidified by saturated hydrochloric acid to pH 1. The precipitate formed was filtered off, washed with 2×200 ml of cold water, and dried in air. The dibacic acid obtained was then dehcarboxylated by heating it at 160° C. for 2 h. To the viscous oil obtained, 40 ml of dichloromethane and 60 ml of $SOCl_2$ were added, and the resulting mixture was refluxed for 2 h. Dichloromethane and an excess of $SOCl_2$ were distilled off, and the residue was dissolved in 50 ml of anhydrous dichloromethane. The solution obtained was added dropwise to a suspension of 25.3 g (0.19 mol) of $AlCl_3$ in 260 ml of dichloromethane for 1 h at 0° C. The reaction mixture was refluxed for 3 h, then cooled to room temperature, poured on 500 cm$^3$ of ice, and finally acidified by saturated HCl to pH 3. The organic layer was separated, and the aqueous layer was washed with 3×300 ml of methyl-tert-butyl ether. The combined organic fractions were dried over $K_2CO_3$ and then evaporated to dryness. The title product was isolated fractional distillation in vacuum, bp 135-138° C./1 mm Hg. Yield 37.0 g (86%).

Anal. calc. for $C_{10}H_8Cl_2O$: C, 55.84; H, 3.75. Found: C, 56.02; H, 3.62.

$^1$H NMR ($CDCl_3$): δ 7.41 (m, 1H, 7-H), 7.39 (d, J=1.9 Hz, 1H, 5-H), 3.23 (dd, J=17.8 Hz, J=7.9 Hz, 1H, 3-H), 2.61-2.70 (m, 1H, 2-H), 2.53 (dd, J=17.8 Hz, J=4.1 Hz, 1H, 3'-H), 1.21 (d, J=7.4 Hz, 3H, 2-Me).

$^{13}$C NMR ($CDCl_3$): δ 206.3, 149.0, 138.8, 134.2, 133.5, 133.1, 121.9, 42.0, 33.2, 15.8.

5,7-Dichloro-2-methyl-1H-indene

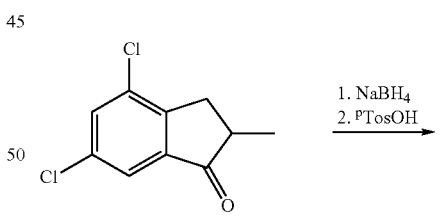

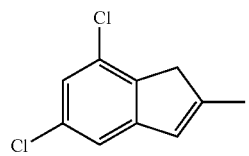

To a solution of 29.3 g (0.136 mol) of 4,6-dichloro-2-methylindan-1-one in 370 ml of a mixture of THF-methanol (2:1, vol.), 11.8 g (0.312 mol) of NaBH$_4$ was added in small portions, while vigorously stirring, over 2 h at 0° C. This mixture was stirred for 12 h at room temperature and then added to 1000 ml of cold water. The organic layer was separated, the aqueous layer was extracted with 3×300 ml of methyl-tert-butyl ether. The combined organic fractions were dried over K$_2$CO$_3$ and then evaporated to dryness. The residue was dissolved in 700 ml of toluene, and 2.0 g of p-TosOH was added. The resulting solution was refluxed for 4 h using a Dean-Stark trap to remove the water formed, and then it was passed through a short Silica Gel 60 column (40-63 um, d 100 mm, l 80 mm, eluent: hexanes). This column was additionally washed with 250 ml of toluene. The combined organic fractions were evaporated to dryness. The product was isolated by flash chromatography on Silica Gel 60 (40-63 um, d 60 mm, l 150 mm). Yield 24.6 g (91%).

Anal. calc. for C$_{10}$H$_8$Cl$_2$: C, 60.33 H, 4.05. Found: C, 60.49; H, 4.24.

$^1$H NMR (CDCl$_3$): δ 7.05 (m, 2H, 4,6-H), 6.37 (m, 1H, 3-H), 3.23 (s, 2H, 1-H), 2.14 (s, 3H, 2-CH$_3$).

$^{13}$C NMR (CDCl$_3$): δ 148.8, 148.4, 139.2, 132.9, 129.4, 126.4, 123.3, 118.6, 41.9, 16.7.

Rac-bis(4,6-dichloro-2-methyl-1H-inden-1-yl)(dimethyl)silane

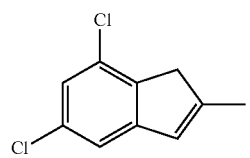

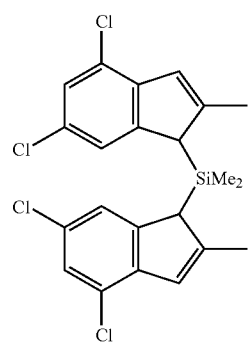

To a solution of 16.2 g (81.4 mmol) of 5,7-dichloro-2-methyl-1H-indene in 800 ml of ether, 32.6 ml (81.4 mmol) of 2.5 M $^n$BuLi in hexanes was added at room temperature. The mixture was stirred for 12 h at this temperature, and then 5.25 g (40.7 mmol) of dichlorodimethylsilane was added. The resulting mixture was stirred for 24 h at ambient temperature, and then 100 ml of water was added. The organic layer was separated, dried over Na$_2$SO$_4$, and evaporated to dryness. The residue was washed with 3×50 ml of hexanes and dried in vacuum. Yield 4.86 g (26%) of pure rac-bis(4,6-dichloro-2-methyl-1H-inden-1-yl)(dimethyl)silane.

Anal. calc. for C$_{22}$H$_{20}$Cl$_4$Si: C, 58.16; H, 4.44. Found: C, 58.46; H, 4.59.

$^1$H NMR (CDCl$_3$): δ 7.23 (d, J=1.2 Hz, 2H, 7,7'-H), 7.11 (m, 2H, 5,5'-H), 6.64 (m, 2H, 3,3'-H), 3.61 (s, 2H, 1,1'-H), 2.16 (m, 6H, CH$_3$), −0.12 (s, 6H, SiMe$_2$).

$^{13}$C NMR (CDCl$_3$): δ 148.5, 146.7, 141.8, 129.1, 125.6, 125.5, 124.3, 121.6, 48.5, 17.9, −4.7.

Rac-[dimethylsilyl-bis(η$^5$-4,6-dichloro-2-methylinden-1-yl)](N$^1$,N$^3$-diphenyl-1,3-propanediamido)zirconium

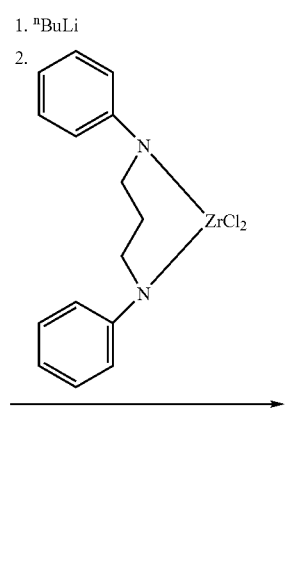

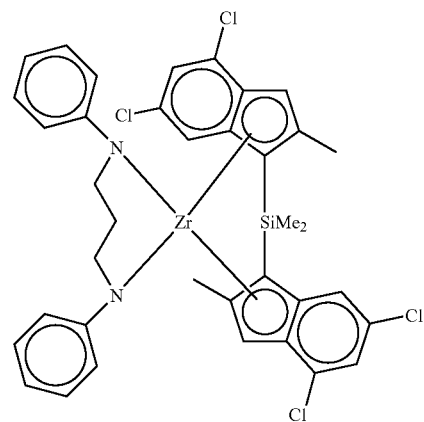

In the Glove Box, to a solution of 4.54 g (10.0 mmol) of rac-bis(4,6-dichloro-2-methyl-1H-inden-1-yl)(dimethyl)silane in 480 ml of diethyl ether, 8.00 ml (20.0 mmol) of 2.5 M $^n$BuLi in hexanes was added at room temperature. This mixture was stirred for 20 h at room temperature. To the solution obtained, 5.31 g (10.0 mmol) of (N$^1$,N$^3$-diphenyl-1,3-propanediamido)bis(tetrahydrofurano)zirconium dichloride was added at −80° C. The resulting mixture was slowly warmed to room temperature and then stirred for 48 h at this temperature, and, finally, evaporated to dryness. The residue was treated with 200 ml of toluene. This toluene solution was filtered through Celite 503. The Celite layer was additionally washed with 3×20 ml of toluene. The combined filtrate was evaporated to dryness. The residue was washed with 4×15 ml of hexanes and recrystallized from 20 ml of dichloromethane. Crystals that precipitated at room temperature were collected, washed with 5 ml of hexanes, and dried in vacuum. Yield 2.53 g (54%) of orange solid.

Anal. calc. for $C_{37}H_{34}Cl_4N_2SiZr$: C, 57.88; H, 4.46. Found: C, 57.59; H, 4.31.

$^1$H NMR (CD$_2$Cl$_2$): δ 7.77 (m, 2H, 7,7'-H in indenyl), 7.24 (m, 4H, 3,3',5,5'-H in Ph), 7.01 (d, J=1.5 Hz, 2H, 5,5'-H in indenyl), 6.98 (m, 2H, 4,4'-H in Ph), 6.51 (m, 4H, 2,2',6,6'-H in Ph), 6.30 (m, 2H, 3,3'-H in indenyl), 3.81 (dt, J=15.3 Hz, J=8.2 Hz, 2H, 1,3-H in propylidene), 3.00 (dt, J=15.0 Hz, J=3.2 Hz, 2H, 1',3'-H in propylidene), 2.03 (s, 6H, 2,2'-CH$_3$), 1.36 (m, 2H, 2,2'-H in propylidene), 1.16 (s, 6H, SiMe$_2$).

$^{13}$C NMR (CD$_2$Cl$_2$): δ 160.4, 133.1, 130.1, 129.8, 128.8, 128.4, 125.9, 124.3, 124.0, 122.5, 121.4, 115.3, 94.9, 58.0, 21.4, 18.5, 1.7.

Rac-dimethylsilyl-bis($\eta^5$-4,6-dichloro-2-methylinden-1-yl)zirconium dichloride (26)

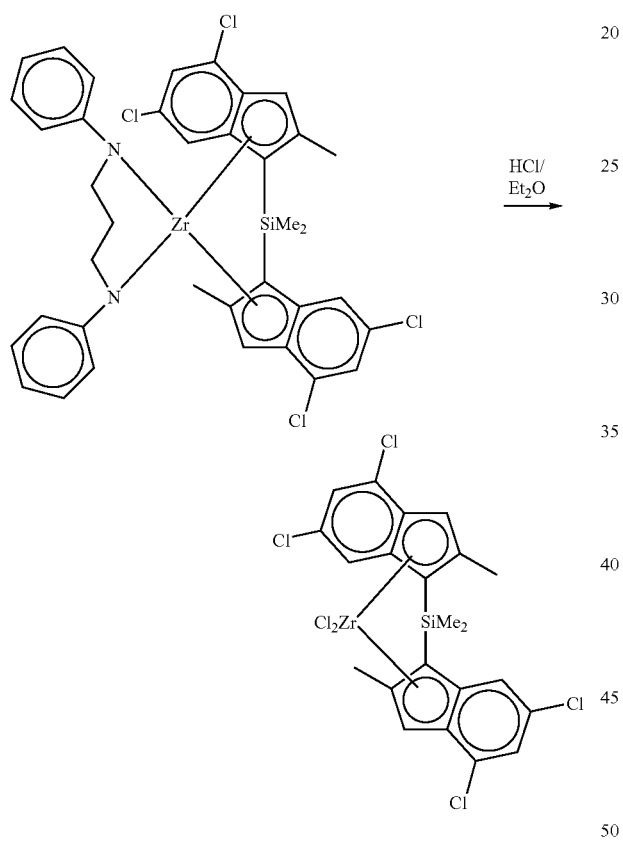

In the Glove Box, to a solution of 1.94 g (2.53 mmol) of rac-[dimethylsilyl-bis($\eta^5$-4,6-dichloro-2-methylinden-1-yl)] (N$^1$,N$^3$-diphenyl-1,3-propanediamido)zirconium in 200 ml of diethyl ether-CH$_2$Cl$_2$ (1:1, vol.), 5.31 ml of cold 1.0 M solution of HCl in ether was added at −80° C. over 5 min. This mixture was stirred and slowly warmed to ca. 0° C. during ca. 4 h and then evaporated (at this temperature) to dryness. The residue was washed with 2×10 ml of hot toluene, 2×30 ml of dichloromethane, 30 ml of THF, and 30 ml of dichloromethane, and dried in vacuum. Yield 0.43 g (28%) of yellow solid which is insoluble in all common solvents. This complex seems to be pure racemate.

Anal. calc. for $C_{22}H_{18}Cl_6SiZr$: C, 43.01; H, 2.95; Cl, 34.62. Found: C, 42.78; H, 4.74, Cl, 34.80.

MALDI mass, m/z: 614.4. Mass calc. for $C_{22}H_{18}Cl_6SiZr$: 614.40.

EXAMPLE 27

Synthesis of mixture of rac- and meso-isopropylidene-bis($\eta^5$-4-bromo-3-methylinden-1-yl)zirconium dichloride (27)

1-Bromo-2-(1-bromoethyl)benzene

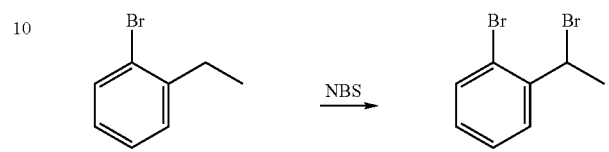

A mixture of 99.4 g (0.537 mol) of 2-bromoethylbenzene, 95.6 g (0.537 mol) of N-bromosuccinimide, 1 g of benzoyl peroxide, and 1000 ml of carbon tetrachloride were refluxed for 3 h. The resulting mixture was cooled to room temperature and then filtered through a glass frit (G3). The precipitate was additionally washed with 3×100 ml of carbon tetrachloride. The combined filtrate was evaporated to dryness. Fractional distillation of the residue gave pure title product, bp 95-98° C./3 mm Hg. Yield 137 g (97%).

Anal. calc. for $C_8H_8Br_2$: C, 36.40; H, 3.05. Found: C, 36.45; H, 2.96.

$^1$H NMR (CDCl$_3$): δ 7.63 (dd, J=8.1 Hz, J=1.9 Hz, 1H, 6-H), 7.52 (dd, J=7.6 Hz, J=1.2 Hz, 1H, 3-H), 7.32 (m, 1H, 4-H), 7.11 (m, 1H, 5-H), 5.59 (q, J=6.9 Hz, 1H, CH), 2.01 (d, J=6.9 Hz, 3H, CH$_3$).

4-Bromo-3-methylindan-1-one

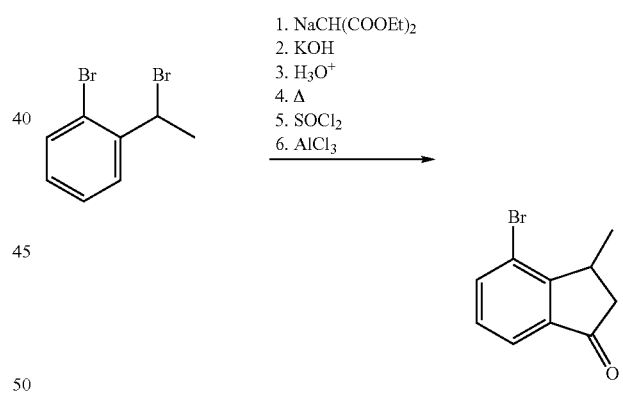

To a solution of sodium ethoxide in ethanol obtained from 15.4 g (0.67 mmol) of sodium and 360 ml of anhydrous ethanol, a solution of 215 g (1.34 mmol) of diethyl malonate in 240 ml of ethanol was added dropwise, while vigorously stirring, over 15 min. Then, 137 g (0.52 mmol) of 1-bromo-2-(1-bromoethyl)benzene in 50 ml of ethanol was added dropwise with such a rate, so the reaction mixture would be slowly refluxing. The resulting mixture was additionally refluxed for 4 h, then cooled to room temperature, and a solution of 105 g of potassium hydroxide in 280 ml of water was added. This mixture was refluxed for 3 h, and then ethanol was distilled off at atmospheric pressure. The solution obtained was cooled to ambient temperature and acidified by saturated hydrochloric acid to pH 1. The precipitate formed was filtered off, washed with 2×200 ml of cold water, and dried in air. The dibacic acid obtained was then dehcarboxylated by heating it at 160° C. for 2 h. To the viscous oil obtained, 130 ml of $SOCl_2$ was added, and the resulting mixture was stirred for 24 h at room temperature. The excess of $SOCl_2$ was distilled off, and the residue was dissolved in 160 ml of anhydrous dichloromethane. The solution obtained was added dropwise to a suspension of 80.0 g (0.60 mmol) of $AlCl_3$ in 800 ml of dichloromethane for 1 h at 0° C. The reaction mixture was refluxed for 3 h, then cooled to room temperature, poured on 500 cm³ of ice, and finally acidified by saturated HCl to pH 3. The organic layer was separated, and the aqueous layer was washed with 3×300 ml of methyl-tert-butyl ether. The combined organic extract was dried over $K_2CO_3$ and then evaporated to dryness. The title product was isolated fractional distillation in vacuum, bp 108-112° C./3 mm Hg. Yield 101 g (86%).

Anal. calc. for $C_{10}H_9BrO$: C, 53.36; H, 4.03. Found: C, 53.48; H, 3.90.

$^1$H NMR (CDCl$_3$): δ 7.75 (dd, J=7.8 Hz, J=0.6 Hz, 1H, 7-H), 7.68 (dd, J=7.5 Hz, J=0.6 Hz, 1H, 5-H), 7.26 (t, J=7.6 Hz, 1H, 6-H), 3.48-3.58 (m, 1H, 3-H), 2.96 (dd, J=19.0 Hz, J=7.8 Hz, 1H, 2-H), 2.39 (dd, J=19.0 Hz, J=1.6 Hz, 1H, 2'-H), 2.43 (d, J=7.1 Hz, 3H, 2-CH$_3$).

$^{13}$C NMR (CDCl$_3$): δ 205.4, 158.3, 138.3, 129.3, 122.6, 121.4, 109.6, 45.6, 34.0, 20.6.

7-Bromo-1-methyl-1H-indene

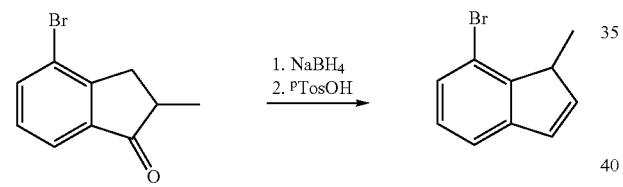

To a solution of 116 g (0.52 mol) of 4-bromo-3-methylindan-1-one in 950 ml of a mixture of THF-methanol (2:1, vol.) 38.3 g (1.02 mol) of NaBH$_4$ was added in small portions, while vigorously stirring, over 2 h at 0° C. This mixture was stirred for 12 h at room temperature and then added to 1000 ml of cold water. The organic layer was separated, the aqueous layer was extracted with 3×300 ml of methyl-tert-butyl ether. The combined organic fractions were dried over $K_2CO_3$ and then evaporated to dryness. The residue was dissolved in 1500 ml of toluene, and 2.0 g of p-TosOH was added. The resulting solution was refluxed for 2 h using a Dean-Stark trap to remove the water formed, and then it was passed through a short Silica Gel 60 column (40-63 um, d 100 mm, l 80 mm, eluent: hexanes). This column was additionally washed with 250 ml of toluene. The combined organic extract was evaporated to dryness. The product was isolated by vacuum distillation (bp 104-108° C./5 mm Hg). Yield 100 g (93%).

Anal. calc. for $C_{10}H_9Br$: C, 57.44; H, 4.34. Found: C, 57.38; H, 4.40.

$^1$H NMR (CDCl$_3$): δ 7.24 (d, J=8.1 Hz, 1H, 6-H), 7.21 (d, J=7.5 Hz, 1H, 4-H), 7.24 (m, 1H, 5-H), 6.65 (dd, J=5.4 Hz, J=1.5 Hz, 1H, 3-H), 6.65 (dd, J=5.4 Hz, J=2.2 Hz, 1H, 2-H), (ddq, J=7.5 Hz, J=2.2 Hz, J=1.5 Hz, 1H, 1-H), 1.38 (d, J=7.5 Hz, 3H, 1-CH$_3$).

$^{13}$C NMR (CDCl$_3$): δ 147.4, 146.0, 142.5, 129.3, 128.4 (two resonance), 120.1, 118.9, 46.9, 13.8.

Bis(4-bromo-3-methylinden-1-yl)isopropylidene

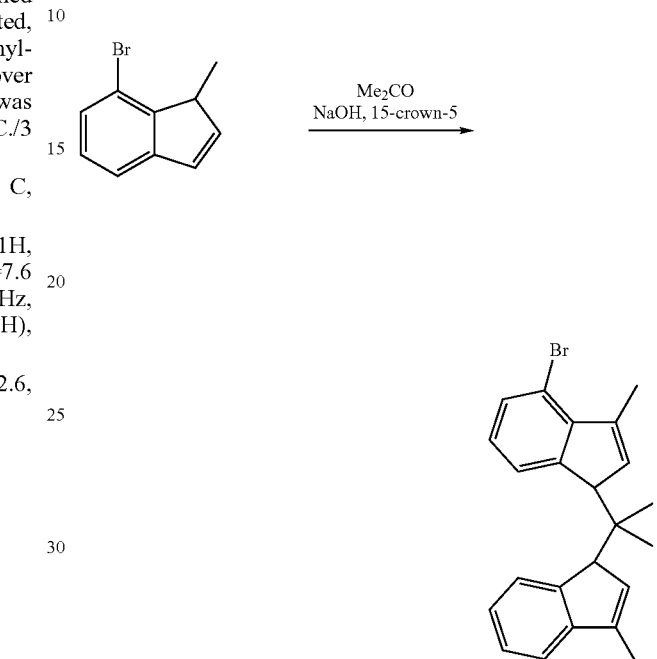

A mixture of 6.00 g (28.7 mmol) of 7-bromo-1-methyl-1H-indene, 2.87 g (71.8 mmol) of NaOH (powder), 0.83 g (14.3 mmol) of acetone, 70 mg of 15-crown-5, and 20 ml of dry THF were stirred for 3 h at room temperature and then added to 500 ml of hexanes. The organic solution was washed with 2×200 ml of water, dried over Na$_2$SO$_4$, and evaporated to dryness. The product was isolated by flash chromatography on Silica Gel 60 (40-63 um, d 30 mm, l 300 mm, eluent: hexanes). Yield 5.40 g (82%) of ca. 1:1 mixture of rac- and meso-isomers.

Anal. calc. for $C_{23}H_{22}Br_2$: C, 60.29; H, 4.84. Found: C, 60.31; H, 4.78.

$^1$H NMR (CDCl$_3$): δ 7.22 (m, 2H, 7,7'-H in rac- and meso-isomers), 7.20 (m, 5,5'-H in rac- and meso-isomers), 6.88 (m, 6,6'-H in rac- and meso-isomers), 6.46 (m, 2H, 3,3'-H in rac- and meso-isomers), 3.59 (m, 1,1'-H in rac- and meso-isomers), 1.69 (s, 3H, 3-Me in meso-isomer), 1.67 (s, 6H, 3,3'-Me in rac-isomer), 1.65 (s, 3H, 3'-Me in meso-isomer), 1.45 (d, J=2.1 Hz, 6H, CMe$_2$ in meso- or rac-isomer), 1.44 (d, J=2.1 Hz, 6H, CMe$_2$ in rac- or meso-isomer).

$^{13}$C NMR (CDCl$_3$): δ 148.7, 147.6, 145.2, 135.8, 128.2, 127.8, 120.6, 118.6, 44.7, 37.6, 30.9, 28.0, 27.9, 27.8, 14.2, 14.1.

Mixture of rac- and meso-isopropylidene-bis($\eta^5$-4-bromo-3-methylinden-1-yl)zirconium dichloride (27)

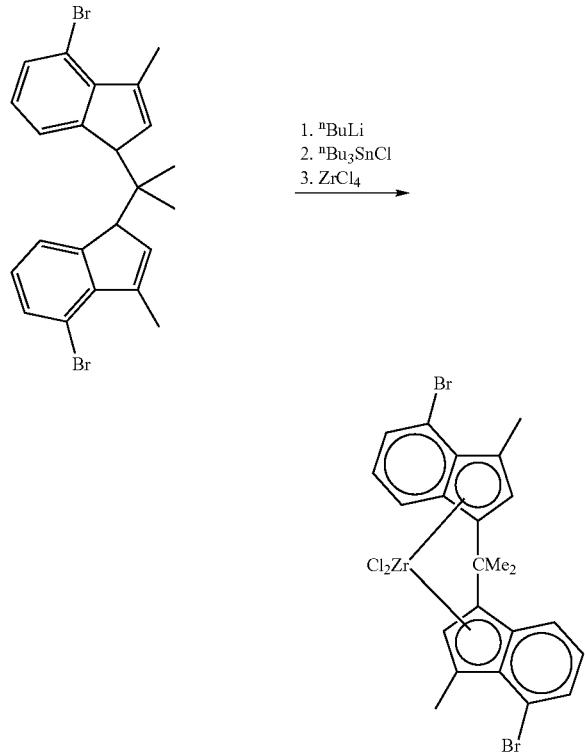

To a solution of 2.70 g (5.89 mmol) of bis(4-bromo-3-methylinden-1-yl)isopropylidene in 70 ml of ether, 4.72 ml (11.8 mmol) of 2.5M $^n$BuLi in hexanes was added. The reaction mixture was stirred for 12 h, then cooled to –80° C., and 4.03 g (12.4 mmol) of tri(n-butyl)tin chloride was added. The resulting mixture was slowly (20 min) warmed to room temperature and then evaporated to dryness. The residue was dissolved in 70 ml of toluene, and the solution filtered through Celite 503. The Celite layer was washed with 3×15 ml of toluene. The combined filtrate was evaporated to dryness to remove traces of THF, and the residue was dissolved in 50 ml of toluene. To this solution, 1.37 g (5.89 mmol) of $ZrCl_4$ was added. The resulting mixture was refluxed for 70 h and then filtered through a glass frit (G4). The precipitate was additionally washed with 2×5 ml of hot toluene. The combined filtrate was additionally stirred at reflux for 30 h and then filtered through a glass frit (G4). The filtrate was evaporated to dryness. The residue was recrystallized from 30 ml of toluene. Crystals that precipitated at –30° C. were collected, washed with 10 ml of hexanes and dried in vacuum. Yield 0.21 g (6%) of ca. 1 to 1 mixture of rac- and meso-complexes.

Anal. calc. for $C_{23}H_{20}Br_2Cl_2Zr$: C, 44.68; H, 3.26. Found: C, 44.85; H, 3.34.

$^1$H NMR ($CD_2Cl_2$): rac-complex, δ 7.63 (m, 2H, 5,5'-H in indenyl of rac-complex), 7.42 (m, 2H, 6,6'-H in indenyl of rac-complex), 7.26 (m, 1H, 6-H in indenyl of rac-complex), 6.75 (m, 1H, 7'-H in indenyl of rac-complex), 5.83 (m, 2H, 2,2'-H in indenyl of rac-complex), 2.55 (s, 3H, 3-Me in indenyl of rac-complex), 2.53 (s, 3H, 3'-Me in indenyl of rac-complex), 2.28 (s, 6H, $CMe_2$ in rac-complex); meso-complex, δ 7.78 (m, 2H, 5,5'-H in indenyl of meso-complex), 7.10 (m, 1H, 6-H in indenyl of meso-complex), 6.99 (m, 1H, 6'-H in indenyl of meso-complex), 5.56 (m, 2H, 2,2'-H in indenyl of meso-complex), 2.65 (s, 3H, 3-Me in indenyl of meso-complex), 2.61 (s, 3H, 3'-Me in indenyl of meso-complex), 2.39 (s, 3H, CMeMe' in meso-complex), 2.05 (s, 3H, CMeMe' in meso-complex).

EXAMPLE 28

Synthesis of rac-dimethylsilyl-bis($\eta^5$-4-bromo-6-fluoro-2-methylinden-1-yl)zirconium dichloride (28)

2-Bromo-1-(bromomethyl)-4-fluorobenzene

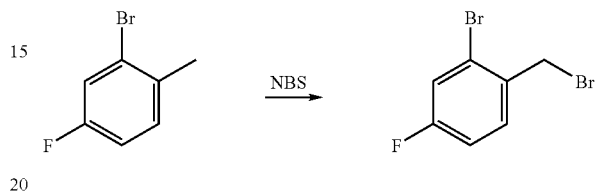

A mixture of 18.9 g (100 mmol) of 2-bromo-4-fluorotoluene, 17.8 g (100 mmol) of N-bromosuccinimide, 400 mg of benzoyl peroxide, and 200 ml of $CCl_4$ were refluxed for 2 h. The reaction mixture was filtered through a glass frit (G2), and the precipitate was additionally washed with 3×50 ml of $CCl_4$. The combined filtrate was evaporated to dryness. Fractional distillation of the residue (bp 92-96° C./4 mm Hg) gave the title product as colorless oil. Yield 20.4 g (76%).

Anal. calc. for $C_7H_5Br_2F$: C, 31.38; H, 1.88. Found: C, 31.49; H, 1.75.

$^1$H NMR ($CDCl_3$): δ 7.43 (dd, J=8.6 Hz, J=5.8 Hz, 1H, 6-H), 7.32 (dd, J=8.1 Hz, J=2.5 Hz, 1H, 5-H), 7.02 (dt, J=8.6 Hz, J=5.8 Hz, 1H, 3-H), 4.57 (m, 2H, $CH_2$).

4-Bromo-6-fluoro-2-methylindan-1-one

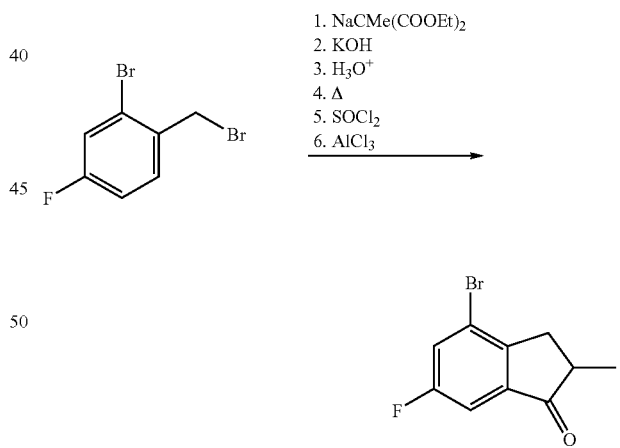

To a solution of sodium ethoxide in ethanol obtained from 5.95 g (0.26 mmol) of sodium and 200 ml of anhydrous ethanol, a solution of 45.1 g (0.26 mmol) of diethyl methylmalonate in 200 ml of ethanol was added dropwise, while vigorously stirring, over 15 min. Then, 64.3 g (0.24 mmol) of 2-bromo-1-(bromomethyl)-4-fluorobenzene in 50 ml of ethanol was added dropwise with such a rate, so the reaction mixture would be slowly refluxing. The resulting mixture was additionally refluxed for 4 h, then cooled to room temperature, and a solution of 51.8 g of potassium hydroxide in 150 ml of water was added. This mixture was refluxed for 3 h, and then ethanol was distilled off at atmospheric pressure. The solution obtained was cooled to ambient temperature and acidified by saturated hydrochloric acid to pH 1. The precipitate formed was filtered off, washed with 2×150 ml of cold water, and dried in air. The dibacic acid obtained was then dehcarboxylated by heating it at 160° C. for 2 h. To the viscous oil obtained, 60 ml of $SOCl_2$ was added, and the resulting mixture was stirred for 24 h at room temperature. The excess of $SOCl_2$ was distilled off, and the residue was dissolved in 200 ml of anhydrous dichloromethane. The solution obtained was added dropwise to a suspension of 37.7 g (0.28 mmol) of $AlCl_3$ in 800 ml of dichloromethane for 1 h at 0° C. The reaction mixture was refluxed for 3 h, then cooled to room temperature, poured on 300 $cm^3$ of ice, and finally acidified by saturated HCl to pH 3. The organic layer was separated, and the aqueous layer was washed with 3×200 ml of methyl-tert-butyl ether. The combined organic fractions were dried over $K_2CO_3$ and then evaporated to dryness. The title product was isolated using flash chromatography (d 50 mm, 1800 mm, eluent: hexanes-$CH_2Cl_2$, 2:1, vol.). Yield 47.3 g (81%).

Anal. calc. for $C_{10}H_8BrFO$: C, 49.41; H, 3.32. Found: C, 49.61; H, 3.30.

$^1$H NMR ($CDCl_3$): δ 7.52 (dd, J=8.1 Hz, J=2.2 Hz, 1H, 7-H), 7.36 (dd, J=7.0 Hz, J=2.2 Hz, 1H, 5-H), 3.32 (dd, J=17.4 Hz, J=7.9 Hz, 1H, 3-H), 2.76-2.84 (m, 1H, 2-H), 2.62 (dd, J=17.4 Hz, J=2.5 Hz, 1H, 3'-H), 1.34 (d, J=7.4 Hz, 3H, 2-Me).

$^{13}$C NMR ($CDCl_3$): δ 207.3, 162.1 (d, J=252.5 Hz), 148.6, 139.1 (d, J=7.3 Hz), 125.1 (d, J=26.4 Hz), 122.1 (d, J=8.8 Hz), 109.0 (d, J=22.0 Hz), 42.7, 35.2, 16.0.

7-Bromo-5-fluoro-2-methyl-1H-indene

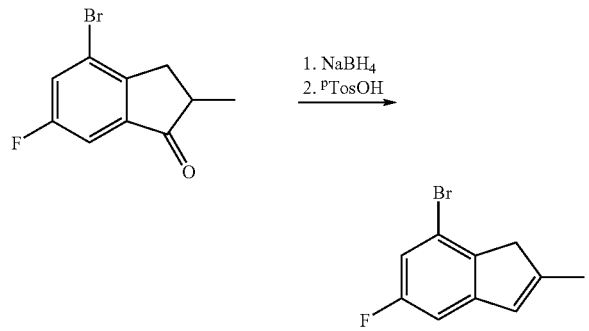

To a solution of 48.4 g (199 mmol) of 4-bromo-6-fluoro-2-methylindan-1-one in 270 ml of a mixture of THF-methanol (2:1, vol.), 11.3 g (299 mmol) of $NaBH_4$ was added in small portions, while vigorously stirring, over 2 h at 0° C. This mixture was stirred for 12 h at room temperature and then added to 500 ml of cold water. The organic layer was separated, the aqueous layer was extracted with 3×200 ml of methyl-tert-butyl ether. The combined organic fractions were dried over $K_2CO_3$ and then evaporated to dryness. The residue was dissolved in 500 ml of toluene, and 2.0 g of p-TosOH was added. The resulting solution was refluxed for 4 h using a Dean-Stark trap to remove the water formed, and then it was passed through a short Silica Gel 60 column (40-63 um, d 100 mm, 180 mm, eluent: hexanes). This column was additionally washed with 250 ml of toluene. The combined organic extract was evaporated to dryness. The residue was dried in vacuum to give the title compound. Yield 38.0 g (84%).

Anal. calc. for $C_{10}H_8BrF$: C, 52.89; H, 3.55. Found: C, 53.08; H, 3.69.

$^1$H NMR ($CDCl_3$): δ 6.91 (dd, J=8.9 Hz, J=2.0 Hz, 1H, 6-H), 6.82 (dd, J=8.9 Hz, J=2.0 Hz, 1H, 4-H), 6.38 (m, 1H, 3-H), 3.14 (s, 2H, 1-H), 2.11 (m, 3H, 2-Me).

$^{13}$C NMR ($CDCl_3$): δ 162.1 (d, J=245.9 Hz), 149.2, 148.1 (d, J =9.5 Hz), 138.6, 126.8 (d, J=2.2 Hz), 117.3 (d, J=11.7 Hz), 113.4 (d, J=26.4 Hz) 106.2 (d, J=22.7 Hz) 43.5, 16.7.

Bis(4-bromo-6-fluoro-2-methyl-1H-inden-1-yl)(dimethyl)silane

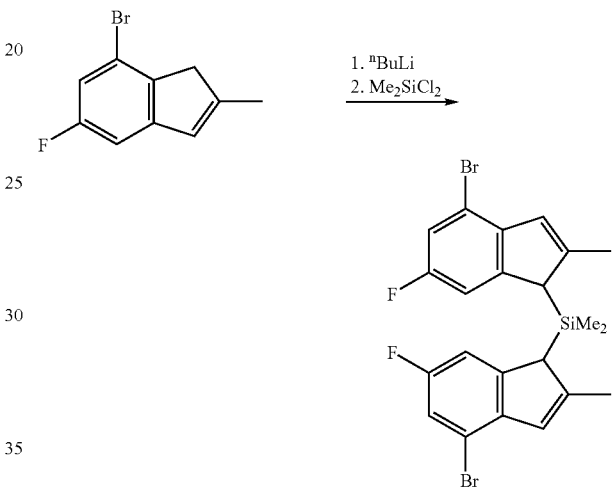

To a solution of 22.2 g (97.8 mmol) of 7-bromo-5-fluoro-2-methyl-1H-indene in 900 ml of ether, 39.1 ml (97.8 mmol) of 2.5 M "BuLi in hexanes was added dropwise, while vigorously stirring, at room temperature. This mixture was stirred for 24 h, and then 6.31 g (48.9 mmol) of dichlorodimethylsilane was added. The resulting mixture was stirred for 36 h, and then 200 ml of water was added. The organic layer was separated, dried over $Na_2SO_4$, and evaporated to dryness. The product was isolated by flash chromatography on Silica Gel 60 (40-63 um, d 50 mm, 1 400 mm, eluent: hexanes). Yield 14.2 g (57%) of a mixture of rac-/meso-isomers (ca. 4:5).

Anal. calc. for $C_{22}H_{22}Br_2Si$: C, 55.71; H, 4.68. Found: C, 56.02; H, 4.77.

$^1$H NMR ($CDCl_3$): δ 7.15 (dd, J=8.7 Hz, J=2.0 Hz, 2H, 7,7'-H in meso-compound), 7.12 (dd, J=8.7 Hz, J=2.0 Hz, 2H, 7,7'-H in rac-compound), 6.94 (t, J=8.1 Hz, 2H, 5,5'-H in rac- and meso-compound), 6.61 (m, 2H, 3,3'-H in meso- and rac-compound), 3.66 (s, 2H, 1,1'-H in meso-compound), 3.62 (s, 2H, 1,1'-H in rac-compound) 2.18 (s, 6H, 2,2'-Me in rac-compound), 2.15 (s, 6H, 2,2'-Me in meso-compound), −0.08 (s, 3H, SiMe in meso-compound), −0.15 (s, 3H, SiMe' in meso-compound), −0.17 (s, 6H, $SiMe_2$ in rac-compound).

$^{13}$C NMR ($CDCl_3$): δ 159.6 (d, J=245.2 Hz)*, 147.5*, 146.5 (d, J=8.1 Hz)*, 141.3 (d, J=10.3 Hz)*, 125.9*, 116.1 (d, J=25.6 Hz)*, 113.1 (d, J=4.4 Hz), 113.2 (d, J=5.1 Hz), 109.5 (d, J=23.4 Hz)*, 48.9*, 17.8*, −4.7, −4.8, −5.2 (* two resonance of rac- and meso-isomers).

125

Rac-dimethylsilyl-bis(η⁵-4-bromo-6-fluoro-2-methylinden-1-yl)zirconium dichloride (28)

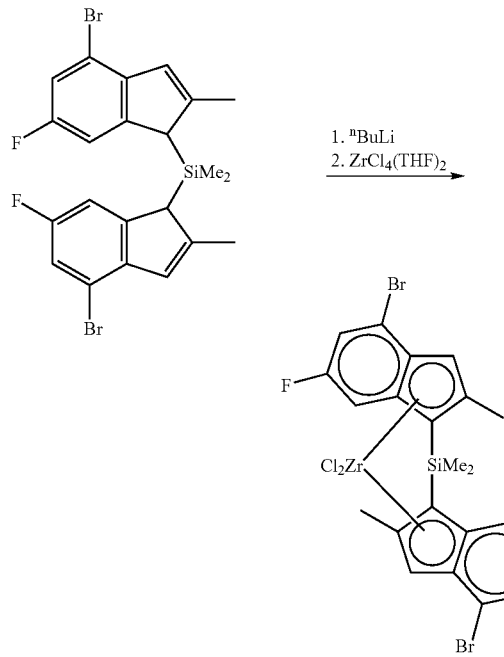

To a solution of 3.83 g (7.51 mmol) of bis(4-bromo-6-fluoro-2-methyl-1H-inden-1-yl)(dimethyl)silane in 150 ml of ether, 6.00 ml (15.0 mmol) of 2.5 M $^n$BuLi in hexanes was added. This mixture was stirred for 24 h at room temperature, then cooled to −30° C., and 2.83 g (7.51 mmol) of ZrCl$_4$(THF)$_2$ was added. The resulting mixture was stirred for 36 h at room temperature and then evaporated to dryness. A mixture of the residue and 140 ml of toluene was stirred for 6 h at 100° C. and then filtered through a glass frit (G4). The filtrate was evaporated to dryness, and the residue was washed with 6×20 ml of dichloromethane and dried in vacuum. Yield 0.81 g (16%) of yellow powder. This product insoluble in all common solvents is considered to be a pure racemate.

Anal. calc. for C$_{22}$H$_{18}$Br$_2$Cl$_2$F$_2$SiZr: C, 39.41; H, 2.71. Found: C, 39.17; H, 4.59.

MALDI-TOF mass, m/z: 670.4. Calc. for C$_{22}$H$_{18}$Br$_2$Cl$_2$F$_2$SiZr: 670.40.

EXAMPLE 29

Synthesis of (η⁵-2-bromoindenyl)(η⁵-2-mesitylindenyl)zirconium dibromide 29)

2-Mesityl-1H-indene

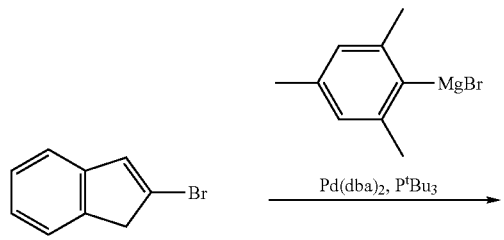

-continued

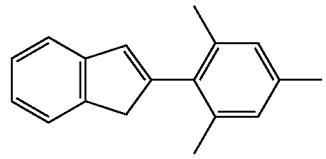

A mixture of 50.0 ml (20.0 mmol) of 0.4 M mesitylmagnesium bromide in THF, 230 mg (0.40 mmol) of Pd(dba)$_2$, 162 mg (0.80 mmol) of P$^t$Bu$_3$, and 3.90 g (20.0 mmol) of 2-bromo-1H-indene was stirred for 48 h at ambient temperature. Then, to the resulting mixture 200 ml of brine was added. The organic layer was separated, and the aqueous layer was extracted with 3×100 ml of ether. The combined organic fractions were dried over K$_2$CO$_3$ and then evaporated to dryness. The product was isolated by flash chromatography on Silica Gel 60 (40-63 um, d 30 mm, 1300 mm, eluent: hexanes-dichloromethane, 20:1, vol.). Yield 3.19 g (68%) of white solid.

Anal. calc. for C$_{18}$H$_{18}$: C, 92.26; H, 7.74. Found: C, 92.33; H, 7.73.

$^1$H NMR (CDCl$_3$): δ 7.52 (m, 1H, 7-H in indenyl), 7.46 (m, 1H, 4-H in indenyl), 7.35 (m, 1H, 6-H in indenyl), 7.24 (m, 1H, 5-H in indenyl), 6.97 (s, 2H, 3,5-H in mesityl), 6.68 (m, 1H, 3-H in indenyl), 3.60 (m, 2H, CH$_2$), 2.36 (s, 3H, 4-Me in mesityl), 2.22 (s, 6H, 2,6-Me in mesityl).

(η⁵-2-Mesitylindenyl)zirconium tribromide

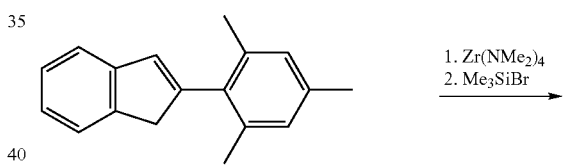

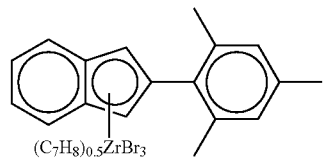

To a suspension of 5.37 g (22.9 mmol) of 2-mesityl-1H-indene in 300 ml of ether 5.89 g (22.0 mmol) of Zr(NMe$_2$)$_4$ was added at room temperature. This mixture was stirred for 12 h at this temperature and then evaporated to dryness in vacuum. To the residue dissolved in 200 ml of toluene, 11.4 g (74.5 mmol) of trimethylbromosilane was added. The resulting mixture was stirred for 12 h at room temperature and then evaporated to dryness. To this residue, 30 ml of toluene and 50 ml of hexanes were added. The precipitate formed was filtered off (using a glass frit G4) and dried in vacuum. Yield 8.98 g (64%) of yellowish powder.

Anal. calc. for $C_{21.5}H_{21}Br_3Zr$: C, 42.31; H, 3.47. Found: C, 38.17; H, 3.29.

$^1$H NMR (CD$_2$Cl$_2$): δ 7.89 (dd, 2H, J=6.6 Hz, J=3.1 Hz, 5,6-H), 7.41 (dd, J=6.6 Hz, J=3.1 Hz, 2H, 4,7-H), 7.16-7.27 (m, 2.5H, C$_6$H$_5$Me), 7.15 (s, 2H, 3,5-H in Me$_3$C$_6$H$_2$), 7.00 (s, 2H, 1,3-H in indenyl), 2.51 (s, 6H, 2-Me and 6-Me in Me$_3$C$_6$H$_2$), 2.36 (s, 1.5H, C$_6$H$_5$Me), 2.33 (s, 3H, 4-Me in Me$_3$C$_6$H$_2$).

$^{13}$C NMR (CD$_2$Cl$_2$): δ 144.4, 140.6, 139.5, 138.2, 131.9, 131.6, 130.5, 130.3, 129.7, 129.2, 128.1, 126.8, 111.0, 25.9, 22.7, 22.2.

($η^5$-2-bromoindenyl)($η^5$-2-mesityl-indenyl)zirconium dibromide (29)

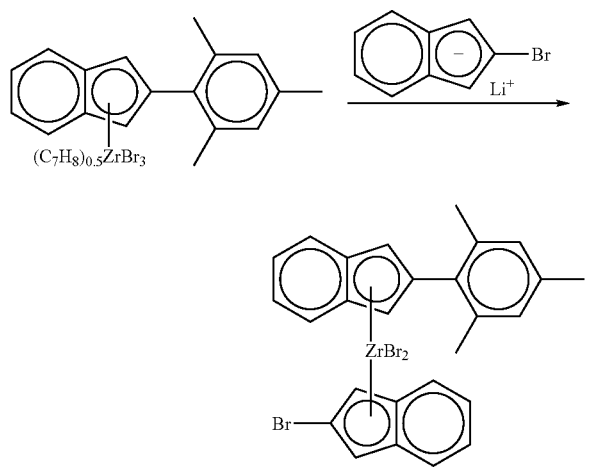

To a suspension of 1.08 g (1.77 mmol) of ($η^5$-2-mesitylindene)zirconium tribromide in 36 ml of a 1:1 mixture of toluene-ether, 356 mg (1.77 mmol) of lithium salt of 2-bromo-1H-indene was added at −30° C. This mixture was stirred for 24 h at room temperature and then evaporated to dryness. The residue was dissolved in 50 ml of toluene. The resulting mixture was stirred for 2 h at 80° C. and then filtered through Celite 503. The Celite layer was additionally washed with 3×10 ml of hot toluene. The combined filtrate was evaporated to dryness, and the residue washed with 4×10 ml of hexanes and dried in vacuum. Yield 0.50 g (42%) of yellowish powder.

Anal. calc. for $C_{27}H_{23}Br_3Zr$: C, 47.80; H, 3.42. Found: C, 47.62; H, 3.30.

$^1$H NMR (CDCl$_3$): δ 7.60 (dd, J=6.4 Hz, J=3.1 Hz, 2H, 4,7-H in (2,4,6-trimethylphenyl)indenyl), 7.26 (m, 6H, 5,6-H in (2,4,6-trimethylphenyl)indenyl and 4,5,6,7-H in 2-bromoindenyl), 7.09 (s, 2H, 3,5-H in Me$_3$C$_6$H$_2$), 6.36 (s, 2H, 1,3-H in 2,4,6-trimethylphenyl)indenyl), 6.02 (s, 2H, 1,3-H in 2-bromoindenyl).

EXAMPLE 30

Synthesis of ($η^5$-2-bromoindenyl)($η^5$-2-pyrrolidinyl-indenyl)zirconium dibromide (30)

1-(1H-Inden-2-yl)pyrrolidine

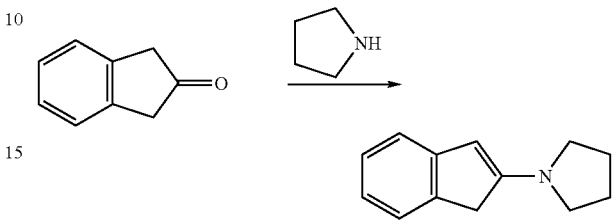

A mixture of 12.5 g (94.7 mmol) of indanone-2, 8.52 g (120 mmol) of pyrrolidine, 30 g of activated molecular sieves (4A), and 210 ml of toluene were stirred for 24 h at 70° C. This mixture was cooled to room temperature, filtered through a glass frit (G2), and the precipitate (crushed molecular shieves) was washed with 3×30 ml of hexanes. The combined filtrate was evaporated to dryness, and the residue was recrystallized from 100 ml of hot hexanes. Crystals that precipitated at 0° C. were collected, washed with 2×10 ml of cold hexanes, and dried in vacuum. Yield 8.40 g (48%).

Anal. calc. for $C_{13}H_{15}N$: C, 84.28; H, 8.16. Found: C, 84.11; H, 8.21.

$^1$H NMR (CDCl$_3$): δ 7.20 (d, J=7.3 Hz, 1H, 7-H), 7.10 (t, J=7.3 Hz, 1H, 6-H), 7.00 (d, J=7.3 Hz, 1H, 4-H), 6.81 (t, J=7.3 Hz, 1H, 5-H), 5.21 (br.s., 1H, 3-H), 3.39 (s, 2H, 1-H), 3.25 (m, 4H, 2,2',5,5'-H in pyrrolidinyl), 1.97 (m, 4H, 3,3',4,4'-H in pyrrolidinyl).

($η^5$-2-Bromoindenyl)zirconium tribromide

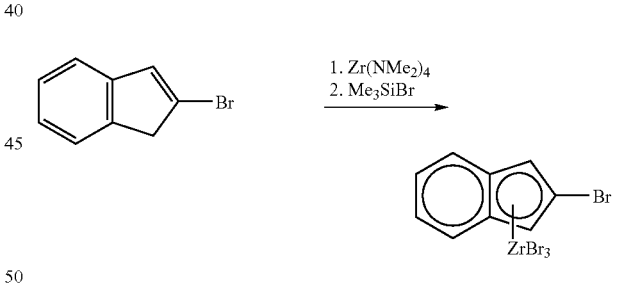

To a solution of 9.49 g (48.7 mmol) of 2-bromo-1H-indene in 490 ml of ether, 12.3 g (46.3 mmol) of Zr(NMe$_2$)$_4$ was added. The reaction mixture was stirred for 12 h and then evaporated to dryness. The residue was dissolved in 500 ml of toluene, and 23.1 g (151 mmol) of bromotrimethylsilane was added. The mixture was stirred for 24 h at room temperature, evaporated to a volume equal to ca. 250 ml, and filtered through a glass frit (G4). Crystals that precipitated at a temperature of 30° C. from the filtrate were separated, washed with 3×20 ml of cold dichloromethane, and dried in vacuum. Yield 16.1 g (66%) of yellow crystalline product.

Anal. calc. for $C_9H_6Br_4Zr$: C, 20.59; H, 1.15. Found: C, 20.68; H, 1.20.

$^1$H NMR (CDCl$_3$): δ 7.75 (dd, 2H, J=6.5 Hz, J=3.0 Hz, 5,6-H), 7.43 (dd, J=6.5 Hz, J=3.0 Hz, 2H, 4,7-H), 7.13 (s, 2H, 1,3-H).

($\eta^5$-2-bromoindenyl)($\eta^5$-2-pyrrolidinyl-indenyl)zirconium dibromide (30)

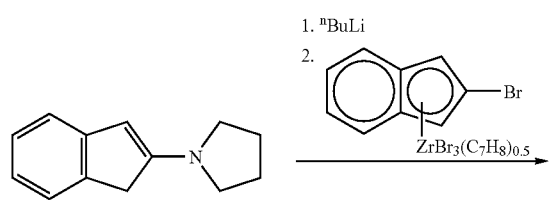

To a solution of 0.53 g (2.86 mmol) of 1-(1H-inden-2-yl)pyrrolidine in 25 ml of ether, 1.14 ml (2.86 mmol) of 2.5 M "BuLi in hexanes was added at room temperature. This mixture was stirred for 12 h and then added to a suspension of 1.63 g (2.86 mmol) of ($\eta^5$-2-bromoindenyl)zirconium tribromide in 60 ml of a mixture of toluene-ether (1:1, vol.) at −30° C. The resulting mixture was stirred for 24 h at room temperature and then it was evaporated to dryness. The residue was dissolved in 80 ml of toluene; the mixture stirred for 2 h at 100° C. and then filtered through Celite 503. The Celite layer was additionally washed with 2×20 ml of hot toluene. The combined filtrate was evaporated to dryness, and the residue was recrystallized from 15 ml of hot toluene. Crystals that precipitated at 0° C. were collected, washed with 5 ml of cold toluene, and dried in vacuum. Yield 0.80 g (44%) of yellowish crystalline solid.

Anal. calc. for $C_{22}H_{20}Br_3NZr$: C, 41.99; H, 3.20. Found: C, 41.78; H, 3.05.

$^1$H NMR ($C_6D_6$): δ 7.42 (dd, J=6.3 Hz, J=3.0 Hz, 2H, 4,7-H in 2-bromoindenyl), 7.02 (dd, J=6.3 Hz, J=3.0 Hz, 2H, 4,7-H in 2-pyrrolidinylindenyl), 6.84 (dd, J=6.3 Hz, J=3.0 Hz, 4H, 5,6,5',6'-H), 6.04 (s, 2H, 1,3-H in 2-bromoindenyl), 5.18 (s, 2H, 1,3-H in 2- pyrrolidinylindenyl), 3.26 (m, 2H, 2,5-H in pyrrolidinyl), 2.70 (m, 2H, 2',5'-H in pyrrolidinyl), 1.66 (m, 2H, 3,4-H in pyrrolidinyl), 1.39 (m, 2H, 3',4'-H in pyrrolidinyl).

EXAMPLE 31

Synthesis of ($\eta^5$-2-bromoindenyl)($\eta^5$-2-(3,5-dibromophenyl)-indenyl)zirconium dibromide (31)

2-(3,5-Dibromophenyl)-1H-indene

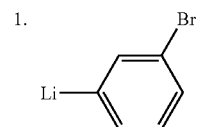

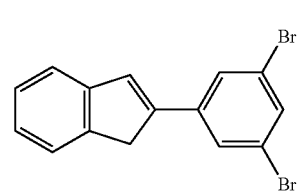

To a solution of 12.6 g (40.0 mmol) of 1,3,5-tribromobenzene in 400 ml of ether, 160 ml (40.0 mmol) of 0.25 M "BuLi in hexanes was added for 1 h at −80° C. The mixture was stirred for 1.5 h at this temperature, and then a solution of 5.29 g (40.0 mmol) of indanone-2 in 200 ml of ether was added dropwise over 1 hour while vigorously stirring. The reaction mixture was allowed to warm to room temperature and it was stirred at this temperature for 24 h. Then, 100 ml of water was added. The organic layer was separated; the aqueous layer was extracted with 3×50 ml of dichloromethane. The combined organic layers were dried over $Na_2SO_4$ and then evaporated to dryness. The residue was dissolved in 250 ml of toluene, and 0.75 g of p-TosOH was added. The resulting solution was refluxed for 1 hours using a Dean-Stark trap to remove the water formed. Next, the mixture was evaporated to dryness, and the product was isolated by flash-chromatography on Silica Gel 60 (d 50 mm, l 400 mm, eluent: hexanes). Yield 8.54 g (61%) of white powder.

Anal. calc. for $C_{15}H_{10}Br_2$: C, 51.47; H, 2.88. Found: C, 51.66; H, 2.80.

$^1$H NMR ($CDCl_3$): δ 7.60 (d, 2H, J=1.5 Hz, 2,6-H in $Br_2C_6H_3$), 7.49 (m, 1H, 4-H in $Br_2C_6H_3$), 7.43 (d, J=7.3 Hz, 1H, 7-H in indenyl), 7.38 (d, J=7.3 Hz, 1H, 4-H in indenyl), 7.27 (t, J=7.3 Hz, 1H, 5-H in indenyl), 7.20 (t, J=7.3 Hz, 1H, 6-H in indenyl), 7.18 (m, 1H, 3-H in indenyl), 3.63 (br.s., 1H, 1-H in indenyl).

$^{13}$C NMR ($CDCl_3$): δ 144.4, 143.1, 143.0, 139.4, 132.4, 129.1, 127.2, 126.8, 125.6, 123.7, 123.2, 121.5, 38.8.

($\eta^5$-2-bromoindenyl)($\eta^5$-2-(3,5-dibromophenyl)-indenyl)zirconium dibromide (31)

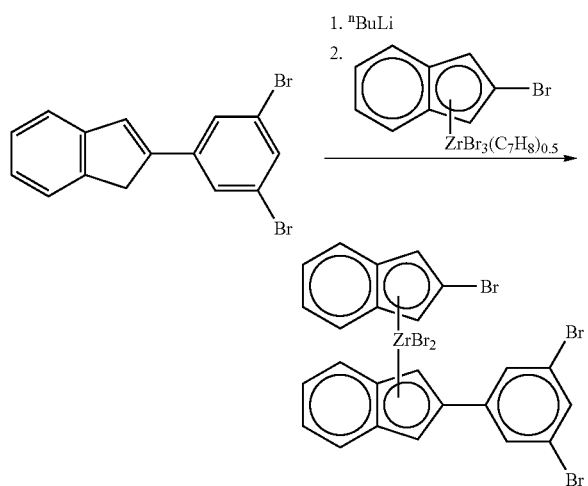

To a suspension of 1.08 g (1.90 mmol) of ($\eta^5$-2-bromoindenyl)zirconium tribromide in 40 ml of a mixture of toluene-ether (1:1, vol.), 0.71 g (1.90 mmol) of the sodium salt of 2-(3,5-dibromophenyl)-1H-indene was added at −30° C. This mixture was stirred for 48 h at room temperature and then it was evaporated to dryness. To the residue, 40 ml of toluene was added. The resulting mixture was stirred for 5 h at 70° C. and then filtered through Celite 503. The Celite layer was additionally washed with 3×10 ml of hot toluene. The combined filtrate was evaporated to dryness, and the residue was recrystallized from 30 ml of hot toluene. Crystals that precipitated at room temperature were collected, washed with 2×5 ml of cold toluene, and dried in vacuum. Yield 0.85 g (56%) of yellowish crystalline solid.

Anal. calc. for $C_{24}H_{15}Br_5Zr$: C, 36.30; H, 1.90. Found: C, 36.47; H, 2.04.

$^1$H NMR ($C_6D_6$): δ 7.59 (d, J=1.7 Hz, 2H, 2,6-H in $Br_2C_6H_3$), 7.42 (t, J=1.7 Hz, 1H, 4-H in $Br_2C_6H_3$), 7.31 (dd, J=6.6 Hz, J=3.1 Hz, 2H, 4,7-H in 2-(3,5-dibromophenyl)indenyl), 6.92 (dd, J=6.3 Hz, J=3.1 Hz, 2H, 4,7-H in 2-bromoindenyl), 6.81 (m, 4H, 5,6-H in 2-(3,5-dibromophenyl)indenyl and 5,6-H in 2-bromoindenyl), 6.27 (m, 2H, 1,3-H in 2-(3,5-dibromophenyl)indenyl, 5.92 (m, 2H, 1,3-H in 2-bromoindenyl).

$^{13}$C NMR ($C_6D_6$): δ 134.0, 129.3, 128.7, 128.2, 128.0, 127.9, 127.8, 127.1, 126.7, 125.9, 124.8, 123.4, 109.2, 103.8.

EXAMPLE 32

Synthesis of ($\eta^5$-2-bromoindenyl)($\eta^5$-2-phenylindenyl)zirconium dibromide (32)

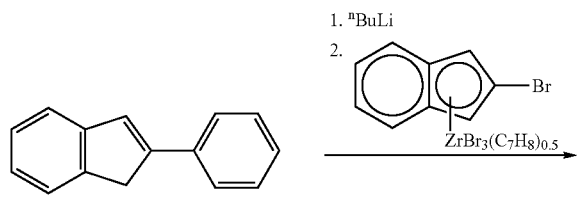

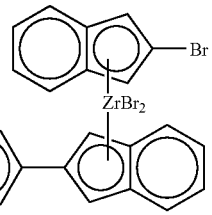

To a suspension of 0.55 g (2.86 mmol) of 2-phenyl-1H-indene in a mixture of toluene-ether (1/1, vol.), 1.14 ml (2.86 mmol) of 2.5 M "BuLi in hexanes was added at −30° C. This mixture was stirred for 24 h at room temperature, then cooled to −30° C., and 1.63 g (2.86 mmol) of ($\eta^5$-2-bromoindenyl)zirconium tribromide was added. The resulting mixture was stirred for 24 h at room temperature and then evaporated to dryness. The residue was dissolved in 50 ml of toluene, and this mixture was stirred for 5 h at 100° C., and then filtered through Celite 503. The filtrate was evaporated to dryness under vacuum. The residue was recrystallized from 15 ml of hot toluene. Crystals that precipitated at ambient temperature were collected, washed with 2×3 ml of cold toluene, and dried in vacuum. Yield 900 mg (49%) of yellowish crystalline solid.

Anal. calc. for $C_{24}H_{17}Br_3Zr$: C, 45.30; H, 2.69. Found: C, 45.42; H, 2.80.

$^1$H NMR ($CD_2Cl_2$): δ 7.74 (m, 2H, 4,7-H in 2-phenylindenyl), 7.61 (dd, J=6.3 Hz, J=3.0 Hz, 2H, 5,6-H in 2-phenylindenyl), 7.52 (m, 2H, 4,7-H in 2-bromindenyl), 7.43 (tt, J=7.6 Hz, J=1.2 Hz, 1H, 4-H in Ph), 7.28 (dd, J=6.4 Hz, J=2.8 Hz, 2H, 5,6-H in 2-bromindenyl), 7.1 (m, 4H, 2,3,5,6-H in Ph), 7.03 (s, 2H, 1,3-H in 2-phenylindenyl), 6.35 (s, 2H, 1,3-H in 2-bromindenyl).

$^{13}$C NMR ($CD_2Cl_2$): δ 135.0, 134.4, 130.7, 130.6, 129.7, 128.9, 128.6, 128.3, 127.5, 127.2, 126.4, 126.0, 111.1, 105.5.

Experimental—Polymerizations

In the following experiments pressure is reported in atmospheres (atm) and pounds per square inch (psi). The conversion factors to S. I. Units are: 1 psi equals 6.894757 kPa and 1 atm equals 101.325 kPa.

Transition metal compound (TMC) solutions were typically prepared using toluene (ExxonMobil Chemical—anhydrous, stored under $N_2$) (98%). Unless otherwise mentioned, TMC solutions are 0.2 mmol/L for $C_2$ and $C_2/C_8$ (co)polymerizations, and 0.6 mmol/L for $C_3$ and $C_3/C_2$ (co)polymerizations.

Solvents, polymerization grade toluene and hexanes were supplied by ExxonMobil Chemical Co. and thoroughly dried and degassed prior to use.

1-octene (98%) was purchased from Aldrich Chemical Company and dried by stirring over NaK overnight followed by filtration through basic alumina (Aldrich Chemical Company, Brockman Basic 1).

Polymerization grade ethylene was used and further purified by passing it through a series of columns: 500 cc Oxyclear cylinder from Labclear (Oakland, Calif.) followed by a 500 cc column packed with dried 3 Å mole sieves purchased from Aldrich Chemical Company, and a 500 cc column packed with dried 5 Å mole sieves purchased from Aldrich Chemical Company.

Polymerization grade propylene was used without further purification.

MAO (methylalumoxane, 10 wt % in toluene) was purchased from Albemarle Corporation and was used as a 1 or 2 wt % in toluene solution. Micromoles of MAO reported in the experimental section are based on the micromoles of aluminum in MAO. The formula weight of MAO is 58.0 grams/mole. TiBAl (triisobutylaluminum, NEAT) and TnOAl (tri-n-octylaluminum, NEAT) were purchased from AKZO Nobel. TnOAl was used as a 0.01 mol/L solution in hexanes, and TiBAl was used as a 5 mmol/L solution in toluene. Dimethylanilinium tetrakis(perfluorophenyl)borate ([DMAH][B(pfp)$_4$], [PhNMe$_2$H][B(C$_6$F$_5$)$_4$], D4) was purchased from Albemarle Corporation or Boulder Scientific Company and used without further purification.

Reactor Description and Preparation:

Polymerizations were conducted in an inert atmosphere (N2) drybox using autoclaves equipped with an external heater for temperature control, glass inserts (internal volume of reactor=23.5 mL for C2 and C2/C8 runs; 22.5 mL for C3 and C2/C3 runs), septum inlets, regulated supply of nitrogen, ethylene and propylene, and equipped with disposable PEEK mechanical stirrers (800 RPM). The autoclaves were prepared by purging with dry nitrogen at 110° C. or 115° C. for 5 hours and then at 25° C. for 5 hours.

Ethylene Polymerization or Ethylene/1-octene Copolymerization:

The reactor was prepared as described above, and then purged with ethylene. Toluene, 1-octene (100 μL when used), and activator (MAO) were added via syringe at room temperature and atmospheric pressure. The reactor was then brought to process temperature (80° C.) and charged with ethylene to process pressure (75 psig=618.5 kPa) while stirring at 800 RPM. The transition metal compound (TMC, 0.02 μmol) was added via syringe with the reactor at process conditions. In cases where some MAO (0.4 μmol of Al) or TIBAL (0.08 μmol, 5 mmol/L in toluene) was also precontacted with the TMC, the MAO or TIBAL was added to the TMC first and then the resulting solution was added to the reactor at process conditions. Amounts of reagents not specified above are given in Tables 1 and 3. Ethylene was allowed to enter (through the use of computer controlled solenoid valves) the autoclaves during polymerization to maintain reactor gauge pressure (±2 psig). Reactor temperature was monitored and typically maintained within ±1° C. Polymerizations were halted by addition of approximately 50 psi O2/Ar (5 mole % O2) gas mixture to the autoclaves for approximately 30 seconds. The polymerizations were quenched after a predetermined cumulative amount of ethylene had been added or for a maximum of 20 minutes polymerization time. The final conversion (in psi) of ethylene added/consumed is reported in the Tables 1 and 3, in addition to the quench time for each run. The reactors were cooled and vented. The polymer was isolated after the solvent was removed in-vacuo. Yields reported include total weight of polymer and residual catalyst. Catalyst activity is reported as grams of polymer per mmol transition metal compound per atmosphere ethylene per hour of reaction time (g/mmol·hr·atm).

Propylene Polymerization:

The reactor was prepared as described above, then heated to 40° C. and then purged with propylene gas at atmospheric pressure. Hexanes, MAO, and liquid propylene (1.066 mL, unless indicated otherwise in Table 5) were added via syringe. The reactor was then heated to process temperature (70° C.) while stirring at 800 RPM. The TMC was added via syringe with the reactor at process conditions. Amounts of reagents not specified above are given in Table 5. Reactor temperature was monitored and typically maintained within ±1° C. Polymerizations were halted by addition of approximately 50 psi O$_2$/Ar (5 mole % O$_2$) gas mixture to the autoclaves for approximately 30 seconds. The polymerizations were quenched based on a predetermined pressure loss of approximately 5 psi. The actual quench time is reported in Table 5 for each run. The reactors were cooled and vented. The polymer was isolated after the solvent was removed in-vacuo. Yields reported include total weight of polymer and residual catalyst. Catalyst activity is reported as grams of polymer per mmol transition metal compound per hour of reaction time (g/mmol·hr).

Ethylene/Propylene Copolymerization:

The reactor was prepared as described above, and then purged with ethylene. Reactors were heated to 40° C. and ethylene was then added to the reactor to a target pressure of 10 psig (single addition), followed by the addition of hexanes, MAO, and then liquid propylene (1.066 mL). All additions were made via syringe. The reactor was then heated to process temperature (70° C.) while stirring at 800 RPM. The TMC was added via syringe with the reactor at process conditions. Amounts of reagents not specified above are given in Table 7. Reactor temperature was monitored and typically maintained within ±1° C. Polymerizations were halted by addition of approximately 50 psi O$_2$/Ar (5 mole % O$_2$) gas mixture to the autoclaves for approximately 30 seconds. The polymerizations were quenched based on a predetermined pressure loss of approximately 5 psi. The actual quench time is reported in Table 8 for each run. The reactors were cooled and vented. The polymer was isolated after the solvent was removed in-vacuo. Yields reported include total weight of polymer and residual catalyst. Catalyst activity is reported as grams of polymer per mmol transition metal compound per hour of reaction time (g/mmol·hr).

Polymer characterization:

Polymer characterization results for polyethylene samples are reported in Table 2, for ethylene-1-octene copolymers are reported in Table 4, for polypropylene are reported in Table 6, and for ethylene-propylene copolymers are reported in Table 8.

For analytical testing, polymer sample solutions were prepared by dissolving polymer in 1,2,4-trichlorobenzene (TCB, 99+% purity from Sigma-Aldrich) containing 2,6-di-tert-butyl-4-methylphenol (BHT, 99% from Aldrich) at 160° C. in a shaker oven for approximately 3 hours. The typical concentration of polymer in solution is between 0.4 to 0.9 mg/mL with a BHT concentration of 1.25 mg BHT/mL of TCB. Samples are cooled to 135° C. for testing.

Molecular weights (weight average molecular weight (Mw) and number average molecular weight (Mn)) and molecular weight distribution (MWD=Mw/Mn), which is also sometimes referred to as the polydispersity (PDI) of the polymer, were measured by Gel Permeation Chromatography using a Symyx Technology GPC equipped with evaporative light scattering detector and calibrated using polystyrene standards (Polymer Laboratories: Polystyrene. Calibration Kit S-M-10: Mp (peak Mw) between 5000 and 3,390,000). Samples were run in TCB at (135° C. sample temperatures, 160° C. oven/columns) using three Polymer Laboratories: PLgel 10 μm Mixed-B 300×7.5 mm columns in series. No column spreading corrections were employed. Numerical analyses were performed using Epoch® software available from Symyx Technologies.

The sample preparation for SAMMS (Sensory Array Modular Measurement System) thermal analysis measurements involved depositing the stabilized polymer solution onto a silanized wafer (Part Number S10457, Symyx). The solvent was then evaporated off at ~145° C. By this method, approximately between 0.12 and 0.24 mg of polymer is deposited onto each corresponding wafer cell. Thermal analysis was measured on a Symyx Technologies SAMMS instrument that measures polymer melt temperatures via the 3 ω technique. The analysis first employs a rapid-scan protocol that heats each cell from 27° C. to 200° C. in ~35 seconds and then rapidly cools the sample to room temperature. This complete procedure takes approximately 60 seconds per cell and is used to minimize each sample's thermal history. The second step involves running a high-resolution scan protocol to measure the second melt of the sample. The protocol heats each cell from 27° C. to 200° C. in ~3 minutes and then rapidly cools the sample to room temperature. The high-resolution scan takes approximately three times the amount of time to complete as the rapid-scan protocol. If multiple melting peaks are present, Epoch® Software reports the largest amplitude peak. SAMMS data is reported under the heading of Tm (° C.) in Tables 2, 4, and 6.

Samples for infrared analysis were prepared by depositing the stabilized polymer solution onto a silanized wafer (Part number S10860, Symyx). By this method, approximately between 0.12 and 0.24 mg of polymer is deposited on the wafer cell. The samples were subsequently analyzed on a Brucker Equinox 55 FTIR spectrometer equipped with Pikes's MappIR specular reflectance sample accessory. Spectra, covering a spectral range of 5000 $cm^{-1}$ to 500 $cm^{-1}$, were collected at a 2 $cm^{-1}$ resolution with 32 scans.

For ethylene-1-octene copolymers, the wt. % copolymer is determined via measurement of the methyl deformation band at ~1375 $cm^{-1}$. The peak height of this band is normalized by the combination and overtone band at ~4321 $cm^{-1}$, which corrects for path length differences. The normalized peak height is correlated to individual calibration curves from $^1$H NMR data to predict the wt. % copolymer content within a concentration range of 2 to 35 wt. % for octene. Typically, $R^2$ correlations of 0.98 or greater are achieved. These numbers are reported in Table 4 under the heading Octene wt %).

For ethylene-propylene copolymers, the wt. % ethylene is determined via measurement of the methylene rocking band (~770 $cm^{-1}$ to 700 $cm^{-1}$). The peak area of this band is normalized by sum of the band areas of the combination and overtone bands in the 4500 $cm^{-1}$ to 4000 $cm^{-1}$ range. The normalized band area is then correlated to a calibration curved from $^{13}$C NMR data to predict the wt. % ethylene within a concentration range of ~5 to 40 wt. %. Typically, $R^2$ correlations of 0.98 or greater are achieved. These numbers are reported in Table 8 under the heading, Ethylene (wt %).

TABLE 1

Ethylene Polymerization Runs - Part I.

| Ex # | TMC | Activator | Activator[a] μmol | Total Toluene (mL) | Total Hexanes (mL) | Final Conversion (psi) | Quench Time (sec) | Polymer Yield (g) | Activity (g/(mmol · hr · atm)) |
|---|---|---|---|---|---|---|---|---|---|
| PE-1 | 1 | MAO | 10.00 | 5.00 | 0 | 20.1 | 124.5 | 0.0771 | 18,268 |
| PE-2 | 1 | MAO | 10.00 | 5.00 | 0 | 20.1 | 130.0 | 0.0738 | 16,746 |
| PE-3 | 1 | MAO | 10.00 | 5.00 | 0 | 20.1 | 185.1 | 0.0782 | 12,461 |
| PE-4 | 1 | MAO | 10.00 | 5.00 | 0 | 20.3 | 154.0 | 0.0790 | 15,136 |
| PE-5 | 1[f] | D4 | 0.02 | 4.90 | 0.099 | 20.1 | 349.6 | 0.0572 | 4,826 |
| PE-6 | 1[f] | D4 | 0.02 | 4.90 | 0.099 | 20.1 | 96.0 | 0.0539 | 16,557 |
| PE-7 | 1[f] | D4 | 0.02 | 4.90 | 0.099 | 20.1 | 171.1 | 0.0410 | 7,068 |
| PE-8 | 1[f] | D4 | 0.02 | 4.90 | 0.099 | 20.1 | 121.9 | 0.0558 | 13,501 |
| PE-9 | 4 | MAO | 10.00 | 5.00 | 0 | 20.1 | 183.2 | 0.0517 | 8,324 |
| PE-10 | 4 | MAO | 10.00 | 5.00 | 0 | 20.1 | 201.1 | 0.0587 | 8,611 |
| PE-11 | 4 | MAO | 10.00 | 5.00 | 0 | 20.3 | 224.0 | 0.0549 | 7,229 |
| PE-12 | 4 | MAO | 10.00 | 5.00 | 0 | 20.3 | 203.3 | 0.0503 | 7,299 |
| PE-13 | 5 | MAO | 10.00 | 5.00 | 0 | 20.6 | 38.2 | 0.0781 | 60,368 |
| PE-14 | 5 | MAO | 10.00 | 5.00 | 0 | 20.8 | 35.5 | 0.0821 | 68,157 |
| PE-15 | 5 | MAO | 10.00 | 5.00 | 0 | 20.6 | 30.8 | 0.0831 | 79,505 |
| PE-16 | 5 | MAO | 10.00 | 5.00 | 0 | 20.1 | 34.0 | 0.0740 | 64,160 |
| PE-17 | 6 | MAO | 10.00 | 5.00 | 0 | 20.3 | 42.9 | 0.0732 | 50,341 |
| PE-18 | 6 | MAO | 10.00 | 5.00 | 0 | 20.1 | 36.9 | 0.0786 | 62,880 |
| PE-19 | 6 | MAO | 10.00 | 5.00 | 0 | 21.1 | 40.0 | 0.0756 | 55,803 |
| PE-20 | 6 | MAO | 10.00 | 5.00 | 0 | 20.6 | 43.0 | 0.0679 | 46,598 |
| PE-21 | 6[f] | D4 | 0.02 | 4.90 | 0.099 | 20.1 | 666.3 | 0.0319 | 1,412 |
| PE-22 | 6[f] | D4 | 0.02 | 4.90 | 0.099 | 17.2 | 1201.7 | 0.0240 | 589 |
| PE-23 | 6[f] | D4 | 0.02 | 4.90 | 0.099 | 13.9 | 1200.6 | 0.0175 | 430 |
| PE-24 | 6[f] | D4 | 0.02 | 4.90 | 0.099 | 20.1 | 520.0 | 0.0299 | 1,696 |
| PE-25 | 8 | MAO | 10.00 | 5.00 | 0 | 20.6 | 42.6 | 0.0785 | 54,340 |
| PE-26 | 8 | MAO | 10.00 | 5.00 | 0 | 20.3 | 42.8 | 0.0831 | 57,282 |
| PE-27 | 8 | MAO | 10.00 | 5.00 | 0 | 20.5 | 72.2 | 0.0581 | 23,742 |
| PE-28 | 8 | MAO | 10.00 | 5.00 | 0 | 20.3 | 51.6 | 0.0703 | 40,170 |
| PE-29 | 9 | MAO | 10.00 | 5.00 | 0 | 20.1 | 375.5 | 0.0781 | 6,134 |
| PE-30 | 9 | MAO | 10.00 | 5.00 | 0 | 20.1 | 374.6 | 0.0765 | 6,024 |
| PE-31 | 9 | MAO | 10.00 | 5.00 | 0 | 20.1 | 434.5 | 0.0653 | 4,433 |
| PE-32 | 9 | MAO | 10.00 | 5.00 | 0 | 20.1 | 388.6 | 0.0722 | 5,480 |
| PE-33 | 10 | MAO | 10.00 | 5.00 | 0 | 20.1 | 794.8 | 0.0402 | 1,492 |
| PE-34 | 10 | MAO | 10.00 | 5.00 | 0 | 20.3 | 1070.9 | 0.0364 | 1,003 |
| PE-35 | 10 | MAO | 10.00 | 5.00 | 0 | 20.1 | 772.8 | 0.0428 | 1,634 |
| PE-36 | 10 | MAO | 10.00 | 5.00 | 0 | 20.1 | 731.21 | 0.0369 | 1,489 |
| PE-37 | 15 | MAO | 10.00 | 5.00 | 0 | 20.1 | 132.6 | 0.0920 | 20,463 |
| PE-38 | 15 | MAO | 10.00 | 5.00 | 0 | 20.1 | 147.7 | 0.0867 | 17,313 |
| PE-39 | 15 | MAO | 10.00 | 5.00 | 0 | 20.1 | 132.7 | 0.0862 | 19,159 |
| PE-40 | 15 | MAO | 10.00 | 5.00 | 0 | 20.1 | 137.1 | 0.0886 | 19,057 |
| PE-41 | 18 | MAO | 10.00 | 5.00 | 0 | 20.3 | 35.4 | 0.0857 | 71,326 |
| PE-42 | 18 | MAO | 10.00 | 5.00 | 0 | 20.5 | 32.3 | 0.0876 | 79,995 |

TABLE 1-continued

Ethylene Polymerization Runs - Part I.

| Ex # | TMC | Activator | Activator[a] μmol | Total Toluene (mL) | Total Hexanes (mL) | Final Conversion (psi) | Quench Time (sec) | Polymer Yield (g) | Activity (g/(mmol · hr · atm)) |
|---|---|---|---|---|---|---|---|---|---|
| PE-43 | 18 | MAO | 10.00 | 5.00 | 0 | 20.1 | 32.4 | 0.0808 | 73,580 |
| PE-44 | 18 | MAO | 10.00 | 5.00 | 0 | 20.8 | 33.8 | 0.0794 | 69,269 |
| PE-45 | 23 | MAO | 10.00 | 5.00 | 0 | 20.5 | 26.6 | 0.0943 | 104,724 |
| PE-46 | 23 | MAO | 10.00 | 5.00 | 0 | 20.6 | 26.7 | 0.0892 | 98,578 |
| PE-47 | 23 | MAO | 10.00 | 5.00 | 0 | 20.6 | 32.6 | 0.0894 | 80,838 |
| PE-48 | 23 | MAO | 10.00 | 5.00 | 0 | 20.8 | 31.0 | 0.0911 | 86,737 |

[a] Micromoles refers to the micromoles of Al in MAO.
[f] In this experiment, TiBAl was premixed with the indicated TMC.

TABLE 2

Ethylene Polymerization Runs - Part II.

| Ex # | TMC | Mw | Mn | PDI | Tm (° C.) |
|---|---|---|---|---|---|
| PE-1 | 1 | 839,200 | 439,031 | 1.9 | — |
| PE-2 | 1 | 841,340 | 447,738 | 1.9 | — |
| PE-3 | 1 | 821,613 | 419,726 | 2.0 | — |
| PE-4 | 1 | 860,729 | 447,300 | 1.9 | — |
| PE-5 | 1 | 684,677 | 340,517 | 2.0 | — |
| PE-6 | 1 | 676,786 | 365,728 | 1.9 | — |
| PE-7 | 1 | 719,991 | 396,051 | 1.8 | — |
| PE-8 | 1 | 740,976 | 391,500 | 1.9 | — |
| PE-9 | 4 | 250,700 | 150,990 | 1.7 | — |
| PE-10 | 4 | 254,392 | 158,308 | 1.6 | — |
| PE-11 | 4 | 258,444 | 157,887 | 1.6 | — |
| PE-12 | 4 | 259,250 | 161,879 | 1.6 | — |
| PE-13 | 5 | 257,041 | 154,974 | 1.7 | — |
| PE-14 | 5 | 264,720 | 162,920 | 1.6 | — |
| PE-15 | 5 | 264,773 | 160,685 | 1.6 | — |
| PE-16 | 5 | 275,780 | 170,048 | 1.6 | — |
| PE-17 | 6 | 197,289 | 122,065 | 1.6 | — |
| PE-18 | 6 | 201,051 | 125,397 | 1.6 | — |
| PE-19 | 6 | 201,397 | 125,250 | 1.6 | — |
| PE-20 | 6 | 204,375 | 127,191 | 1.6 | — |
| PE-21 | 6 | 216,167 | 119,865 | 1.8 | — |
| PE-22 | 6 | 205,782 | 119,200 | 1.7 | — |
| PE-23 | 6 | 445,470 | 186,570 | 2.4 | — |
| PE-24 | 6 | 207,003 | 116,219 | 1.8 | — |
| PE-25 | 8 | 257,931 | 154,684 | 1.7 | — |
| PE-26 | 8 | 260,080 | 158,272 | 1.6 | — |
| PE-27 | 8 | 245,081 | 157,351 | 1.6 | — |
| PE-28 | 8 | 249,871 | 158,712 | 1.6 | — |
| PE-29 | 9 | 1,008,148 | 514,269 | 2.0 | — |
| PE-30 | 9 | 998,474 | 520,443 | 1.9 | — |
| PE-31 | 9 | 1,002,301 | 535,137 | 1.9 | — |
| PE-32 | 9 | 1,016,772 | 537,999 | 1.9 | — |
| PE-33 | 10 | — | — | — | 133.5 |
| PE-34 | 10 | — | — | — | 133.3 |
| PE-35 | 10 | — | — | — | 132.9 |
| PE-36 | 10 | — | — | — | 133.9 |
| PE-37 | 15 | 909,030 | 524,250 | 1.7 | — |
| PE-38 | 15 | 899,999 | 531,896 | 1.7 | — |
| PE-39 | 15 | 844,805 | 505,993 | 1.7 | — |
| PE-40 | 15 | 885,067 | 527,046 | 1.7 | — |
| PE-41 | 18 | 270,183 | 156,223 | 1.7 | — |
| PE-42 | 18 | 295,683 | 169,333 | 1.7 | — |
| PE-43 | 18 | 291,353 | 168,907 | 1.7 | — |
| PE-44 | 18 | 274,783 | 159,030 | 1.7 | — |
| PE-45 | 23 | 492,523 | 261,539 | 1.9 | — |
| PE-46 | 23 | 494,365 | 257,816 | 1.9 | — |
| PE-47 | 23 | 496,834 | 263,764 | 1.9 | — |
| PE-48 | 23 | 507,291 | 259,433 | 2.0 | — |

TABLE 3

Ethylene-1-Octene Polymerization Runs - Part I.

| Ex # | TMC | Activator | Activator[a] μmol | Total Toluene mL | Total Hexanes mL | Final Conversion (psi) | Quench Time (sec) | Polymer Yield (g) | Activity (g/(mmol · hr · atm)) |
|---|---|---|---|---|---|---|---|---|---|
| EO-1 | 1 | MAO | 10.00 | 4.90 | 0 | 20.1 | 75.3 | 0.0569 | 22,298 |
| EO-2 | 1 | MAO | 10.00 | 4.90 | 0 | 20.1 | 88.5 | 0.0575 | 19,160 |
| EO-3 | 1 | MAO | 10.00 | 4.90 | 0 | 20.1 | 93.0 | 0.0615 | 19,505 |
| EO-4 | 1 | MAO | 10.00 | 4.90 | 0 | 20.3 | 96.0 | 0.0594 | 18,249 |
| EO-5 | 1[f] | D4 | 0.02 | 4.80 | 0.099 | 20.1 | 151.8 | 0.0250 | 4,857 |
| EO-6 | 1[f] | D4 | 0.02 | 4.80 | 0.099 | 20.1 | 108.8 | 0.0416 | 11,279 |
| EO-7 | 1[f] | D4 | 0.02 | 4.80 | 0.099 | 20.1 | 205.6 | 0.0421 | 6,041 |
| EO-8 | 1[f] | D4 | 0.02 | 4.80 | 0.099 | 20.1 | 677.4 | 0.0408 | 1,777 |
| EO-9 | 4 | MAO | 10.00 | 4.90 | 0 | 20.1 | 284.0 | 0.0596 | 6,190 |
| EO-10 | 4 | MAO | 10.00 | 4.90 | 0 | 20.1 | 247.0 | 0.0564 | 6,735 |
| EO-11 | 4 | MAO | 10.00 | 4.90 | 0 | 20.1 | 296.0 | 0.0590 | 5,879 |
| EO-12 | 4 | MAO | 10.00 | 4.90 | 0 | 20.1 | 384.3 | 0.0531 | 4,076 |
| EO-13 | 5 | MAO | 10.00 | 4.90 | 0 | 20.1 | 56.2 | 0.0639 | 33,567 |
| EO-14 | 5 | MAO | 10.00 | 4.90 | 0 | 20.5 | 59.0 | 0.0637 | 31,845 |
| EO-15 | 5 | MAO | 10.00 | 4.90 | 0 | 20.3 | 57.8 | 0.0668 | 34,083 |
| EO-16 | 5 | MAO | 10.00 | 4.90 | 0 | 20.3 | 59.1 | 0.0683 | 34,093 |
| EO-17 | 6 | MAO | 10.00 | 4.90 | 0 | 20.8 | 45.9 | 0.0856 | 54,984 |
| EO-18 | 6 | MAO | 10.00 | 4.90 | 0 | 20.1 | 48.6 | 0.0775 | 47,007 |

TABLE 3-continued

Ethylene-1-Octene Polymerization Runs - Part I.

| Ex # | TMC | Activator | Activator[a] μmol | Total Toluene mL | Total Hexanes mL | Final Conversion (psi) | Quench Time (sec) | Polymer Yield (g) | Activity (g/(mmol · hr · atm)) |
|---|---|---|---|---|---|---|---|---|---|
| EO-19 | 6 | MAO | 10.00 | 4.90 | 0 | 20.1 | 44.2 | 0.0864 | 57,644 |
| EO-20 | 6 | MAO | 10.00 | 4.90 | 0 | 20.3 | 45.8 | 0.0872 | 56,159 |
| EO-21 | 6[f] | D4 | 0.02 | 4.80 | 0.099 | 20.1 | 879.4 | 0.0325 | 1,090 |
| EO-22 | 6[f] | D4 | 0.02 | 4.80 | 0.099 | 20.1 | 1195.2 | 0.0328 | 809 |
| EO-23 | 6[f] | D4 | 0.02 | 4.80 | 0.099 | 20.1 | 667.7 | 0.0331 | 1,462 |
| EO-24 | 6[f] | D4 | 0.02 | 4.80 | 0.099 | 20.1 | 366.0 | 0.0355 | 2,861 |
| EO-25 | 8 | MAO | 10.00 | 4.90 | 0 | 20.1 | 70.8 | 0.0662 | 27,599 |
| EO-26 | 8 | MAO | 10.00 | 4.90 | 0 | 20.9 | 66.7 | 0.0730 | 32,306 |
| EO-27 | 8 | MAO | 10.00 | 4.90 | 0 | 20.3 | 72.5 | 0.0704 | 28,650 |
| EO-28 | 8 | MAO | 10.00 | 4.90 | 0 | 20.3 | 75.3 | 0.0676 | 26,490 |
| EO-29 | 9 | MAO | 10.00 | 4.90 | 0 | 20.1 | 167.1 | 0.0483 | 8,525 |
| EO-30 | 9 | MAO | 10.00 | 4.90 | 0 | 20.1 | 187.9 | 0.0520 | 8,165 |
| EO-31 | 9 | MAO | 10.00 | 4.90 | 0 | 20.1 | 181.7 | 0.0515 | 8,360 |
| EO-42 | 9 | MAO | 10.00 | 4.90 | 0 | 20.1 | 180.2 | 0.0483 | 7,905 |
| EO-43 | 10[d] | MAO | 10.00 | 4.90 | 0 | 20.1 | 609.6 | 0.0381 | 1,844 |
| EO-44 | 10[d] | MAO | 10.00 | 4.90 | 0 | 20.1 | 1048.5 | 0.0468 | 1,317 |
| EO-45 | 10[d] | MAO | 10.00 | 4.90 | 0 | 20.1 | 693.7 | 0.0402 | 1,709 |
| EO-46 | 10[d] | MAO | 10.00 | 4.90 | 0 | 20.1 | 623.8 | 0.0351 | 1,660 |
| EO-47 | 10[c] | MAO | 10.00 | 4.90 | 0 | 20.1 | 976.5 | 0.0324 | 979 |
| EO-48 | 10[c] | MAO | 10.00 | 4.90 | 0 | 20.1 | 945.9 | 0.0357 | 1,113 |
| EO-49 | 10[c] | MAO | 10.00 | 4.90 | 0 | 20.1 | 689.1 | 0.0340 | 1,455 |
| EO-40 | 10[c] | MAO | 10.00 | 4.90 | 0 | 19.1 | 1200.7 | 0.0326 | 801 |
| EO-41 | 11[c,e] | MAO | 10.00 | 4.90 | 0 | 4.0 | 1201.2 | 0.0000 | 0 |
| EO-42 | 11[c,e] | MAO | 10.00 | 4.90 | 0 | 2.0 | 1200.3 | 0.0000 | 0 |
| EO-43 | 11[c,e] | MAO | 10.00 | 4.90 | 0 | 4.6 | 1200.8 | 0.0000 | 0 |
| EO-44 | 12[b] | MAO | 10.00 | 4.90 | 0 | 20.1 | 502.3 | 0.0842 | 4,945 |
| EO-45 | 12[b] | MAO | 10.00 | 4.90 | 0 | 20.1 | 327.7 | 0.0874 | 7,867 |
| EO-46 | 12[b] | MAO | 10.00 | 4.90 | 0 | 20.1 | 446.1 | 0.0856 | 5,660 |
| EO-47 | 13[b] | MAO | 10.00 | 4.90 | 0 | 20.1 | 229.8 | 0.0413 | 5,301 |
| EO-48 | 13[b] | MAO | 10.00 | 4.90 | 0 | 20.1 | 197.9 | 0.0474 | 7,065 |
| EO-49 | 13[b] | MAO | 10.00 | 4.90 | 0 | 20.1 | 198.0 | 0.0487 | 7,255 |
| EO-50 | 15 | MAO | 10.00 | 4.90 | 0 | 20.3 | 66.4 | 0.0885 | 39,290 |
| EO-51 | 15 | MAO | 10.00 | 4.90 | 0 | 20.1 | 85.4 | 0.0995 | 34,358 |
| EO-52 | 15 | MAO | 10.00 | 4.90 | 0 | 20.3 | 75.3 | 0.0965 | 37,816 |
| EO-53 | 15 | MAO | 10.00 | 4.90 | 0 | 20.3 | 72.4 | 0.0865 | 35,226 |
| EO-54 | 16[b] | MAO | 10.00 | 4.90 | 0 | 20.1 | 93.7 | 0.0898 | 28,270 |
| EO-55 | 16[b] | MAO | 10.00 | 4.90 | 0 | 20.1 | 98.2 | 0.0966 | 29,018 |
| EO-56 | 16[b] | MAO | 10.00 | 4.90 | 0 | 20.1 | 80.2 | 0.0858 | 31,558 |
| EO-57 | 18 | MAO | 10.00 | 4.90 | 0 | 20.1 | 51.8 | 0.0746 | 42,503 |
| EO-58 | 18 | MAO | 10.00 | 4.90 | 0 | 20.9 | 50.1 | 0.0736 | 43,323 |
| EO-59 | 18 | MAO | 10.00 | 4.90 | 0 | 20.9 | 48.5 | 0.0732 | 44,508 |
| EO-60 | 18 | MAO | 10.00 | 4.90 | 0 | 20.1 | 45.6 | 0.0727 | 47,016 |
| EO-61 | 18[b] | MAO | 10.00 | 4.90 | 0 | 20.3 | 78.7 | 0.0630 | 23,614 |
| EO-62 | 18[b] | MAO | 10.00 | 4.90 | 0 | 20.3 | 78.7 | 0.0612 | 22,939 |
| EO-63 | 18[b] | MAO | 10.00 | 4.90 | 0 | 20.3 | 72.7 | 0.0647 | 26,252 |
| EO-64 | 19[c] | MAO | 10.00 | 4.90 | 0 | 20.6 | 65.6 | 0.0723 | 32,511 |
| EO-65 | 19[c] | MAO | 10.00 | 4.90 | 0 | 20.3 | 59.5 | 0.0736 | 36,489 |
| EO-66 | 19[c] | MAO | 10.00 | 4.90 | 0 | 20.5 | 68.8 | 0.0745 | 31,942 |
| EO-67 | 20[b] | MAO | 10.00 | 4.90 | 0 | 20.1 | 330.3 | 0.0684 | 6,109 |
| EO-68 | 20[b] | MAO | 10.00 | 4.90 | 0 | 20.1 | 255.9 | 0.0685 | 7,896 |
| EO-69 | 20[b] | MAO | 10.00 | 4.90 | 0 | 20.1 | 311.4 | 0.0711 | 6,735 |
| EO-70 | 21[c] | MAO | 10.00 | 4.90 | 0 | 20.1 | 61.0 | 0.0846 | 40,911 |
| EO-71 | 21[c] | MAO | 10.00 | 4.90 | 0 | 20.1 | 59.4 | 0.0888 | 44,099 |
| EO-72 | 23 | MAO | 10.00 | 4.90 | 0 | 20.6 | 33.9 | 0.1043 | 90,670 |
| EO-73 | 23 | MAO | 10.00 | 4.90 | 0 | 20.3 | 35.3 | 0.1083 | 90,442 |
| EO-74 | 23 | MAO | 10.00 | 4.90 | 0 | 20.5 | 33.5 | 0.1099 | 96,706 |
| EO-75 | 23 | MAO | 10.00 | 4.90 | 0 | 20.1 | 32.4 | 0.1026 | 93,346 |
| EO-76 | 24[c] | MAO | 10.00 | 4.90 | 0 | 20.1 | 548.4 | 0.0470 | 2,528 |
| EO-77 | 24[c] | MAO | 10.00 | 4.90 | 0 | 20.1 | 536.6 | 0.0492 | 2,705 |
| EO-78 | 24[c] | MAO | 10.00 | 4.90 | 0 | 20.1 | 623.9 | 0.0482 | 2,279 |
| EO-79 | 25[b] | MAO | 10.00 | 4.90 | 0 | 20.3 | 56.8 | 0.1053 | 54,686 |
| EO-80 | 25[b] | MAO | 10.00 | 4.90 | 0 | 20.6 | 55.4 | 0.1048 | 55,801 |
| EO-81 | 26[c,e] | MAO | 10.00 | 4.90 | 0 | 9.8 | 1200.9 | 0.0184 | 452 |
| EO-82 | 26[c,e] | MAO | 10.00 | 4.90 | 0 | 7.6 | 1200.9 | 0.0175 | 430 |
| EO-83 | 26[c,e] | MAO | 10.00 | 4.90 | 0 | 8.2 | 1200.4 | 0.0176 | 432 |
| EO-84 | 27[b] | MAO | 10.00 | 4.90 | 0 | 20.1 | 45.3 | 0.0737 | 47,992 |
| EO-85 | 27[b] | MAO | 10.00 | 4.90 | 0 | 20.8 | 34.8 | 0.0807 | 68,404 |
| EO-86 | 27[b] | MAO | 10.00 | 4.90 | 0 | 20.8 | 49.8 | 0.0770 | 45,601 |
| EO-87 | 30[c] | MAO | 10.00 | 4.90 | 0 | 20.1 | 1011.8 | 0.0322 | 939 |
| EO-88 | 30[c] | MAO | 10.00 | 4.90 | 0 | 20.1 | 1150.0 | 0.0274 | 703 |
| EO-89 | 30[c] | MAO | 10.00 | 4.90 | 0 | 20.1 | 810.6 | 0.0319 | 1,161 |
| EO-90 | 31[b] | MAO | 10.00 | 4.90 | 0 | 20.1 | 223.1 | 0.0442 | 5,844 |

TABLE 3-continued

Ethylene-1-Octene Polymerization Runs - Part I.

| Ex # | TMC | Activator | Activator[a] μmol | Total Toluene mL | Total Hexanes mL | Final Conversion (psi) | Quench Time (sec) | Polymer Yield (g) | Activity (g/(mmol · hr · atm)) |
|---|---|---|---|---|---|---|---|---|---|
| EO-91 | 31[b] | MAO | 10.00 | 4.90 | 0 | 20.1 | 472.4 | 0.0629 | 3,928 |
| EO-92 | 31[b] | MAO | 10.00 | 4.90 | 0 | 20.3 | 212.0 | 0.0444 | 6,178 |

[a] Micromoles refers to the micromoles of Al in MAO.
[b] In this experiment, an additional 20 equivalents (relative to the TMC) of MAO was premixed with the indicated TMC.
[c] In this experiment, an additional 20 equivalents (relative to the TMC) of MAO was premixed with the indicated TMC and the complex formed was heated for 20 min using a hot plate set at 80° C.
[d] In this experiment, an additional 8 equivalents (relative to the TMC) of TiBAl was premixed with the indicated TMC and the complex formed was heated for 20 min using a hot plate set at 80° C.
[e] In this experiment, the TMC was significantly insoluble. How much catalyst, if any, was added to the reactor is, therefore, unknown.
[f] In this experiment, TiBAl was premixed with the indicated TMC.

TABLE 4

Ethylene-1-Octene Polymerization Runs - Part II.

| Ex # | TMC | Mw | Mn | PDI | Octene (wt %) | Tm (° C.) |
|---|---|---|---|---|---|---|
| EO-1 | 1 | 791,546 | 431,506 | 1.8 | 5.1 | — |
| EO-2 | 1 | 772,701 | 414,829 | 1.9 | 4.8 | — |
| EO-3 | 1 | 809,161 | 425,614 | 1.9 | 5.0 | — |
| EO-4 | 1 | 789,787 | 431,932 | 1.8 | 4.9 | — |
| EO-5 | 1 | 697,076 | 395,779 | 1.8 | 2.4 | — |
| EO-6 | 1 | 668,176 | 370,227 | 1.8 | 2.2 | — |
| EO-7 | 1 | 683,109 | 371,015 | 1.8 | 2.9 | — |
| EO-8 | 1 | 659,623 | 289,568 | 2.3 | 2.7 | — |
| EO-9 | 4 | 257,555 | 148,511 | 1.7 | 14.1 | — |
| EO-10 | 4 | 235,786 | 148,093 | 1.6 | 14.4 | — |
| EO-11 | 4 | 222,962 | 142,764 | 1.6 | 13.7 | — |
| EO-12 | 4 | 232,924 | 147,475 | 1.6 | 13.4 | — |
| EO-13 | 5 | 219,670 | 138,899 | 1.6 | 16.4 | — |
| EO-14 | 5 | 224,942 | 141,482 | 1.6 | 16.2 | — |
| EO-15 | 5 | 218,088 | 138,534 | 1.6 | 16.1 | — |
| EO-16 | 5 | 222,205 | 140,414 | 1.6 | 15.3 | — |
| EO-17 | 6 | 168,429 | 107,438 | 1.6 | 17.6 | — |
| EO-18 | 6 | 174,117 | 111,939 | 1.6 | 17.4 | — |
| EO-19 | 6 | 171,109 | 109,718 | 1.6 | 18.8 | — |
| EO-20 | 6 | 175,634 | 112,896 | 1.6 | 17.3 | — |
| EO-21 | 6 | 199,726 | 116,145 | 1.7 | 11.9 | — |
| EO-22 | 6 | 195,820 | 113,868 | 1.7 | 13.0 | — |
| EO-23 | 6 | 198,696 | 114,683 | 1.7 | 10.5 | — |
| EO-24 | 6 | 195,487 | 112,230 | 1.7 | 10.3 | — |
| EO-25 | 8 | 224,706 | 138,186 | 1.6 | 16.0 | — |
| EO-26 | 8 | 226,327 | 140,870 | 1.6 | 15.9 | — |
| EO-27 | 8 | 216,049 | 138,370 | 1.6 | 15.6 | — |
| EO-28 | 8 | 218,343 | 140,799 | 1.6 | 14.9 | — |
| EO-29 | 9 | 814,165 | 518,678 | 1.6 | 9.9 | — |
| EO-30 | 9 | 877,607 | 548,944 | 1.6 | 9.1 | — |
| EO-31 | 9 | 1,001,190 | 605,667 | 1.7 | 9.2 | — |
| EO-42 | 9 | 1,002,231 | 599,846 | 1.7 | 10.5 | — |
| EO-43 | 10 | — | — | — | 6.7 | 109.5 |
| EO-44 | 10 | — | — | — | 6.9 | 110.6 |
| EO-45 | 10 | — | — | — | 6.6 | 110.7 |
| EO-46 | 10 | — | — | — | 7.1 | 109.9 |
| EO-47 | 10 | 824,540 | 453,060 | 1.8 | 7.8 | 111.8 |
| EO-48 | 10 | 1,032,248 | 632,493 | 1.6 | 6.4 | 113.1 |
| EO-49 | 10 | 1,009,449 | 540,891 | 1.9 | 6.7 | 112.6 |
| EO-40 | 10 | 916,961 | 476,467 | 1.9 | 6.9 | 111.8 |
| EO-41 | 11 | — | — | — | — | — |
| EO-42 | 11 | — | — | — | — | — |
| EO-43 | 11 | — | — | — | — | — |
| EO-44 | 12 | 740,828 | 364,167 | 2.0 | 9.8 | 115.2 |
| EO-45 | 12 | 842,773 | 576,005 | 1.5 | 11.0 | — |
| EO-46 | 12 | 832,670 | 443,784 | 1.9 | 10.0 | 115.3 |
| EO-47 | 13 | 797,338 | 486,096 | 1.6 | 6.7 | 117.7 |
| EO-48 | 13 | 739,564 | 455,362 | 1.6 | 7.4 | 115.9 |
| EO-49 | 13 | 870,428 | 577,646 | 1.5 | 7.4 | 115.9 |
| EO-50 | 15 | 595,182 | 346,916 | 1.7 | 11.3 | — |
| EO-51 | 15 | 566,453 | 306,683 | 1.8 | 13.2 | — |
| EO-52 | 15 | 566,254 | 320,247 | 1.8 | 12.4 | — |
| EO-53 | 15 | 606,301 | 343,422 | 1.8 | 10.3 | — |
| EO-54 | 16 | 630,109 | 380,420 | 1.7 | 11.7 | 108.3 |
| EO-55 | 16 | 636,391 | 382,316 | 1.7 | 11.3 | 109.7 |
| EO-56 | 16 | 635,888 | 389,667 | 1.6 | 10.4 | 110.1 |
| EO-57 | 18 | 207,069 | 129,267 | 1.6 | 15.6 | — |
| EO-58 | 18 | 214,083 | 135,397 | 1.6 | 15.5 | — |
| EO-59 | 18 | 213,293 | 134,098 | 1.6 | 15.5 | — |
| EO-60 | 18 | 216,006 | 135,003 | 1.6 | 15.2 | — |
| EO-61 | 18 | 220,149 | 152,185 | 1.4 | 11.7 | 109.9 |
| EO-62 | 18 | 193,495 | 135,279 | 1.4 | 11.9 | 108.9 |
| EO-63 | 18 | 207,711 | 145,175 | 1.4 | 12.5 | 108.8 |
| EO-64 | 19 | 312,070 | 184,443 | 1.7 | 11.0 | 103.7 |
| EO-65 | 19 | 318,422 | 188,171 | 1.7 | 10.0 | 105.9 |
| EO-66 | 19 | 314,060 | 186,201 | 1.7 | 9.9 | 106.9 |
| EO-67 | 20 | 981,925 | 512,305 | 1.9 | 4.1 | 122.4 |
| EO-68 | 20 | 952,584 | 497,202 | 1.9 | 4.3 | 122.3 |
| EO-69 | 20 | 971,157 | 497,833 | 2.0 | 4.1 | 123.5 |
| EO-70 | 21 | 395,726 | 229,433 | 1.7 | 10.5 | 106.8 |
| EO-71 | 21 | 384,613 | 221,222 | 1.7 | 11.4 | 106.1 |
| EO-72 | 23 | 228,022 | 134,554 | 1.7 | 21.5 | — |
| EO-73 | 23 | 229,684 | 136,452 | 1.7 | 20.1 | — |
| EO-74 | 23 | 227,098 | 132,807 | 1.7 | 19.4 | — |
| EO-75 | 23 | 223,493 | 133,650 | 1.7 | 20.2 | — |
| EO-76 | 24 | 699,798 | 385,110 | 1.8 | 14.0 | — |
| EO-77 | 24 | 848,599 | 488,657 | 1.7 | 15.3 | — |
| EO-78 | 24 | 681,865 | 378,128 | 1.8 | 15.7 | — |
| EO-79 | 25 | 356,706 | 189,278 | 1.9 | 14.6 | — |
| EO-80 | 25 | 357,679 | 188,823 | 1.9 | 16.1 | — |
| EO-81 | 26 | 178,492 | 83,674 | 2.1 | 8.9 | 118.8 |
| EO-82 | 26 | 160,450 | 79,038 | 2.0 | 11.4 | 116.8 |
| EO-83 | 26 | 159,528 | 86,199 | 1.9 | 12.4 | 99.6 |
| EO-84 | 27 | 85,975 | 38,435 | 2.2 | 7.2 | 116.1 |
| EO-85 | 27 | 80,266 | 34,268 | 2.3 | 8.9 | 112.6 |
| EO-86 | 27 | 84,112 | 37,903 | 2.2 | 7.8 | 115.1 |
| EO-87 | 30 | 903,208 | 323,364 | 2.8 | 2.3 | 127.2 |
| EO-88 | 30 | 922,531 | 371,483 | 2.4 | 2.2 | 127.2 |
| EO-89 | 30 | 930,088 | 331,643 | 2.8 | 2.3 | 127.5 |
| EO-90 | 31 | 804,553 | 437,627 | 1.8 | 3.9 | 121.4 |
| EO-91 | 31 | 814,647 | 438,906 | 1.9 | 3.9 | 122.4 |
| EO-92 | 31 | 845,833 | 477,666 | 1.8 | 3.9 | 121.4 |

TABLE 5

Propylene Polymerization Runs.

| Ex # | TMC | TMC μmol | MAO[a] μmol | Toluene μL | Hexanes μL | Propene μL | Quench Time (sec) | Yield (g) | Activity (g/(mmol·hr)) |
|---|---|---|---|---|---|---|---|---|---|
| PP-1  | 9        | 0.10 | 50 | 331 | 3700 | 1066 | 901   | 0.0075 | 300    |
| PP-2  | 9        | 0.10 | 50 | 331 | 3700 | 1066 | 901   | 0.0065 | 260    |
| PP-3  | 9        | 0.08 | 40 | 265 | 3767 | 1066 | 901   | 0.0013 | 65     |
| PP-4  | 9        | 0.08 | 40 | 265 | 3767 | 1066 | 900   | 0.0009 | 45     |
| PP-5  | 16[b]    | 0.08 | 40 | 259 | 3773 | 1066 | 324.4 | 0.0686 | 9,516  |
| PP-6  | 16[b]    | 0.08 | 40 | 259 | 3773 | 1066 | 373.2 | 0.0773 | 9,320  |
| PP-7  | 18[b]    | 0.08 | 40 | 259 | 3773 | 1066 | 129.7 | 0.0724 | 25,119 |
| PP-8  | 18[b]    | 0.08 | 40 | 259 | 3773 | 1066 | 172.3 | 0.0845 | 22,069 |
| PP-9  | 18[b]    | 0.08 | 40 | 259 | 3773 | 1066 | 144.2 | 0.0765 | 23,873 |
| PP-10 | 19[c]    | 0.08 | 40 | 259 | 3773 | 1066 | 117.6 | 0.0923 | 35,319 |
| PP-11 | 19[c]    | 0.08 | 40 | 259 | 3773 | 1066 | 125.1 | 0.1016 | 36,547 |
| PP-12 | 21[c]    | 0.08 | 40 | 259 | 3773 | 1066 | 273.7 | 0.0618 | 10,161 |
| PP-13 | 21[c]    | 0.08 | 40 | 259 | 3773 | 1066 | 263.5 | 0.0623 | 10,639 |
| PP-14 | 21[c]    | 0.08 | 40 | 259 | 3773 | 1066 | 289.8 | 0.0669 | 10,388 |
| PP-15 | 23[c]    | 0.08 | 40 | 259 | 3773 | 1066 | 75.5  | 0.1611 | 96,020 |
| PP-16 | 23[c]    | 0.08 | 40 | 259 | 3773 | 1066 | 75.6  | 0.1456 | 86,666 |
| PP-17 | 23[c]    | 0.08 | 40 | 259 | 3773 | 1066 | 82.2  | 0.1473 | 80,638 |
| PP-18 | 24[c]    | 0.08 | 40 | 259 | 3773 | 1066 | 208.1 | 0.0655 | 14,164 |
| PP-19 | 24[c]    | 0.08 | 40 | 259 | 3773 | 1066 | 216.9 | 0.0728 | 15,104 |
| PP-20 | 24[c]    | 0.08 | 40 | 259 | 3773 | 1066 | 213.9 | 0.0672 | 14,137 |
| PP-21 | 25[c]    | 0.08 | 40 | 259 | 3773 | 1066 | 125.4 | 0.1283 | 46,041 |
| PP-22 | 25[c]    | 0.08 | 40 | 259 | 3773 | 1066 | 131.7 | 0.1383 | 47,255 |
| PP-23 | 25[c]    | 0.08 | 40 | 259 | 3773 | 1066 | 133.3 | 0.1508 | 50,908 |
| PP-24 | 26[c,e]  | 0.08 | 40 | 259 | 3773 | 1066 | 900.6 | 0.0087 | 435    |
| PP-25 | 26[c,e]  | 0.08 | 40 | 259 | 3773 | 1066 | 900.5 | 0.0092 | 460    |
| PP-26 | 26[c,e]  | 0.08 | 40 | 259 | 3773 | 1066 | 901.3 | 0.0087 | 434    |

[a]Micromoles refers to the micromoles of Al in MAO.
[b]In this experiment, an additional 20 equivalents (relative to the TMC) of MAO was premixed with the indicated TMC.
[c]In this experiment, an additional 20 equivalents (relative to the TMC) of MAO was premixed with the indicated TMC and the complex formed was heated for 20 min using a hot plate set at 80° C.
[d]In this experiment, an additional 8 equivalents (relative to the TMC) of MAO was premixed with the indicated TMC and the complex formed was heated for 20 min using a hot plate set at 80° C.
[e]In this experiment, the TMC was significantly insoluble. How much catalyst, if any, was added to the reactor is, therefore, unknown.

TABLE 6

Propylene Polymerization Runs - Part II.

| Ex # | TMC | Mw | Mn | PDI | Tm (° C.) |
|---|---|---|---|---|---|
| PP-1  | 9  | —       | —       | —   | —     |
| PP-2  | 9  | —       | —       | —   | —     |
| PP-3  | 9  | —       | —       | —   | —     |
| PP-4  | 9  | —       | —       | —   | —     |
| PP-5  | 16 | 136,408 | 91,584  | 1.5 | 139.1 |
| PP-6  | 16 | 139,660 | 93,108  | 1.5 | 140.2 |
| PP-7  | 18 | 236,736 | 160,090 | 1.5 | 147.6 |
| PP-8  | 18 | 253,292 | 178,260 | 1.4 | 146.3 |
| PP-9  | 18 | 258,194 | 177,075 | 1.5 | 146.1 |
| PP-10 | 19 | 235,660 | 161,738 | 1.5 | 143.0 |
| PP-11 | 19 | 245,757 | 167,924 | 1.5 | 145.4 |
| PP-12 | 21 | 288,202 | 201,778 | 1.4 | 143.0 |
| PP-13 | 21 | 270,371 | 184,264 | 1.4 | 142.5 |
| PP-14 | 21 | 285,363 | 196,662 | 1.5 | 142.8 |
| PP-15 | 23 | 216,068 | 143,102 | 1.5 | 141.7 |
| PP-16 | 23 | 219,941 | 145,507 | 1.5 | 142.6 |
| PP-17 | 23 | 228,642 | 147,118 | 1.6 | 144.0 |
| PP-18 | 24 | 36,007  | 23,392  | 1.5 | —     |
| PP-19 | 24 | 38,166  | 24,963  | 1.5 | —     |
| PP-20 | 24 | 38,830  | 25,921  | 1.5 | —     |
| PP-21 | 25 | 292,381 | 194,567 | 1.5 | 140.9 |
| PP-22 | 25 | 293,861 | 192,920 | 1.5 | 140.6 |
| PP-23 | 25 | 290,722 | 190,422 | 1.5 | 140.7 |
| PP-24 | 26 | —       | —       | —   | —     |
| PP-25 | 26 | —       | —       | —   | —     |
| PP-26 | 26 | —       | —       | —   | —     |

TABLE 7

Ethylene-Propylene Polymerization Runs - Part I.

| Ex # | TMC | TMC µmol | MAO[a] µmol | Hexanes µL | Toluene µL | Propene µL | Quench Time (sec) | Yield (g) | Activity (g/(mmol · hr)) |
|---|---|---|---|---|---|---|---|---|---|
| EP-1 | 9 | 0.08 | 40 | 3724 | 265 | 1066 | 901.0 | 0.0061 | 305 |
| EP-2 | 9 | 0.08 | 40 | 3724 | 265 | 1066 | 901.6 | 0.0047 | 235 |
| EP-3 | 9 | 0.10 | 50 | 3657 | 331 | 1066 | 525.3 | 0.0298 | 2042 |

[a]Micromoles refers to the micromoles of Al in MAO.

TABLE 8

Ethylene-Propylene Polymerization Runs - Part II.

| Ex # | TMC | Mw | Mn | PDI | Ethylene (wt %) |
|---|---|---|---|---|---|
| EP-1 | 9 | — | — | — | — |
| EP-2 | 9 | — | — | — | — |
| EP-3 | 9 | 53,966 | 29,105 | 1.9 | 28.0 |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention. All documents described herein are incorporated by reference herein, including any priority documents and/or testing procedures to the extent they are not inconsistent with this text. Likewise, the term "comprising" is considered synonymous with the term "including" for purposes of Australian law.

What we claim is:

1. A metallocene compound represented by the formula (1):

wherein:

M is a transition metal atom having a coordination number of n selected from Group 3, 4, 5 or 6 of the Periodic Table of Elements, or a lanthanide metal atom, or actinide metal atom;

each A is independently a substituted polycyclic arenyl ligand pi-bonded to M selected from the group consisting of a substituted fluorenyl ligand, a substituted cyclopentanaphthyl ligand, and a substituted indenyl ligand, wherein each A ligand includes at least one bromo substituent directly bonded to an $sp^2$ carbon at a bondable ring position and, when each A is a substituted indenyl ligand and y is equal to one and the ligand includes at least one bromo substituent at the 4, 5, or 6 position of the indenyl ligand, then A also includes at least one other substituent in the indenyl ligand selected from hydrocarbyl, substituted hydrocarbyl, halogen, halocarbyl, substituted halocarbyl, silylcarbyl, substituted silylcarbyl, germylcarbyl, substituted germylcarbyl, or other heteroatom substituents wherein the heteroatom is bonded directly to a ring carbon of the ring structure ligand and is boron, a Group 15 atom, or a Group 16 atom, preferably boron, nitrogen, oxygen, phosphorus, or sulfur;

Y is an optional bridging group containing at least one Group 13, 14, 15, or 16 element and is bonded to any single position of the ring structure of A, y is zero or 1, indicating the absence (y=0) or presence (y=1) of Y; and each X is a univalent anionic ligand, or two X are joined and bound to the metal atom to form a metallocycle ring, or two X are joined to form a chelating ligand, a diene ligand, or an alkylidene ligand.

2. The metallocene compound of claim 1 wherein M is a Group 4 transition metal selected from titanium, zirconium and hafnium.

3. The metallocene compound of claim 1 wherein each A is independently a substituted indenyl ligand with at least one bromo substituent at the 4, 5, or 6 position of the indenyl ligand, and said at least one other substituent is connected to the 2 position of the indenyl ligand.

4. The compound of claim 1 wherein Y is present and is a bridging group containing boron or a Group 14, 15 or 16 element.

5. The compound of claim 1 wherein Y is present and is selected from the group consisting of: S, O, NR', PR', P(=S)R', AsR', SbR', O—O, S—S, R'N—NR', R'P—PR', O—S, O—NR', O—PR', S—NR', S—PR', R'N—PR', R'$_2$C, R'$_2$Si, R'$_2$Ge, R'$_2$CCR'$_2$, R'$_2$CCR'$_2$CR'$_2$, R'$_2$CCR'$_2$CR'$_2$CR'$_2$, R'C=CR', R'C=CR'CR'$_2$, R'$_2$CCR'=CR'CR'$_2$, R'C=CR'CR'=CR', R'C=CR'CR'$_2$CR'$_2$, R'$_2$CSiR'$_2$, R'$_2$SiSiR'$_2$, R'$_2$CSiR'$_2$CR'$_2$, R'$_2$SiCR'$_2$SiR'$_2$, R'C=CR'SiR'$_2$, R'$_2$CGeR'$_2$, R'$_2$GeGeR'$_2$, R'$_2$CGeR'$_2$CR'$_2$, R'$_2$GeCR'$_2$GeR'$_2$, R'$_2$SiGeR'$_2$, R'C=CR'GeR'$_2$, R'B, R'$_2$C—BR', R'$_2$C—BR'—CR'$_2$, R'$_2$C—O—CR'$_2$, R'$_2$CR'$_2$C—O—CR'$_2$CR'$_2$, R'$_2$C—O—CR'$_2$CR'$_2$, R'$_2$C—O—CR'=CR', R'$_2$C—S—CR'$_2$, R'$_2$CR'$_2$C—S—CR'$_2$CR'$_2$, R'$_2$C—S—CR'$_2$CR'$_2$, R'$_2$C—S—CR'=CR', R'$_2$C—Se—CR'$_2$, R'$_2$CR'$_2$C—Se—CR'$_2$CR'$_2$, R'$_2$C—Se—CR'$_2$CR'$_2$, R'$_2$C—Se—CR'=CR', R'$_2$C—N=CR', R'$_2$C—NR'—CR'$_2$, R'$_2$C—NR'—CR'$_2$CR'$_2$, R'$_2$C—NR'—CR'=CR', R'$_2$CR'$_2$C—NR'—CR'$_2$CR'$_2$, R'$_2$C—P=CR', and R'$_2$C—PR'—CR'$_2$ where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

6. The compound of claim 1 wherein Y is present and is selected from The group consisting of: O, S, NMe, Net, NPr, NPh, N-Ph-p-Me, PMe, PEt, PPr, PPh, P(=S)Ph, CH$_2$, CH$_2$CH$_2$, CH(CH$_3$)$_2$, SiMe$_2$, SiEt$_2$, SiPh$_2$, SiMePh, Si(CH$_2$)$_3$, and Si(CH$_2$)$_4$.

7. A metallocene compound represented by the formula (2):

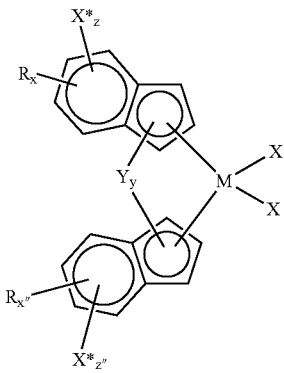

or formula (3):

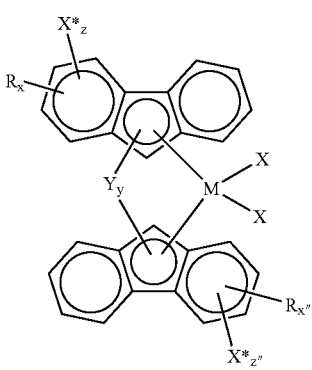

or formula (4):

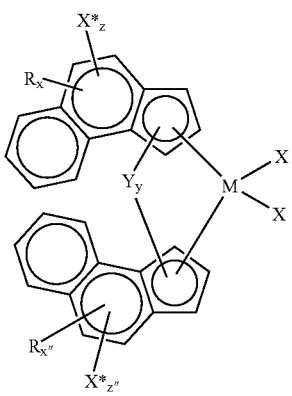

or formula (5):

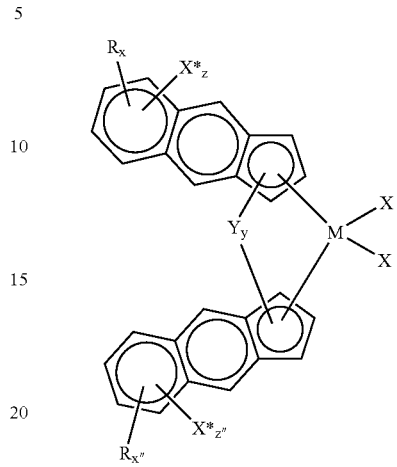

wherein

M is a group 3, 4, 5 or 6 transition metal atom, or a lanthanide metal atom, or actinide metal atom;

each R is bonded to any position of the ring structure ligand and is, independently, hydrogen, or a hydrocarbyl, substituted hydrocarbyl, halocarbyl, substituted halocarbyl, silylcarbyl, substituted silylcarbyl, germylcarbyl, substituted germylcarbyl, or other heteroatom substituents wherein the heteroatom is bonded directly to a ring carbon of the ring structure ligand and is boron, a Group 15 atom, or a Group 16 atom, preferably boron, nitrogen, oxygen, phosphorus, or sulfur, and optionally, two or more adjacent R may join together to form a substituted or unsubstituted, saturated, partially unsaturated, or aromatic cyclic or polycyclic substituent;

x and x" represent the number of R substituents bonded to the ring structure ligand; x and x" are, independently, 4, 5, 6, or 7 for formula (2); x and x" are, independently, 6, 7, 8, or 9 for each of formulae (3), (4) and (5);

each X* is bonded to any position of the ring structure ligand and is a bromo substitutent; provided that when one X* substituent is bonded to the 4,5, or 6 position of each indenyl ligand in formula (2), then at least one other substituent is selected from hydrocarbyl, substituted hydrocarbyl, halogen, halocarbyl, substituted halocarbyl, silylcarbyl, substituted silylcarbyl, germylcarbyl, substituted germylcarbyl, or other heteroatom substituents wherein the heteroatom is bonded directly to a ring carbon of the ring structure ligand and is boron, a Group 15 atom, or a Group 16 atom, preferably boron, nitrogen, oxygen, phosphorus, or sulfur;

z and z" represent the number of X* substituents bonded to its respective ring structure ligand; z and z" are, independently, 0, 1 or 2; z+z"=1, 2, 3, or 4;

when present, Y is bonded to any single position of each ring structure ligand, and is a bridging group containing a Group 13, 14, 15, or 16 element;

y is 0 or 1, indicating the absence (y=0) or presence (y=1) of Y;

x+y+z=7, and x"+y+z"=7 for formula (2);

x+y+z=9, and x"+y+z"=9 for each of formulae (3), (4) and (5); and each X is a univalent anionic ligand, or two X are joined and bound to the metal atom to form a metallocycle ring, or two X are joined to form a chelating ligand, a diene ligand, or an alkylidene ligand.

8. The metallocene compound of claim 7 wherein the transition metal is a Group 4 transition metal selected from titanium, zirconium and hafnium.

9. The compound of claim 7 wherein Y is present and is a bridging group containing boron or a Group 14, 15 or 16 element.

10. The compound of claim 7 wherein Y is 1 and is selected from the group consisting of: S, O, NR', PR', P(=S)R', AsR', SbR', O—O, S—S, R'N—NR', R'P—PR', O—S, O—NR', O—PR', S—NR', S—PR', R'N—PR', R'$_2$C, R'$_2$Si, R'$_2$Ge, R'$_2$CCR'$_2$, R'$_2$CCR'$_2$CR'$_2$, R'$_2$CCR'$_2$CR'$_2$CR'$_2$, R'C=CR', R'C=CR'CR'$_2$, R'$_2$CCR'=CR'CR'$_2$, R'C=CR'CR'=CR', R'C=CR'CR'$_2$CR'$_2$, R'$_2$CSiR'$_2$, R'$_2$SiSiR'$_2$, R'$_2$CSiR'$_2$CR'$_2$, R'$_2$SiCR'$_2$SiR'$_2$, R'C=CR'SiR'$_2$, R'$_2$CGeR'$_2$, R'$_2$GeGeR'$_2$, R'$_2$CGeR'$_2$CR'$_2$, R'$_2$GeCR'$_2$GeR'$_2$, R'$_2$SiGeR'$_2$, R'C=CR'GeR'$_2$, R'B, R'$_2$C—BR', R'$_2$C—BR'—CR'$_2$, R'$_2$C—O—CR'$_2$, R'$_2$CR'$_2$C—O—CR'$_2$CR'$_2$, R'$_2$C—O—CR'$_2$CR'$_2$, R'$_2$C—O—CR'=CR', R'$_2$C—S—CR'$_2$, R'$_2$CR'$_2$C—S—CR'$_2$CR'$_2$, R'$_2$C—S—CR'$_2$CR'$_2$, R'$_2$C—S—CR'=CR', R'$_2$C—Se—CR'$_2$, R'$_2$CR'$_2$C—Se—CR'$_2$CR'$_2$, R'$_2$C—Se—CR'$_2$CR'$_2$, R'$_2$C—Se—CR'=CR', R'$_2$C—N=CR', R'$_2$C—NR'—CR'$_2$, R'$_2$C—NR'—CR'$_2$CR'$_2$, R'$_2$C—NR'—CR'=CR', R'$_2$CR'$_2$C—NR'—CR'$_2$CR'$_2$, R'$_2$C—P=CR', and R'$_2$C—PR'—CR'$_2$ where R' is hydrogen or a C$_1$-C$_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

11. The compound of claim 1 wherein Y is present and is selected from the group consisting of: O, S, NMe, NEt, NPr, NPh, N—Ph—p—Me, PMe, PEt, PPr, PPh, P(=S)Ph, CH$_2$, CH$_2$CH$_2$, CH(CH$_3$)$_2$, SiMe$_2$, SiEt$_2$, SiPh$_2$, SiMePh, Si(CH$_2$)$_3$, and Si(CH$_2$)$_4$.

12. A metallocene compound selected from:

rac-bis($\eta^5$-2-methyl-4-bromoinden-1-yl)zirconium dichloride, meso-bis($\eta^5$-2-methyl-4-bromoinden-1-yl)zirconium dichloride, rac-bis($\eta^5$-2-methyl-4-bromoinden-1-yl)hafnium dichloride, meso-bis($\eta^5$-2-methyl-4-bromoinden-1-yl)hafnium dichloride, rac-dimethylsilyl-bis($\eta^5$-4-bromo-2-methylinden-1-yl)zirconium dichloride, meso-dimethylsilyl-bis($\eta^5$-4-bromo-2-methylinden-1-yl)zirconium dichloride, meso-dimethylsilyl-bis($\eta^5$-4-bromo-2-methylinden-1-yl)hafnium dichloride, rac-dimethylsilyl-bis($\eta^5$-4-bromo-2-methylinden-1-yl)zirconium dibromide, rac-[dimethylsilyl-bis($\eta^5$-5-bromo-2-methyl-6,7,8,9-tetrahydro-3H-cyclopenta[a]naphthalen-3-yl)]zirconium dichloride, rac-diethylsilyl-bis($\eta^5$-5-bromo-2-methyl-6,7,8,9-tetrahydro-3H-cyclopenta[a]naphthalen-3-yl)zirconium dichloride, rac-diethylsilyl-bis($\eta^5$-4-bromo-2-methylinden-1-yl)zirconium dichloride, rac-dimethylsilyl-bis($\eta^5$-4-bromo-2,6-dimethylinden-1-yl)zirconium dichloride, rac-[dimethylsilyl-bis($\eta^5$-4-bromo-2-methyl-5,6,7,8,-tetrahydro-1H-cyclopenta[b]naphthalen-1-yl)]zirconium dichloride, rac-dimethylsilyl-bis($\eta^5$-4-bromo-2,5-dimethylinden-1-yl)zirconium dichloride, rac-dimethylsilyl-bis($\eta^5$-4-bromo-2,5-dimethylinden-1-yl)zirconium dichloride, rac-dimethylsilyl-bis($\eta^5$-4-bromo-2-isopropylinden-1-yl)zirconium dichloride, rac-dimethylsilyl-bis($\eta^5$-4-bromo-2-methyl-6-isopropylinden-1-yl)zirconium dichloride, rac-isopropylidene-bis($\eta^5$-4-bromo-3-methylinden-1-yl)zirconium dichloride, meso-isopropylidene-bis($\eta^5$-4-bromo-3-methylinden-1-yl)zirconium dichloride, and rac-dimethylsilyl-bis($\eta^5$-4-bromo-6-fluoro-2-methylinden-1-yl)zirconium dichloride.

13. A catalyst system comprising the metallocene compound of claim 1 and an activator.

14. A process for polymerizing olefins comprising contacting the catalyst system of claim 13 with at least one olefin.

15. The process of claim 14 wherein said at least one olefin comprises ethylene and/or propylene.

16. A catalyst system comprising the metallocene compound of claim 7 and an activator.

17. A process for polymerizing olefins comprising contacting the catalyst system of claim 16 with at least one olefin.

18. The process of claim 17 wherein said at least one olefin comprises ethylene and/or propylene.

19. A catalyst system comprising the metallocene compound of claim 12 and an activator.

20. A process for polymerizing olefins comprising contacting the catalyst system of claim 19 with at least one olefin.

21. The process of claim 20 wherein said at least one olefin comprises ethylene and/or propylene.

* * * * *